US008986697B2

(12) United States Patent
Ma et al.

(10) Patent No.: US 8,986,697 B2
(45) Date of Patent: Mar. 24, 2015

(54) **ANTIBODIES FOR THE TREATMENT OF *CLOSTRIDIUM DIFFICILE*-ASSOCIATED INFECTION AND DISEASE**

(75) Inventors: Dangshe Ma, Millwood, NY (US); Kirsten Nagashima, Valhalla, NY (US); Brian Kennedy, Yorktown Heights, NY (US); Gerald P. Donovan, Kittery, ME (US); Yun Kang, Livingstone, NJ (US); William C. Olson, Yorktown Heights, NY (US); Shankar Kumar, Pleasanton, CA (US); Naoya Tsurushita, Palo Alto, CA (US); Andre J. Marozsan, Port Chester, NY (US); Albert Cupo, Stamford, CT (US)

(73) Assignee: Progenics Pharmaceuticals, Inc., Tarrytown, NY (US)

( * ) Notice: Subject to any disclaimer, the term of this patent is extended or adjusted under 35 U.S.C. 154(b) by 33 days.

(21) Appl. No.: 13/641,315

(22) PCT Filed: Apr. 15, 2011

(86) PCT No.: PCT/US2011/032713
§ 371 (c)(1),
(2), (4) Date: Mar. 26, 2013

(87) PCT Pub. No.: WO2011/130650
PCT Pub. Date: Oct. 20, 2011

(65) Prior Publication Data
US 2013/0202618 A1   Aug. 8, 2013

Related U.S. Application Data

(60) Provisional application No. 61/324,503, filed on Apr. 15, 2010, provisional application No. 61/381,669, filed on Sep. 10, 2010.

(51) Int. Cl.
*A61K 39/40* (2006.01)
*C07K 16/12* (2006.01)
*A61K 45/06* (2006.01)
*A61K 39/00* (2006.01)

(52) U.S. Cl.
CPC .............. *C07K 16/1282* (2013.01); *A61K 39/40* (2013.01); *A61K 45/06* (2013.01); *A61K 2039/505* (2013.01); *C07K 2317/24* (2013.01); *C07K 2317/33* (2013.01); *C07K 2317/55* (2013.01); *C07K 2317/76* (2013.01); *C07K 2317/92* (2013.01)
USPC .................. 424/167.1; 424/150.1; 424/136.1

(58) Field of Classification Search
None
See application file for complete search history.

(56) References Cited

U.S. PATENT DOCUMENTS

| | | |
|---|---|---|
| 4,879,218 A | 11/1989 | Wilkins et al. |
| 5,231,003 A | 7/1993 | Coughlin et al. |
| 5,292,668 A | 3/1994 | Paulus |
| 5,545,806 A | 8/1996 | Lonberg et al. |
| 5,545,807 A | 8/1996 | Surani et al. |
| 5,585,089 A | 12/1996 | Queen et al. |
| 5,591,669 A | 1/1997 | Krimpenfort et al. |
| 5,598,369 A | 1/1997 | Chen et al. |
| 5,693,761 A | 12/1997 | Queen et al. |
| 5,693,762 A | 12/1997 | Queen et al. |
| 5,932,448 A | 8/1999 | Tso et al. |
| 6,071,517 A | 6/2000 | Fanger et al. |
| 6,150,584 A | 11/2000 | Kucherlapati et al. |
| 6,180,370 B1 | 1/2001 | Queen et al. |
| 7,235,641 B2 | 6/2007 | Kufer et al. |
| 7,442,778 B2 | 10/2008 | Gegg et al. |
| 2005/0287150 A1 | 12/2005 | Ambrosino et al. |
| 2007/0071675 A1 | 3/2007 | Wu et al. |
| 2009/0060910 A1 | 3/2009 | Johnson et al. |
| 2009/0087478 A1 | 4/2009 | Hansen et al. |
| 2013/0202618 A1 | 8/2013 | Ma et al. |

FOREIGN PATENT DOCUMENTS

| | | |
|---|---|---|
| CN | 101014620 A | 8/2007 |
| WO | WO 2006/071877 A2 | 7/2006 |
| WO | WO 2006/121422 A2 | 11/2006 |
| WO | WO 2006/121422 A3 | 3/2007 |
| WO | WO 2006/071877 A3 | 4/2007 |
| WO | WO 2006/121422 A8 | 4/2007 |
| WO | WO 2007/093630 A1 | 8/2007 |
| WO | WO 2008/024188 A2 | 2/2008 |
| WO | WO 2008/024188 A8 | 7/2008 |
| WO | WO 2008/024188 A3 | 9/2008 |
| WO | WO 2009/030734 A1 | 3/2009 |

(Continued)

OTHER PUBLICATIONS

Babcock et al. (Infect. Immun., 74:6339-6347, 2006).*
Vajdos et al. (J Mol Biol. Jul. 5, 2002;320(2):415-28.*
Brown et al. (J Immunol. May 1996;156(9):3285-91.*
U.S. Appl. No. 61/324,503, filed Apr. 15, 2010, Ma et al.
U.S. Appl. No. 61/381,669, filed Sep. 10, 2010, Ma et al.
American Type Culture Collection, "ATTC® 43255-FZ," organism:

(Continued)

*Primary Examiner* — Brian J Gangle
(74) *Attorney, Agent, or Firm* — Mueting, Raasch & Gebhardt, P.A.

(57) ABSTRACT

Provided herein are reagents, compositions, and therapies with which to treat *Clostridium difficile* infection and related disease conditions and pathologies, such as *Clostridium difficile*-associated diarrhea, resulting from infection by *Clostridium difficile* bacteria and the enterotoxins produced by these bacteria. In particular, antibodies or antigen-binding fragments thereof that bind specifically to toxin A and/or toxin B of *C difficile* and neutralize the activities of these toxins; compositions comprising such antibodies; and methods of using the antibodies and the compositions are provided.

24 Claims, 54 Drawing Sheets

(56) References Cited

FOREIGN PATENT DOCUMENTS

| WO | WO 2009/058383 A2 | 5/2009 |
|---|---|---|
| WO | WO 2009/058383 A3 | 12/2009 |
| WO | WO 2011/130650 A2 | 10/2011 |
| WO | WO 2011/130650 A3 | 4/2012 |

OTHER PUBLICATIONS

*Clostridium difficile*; designation: VPI 10463 [online]; Manassas, VA [retrieved on Feb. 4, 2014] from the Internet. Retrieved from the Internet: <www.atcc.org>; 2 pgs.
American Type Culture Collection, "ATTC® 43596," organism: *Cricetulus griseus*; designation 545 [online]; Manassas, VA [retrieved on Feb. 4, 2014] from the Internet. Retrieved from the Internet: <www.atcc.org>; 2 pgs.
American Type Culture Collection, "ATTC® CCL-61," organism: *Clostridium difficile* [online]; Manassas, VA [retrieved on Feb. 4, 2014] from the Internet. Retrieved from the Internet: <www.atcc.org>; 2 pgs.
Anton et al., "Rifalazil treats and prevents relapse of *Clostridium difficile*-associated diarrhea in hamsters," *Antimicrob. Agents Chemother.*, Oct. 2004; 48:3975-3979.
Aslam et al., "Treatment of *Clostridium difficile*-associated disease: old therapies and new strategies," *Lancet Infect. Dis.*, Sep. 2005; 5:549-557.
Ausubel et al. (Eds.), *Current Protocols in Molecular Biology*, John Wiley & Sons: New York, NY; 1994. Title page, publisher's page, and table of contents; 14 pages.
Babcock et al., "Human Monoclonal Antibodies Neutralize Toxins Produced by Epidemic Strains of *Clostridium difficile*," meeting abstract presented at the *Infectious Diseases Society of America 43rd Annual Meeting*: San Francisco, CA; Oct. 6-9, 2005; 1 page.
Babcock et al., "Human monoclonal antibodies directed against toxins A and B prevent *Clostridium difficile*-induced mortality in hamsters," *Infect. Immun.* Nov. 2006 74(11):6339-6349. Available online on Sep. 11, 2006.
Barbut et al., "Epidemiology of recurrences or reinfections of *Clostridium difficile*-associated diarrhea," *J. Clin. Microbiol.*, Jun. 2000; 38(6):2386-2388.
Bartlett, "Antibiotic-associated pseudomembranous colitis due to toxin-producing clostridia," *The New England Journal of Medicine*, Mar. 1978; 298(10):531-534.
Bartlett, "Antimicrobial agents implicated in *Clostridium difficile* toxin-associated diarrhea of colitis," *Johns Hopkins Med. J.*, Jul. 1981; 149:6-9.
Berge et al., "Pharmaceutical salts," *J. Pharm. Sci.*, Jan. 1977; 66(1):1-19.
Bird et al., "Single-chain antigen-binding proteins," *Science*, Oct. 1988; 242(4877):423-426.
Boss et al., "Use of vancomycin hydrochloride for treatment of *Clostridium difficile* enteritis in Syrian hamsters," *Lab Anim. Sci.*, Feb. 1994; 44(1):31-37.
Campbell, "Chapter 3: Selection of animals and cell lines," in *Monoclonal Antibody Technology: The Production and Characterization of Rodent and Human Hybridomas*, Campbell (Ed.); in *Laboratory Techniques in Biochemistry and Molecular Biology*, vol. 13, Burdon et al. (Eds.); Elsevier: New York, NY, 1984; Title page, publisher's page, and pp. 66-85.
Carswell et al., "Daclizumab: a review of its use in the management of organ transplantation," *BioDrugs*, 2001; 15(11):745-773.
Carter et al., "Humanization of an anti-p185$^{HER2}$ antibody for human cancer therapy," *Proc. Natl. Acad. Sci. USA*, May 1992; 89:4285-4289.
Casale, "Omalizumab: an effective anti-IgE treatment for allergic asthma and rhinitis," *Drugs Today (Barc.)*, Apr. 2004; 40(4):367-376.
Chase et al., (Eds.), *Remington's Pharmaceutical Sciences*, Mack Publishing Company: Easton, PA; 1965. Cover page, title page and table of contents only, 3 pgs.
Cheknis et al., "Distribution of *Clostridium difficile* strains from a North American, European and Australian trial of treatment for *C.*

*difficile* infections: 2005-2007," *Anaerobe*, Sep. 2009; 15:230-233. Available online on Sep. 6, 2009.
Clark et al., "Toxin A from *Clostridium difficile* binds to rabbit erythrocyte glycolipids with terminal Galα1-3Galβ1-4GlcNAc sequences," *Arch. Biochem. Biophys.*, Aug. 1987; 257(1):217-229.
Co et al., "Chimeric and humanized antibodies with specificity for the CD33 antigen," *J. Immunol.*, Feb. 1992; 148:1149-1154.
Cole et al., *Monoclonal Antibodies and Cancer Therapy*, 1995, Alan R. Liss: New York, NY. Title page, publisher's page, and pp. 77-96.
Delmee et al., "Serogrouping of *Clostridium difficile* strains by slide agglutination," *J. Clin. Microbiol.*, Mar. 1985; 21(3):323-327.
Delmee et al., "Characterization of flagella of *Clostridium difficile* and their role in serogrouping reactions," *J. Clin. Microbiol.*, Oct. 1990; 28(10):2210-2214.
Demarest et al., "Neutralization of *Clostridium difficile* toxin A using antibody combinations," *MAbs* Mar.-Apr. 2010; 2:190-198. Available online on Mar. 1, 2010.
Drudy et al., "High-level resistance to moxifloxacin and gatifloxacin associated with a novel mutation in gyrB in toxin-A-negative, toxin-B-positive *Clostridium difficile*," *J. Antimicrob. Chemother.*, Oct. 2006; 58:1264-1267.
Emens, "Trastuzumab: targeted therapy for the management of HER-2/neu-overexpressing metastatic breast cancer," *Am. J. Ther.*, May-Jun. 2005; 12:243-253.
Fagnani, "The immunogenicity of foreign monoclonal antibodies in human disease applications: problems and current approaches," in *Immunology Series* vol. 61: *Tumor Immunology and Cancer Therapy*, Goldfarb and Whiteside (Eds.); Marcel Dekker, Inc.: New York, NY; 1994. Cover page, publisher's page, and pp. 3-22.
Fanger et al., "Bispecific Antibodies," *Drug News and Perspectives*, 1995; 8(3):133-137.
Fekety et al., "Diagnosis and treatment of *Clostridium difficile* colitis," *JAMA*, Jan. 1993; 269(1):71-75.
Fekety et al., "Recurrent *Clostridium difficile* diarrhea: characteristics of and risk factors for patients enrolled in a prospective, randomized, double-blinded trial," *Clin. Infect. Dis.*, Mar. 1997; 24:324-333.
Fenton et al., "Palivizumab: a review of its use as prophylaxis for serious respiratory syncytial virus infection," *Paediatr. Drugs*, 2004; 6:177-197.
Fernie et al., "Active and passive immunization to protect against antibiotic associated caecitis in hamsters," *Developmental Biology Standard*, 1983; 53:325-332.
Ferrara et al., "Discovery and development of bevacizumab, an anti-VEGF antibody for treating cancer," *Nat. Rev. Drug Discov.*, May 2004, 3:391-400.
Finn et al., "Monoclonal antibody therapy for breast cancer: Herceptin," in *Cancer Chemotherapy and Biological Response Modifiers Annual 21*; Giaccone et al. (Eds.). Elsevier, copyright 2003. Title page and pp. 223-233.
Freeman et al., "Comparison of the efficacy of ramoplanin and vancomycin in both in vitro and in vivo models of clindamycin-induced *Clostridium difficile* infection," *J. Antimicrob. Chemother.*, Sep. 2005; 56:717-725.
Gerding et al., "Restriction endonuclease analysis (REA) typing of *Clostridium difficile* in a phase 3 treatment trial of fidaxomicin vs vancomycin: Decreased cure rate for epidemic BI/NAP1/027 strain," meeting Abstract L1-1642 presented at the American Society of Microbiology *49th Interscience Conference on Antimicrobial Agents and Chemotherapy*: San Francisco, CA; Sep. 12-15, 2009; 3 pgs.
Giannasca et al., "Serum antitoxin antibodies mediate systemic and mucosal protection from *Clostridium difficile* disease in hamsters," *Infect. Immun.*, Feb. 1999; 67(2):527-538.
Giles et al., "Gemtuzumab ozogamicin in the treatment of acute myeloid leukemia," *Cancer*, Nov. 2003; 98:2095-2104.
Goding, *Monoclonal Antibodies: Principles and Practice*, Academic Press: London, UK, 1983; pp. 98-118.
Goding (Ed.), *Monoclonal Antibodies: Principles and Practice, 2nd Edition*, Academic Press: Orlando, FL; 1986. Title page, publishers page, and p. 60-61 and 65-66.
Harlow et al., *Antibodies, a laboratory manual*, Cold Spring Harbor Laboratory Press, Cold Spring Harbor, New York, NY, 1988; cover page, title page, and table of contents only, 9 pgs.

(56) References Cited

OTHER PUBLICATIONS

Holgate et al., "Anti-immunoglobulin E treatment with omalizumab in allergic diseases: an update on anti-inflammatory activity and clinical efficacy," *Clin. Exp. Allergy*, Apr. 2005; 35:408-416.

Holliger et al., "'Diabodies': Small bivalent and bispecific antibody fragments," *Proc. Natl. Acad. Sci.*, Jul. 1993; 90:6444-6448.

Hussack et al., "Neutralization of *Clostridium difficile* toxin A with single-domain antibodies targeting the cell receptor binding domain," *J. Biol. Chem.* Mar. 2011; 286(11):8961-8976. Available online on Jan. 7, 2011.

Huston et al., "Protein engineering of antibody binding sites: Recovery of specific activity in an anti-digoxin single-chain Fv analogue produced in *Escherichia coli*," *Proc. Natl. Acad. Sci.*, Aug. 1988; 85:5879-5883.

Jodlowski et al., "Emerging therapies in the treatment of *Clostridium difficile*-associated disease," *Ann. Pharmacother.*, Dec. 2006; 40:2164-2169. Available online on Nov. 21, 2006.

Jordan, "Efalizumab for the treatment of moderate to severe plaque psoriasis," *Ann. Pharmacother.*, Sep. 2005; 39:1476-1482. Available online on Jul. 5, 2005.

Kabat et al., *Sequences of Proteins of Immunological Interest*, vol. 1, 5th Ed. U.S. Public Health Service, National Institutes of Health. NIH Publication No. 91/3242; Copyright 1991. Cover page, publisher's page, and table of contents; 13 pgs.

Kamiya et al., "Production of monoclonal antibody to *Clostridium difficile* toxin A which neutralizes enterotoxicity but not haemagglutination activity," *FEMS Microbiol. Lett.*, Jul. 1991; 65:311-315.

Kelly et al., "Human colonic aspirates containing immunoglobulin A antibody to *Clostridium difficile* toxin A inhibit toxin A-receptor binding," *Gastroenterology*, Jan. 1992; 102:35-40.

Kelly et al., "*Clostridium difficile* colitis," *New Eng. J. Med.*, Jan. 1994; 330(4):257-262.

Kelly et al., "Anti-*Clostridium difficile* bovine immunoglobulin concentrate inhibits cytotoxicity and enterotoxicity of *C. difficile* toxins," *Antimicrob. Agents Chemother.*, Feb. 1996; 40(2):373-379.

Kelly et al., "*Clostridium difficile*—more difficult than ever," *The New England Journal of Medicine*, Oct. 2008; 359:1932-1940.

Kim et al, "Immunization of adult hamsters against *Clostridium difficile* -associated ileocecitis and transfer of protection to infant hamsters," *Infect Immun.*, Dec. 1987; 55(12):2984-2992.

Kink et al., "Antibodies to recombinant *Clostridium difficile* toxins A and B are an effective treatment and prevent relapse of *C. difficile*-associated disease in a hamster model of infection," *Infect. Immun.*, May 1998; 66(5):2018-2025.

Kohler and Milstein, "Continuous cultures of fused cells secreting antibody of predefined specificity," *Nature*, Aug. 1975; 256:495-497.

Kohler and Milstein, "Derivation of specific antibody-producing tissue culture and tumor lines by cell fusion," *Eur. J. Immunol.*, Jul. 1976; 6:511-519.

Kokkotou et al., "Comparative efficacies of rifaximin and vancomycin for treatment of *Clostridium difficile* -associated diarrhea and prevention of disease recurrence in hamsters," *Antimicrob. Agents Chemother.*, Mar. 2008; 52(3):1121-1126.

Kurtz et al., "GT160-246, a toxin binding polymer for treatment of *Clostridium difficile* colitis," *Antimicrob. Agents Chemother.*, Aug. 2001; 45(8):2340-2347.

Kyne et al., "Asymptomatic carriage of *Clostridium difficile* and serum levels of IgG antibody against toxin A," *New Eng. J. Med.*, Feb. 2000; 342:390-397.

Kyne et al., "Association between antibody response to toxin A and protection against recurrent *Clostridium difficile* diarrhoea," *Lancet*, Jan. 2001; 357:189-193.

Kyne et al., "*Clostridium difficile*," *Gastroenterol. Clin. North Am.*, Sep. 2001; 30(3):753-777.

Leav et al., "Serum anti-toxin B antibody correlates with protection from recurrent *Clostridium difficile* associated diarrhea (CDAD)," meeting abstract B-1925 presented at the *48th Interscience Conference On Antimicrobial Agents And Chemotherapy (ICCAC) Held Jointly With The 46th Annual Meeting Of The Infectious Diseases Society Of America (IDSA)*: Washington, DC; Oct. 25, 2008; 1 page.

Leonardi, "Current concepts and review of efalizumab in the treatment of psoriasis," *Dermatol. Clin.*, Oct. 2004; 22:427-435.

Leung et al., "Treatment with intravenously administered gamma globulin of chronic relapsing colitis induced by *Clostridium difficile* toxin," *J. Pediatr.*, Apr. 1991; 118:633-637.

Loo et al., "A predominantly clonal multi-institutional outbreak of *Clostridium difficile*-associated diarrhea with high morbidity and mortality," *The New England Journal of Medicine*, Dec. 2005; 353:2442-2449.

Louie et al., "Tolevamer, a novel nonantibiotic polymer, compared with vancomycin in the treatment of mild to moderately severe *Clostridium difficile*-associated diarrhea," *Clin. Infect. Dis.*, Aug. 2006; 43:411-420.

Louie et al., "Results of a phase III trial comparing tolevamer, vancomycin and metronidazole in patients with *Clostridium difficile*-associated diarrhea (CDAD)," Presentation No. K-425a presented at the *47th Annual Interscience Conference on Antimicrobial Agents and Chemotherapy*; Chicago, IL: Sep. 17-20, 2007; 5 pgs.

Lowy et al., "Treatment with monoclonal antibodies against *Clostridium difficile* toxins," *N. Engl. J. Med.*, Jan. 21, 2010; 362(3):197-205.

Lyerly et al., "Biological activities of toxins A and B of *Clostridium difficile* ," *Infect. Immun.*, Mar. 1982; 35(3):1147-1150.

Lyerly et al., "Characterization of toxins A and B of *Clostridium difficile* with monoclonal antibodies," *Infect. Immun.*, Oct. 1986; 54(1):70-76.

Lyerly et al., "Passive immunization of hamsters against disease caused by *Clostridium difficile* by use of bovine immunoglobulin G concentrate," *Infect. Immun.*, Jun. 1991; 59(6):2215-2218.

MacCannell et al., "Molecular Analysis of *Clostridium difficile* PCR Ribotype 027 Isolates from Eastern and Western Canada," *J. Clin. Microbiol.*, Jun. 2006; 44(6):21472152.

Mateo et al., "Humanization of a mouse monoclonal antibody that blocks the epidermal growth factor receptor: recovery of antagonistic activity," *Immunotechnology*, Mar. 1997; 3:71-81.

McDonald et al., "An epidemic, toxin gene-variant strain of *Clostridium difficile* ," *The New England Journal of Medicine*, Dec. 2005; 353(23):2433-2441.

McFarland et al., "Nosocomial acquisition of *Clostridium difficile* infection," *The New England Journal of Medicine*, Jan. 1989; 320:204-210.

McFarland et al., "A randomized placebo-controlled trial of *Saccharomyces boulardii* in combination with standard antibiotics for *Clostridium difficile* disease," *JAMA*, Jun. 1994; 271(24):1913-1918.

McFarland et al., "Breaking the cycle: treatment strategies for 163 cases of recurrent *Clostridium difficile* disease," *Am. J. Gastroenterol.*, Jul. 2002; 97:1769-1775.

McFarland et al., "Implications of the changing face of *Clostridium difficile* disease for health care practitioners," *Am. J. Infect. Control.*, May 2007; 35(4):237-253.

McVay et al., "In vitro and in vivo activities of nitazoxanide against *Clostridium difficile*," *Antimicrob. Agents Chemother.*, Sep. 2000; 44(9):2254-2258.

Medarex and Massachusetts Biologic Laboratories, "Medarex and Massachusetts Biologic Laboratories Announce Primary Objective Achieved In Phase 2 Trial of Monoclonal Antibody Combination for the Treatment of *Clostridium difficile* Associated Diarrhea (CDAD)," News Release, Nov. 3, 2008; 4 pgs.

Missaghi et al., "*Clostridium difficile* Infection: A Critical Overview," *Curr. Infect. Dis. Rep.*, May 2008; 10:165-173.

Musher et al., "Relatively poor outcome after treatment of *Clostridium difficile* colitis with metronidazole," *Clin. Infect. Dis.*, Jun. 2005; 40:1586-1590.

National Center for Biotechnology Information, National Library of Medicine, National Institutes of Health, GenBank Locus NC_009089, Accession No. NC_009089, "*Clostridium difficile* 630, complete genome," [online]. Bethesda, MD [retrieved on Jul. 10, 2013]. Retrieved from the Internet: <www.ncbi.nlm.nih.gov/nuccore/NC_009089>; 1 pg.

National Center for Biotechnology Information, National Library of Medicine, National Institutes of Health, GenBank Locus NW_001838121, Accession No. NW_001838121, "*Homo sapiens* chromosome 14 genomic scaffold, alternate assembly HuFef

(56) References Cited

OTHER PUBLICATIONS

SCAF_1103279188425, whole genome shotgun sequence," [online]. Bethesda, MD [retrieved on Jul. 10, 2013]. Retrieved from the Internet: <www.ncbi.nlm.nih.gov/nuccore/NW_001838121>; 44 pgs.

National Center for Biotechnology Information, National Library of Medicine, National Institutes of Health, GenBank Locus NW_001838785.1, Accession No. NW_001838785, "*Homo sapiens* chromosome 2 genomic scaffold, alternate assembly HuRef SCAF_1103279188045, whole genome shotgun sequence," [online]. Bethesda, MD [retrieved on Jul. 9, 2013]. Retrieved from the Internet: <www.ncbi.nlm.nih.gov/nuccore/NW_001838785>; 2 pgs.

National Center for Biotechnology Information, National Library of Medicine, National Institutes of Health, GenBank Locus X92982.1, Accession No. X92982, "*C.difficile* cdu2, cdu1, tcdD, tcdB, tcdE, tcdA, tcdC, cdd1, cdd2, cdd3, and cdd4 genes," [online]. Bethesda, MD [retrieved on Jul. 10, 2013]. Retrieved from the Internet: < www.ncbi.nlm.nih.gov/nuccore/x92982>; 11 pgs.

O'Brien et al., "The emerging infectious challenge of *Clostridium difficile*-associated disease in Massachusetts hospitals: clinical and economic consequences," *Infect. Control Hosp. Epidemiol.*, Nov. 2007; 28(11):1219-1227.

Optimer Pharmaceuticals, "Optimer Pharmaceuticals Reports Positive Data from its North American Phase 3 CDI Study of OPT-80," News Release; Nov. 10, 2008; 2 pgs.

Pepin et al., "Increasing risk of relapse after treatment of *Clostridium difficile* colitis in Quebec, Canada," *Clin. Infect. Dis.*, Jun. 2005; 40:1591-1597.

Poljak, "Production and structure of diabodies," *Structure*, Dec. 1994; 2(12):1121-1123.

Pothoulakis et al., "*Clostridium difficile* colitis and diarrhea," *Gastroenterol. Clin. North Am.*, Sep. 1993; 22(3):623-637.

Presta et al., "Humanization of an antibody directed against IgE," *The Journal of Immunology*, Sep. 1993; 151(5):2623-2632.

Presta et al., "Humanization of an anti-vascular endothelial growth factor monoclonal antibody for the therapy of solid tumors and other disorders," *Cancer Res.*, Oct. 1997; 57:4593-4599.

Razaq et al., "Infection of hamsters with historical and epidemic BI types of *Clostridium difficile*," *J. Infect. Dis.*, Dec. 2007; 196:1813-1819.

Redelings et al., "Increase in *Clostridium difficile*-related Mortality Rates, United States, 1999-2004," *Emerg. Infect. Dis.*, Sep. 2007; 13(9):1417-1419.

Reichert et al., "Monoclonal antibody successes in the clinic," *Nat. Biotechnol.*, Sep. 2005; 23(9):1073-1078.

Reineke et al., "Autocatalytic cleavage of *Clostridium difficile* toxin B," *Nature*, Mar. 2007; 446:415-419.

Riley et al., "Increased length of hospital stay due to *Clostridium difficile*-associated diarrhoea," *Lancet*, Feb. 1995; 345:455-456.

Robinson (Ed.), *Sustained and Controlled Release Drug Delivery Systems*, Marcel Dekker, Inc.: New York, NY; 1978. Title page, publisher's page, and table of contents; 5 pages.

Romero et al., "Palivizumab prophylaxis of respiratory syncytial virus disease from 1998 to 2002: results from four years of palivizumab usage," *Pediatr. Infect. Dis.* Feb. 2003; 22(2):546-554.

Rothman, "Immunochemical and structural similarities in toxin A and toxin B of *Clostridium difficile* shown by binding to monoclonal antibodies," *Toxicon*, 1988; 26(6):583-97.

Rupnik et al., "New types of toxin A-negative, toxin B-positive strains among *Clostridium difficile* isolates from Asia," *J. Clin. Microbiol.*, Mar. 2003; 41(3):11181125.

Salcedo et al., "Intravenous immunoglobulin therapy for severe *Clostridium difficile* colitis," *Gut*, Apr. 1997; 41:366-370.

Sambrook et al. (Eds.), *Molecular Cloning: A Laboratory Manual*, Cold Spring Harbor Laboratory Press: Cold Spring Harbor, NY; 1989. Title page, publisher's page, and table of contents; 30 pages.

Siemoneit et al., "Human monoclonal antibodies for the immunological characterization of a highly conserved protein domain of the hepatitis C virus glycoprotein E1," *Clin. Exp. Immunol.*, Aug. 1995; 101:278-83.

Steinman, "Blocking adhesion molecules as therapy for multiple sclerosis: natalizumab," *Nat. Rev. Drug Discov.*, Jun. 2005; 4:510-518.

Stephens et al., "Comprehensive pharmacokinetics of a humanized antibody and analysis of residual anti-idiotypic responses," *Immunology*, Aug. 1995; 85:668-674.

Voth et al., "*Clostridium difficile* toxins: mechanism of action and role in disease," *Clin. Microbiol. Rev.*, Apr. 2005; 18(2):247-263.

Waldmann, "Monoclonal antibodies in diagnosis and therapy," *Science*, Jun. 1991; 252(5013):1657-1662.

Ward et al., "Binding activities of a repertoire of single immunoglobulin variable domains secreted from *Escherichia coli*," *Nature*, Oct. 1989; 341:544-546.

Warny, "Pathogenicity of *Clostridium difficile* toxins," in *Microbial Pathogenesis and the Intestinal Epithelial Cell*. Hecht (Ed.). ASM Press: 2003. Title page and pp. 503-524.

Warny et al., "Toxin production by an emerging strain of *Clostridium difficile* associated with outbreaks of severe disease in North America and Europe," *Lancet*, Sep. 2005; 366:1079-1084.

Werther et al., "Humanization of an anti-lymphocyte function-associated antigen (LFA)-1 monoclonal antibody and reengineering of the humanized antibody for binding to rhesus LFA-1," *The Journal of Immunology*, Dec. 1996; 157:4986-4995.

Wiland et al., "Daclizumab induction in solid organ transplantation," *Expert Opin. Biol. Ther.*, May 2004; 4:729-740.

Wilcox et al., "Recurrence of symptoms in *Clostridium difficile* infection—relapse or reinfection?" *J. Hosp. Infect.*, Feb. 1998; 38:93-100.

Wu et al., "Ultra-potent antibodies against respiratory syncytial virus: effects of binding kinetics and binding valence on viral neutralization," *J. Mol. Biol.*, Jul. 2005; 350:126-144.

Zilberberg et al., "Increase in Adult *Clostridium difficile*-related Hospitalizations and Case-Fatality Rate, United States, 2000-2005," *Emerg. Infect. Dis.*, Jun. 2008; 14(6):929-931.

PCT/US2011/032713: International Preliminary Report on Patentability issued on Oct. 16, 2012 by the International Bureau of WIPO; 6 pgs.

PCT/US2011/032713: International Search Report mailed Feb. 21, 2012 by the International Search Authority ISA/KR; 5 pgs.

PCT/US2011/032713: Written Opinion mailed Feb. 21, 2012 by the International Search Authority ISA/KR; 5 pgs.

\* cited by examiner

Full length of toxin B

Reducing SDS-PAGE /Coomassie blue

Possible toxin B fragments from caspase-1 treatment

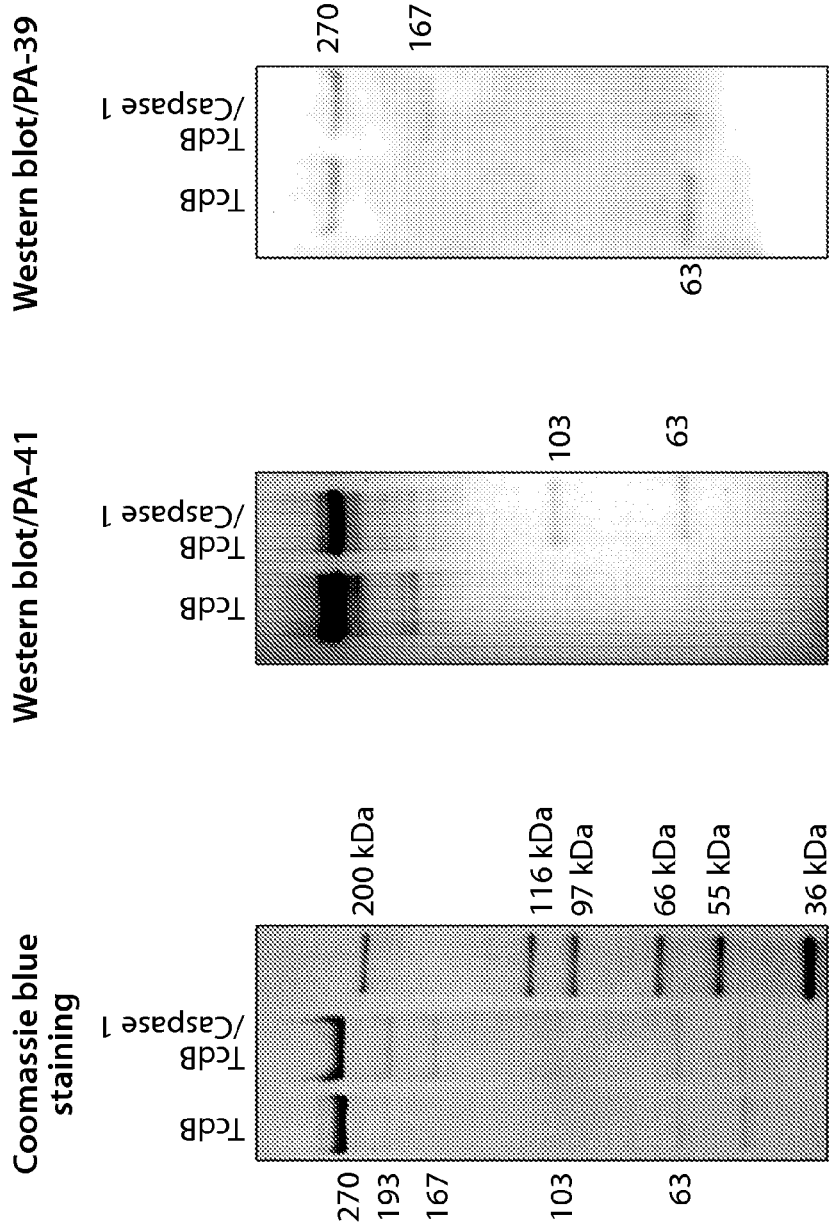

SDS-PAGE /Coomassie staining

Possible EK cleavage sites on *C. diff* toxin A

- C-term containing fragments: 223, 181, 160, 91, and 68 kDa
- N-term containing fragments: 223, 185, and 127 kDa
- Fragments needed further identification: 160, 53 and 42 kDa

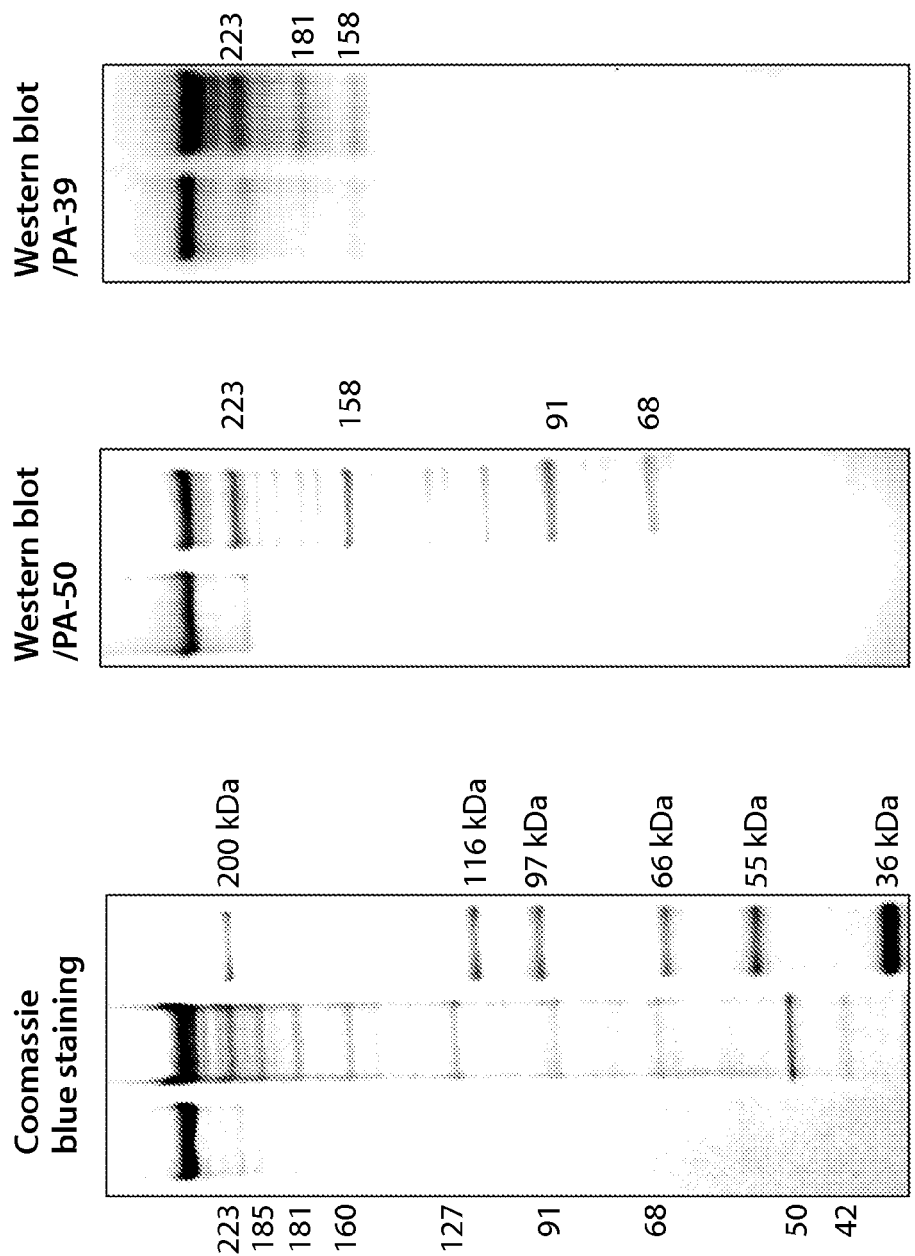

*N/A: NotApplicable; no toxin A was produced from toxin A-/toxin B+ strains F1470, 8864, CCL13820 and CCL14402
"Toxin A titer was very low; no measurable cytotoxicity on T-84 using supernatant
^Not applicable; no toxin A was produced from toxin A-/toxin B+ strains or concentration was too low

*N/A: Not Applicable; no toxin A was produced from toxin A−/toxin B+ strains F1470, 8864, CCL13820 and CCL14402
"Toxin A titer was very low; no measurable cytotoxicity on T-84 using supernatant
^Not applicable; no toxin A was produced from toxin A−/toxin B+ strains or concentration was too low

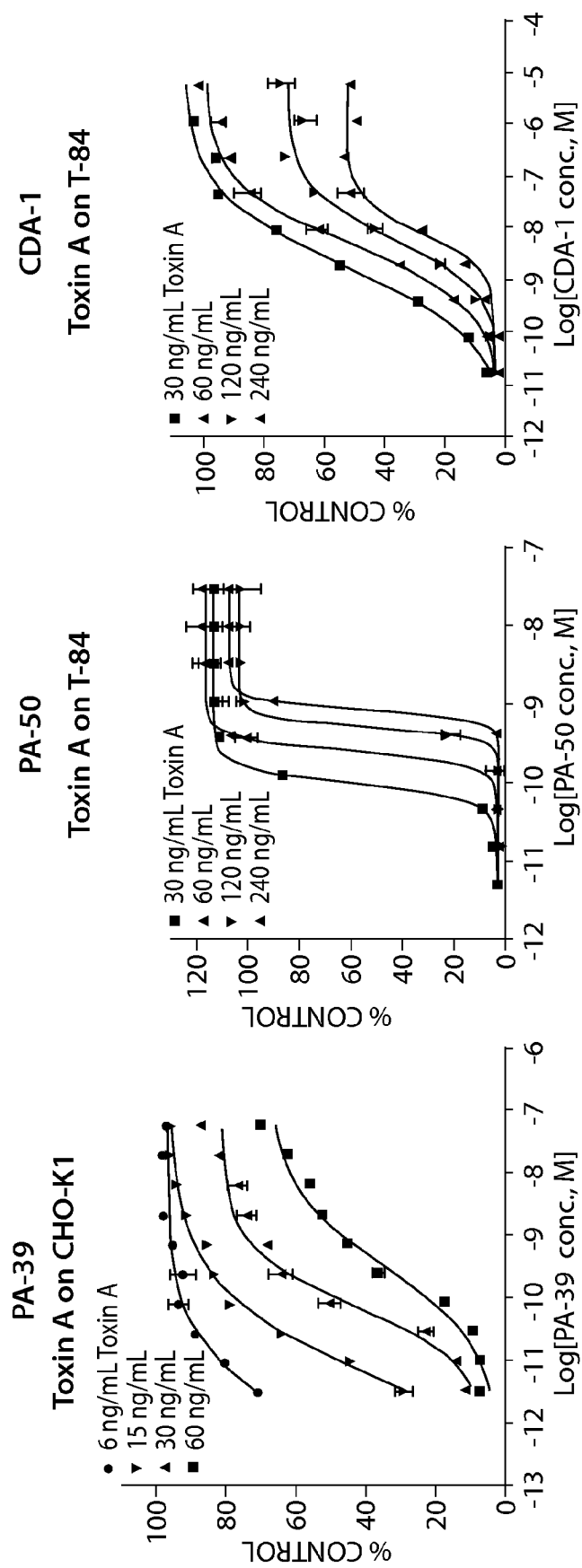

```
          1          2          3
123456789 0123456789 0123456789 0123456789
QVQLVQSGA EVKKPGASVK VSCKASGYTF NDHNIHWVRQ 4         5          6          7
0123456789 01223456789 0123456789 0123456789
APGQGLEWIG YIYPYIGTTVY NQKFKSKATL TVDTSTSTAY 1          1
8             9            0          1
0122223456789 0123456789 0123456789 0123
MELRSLRSDDTAV YYCSRWGHRG FPYWGQGTLV TVSS
(SEQ ID NO:1)
```

Fig. 32A

```
          1          2          3
123456789 0123456789 0123456789 0123456789
QVQLVQSGA EVKKPGASVK VSCKASGYTF NDHNIHWVRQ 4         5          6          7
0123456789 01223456789 0123456789 0123456789
APGQGLEWIG YIYPYIGTTVY NQKFKSKATL TVDNSTSTAY 1          1
8             9            0          1
0122223456789 0123456789 0123456789 0123
MELRSLRSDDTAV YYCSRWGHRG FPYWGQGTLV TVSS
(SEQ ID NO:2)
```

Fig. 32B

```
         1          2          3
123456789 0123456789 0123456789 0123456789
DIQMTQSPS SLSASVGDRV TITCKASQNV GTNVAWYQQK 4          5          6          7
0123456789 0123456789 0123456789 0123456789
PGKAPKALIY SASYRYSGVS SRFSGSGSGT DFTLTISSLQ 1
8          9            0
0123456789 0123456789 01234567
PEDFAVYYCQ QYYSYPYTFG QGTKLEIK
(SEQ ID NO:3)
```

Fig. 33A

```
         1          2          3
123456789 0123456789 0123456789 0123456789
DIQMTQSPS SLSASVGDRV TITCKASQNV GTNVAWYQQK 4          5          6          7
0123456789 0123456789 0123456789 0123456789
PGKAPKVLIY SASYRYSGVS SRFSGSGSGT DFTLTISSLQ 1
8          9            0
0123456789 0123456789 01234567
PEDFAVYYCQ QYYSYPYTFG QGTKLEIK
(SEQ ID NO:4)
```

Fig. 33B

```
                  1          2          3
123456789 0123456789 0123456789 0123456789
QVQLVQSGA EVKKPGASVK VSCKASGYTF TDYNMDWVRQ 4         5          6          7
0123456789 01223456789 0123456789 0123456789
APGQRLEWIG DINPKYDIIGH NPKFMGKATL TVDKSASTAY 1          1
8             9               0          1
01222234567890 123456789 00123456789 0123
MELSSLRSEDTAV YYCARSDRGW YFDVWGQGTLV TVSS
(SEQ ID NO:5)
```

Fig. 34A

```
                  1          2          3
123456789 0123456789 0123456789 0123456789
QVQLVQSGA EVKKPGASVK VSCKASGYTF TDYNMDWVRQ 4         5          6          7
0123456789 01223456789 0123456789 0123456789
APGQRLEWIG DINPKYDIIGH NPKFMGKATI TVDKSASTAY 1          1
8             9               0          1
01222234567890 123456789 00123456789 0123
MELSSLRSEDTAV YYCARSDRGW YFDVWGQGTLV TVSS
(SEQ ID NO:6)
```

Fig. 34B

```
                  1          2          3
123456789 0123456789 0123456789 0123456789
EIVLTQSPA TLSLSPGERA TLSCRASSSV NYMNWYQQKP 4          5          6          7
0123456789 0123456789 0123456789 0123456789
GQAPRPRIYA TSNLASGVPA RFSGSGSGTD YTLTISSLEP 1
8          9                  0
0123456789 0123456789 01234
EDFAVYYCQQ WSSRTFGGGT KVEIK
(SEQ ID NO:7)
```

Fig. 35

```
         1          2          3
123456789  0123456789 0123456789 0123456789
QVQLVQSGA  EVKKPGASVK VSCKASGYPF TNYFMHWVRQ 4          5          6          7
0123456789 0123456789 0123456789 0123456789
APGQRLEWIG RINPYNGATS YSLNFRDKAT LTLDKSASTA 1          1
8          9          0          1
0123456789 0123456789 0123456789 0123456789
YMELSSLRSE DTAVYYCARS TITSPLLDFW GQGTLVTVSS
 (SEQ ID NO:8)
```

Fig. 36A

```
         1          2          3
123456789  0123456789 0123456789 0123456789
QVQLVQSGA  EVKKPGASVK VSCKASGYPF TNYFMHWVRQ 4          5          6          7
0123456789 0123456789 0123456789 0123456789
APGQRLEWIG RINPYNGATS YSLNFRDKAT ITLDKSASTA 1          1
8          9          0          1
0123456789 0123456789 0123456789 0123456789
YMELSSLRSE DTAVYYCARS TITSPLLDFW GQGTLVTVSS
 (SEQ ID NO:9)
```

Fig. 36B

```
         1          2          3
123456789  0123456789 0123456789 0123456789
EIVLTQSPA  TLSLSPGERA TLSCRASQSV GTSIHWYQQK 4          5          6          7
0123456789 0123456789 0123456789 0123456789
PGQAPRLLIK FASESISGIP ARFSGSGSGT DFTLTISSLE 1
8          9          0
0123456789 0123456789 01234567
PEDFAVYYCQ QSNKWPFTFG QGTKLEIK
  (SEQ ID NO:10)
```

Fig. 37

```
  1 atg gat ttt caa gtt cag ata ttc tcc ttt ctt ctc att agc gcc
    M   D   F   Q   V   Q   I   F   S   F   L   L   I   S   A 46 agt gtg att atg tca aga ggg gag att gtc ctg aca cag agt ccc
    S   V   I   M   S   R   G   E   I   V   L   T   Q   S   P 91 gcc aca ctt agc ctg tcc ccc gga gag cgt gct aca ctc tct tgt
    A   T   L   S   L   S   P   G   E   R   A   T   L   S   C 136 cgc gct tcc agc tct gtc aac tac atg aac tgg tat cag cag aaa
    R   A   S   S   S   V   N   Y   M   N   W   Y   Q   Q   K 181 ccc ggt cag gcc cct aga ccc cgg atc tat gcc aca tct aat ctt
    P   G   Q   A   P   R   P   R   I   Y   A   T   S   N   L 226 gcc tcc gga gtg cct gcc cga ttc agc ggg agc gga agt ggt acc
    A   S   G   V   P   A   R   F   S   G   S   G   S   G   T 271 gat tac acc ctc aca atc tct agc ttg gaa cca gag gac ttt gca
    D   Y   T   L   T   I   S   S   L   E   P   E   D   F   A 316 gtc tat tac tgc caa cag tgg tct agt cgc act ttc ggt ggt ggc
    V   Y   Y   C   Q   Q   W   S   S   R   T   F   G   G   G 361 acc aaa ttg gag atc aag agg act gtc gct gcc cca agt gtg ttc
    T   K   L   E   I   K   R   T   V   A   A   P   S   V   F 406 atc ttt cct cca tcc gat gag cag ctg aag agt gga acc gca tcc
    I   F   P   P   S   D   E   Q   L   K   S   G   T   A   S 451 gtg gtt tgc ctg ctg aac aac ttt tac cct cgg gaa gct aaa gtg
    V   V   C   L   L   N   N   F   Y   P   R   E   A   K   V 496 cag tgg aag gtg gac aat gca ctg cag tcc ggc aat agc cag gag
    Q   W   K   V   D   N   A   L   Q   S   G   N   S   Q   E 541 tca gta acc gaa caa gat tcc aag gac tcc acc tac tct ctc tca
    S   V   T   E   Q   D   S   K   D   S   T   Y   S   L   S 586 tct acc ttg acc ctg tca aag gcc gac tat gaa aaa cac aag gtt
    S   T   L   T   L   S   K   A   D   Y   E   K   H   K   V 631 tac gca tgt gag gta act cat caa ggg ctt agc tct cca gtc act
    Y   A   C   E   V   T   H   Q   G   L   S   S   P   V   T 676 aag agc ttt aac agg ggc gaa tgc tag  (SEQ ID NO:17)
    K   S   F   N   R   G   E   C       (SEQ ID NO:16)
```

Fig. 38A

```
  1 atg gaa tgg tcc ggc gtg ttc atc ttt ttg ctg tca gtc acc gct
    M   E   W   S   G   V   F   I   F   L   L   S   V   T   A 46 ggc gtg cac tct caa gtc cag ctt gtt cag agc gga gca gaa gtg
    G   V   H   S   Q   V   Q   L   V   Q   S   G   A   E   V 91 aag aag cca ggg gcc agc gtc aag gtt tct tgt aaa gcc agt ggt
    K   K   P   G   A   S   V   K   V   S   C   K   A   S   G 136 tat acc ttt act gat tac aac atg gat tgg gta cgt cag gca ccc
    Y   T   F   T   D   Y   N   M   D   W   V   R   Q   A   P 181 gga caa cgg ctg gag tgg att ggc gac atc aat ccc aaa tac gac
    G   Q   R   L   E   W   I   G   D   I   N   P   K   Y   D 226 att atc ggc cat aac cct aag ttt atg gga aag gct acc att aca
    I   I   G   H   N   P   K   F   M   G   K   A   T   I   T 271 gta gat aag tct gct tcc acc gct tac atg gag ctc tcc tct ctg
    V   D   K   S   A   S   T   A   Y   M   E   L   S   S   L 316 cgc agt gag gat acc gca gtg tac tat tgc gcc agg agt gac cga
    R   S   E   D   T   A   V   Y   Y   C   A   R   S   D   R 361 ggc tgg tat ttc gac gtt tgg ggg cag ggt aca ttg gtg act gtg
    G   W   Y   F   D   V   W   G   Q   G   T   L   V   T   V 406 tca agc gcc agc aca aag ggc cca tcg gtc ttc ccc ctg gca ccc
    S   S   A   S   T   K   G   P   S   V   F   P   L   A   P 451 tct agc aag agc acc tct ggg ggc aca gcg gcc ctg ggc tgc ctg
    S   S   K   S   T   S   G   G   T   A   A   L   G   C   L 496 gtc aag gac tac ttc ccc gaa ccg gtg acg gtg tcg tgg aac tca
    V   K   D   Y   F   P   E   P   V   T   V   S   W   N   S 541 ggc gcc ctg acc agc ggc gtg cac acc ttc ccg gct gtc cta cag
    G   A   L   T   S   G   V   H   T   F   P   A   V   L   Q 586 tcc tca gga ctc tac tcc ctc agc agc gtg gtg acc gtg ccc tcc
    S   S   G   L   Y   S   L   S   S   V   V   T   V   P   S 631 agc agc ttg ggc acc cag acc tac atc tgc aac gtg aat cac aag
    S   S   L   G   T   Q   T   Y   I   C   N   V   N   H   K 676 ccc agc aac acc aag gtg gac aag aga gtt gag ccc aaa tct tgt
    P   S   N   T   K   V   D   K   R   V   E   P   K   S   C
```

Fig. 38B

```
 721 gac aaa act cac aca tgc cca ccg tgc cca gca cct gaa ctc ctg
      D   K   T   H   T   C   P   P   C   P   A   P   E   L   L 766 ggg gga ccg tca gtc ttc ctc ttc ccc cca aaa ccc aag gac acc
      G   G   P   S   V   F   L   F   P   P   K   P   K   D   T 811 ctc atg atc tcc cgg acc cct gag gtc aca tgc gtg gtg gtg gac
      L   M   I   S   R   T   P   E   V   T   C   V   V   V   D 856 gtg agc cac gaa gac cct gag gtc aag ttc aac tgg tac gtg gac
      V   S   H   E   D   P   E   V   K   F   N   W   Y   V   D 901 ggc gtg gag gtg cat aat gcc aag aca aag ccg cgg gag gag cag
      G   V   E   V   H   N   A   K   T   K   P   R   E   E   Q 946 tac aac agc acg tac cgt gtg gtc agc gtc ctc acc gtc ctg cac
      Y   N   S   T   Y   R   V   V   S   V   L   T   V   L   H 991 cag gac tgg ctg aat ggc aag gag tac aag tgc aag gtc tcc aac
      Q   D   W   L   N   G   K   E   Y   K   C   K   V   S   N 1036 aaa gcc ctc cca gcc ccc atc gag aaa acc atc tcc aaa gcc aaa
      K   A   L   P   A   P   I   E   K   T   I   S   K   A   K 1081 ggg cag ccc cga gaa cca cag gtg tac acc ctg ccc cca tcc cgg
      G   Q   P   R   E   P   Q   V   Y   T   L   P   P   S   R 1126 gag gag atg acc aag aac cag gtc agc ctg acc tgc ctg gtc aaa
      E   E   M   T   K   N   Q   V   S   L   T   C   L   V   K 1171 ggc ttc tat ccc agc gac atc gcc gtg gag tgg gag agc aat ggg
      G   F   Y   P   S   D   I   A   V   E   W   E   S   N   G 1216 cag ccg gag aac aac tac aag acc acg cct ccc gtg ctg gac tcc
      Q   P   E   N   N   Y   K   T   T   P   P   V   L   D   S 1261 gac ggc tcc ttc ttc ctc tat agc aag ctc acc gtg gac aag agc
      D   G   S   F   F   L   Y   S   K   L   T   V   D   K   S 1306 agg tgg cag cag ggg aac gtc ttc tca tgc tcc gtg atg cat gag
      R   W   Q   Q   G   N   V   F   S   C   S   V   M   H   E 1351 gct ctg cac aac cac tac acg cag aag agc ctc tcc ctg tct ccg
      A   L   H   N   H   Y   T   Q   K   S   L   S   L   S   P 1396 ggt aaa tga        (SEQ ID NO:15)
      G   K            (SEQ ID NO:14)
```

Fig. 38B continued

```
  1 atg gaa tct cag act caa gtg ttt gtg tac atg ttg ctg tgg ctg
    M   E   S   Q   T   Q   V   F   V   Y   M   L   L   W   L 46 agc ggc gtt gac ggt gac att cag atg acc caa agc ccc tca agt
    S   G   V   D   G   D   I   Q   M   T   Q   S   P   S   S 91 ctt tct gct agc gtg ggg gac agg gtg acc ata aca tgc aaa gcc
    L   S   A   S   V   G   D   R   V   T   I   T   C   K   A 136 agc caa aat gtg ggg act aac gtt gcc tgg tat cag cag aaa cca
    S   Q   N   V   G   T   N   V   A   W   Y   Q   Q   K   P 181 ggt aaa gca ccc aag gct ctg atc tac agt gca agt tat cga tac
    G   K   A   P   K   A   L   I   Y   S   A   S   Y   R   Y 226 tcc ggc gtg tcc tct cgg ttt tct ggc tct ggg agc gga acc gat
    S   G   V   S   S   R   F   S   G   S   G   S   G   T   D 271 ttc act ctg acc att agt tca ctc caa cca gaa gat ttc gca gtc
    F   T   L   T   I   S   S   L   Q   P   E   D   F   A   V 316 tac tat tgt cag cag tac tat agt tac cca tat aca ttt gga cag
    Y   Y   C   Q   Q   Y   Y   S   Y   P   Y   T   F   G   Q 361 ggc acc aag ctg gaa atc aag aga acc gtt gcc gct cct tca gta
    G   T   K   L   E   I   K   R   T   V   A   A   P   S   V 406 ttc atc ttc cct ccc tcc gat gag cag ttg aag tcc ggc aca gca
    F   I   F   P   P   S   D   E   Q   L   K   S   G   T   A 451 agc gtc gta tgc ctt ttg aac aat ttc tat cca cgc gag gcc aaa
    S   V   V   C   L   L   N   N   F   Y   P   R   E   A   K 496 gtg caa tgg aag gtc gac aac gct ctg cag tca ggc aac tcc caa
    V   Q   W   K   V   D   N   A   L   Q   S   G   N   S   Q 541 gag tca gtc aca gag cag gac agc aaa gat tcc act tat tct ctc
    E   S   V   T   E   Q   D   S   K   D   S   T   Y   S   L 586 tct tct aca ctc act ctg agc aag gcc gac tat gag aag cat aag
    S   S   T   L   T   L   S   K   A   D   Y   E   K   H   K 631 gtt tac gcc tgc gaa gtg acc cac cag gga ttg agt tcc cct gtc
    V   Y   A   C   E   V   T   H   Q   G   L   S   S   P   V 676 act aag tcc ttt aac cgt ggg gag tgt tag     (SEQ ID NO:21)
    T   K   S   F   N   R   G   E   C           (SEQ ID NO:20)
```

Fig. 39A

```
  1 atg gag tgg tcc gga gtg ttc atc ttt ctg ctc tct gtt acc gct
     M   E   W   S   G   V   F   I   F   L   L   S   V   T   A 46 ggc gta cat agc caa gtc cag ctt gtc cag tct ggc gcc gag gtc
     G   V   H   S   Q   V   Q   L   V   Q   S   G   A   E   V 91 aag aaa cca ggg gcc agc gtg aaa gtt agt tgt aag gca tcc ggc
     K   K   P   G   A   S   V   K   V   S   C   K   A   S   G 136 tat acc ttc aac gat cac aat atc cac tgg gta cga cag gct cca
     Y   T   F   N   D   H   N   I   H   W   V   R   Q   A   P 181 ggc caa ggg ctg gaa tgg att ggt tac ata tac cct tac att gga
     G   Q   G   L   E   W   I   G   Y   I   Y   P   Y   I   G 226 aca aca gtg tat aac cag aag ttc aaa tcc aag gca act ctt act
     T   T   V   Y   N   Q   K   F   K   S   K   A   T   L   T 271 gtg gat aca tca acc tca act gcc tac atg gaa ttg aga tcc ctg
     V   D   T   S   T   S   T   A   Y   M   E   L   R   S   L 316 agg agt gac gac act gct gtc tat tac tgc agt cgg tgg gga cat
     R   S   D   D   T   A   V   Y   Y   C   S   R   W   G   H 361 cgc ggc ttt cct tat tgg ggt cag ggg aca ctc gtt act gtg agc
     R   G   F   P   Y   W   G   Q   G   T   L   V   T   V   S 406 tct gcc agt acc aag ggc cca tcg gtc ttc ccc ctg gca ccc tct
     S   A   S   T   K   G   P   S   V   F   P   L   A   P   S 451 agc aag agc acc tct ggg ggc aca gcg gcc ctg ggc tgc ctg gtc
     S   K   S   T   S   G   G   T   A   A   L   G   C   L   V 496 aag gac tac ttc ccc gaa ccg gtg acg gtg tcg tgg aac tca ggc
     K   D   Y   F   P   E   P   V   T   V   S   W   N   S   G 541 gcc ctg acc agc ggc gtg cac acc ttc ccg gct gtc cta cag tcc
     A   L   T   S   G   V   H   T   F   P   A   V   L   Q   S 586 tca gga ctc tac tcc ctc agc agc gtg gtg acc gtg ccc tcc agc
     S   G   L   Y   S   L   S   S   V   V   T   V   P   S   S 631 agc ttg ggc acc cag acc tac atc tgc aac gtg aat cac aag ccc
     S   L   G   T   Q   T   Y   I   C   N   V   N   H   K   P 676 agc aac acc aag gtg gac aag aga gtt ggt gag agg cca gca cag
     S   N   T   K   V   D   K   R   V   G   E   R   P   A   Q 721 gga ggg agg gtg tct gct gga agc cag gct cag cgc tcc tgc ctg
     G   G   R   V   S   A   G   S   Q   A   Q   R   S   C   L
```

Fig. 39B

```
 766 gac gca tcc cgg cta tgc agt ccc agt cca ggg cag caa ggc agg
      D   A   S   R   L   C   S   P   S   P   G   Q   Q   G   R 811 ccc cgt ctg cct ctt cac ccg gag gcc tct gcc cgc ccc act cat
      P   R   L   P   L   H   P   E   A   S   A   R   P   T   H 856 gct cag gga gag ggt ctt ctg gct ttt tcc cca ggc tct ggg cag
      A   Q   G   E   G   L   L   A   F   S   P   G   S   G   Q 901 gca cag gct agg tgc ccc gag ccc aaa tct tgt gac aaa act cac
      A   Q   A   R   C   P   E   P   K   S   C   D   K   T   H 946 aca tgc cca ccg tgc cca gca cct gaa ctc ctg ggg gga ccg tca
      T   C   P   P   C   P   A   P   E   L   L   G   G   P   S 991 gtc ttc ctc ttc ccc cca aaa ccc aag gac acc ctc atg atc tcc
      V   F   L   F   P   P   K   P   K   D   T   L   M   I   S 1036 cgg acc cct gag gtc aca tgc gtg gtg gtg gac gtg agc cac gaa
      R   T   P   E   V   T   C   V   V   V   D   V   S   H   E 1081 gac cct gag gtc aag ttc aac tgg tac gtg gac ggc gtg gag gtg
      D   P   E   V   K   F   N   W   Y   V   D   G   V   E   V 1126 cat aat gcc aag aca aag ccg cgg gag gag cag tac aac agc acg
      H   N   A   K   T   K   P   R   E   E   Q   Y   N   S   T 1171 tac cgt gtg gtc agc gtc ctc acc gtc ctg cac cag gac tgg ctg
      Y   R   V   V   S   V   L   T   V   L   H   Q   D   W   L 1216 aat ggc aag gag tac aag tgc aag gtc tcc aac aaa gcc ctc cca
      N   G   K   E   Y   K   C   K   V   S   N   K   A   L   P 1261 gcc ccc atc gag aaa acc atc tcc aaa gcc aaa ggg cag ccc cga
      A   P   I   E   K   T   I   S   K   A   K   G   Q   P   R 1306 gaa cca cag gtg tac acc ctg ccc cca tcc cgg gag gag atg acc
      E   P   Q   V   Y   T   L   P   P   S   R   E   E   M   T 1351 aag aac cag gtc agc ctg acc tgc ctg gtc aaa ggc ttc tat ccc
      K   N   Q   V   S   L   T   C   L   V   K   G   F   Y   P 1396 agc gac atc gcc gtg gag tgg gag agc aat ggg cag ccg gag aac
      S   D   I   A   V   E   W   E   S   N   G   Q   P   E   N 1441 aac tac aag acc acg cct ccc gtg ctg gac tcc gac ggc tcc ttc
      N   Y   K   T   T   P   P   V   L   D   S   D   G   S   F 1486 ttc ctc tat agc aag ctc acc gtg gac aag agc agg tgg cag cag
      F   L   Y   S   K   L   T   V   D   K   S   R   W   Q   Q 1531 ggg aac gtc ttc tca tgc tcc gtg atg cat gag gct ctg cac aac
      G   N   V   F   S   C   S   V   M   H   E   A   L   H   N 1576 cac tac acg cag aag agc ctc tcc ctg tct ccg ggt aaa tga
      H   Y   T   Q   K   S   L   S   L   S   P   G   K
```
(aa: SEQ ID NO:18)
(na: SEQ ID NO:19)

Fig. 39B continued

```
  1 atg tcc gtt cct act caa gtg ctg gga ctg ctt ctt ctg tgg ctc
    M   S   V   P   T   Q   V   L   G   L   L   L   L   W   L 46 act gac gca agg tgt gag atc gtg ctg acc cag agt cca gcc aca
    T   D   A   R   C   E   I   V   L   T   Q   S   P   A   T 91 ctc agc ttg tca ccc ggg gaa cgg gct aca ctg tcc tgt cgt gca
    L   S   L   S   P   G   E   R   A   T   L   S   C   R   A 136 tca cag agc gtg ggt aca tca att cac tgg tat cag cag aag ccc
    S   Q   S   V   G   T   S   I   H   W   Y   Q   Q   K   P 181 ggt cag gct ccc aga ctc ctg ata aag ttt gcc tcc gaa tcc att
    G   Q   A   P   R   L   L   I   K   F   A   S   E   S   I 226 tct ggc att cca gcc cgc ttc tcc ggc tcc ggc agt gga act gat
    S   G   I   P   A   R   F   S   G   S   G   S   G   T   D 271 ttc acc ctc acc att agt tct ttg gag cct gaa gat ttt gca gta
    F   T   L   T   I   S   S   L   E   P   E   D   F   A   V 316 tac tac tgt caa cag tct aac aag tgg cct ttt act ttt ggg cag
    Y   Y   C   Q   Q   S   N   K   W   P   F   T   F   G   Q 361 gga act aaa ctg gag atc aag cgc act gtc gct gct cca agc gta
    G   T   K   L   E   I   K   R   T   V   A   A   P   S   V 406 ttc atc ttt cct ccc tcc gac gag cag ttg aaa tca ggg aca gcc
    F   I   F   P   P   S   D   E   Q   L   K   S   G   T   A 451 tct gtg gtc tgc ctg ctg aac aat ttc tac cca agg gaa gcc aaa
    S   V   V   C   L   L   N   N   F   Y   P   R   E   A   K 496 gtg cag tgg aag gtc gat aat gca ctt caa tca ggt aat tct caa
    V   Q   W   K   V   D   N   A   L   Q   S   G   N   S   Q 541 gag agt gtg acc gag cag gat tcc aag gac agt acc tac tct ctc
    E   S   V   T   E   Q   D   S   K   D   S   T   Y   S   L 586 agc tca acc ctg acc ctt tct aaa gct gac tat gaa aaa cat aaa
    S   S   T   L   T   L   S   K   A   D   Y   E   K   H   K 631 gtc tac gcc tgc gaa gtg aca cac cag ggt ctg agt agc cct gtt
    V   Y   A   C   E   V   T   H   Q   G   L   S   S   P   V 676 acc aag agc ttt aac cga ggc gag tgc tag      (SEQ ID NO:25)
    T   K   S   F   N   R   G   E   C            (SEQ ID NO:24)
```

Fig. 40A

```
  1 atg gga tgg agc tgg att ttc ttg ttc ctc ctt tcc ggg act gct
    M   G   W   S   W   I   F   L   F   L   L   S   G   T   A 46 ggc gga ctg tcc caa gtc cag ttg gtg cag agc ggc gct gag gtt
    G   G   L   S   Q   V   Q   L   V   Q   S   G   A   E   V 91 aag aag ccc ggt gcc tct gtc aaa gtt agt tgc aaa gca agt ggc
    K   K   P   G   A   S   V   K   V   S   C   K   A   S   G 136 tac cct ttc aca aac tac ttt atg cac tgg gtg cgc cag gcc cct
    Y   P   F   T   N   Y   F   M   H   W   V   R   Q   A   P 181 ggg caa aga ctc gaa tgg atc ggt cgt atc aat cca tac aat ggg
    G   Q   R   L   E   W   I   G   R   I   N   P   Y   N   G 226 gca act agt tat tct ctc aac ttc agg gat aag gct acc att aca
    A   T   S   Y   S   L   N   F   R   D   K   A   T   I   T 271 ctg gac aag tct gcc tct acc gcc tat atg gag ctg agc tcc ctg
    L   D   K   S   A   S   T   A   Y   M   E   L   S   S   L 316 cgg agt gaa gat act gct gtc tat tac tgt gca cga tcc acc ata
    R   S   E   D   T   A   V   Y   Y   C   A   R   S   T   I 361 acc tct ccc ctg ctg gac ttt tgg ggc cag ggc aca ctt gtg act
    T   S   P   L   L   D   F   W   G   Q   G   T   L   V   T 406 gta tca tca gca tcc aca aag ggc cca tcg gtc ttc ccc ctg gca
    V   S   S   A   S   T   K   G   P   S   V   F   P   L   A 451 ccc tct agc aag agc acc tct ggg ggc aca gcg gcc ctg ggc tgc
    P   S   S   K   S   T   S   G   G   T   A   A   L   G   C 496 ctg gtc aag gac tac ttc ccc gaa ccg gtg acg gtg tcg tgg aac
    L   V   K   D   Y   F   P   E   P   V   T   V   S   W   N 541 tca ggc gcc ctg acc agc ggc gtg cac acc ttc ccg gct gtc cta
    S   G   A   L   T   S   G   V   H   T   F   P   A   V   L 586 cag tcc tca gga ctc tac tcc ctc agc agc gtg gtg acc gtg ccc
    Q   S   S   G   L   Y   S   L   S   S   V   V   T   V   P 631 tcc agc agc ttg ggc acc cag acc tac atc tgc aac gtg aat cac
    S   S   S   L   G   T   Q   T   Y   I   C   N   V   N   H 676 aag ccc agc aac acc aag gtg gac aag aga gtt ggt gag agg cca
    K   P   S   N   T   K   V   D   K   R   V   G   E   R   P 721 gca cag gga ggg agg gtg tct gct gga agc cag gct cag cgc tcc
    A   Q   G   G   R   V   S   A   G   S   Q   A   Q   R   S 766 tgc ctg gac gca tcc cgg cta tgc agt ccc agt cca ggg cag caa
    C   L   D   A   S   R   L   C   S   P   S   P   G   Q   Q 811 ggc agg ccc cgt ctg cct ctt cac ccg gag gcc tct gcc cgc ccc
    G   R   P   R   L   P   L   H   P   E   A   S   A   R   P
```

Fig. 40B

```
 856 act cat gct cag gga gag ggt ctt ctg gct ttt tcc cca ggc tct
      T   H   A   Q   G   E   G   L   L   A   F   S   P   G   S 901 ggg cag gca cag gct agg tgc ccc gag ccc aaa tct tgt gac aaa
      G   Q   A   Q   A   R   C   P   E   P   K   S   C   D   K 946 act cac aca tgc cca ccg tgc cca gca cct gaa ctc ctg ggg gga
      T   H   T   C   P   P   C   P   A   P   E   L   L   G   G 991 ccg tca gtc ttc ctc ttc ccc cca aaa ccc aag gac acc ctc atg
      P   S   V   F   L   F   P   P   K   P   K   D   T   L   M 1036 atc tcc cgg acc cct gag gtc aca tgc gtg gtg gtg gac gtg agc
      I   S   R   T   P   E   V   T   C   V   V   V   D   V   S 1081 cac gaa gac cct gag gtc aag ttc aac tgg tac gtg gac ggc gtg
      H   E   D   P   E   V   K   F   N   W   Y   V   D   G   V 1126 gag gtg cat aat gcc aag aca aag ccg cgg gag gag cag tac aac
      E   V   H   N   A   K   T   K   P   R   E   E   Q   Y   N 1171 agc acg tac cgt gtg gtc agc gtc ctc acc gtc ctg cac cag gac
      S   T   Y   R   V   V   S   V   L   T   V   L   H   Q   D 1216 tgg ctg aat ggc aag gag tac aag tgc aag gtc tcc aac aaa gcc
      W   L   N   G   K   E   Y   K   C   K   V   S   N   K   A 1261 ctc cca gcc ccc atc gag aaa acc atc tcc aaa gcc aaa ggg cag
      L   P   A   P   I   E   K   T   I   S   K   A   K   G   Q 1306 ccc cga gaa cca cag gtg tac acc ctg ccc cca tcc cgg gag gag
      P   R   E   P   Q   V   Y   T   L   P   P   S   R   E   E 1351 atg acc aag aac cag gtc agc ctg acc tgc ctg gtc aaa ggc ttc
      M   T   K   N   Q   V   S   L   T   C   L   V   K   G   F 1396 tat ccc agc gac atc gcc gtg gag tgg gag agc aat ggg cag ccg
      Y   P   S   D   I   A   V   E   W   E   S   N   G   Q   P 1441 gag aac aac tac aag acc acg cct ccc gtg ctg gac tcc gac ggc
      E   N   N   Y   K   T   T   P   P   V   L   D   S   D   G 1486 tcc ttc ttc ctc tat agc aag ctc acc gtg gac aag agc agg tgg
      S   F   F   L   Y   S   K   L   T   V   D   K   S   R   W 1531 cag cag ggg aac gtc ttc tca tgc tcc gtg atg cat gag gct ctg
      Q   Q   G   N   V   F   S   C   S   V   M   H   E   A   L 1576 cac aac cac tac acg cag aag agc ctc tcc ctg tct ccg ggt aaa
      H   N   H   Y   T   Q   K   S   L   S   L   S   P   G   K 1621 tga (aa; SEQ ID NO:22)
(na; SEQ ID NO:23)
```

Fig. 40B continued

ANTIBODIES FOR THE TREATMENT OF *CLOSTRIDIUM DIFFICILE*-ASSOCIATED INFECTION AND DISEASE

RELATED APPLICATIONS

This application claims priority under 35 U.S.C. §119 from U.S. Provisional Application Nos. 61/324,503, filed Apr. 15, 2010, and 61/381,669, filed Sep. 10, 2010, the entire contents of each of which are incorporated by reference herein.

FIELD OF THE INVENTION

This invention relates generally to compositions and therapies that can be used to treat *Clostridium difficile* (*C. difficile*) infection and *C. difficile*-associated disease conditions and pathologies, such as *C. diff.*-associated diarrhea (CDAD), which can result from infection by *C. difficile* bacteria. The invention further relates to antibodies or antigen-binding fragments thereof that bind specifically to epitopes on toxin A and/or toxin B of *C. difficile*, compositions comprising such antibodies, as well as methods of using the antibodies or the compositions.

BACKGROUND OF THE INVENTION

*C. difficile* (or *C. diff*) is a Gram-positive, spore-forming, anaerobic bacterium that represents the leading cause of nosocomial (hospital-acquired) antibiotic-associated diarrhea and pseudomembranous colitis. *C. difficile* infection is estimated to total more than 750,000 cases per year in the U.S., and it is responsible for more deaths than all other intestinal infections combined (1). In many hospitals, *C. difficile* constitutes a greater risk to patients than methicillin-resistant *Staphylococcus aureus* (MRSA) or any other bacteria (2). The annual costs for management of *Clostridium difficile*-associated disease (CDAD) are estimated to exceed 3.2 billion dollars in the U.S. (3). Recent outbreaks of *C. difficile* strains with increased virulence or antibiotic resistance have led to treatment failures, more frequent relapses and increased mortality rates (4).

CDAD is typically induced by the disruption of the colonic flora through the use of antibiotics such as clindamycin, cephalosporins, and fluoroquinolones.(3,8) This perturbation in the colonic microenvironment, along with exposure to *C. difficile* spores, leads to colonization. Approximately one-third of all patients that become colonized develop CDAD(9), which can result in severe diarrhea, perforation of the colon, colectomy and death (10). CDAD results following the acquisition and proliferation of *C. difficile* in the gut, where *C. difficile* bacteria produce toxin A and toxin B, two important virulence factors of CDAD. Toxins A and B of *C. difficile* show considerable sequence and structural homology. Both have a C-terminal receptor-binding domain containing multiple repeating sequences, a central hydrophobic domain and an N-terminal glucosyltransferase domain. The receptor-binding domain mediates binding of the toxins to intestinal epithelial cells via host receptors that remain poorly defined in humans. Following internalization via an endosomal pathway, the central hydrophobic domain inserts into the membrane of the endosome. The acidic pH of the endosome triggers pore formation and translocation of the amino-terminal domains of the toxins into the cytosol. Glucosylation of the cytosolic target Rho GTPases leads to disruption of the cytoskeleton and cell death. Toxins A and B demonstrate different pathological profiles with potential synergy in causing disease.

Recent outbreaks of a hypervirulent strain of *C. difficile* have resulted in increased rates of severe disease, more frequent relapses, and increased mortality. One hypervirulent strain, BI/NAP1/027 toxintoype III, was historically uncommon, but is now epidemic. Hypervirulent strains, such as BI/NAP1/027, produce several times more toxin A and toxin B than non-hypervirulent strains of *C. difficile*, making such strains more formidable to treat following infection. Since resistance of hypervirulent strains to commonly-used antimicrobials and antibiotics is a growing problem that makes these strains more difficult to treat and contain, additional treatment approaches and more potent therapies are needed to combat hypervirulence and the recurrence of disease that is associated with hypervirulent *C. difficile* isolates.

Current antibiotic treatments for *C. difficile* infection include the use of vancomycin and/or metronidazole; however these antibiotics are limited by incomplete response rates and increasing reinfection and recurrence rates. Since 2000, substantially higher failure rates have been reported for metronidazole therapy (23-25). The high recurrence rates following antibiotic treatment may result from continued disruption of the normal colonic flora, giving *C. difficile* the opportunity to recover with little competition.(26-28) The risk of recurrence is increased in patients who have already had one recurrence, rising from about 20% after an initial episode to more than 60% after two or more recurrences.(29,30) This increased risk of recurrence has been associated with the failure to mount an adequate antitoxin antibody response.(31) Indeed, patients with the highest titers of serum IgG antitoxin at the end of antimicrobial therapy had a decreased risk of recurrence.(32) In a separate study, serum anti-toxin B antibody levels were correlated with protection from recurrent CDAD.(33)

The prevalence of *C. difficile* infection has been increasing steadily, particularly in the elderly, who are often frail. Approximately one-third of patients with *C. difficile* infection have recurrences of their infection, usually within two months of the initial illness. Repeat infections tend to be more severe than the original disease; they are often more fatal. Older adults and people with weakened immune systems are particularly susceptible to recurring infections. If not treated promptly and appropriately, the complications of *C. difficile* infection include dehydration, kidney failure, bowel perforation, toxic megacolon, which can lead to rupture of the colon, and death.

Although in the United States, *C. difficile* infection is the most common infection acquired by hospitalized patients, it may also be acquired outside of hospitals in the community. It is estimated that 20,000 infections with *C. difficile* occur in the community each year in the United States. Internationally, the incidence is highly variable and depends on multiple factors, including the frequency with which endoscopy is used to establish the diagnosis, antimicrobial use patterns and epidemiologic patterns.

Thus, it is clear that disease caused by *C. difficile* infection puts the lives of people of all ages in jeopardy, both in nosocomial settings and in the community at large. In today's world, there is an ever present risk of *C. difficile* infection for those who face hospitalization or who are in long-term hospital care. Because there is also a chance of contracting *C. difficile* infection outside of a hospital environment, the possibility of young children and babies contracting the disease is great. In addition, there is a potential that current antibiotic regimens used to treat *C. difficile* may be less than optimally effective. Patients who present with *C. difficile*-associated disease require extensive in-patient care and a long duration hospital stay. The costs associated with the high degree of supportive hospital care and treatment needed for *C. difficile*-associated disease patients are large and involve expensive resources, such as greater numbers of physician and nursing staffing, laboratory testing and monitoring, concomitant medications and additional supportive measures.

Consequently, there is a need for more effective medications, drugs and treatments that target the life-threatening diseases caused by *C. difficile*, and, in particular the potent toxins that are produced by *C. difficile*, for prophylactic and therapeutic benefit. There is an unmet medical need for successful and lasting treatments for *C. difficile*-associated disease that offer lower potential for developing resistance and higher potential for successful patient response and disease resolution, leading to disease eradication.

SUMMARY OF THE INVENTION

The invention provides, at least in part, new antibody reagents and compositions comprising anti-*C. difficile* toxin A and/or toxin B antibodies. The reagents and compositions can be beneficial for treating the increasingly prevalent numbers of subjects afflicted with *C. difficile* associated infection and disease, providing improved quality of life, resolving CDAD and *C. difficile* infection and aiding in the survival of these infected individuals.

In one aspect, an isolated antibody or an antigen-binding fragment thereof, which specifically binds toxin A of *C. difficile* and which cross competes for binding to toxin A of *C. difficile* with a monoclonal antibody produced by a hybridoma cell line deposited under ATCC Accession No. PTA-9692, PTA-9694, or PTA-9888 is provided. In an embodiment the hybridoma cell line is deposited under ATCC Accession No. PTA-9692. In an embodiment, the hybridoma cell line is deposited under ATCC Accession No. PTA-9694. In an embodiment, the hybridoma cell line is deposited under ATCC Accession No. PTA-9888. In an embodiment, the monoclonal antibody, or antigen-binding fragment thereof, is in chimeric or humanized form.

In another aspect, an isolated antibody or an antigen-binding fragment thereof which specifically binds to a *C. difficile* toxin A epitope defined by a monoclonal antibody produced by the hybridoma cell line deposited under ATCC Accession No. PTA-9692, PTA-9694, or PTA-9888 is provided. In an embodiment the hybridoma cell line is deposited under ATCC Accession No. PTA-9692. In an embodiment, the hybridoma cell line is deposited under ATCC Accession No. PTA-9694. In an embodiment, the hybridoma cell line is deposited under ATCC Accession No. PTA-9888. In an embodiment, the monoclonal antibody, or antigen-binding fragment thereof, is in chimeric or humanized form.

In another aspect, an isolated antibody or an antigen-binding fragment thereof, which specifically binds toxin B of *C. difficile* and which cross competes for binding to toxin B of *C. difficile* of a monoclonal antibody produced by the hybridoma cell line deposited under ATCC Accession No. PTA-9693 or PTA-9692 is provided. In an embodiment the hybridoma cell line is deposited under ATCC Accession No. PTA-9693. In an embodiment the hybridoma cell line is deposited under ATCC Accession No. PTA-9692. In an embodiment, the monoclonal antibody, or antigen-binding fragment thereof, is in chimeric or humanized form.

In another aspect, an isolated antibody or an antigen-binding fragment thereof which specifically binds to a *C. difficile* toxin B epitope defined by a monoclonal antibody produced by the hybridoma cell line deposited under ATCC Accession No. PTA-9693 or PTA-9692 is provided. In an embodiment the hybridoma cell line is deposited under ATCC Accession No. PTA-9693. In an embodiment the hybridoma cell line is deposited under ATCC Accession No. PTA-9692. In an embodiment, the monoclonal antibody, or antigen-binding fragment thereof, is in chimeric or humanized form. In an embodiment, the isolated antibody or antigen-binding fragment thereof neutralizes the in vivo toxicity of toxin B of *C. difficile*. In an embodiment, the antibody or antigen-binding fragment thereof neutralizes the in vivo toxicity of toxin B of *C. difficile* in an amount of from 0.1-1000 μg.

In another aspect, monoclonal antibody PA-39 (ATCC Accession No. 9692), or an antigen-binding fragment thereof is provided. In another aspect, monoclonal antibody PA-50 (ATCC Accession No. PTA-9694), or an antigen-binding fragment thereof is provided. In another aspect, monoclonal antibody PA-38 (ATCC Accession No. PTA-9888), or an antigen-binding fragment thereof is provided. In another aspect, monoclonal antibody PA-41 (ATCC Accession No. PTA-9693), or an antigen-binding fragment thereof is provided. In an embodiment, the monoclonal antibody, or antigen-binding fragment thereof, is in chimeric or humanized form.

In still another aspect, an expression vector comprising at least one nucleic acid molecule encoding the antibodies or antigen-binding fragments thereof as described above and herein is provided. In still another aspect, an expression vector comprising a nucleic acid molecule encoding the heavy chain or portion thereof of the antibodies or antigen-binding fragments thereof as described above or herein is provided. In still another aspect—an expression vector comprising a nucleic acid molecule encoding the light chain, or portion thereof, of the antibodies or antigen-binding fragments thereof as described above or herein is provided. In still another aspect an expression vector comprising at least one nucleic acid molecule encoding the heavy chain, or portion thereof, and light chain, or portion thereof, of the antibodies or antigen binding fragments thereof as described above or herein is provided.

In another aspect, a host cell transformed or transfected by any of the expression vectors described above and herein is provided. In another aspect, a plasmid which encodes the any of the antibodies or antigen binding fragments thereof as described above and herein is provided.

In another aspect is provided an isolated anti-*C. difficile* toxin A antibody or antigen-binding fragment as described above and herein, wherein the antibody or antigen-binding fragment neutralizes the in vivo toxicity of toxin A of *C. difficile*. In an embodiment, the antibody or antigen-binding fragment neutralizes the in vivo toxicity of toxin A of *C. difficile* in an amount of from 0.1 μg to 1000 μg, or 1 μg/kg to 100,000 μg/kg. In another embodiment, the isolated antibody or antigen-binding fragment neutralizes the in vivo toxicity of toxin A of *C. difficile* in an amount selected from 0.5 μg-1000 μg, or from 5 μg-250 μg, or from 10 mg/kg-50 mg/kg. In an embodiment, the antibody is monoclonal antibody PA-39 (ATCC Accession No. 9692), or an antigen-binding fragment thereof. In an embodiment, the antibody is monoclonal antibody PA-50 (ATCC Accession No. PTA-9694), or an antigen-binding fragment thereof. In an embodiment, the antibody is monoclonal antibody PA-38 (ATCC Accession No. PTA-9888), or an antigen-binding fragment thereof. In an embodiment, the monoclonal antibody, or antigen-binding fragment thereof, is in chimeric or humanized form.

In another aspect is provided an isolated anti-*C. difficile* toxin B antibody or antigen-binding fragment as described above and herein, wherein the antibody or antigen-binding fragment neutralizes the in vivo toxicity of toxin B of *C. difficile*. In an embodiment, the isolated antibody or antigen-binding fragment thereof neutralizes the in vivo toxicity of toxin B of *C. difficile* in an amount selected from 0.5 µg-1000 µg, 0.5 µg, 5 µg, 40 µg, 50 µg, 100 µg, 200 µg, 1000 µg, or from 10 mg/kg-50 mg/kg. In an embodiment, the antibody is monoclonal antibody PA-39 (ATCC Accession No. 9692), or an antigen-binding fragment thereof. In an embodiment, the antibody is monoclonal antibody PA-41 (ATCC Accession No. PTA-9693), or an antigen-binding fragment thereof. In an embodiment, the monoclonal antibody, or antigen-binding fragment thereof, is in chimeric or humanized form.

Another aspect provides an isolated anti-*C. difficile* toxin A antibody or antigen-binding fragment as described above and herein, wherein the antibody or antigen-binding fragment, when administered to a *C. difficile*-infected subject in combination with an isolated antibody or antigen-binding fragment thereof that specifically binds and/or neutralizes toxin B of *C. difficile*, treats CDAD and/or increases the survivability of the subject. In an embodiment, the anti-toxin A and anti-toxin B antibodies or fragments thereof are administered simultaneously. In an embodiment, the anti-toxin A and anti-toxin B antibodies or fragments thereof are administered at different times. In an embodiment, the anti-toxin A and anti-toxin B antibodies or fragments thereof are administered sequentially. In an embodiment, the isolated antibody or antigen-binding fragment that specifically binds toxin A of *C. difficile* is an antibody produced by the hybridoma cell line deposited under ATCC Accession No. PTA-9692, PTA-9694, or PTA-9888, an antigen-binding fragment thereof, a humanized form thereof, or a monoclonal antibody that cross-reacts therewith for binding toxin A. In an embodiment, the isolated antibody or antigen-binding fragment that specifically binds toxin B of *C. difficile* is an antibody produced by the hybridoma cell line deposited under ATCC Accession No. PTA-9693 or PTA-9692, an antigen-binding fragment thereof, a humanized form thereof, or a monoclonal antibody that cross-reacts therewith for binding toxin B.

Another aspect provides an isolated anti-*C. difficile* toxin B antibody or antigen-binding fragment as described above and herein, wherein the antibody or antigen-binding fragment, when administered to a *C. difficile*-infected subject in combination with an isolated antibody or antigen-binding fragment thereof that specifically binds and/or neutralizes toxin A of *C. difficile*, treats CDAD and/or increases the survivability of the subject. In an embodiment the anti-toxin A and anti-toxin B antibodies or fragments thereof are administered simultaneously. In an embodiment the anti-toxin A and anti-toxin B antibodies or fragments thereof are administered at different times. In an embodiment the anti-toxin A and anti-toxin B antibodies or fragments thereof are administered sequentially. In an embodiment, the isolated antibody or antigen-binding fragment that specifically binds toxin A of *C. difficile* is an antibody produced by the hybridoma cell line deposited under ATCC Accession No. PTA-9692, PTA-9694, or PTA-9888, an antigen-binding fragment thereof, a humanized form thereof, or a monoclonal antibody that cross-reacts therewith for binding toxin A. In an embodiment, the isolated antibody or antigen-binding fragment that specifically binds toxin B of *C. difficile* is an antibody produced by the hybridoma cell line deposited under ATCC Accession No. PTA-9693 or PTA-9692, an antigen-binding fragment thereof, a humanized form thereof, or a monoclonal antibody that cross-reacts therewith for binding toxin B.

Another aspect provides an isolated anti-*C. difficile* toxin A antibody or antigen-binding fragment as described above and herein, wherein the antibody or antigen-binding fragment, when administered to a *C. difficile*-infected subject in combination with an isolated antibody or antigen-binding fragment thereof that specifically binds toxin B of *C. difficile*, treats CDAD and/or improves the survivability of the subject. In an embodiment, the anti-toxin A antibody or antigen-binding fragment thereof is administered in an amount of 1 µg-1000 µg, or from 1 µg-250 µg or from 5 µg-100 µg and the dose of the anti-toxin B antibody or antigen-binding fragment thereof is administered in an amount of from 0.1 µg-1000 µg. or from 1 µg-250 µg or from 5 µg-100 µg. In an embodiment, the isolated antibody or antigen-binding fragment that specifically binds toxin A of *C. difficile* is an antibody produced by the hybridoma cell line deposited under ATCC Accession No. PTA-9692, PTA-9694, or PTA-9888, an antigen-binding fragment thereof, a humanized form thereof, or a monoclonal antibody that cross-reacts therewith for binding toxin A. In an embodiment, the isolated antibody or antigen-binding fragment that specifically binds toxin B of *C. difficile* is an antibody produced by the hybridoma cell line deposited under ATCC Accession No. PTA-9693 or PTA-9692, an antigen-binding fragment thereof, a humanized form thereof, or a monoclonal antibody that cross-reacts therewith for binding toxin B.

Another aspect provides an isolated anti-*C. difficile* toxin A antibody or antigen-binding fragment as described above and herein, wherein the antibody or antigen-binding fragment, when administered to a *C. difficile*-infected subject in combination with an isolated antibody or antigen-binding fragment thereof that specifically binds toxin B of *C. difficile*, treats CDAD and/or improves the survivability of the subject. In an embodiment, the anti-toxin A antibody or antigen-binding fragment thereof is administered in an amount of 50 mg/kg, the anti-toxin B antibody or antigen-binding fragment thereof is administered in an amount of 50 mg/kg. In an embodiment, the isolated antibody or antigen-binding fragment that specifically binds toxin A of *C. difficile* is an antibody produced by the hybridoma cell line deposited under ATCC Accession No. PTA-9692, PTA-9694, or PTA-9888, an antigen-binding fragment thereof, a humanized form thereof, or a monoclonal antibody that cross-reacts therewith for binding toxin A. In an embodiment, the isolated antibody or antigen-binding fragment that specifically binds toxin B of *C. difficile* is an antibody produced by the hybridoma cell line deposited under ATCC Accession No. PTA-9693 or PTA-9692, an antigen-binding fragment thereof, a humanized form thereof, or a monoclonal antibody that cross-reacts therewith for binding toxin B.

Another aspect provides an isolated anti-*C. difficile* toxin A antibody or antigen-binding fragment as described above and herein, wherein the antibody or antigen-binding fragment, when administered to a *C. difficile*-infected subject in combination with an isolated antibody or antigen-binding fragment thereof that specifically binds toxin B of *C. difficile*, effects a cure or survivability rate of 50%, 60%, 70%, 80%, 90%, or 100%. In an embodiment, the antibody or antigen-binding fragment is administered q2d×4 at a dose of 40-50 mg/kg. In an embodiment, the isolated antibody or antigen-binding fragment that specifically binds toxin A of *C. difficile* is an antibody produced by the hybridoma cell line deposited under ATCC Accession No. PTA-9692, PTA-9694, or PTA-9888, an antigen-binding fragment thereof, a humanized form thereof, or a monoclonal antibody that cross-competes for binding toxin A with one of more of the monoclonal antibodies deposited under ATCC Accession No. PTA-9692, PTA-9694, or PTA-9888. In an embodiment, the isolated antibody or antigen-binding fragment that specifically binds toxin B of *C. difficile* is an antibody produced by the hybridoma cell line deposited under ATCC Accession No. PTA-9693 or PTA-9692, an antigen-binding fragment thereof, a humanized form thereof, or a monoclonal antibody that cross-competes for binding toxin B with one of more of the monoclonal antibodies deposited under ATCC Accession No. PTA-9692 or PTA-9693.

In another aspect is provided an isolated anti-*C. difficile* toxin A or an anti-*C. difficile* toxin B antibody or antigen-binding fragment thereof as described herein, wherein the antibody or antigen-binding fragment is, is in the form of, or is from, one or more of a monoclonal antibody, a humanized antibody, a human antibody, or a chimeric antibody.

In another aspect is provided an isolated anti-*C. difficile* toxin A or an anti-*C. difficile* toxin B antibody or antigen-binding fragment thereof as described herein, wherein the antibody or antigen-binding fragment thereof is, is in the form of, or is comprised in, a bispecific or bifunctional antibody.

Another aspect provides a bispecific antibody or an antigen-binding fragment thereof which comprises (i) a monoclonal antibody produced by the hybridoma cell line deposited under ATCC Accession No. PTA-9692, PTA-9694, or PTA-9888, an antigen-binding fragment thereof, a humanized version of the antibody or antigen-binding fragment thereof, a heavy chain variable domain of the antibody or antigen-binding fragment thereof, and/or a light chain variable domain of the antibody or antigen-binding fragment thereof; and (ii) a monoclonal antibody produced by the hybridoma cell line deposited under ATCC Accession No. PTA-9693 or PTA-9692, an antigen-binding fragment thereof, a humanized version of the antibody or antigen-binding fragment thereof, a heavy chain variable domain of the antibody or antigen-binding fragment thereof, and/or a light chain variable domain of the antibody or antigen-binding fragment thereof.

Another aspect provides a bispecific antibody or antigen-binding fragment thereof, wherein the antibody comprises (i) a monoclonal antibody produced by the hybridoma cell line deposited under ATCC Accession No. PTA-9692, an antigen-binding fragment thereof, a humanized version of the antibody or antigen-binding fragment thereof, a heavy chain variable domain of the antibody or antigen-binding fragment thereof, and/or a light chain variable domain of the antibody or antigen-binding fragment thereof; and (ii) an isolated monoclonal antibody produced by the hybridoma cell line deposited under ATCC Accession No. PTA-9693 or PTA-9692, an antigen-binding fragment thereof, a humanized version of the antibody or antigen-binding fragment thereof, a heavy chain variable domain of the antibody or antigen-binding fragment thereof, and/or a light chain variable domain of the antibody or antigen-binding fragment thereof.

In various embodiments an antibody or antigen-binding fragment thereof as described above and herein, wherein the antigen-binding fragment is selected from an Fab fragment, an $F(ab')_2$ fragment, and an Fv fragment is provided. In another aspect an isolated antibody or antigen-binding fragment thereof as described above and herein, wherein the antibody or antigen-binding fragment thereof is or comprises a single chain antibody is provided.

In another aspect a composition comprising one or more of the antibodies or antigen-binding fragments thereof of the invention, as described above and herein, and a pharmaceutically acceptable carrier, excipient, vehicle, or diluent is provided. In an embodiment, the composition comprises at least one anti-toxin A antibody of the invention, for example, mAb PTA-9692, mAb PTA-9694, mAb PTA-9888, an antigen-binding fragment thereof, or a humanized form thereof, and at least one anti-toxin B antibody of the invention, for example, mAb PTA-9692, mAb PTA-9693, an antigen-binding fragment thereof, or a humanized form thereof. In an embodiment, the composition comprises one anti-toxin A antibody of the invention, for example, mAb PTA-9888, an antigen-binding fragment thereof, or a humanized form thereof, and one anti-toxin B antibody of the invention, for example, mAb 9693, an antigen-binding fragment thereof, or a humanized form thereof. In an embodiment, the composition comprises one anti-toxin A antibody of the invention, for example, mAb PTA-9694, an antigen-binding fragment thereof, or a humanized form thereof, and one anti-toxin B antibody of the invention, for example, mAb 9693, an antigen-binding fragment thereof, or a humanized form thereof. In an embodiment, each mAb is present in the composition in the same amount. In an embodiment, each mAb is present in the composition in a 1:1 ratio, by weight, relative to each other. In an embodiment, each mAb is present in the composition in different amounts. In an embodiment, each mAb is present in the composition in ratios other than 1:1, by weight, relative to each other, wherein the ratios are as provided herein. In an embodiment, the composition further comprises an additional therapeutic agent. In an embodiment, the additional therapeutic agent is a/an antibiotic, antibacterial, bacteriocide, bacteriostat or a combination thereof. In an embodiment, the additional therapeutic agent is metronizadole, vancomycin, fidaxomicin, or a combination thereof.

In another aspect a composition comprising an expression vector of the invention, as described above and herein, and a pharmaceutically acceptable carrier, excipient, vehicle, or diluent is provided. In another aspect a composition comprising a host cell harboring an expression vector of the invention, as described above and herein, and a pharmaceutically acceptable carrier, excipient, vehicle, or diluent is provided. In another aspect a composition comprising a plasmid of the invention, as described above and herein, and a pharmaceutically acceptable carrier, excipient, vehicle, or diluent is provided.

Another aspect provides a binding protein comprising at least two polypeptide chains comprising binding sites for binding toxin A and toxin B of *C. difficile*, wherein at least one polypeptide chain comprises a first heavy chain variable domain, a second heavy chain variable domain, and a heavy chain constant domain or portion thereof; and at least one polypeptide chain comprises a first light chain variable domain, a second light chain variable domain, and a light chain constant domain or portion thereof, wherein the variable domains comprising the polypeptide chains form functional binding sites for toxin A and toxin B of *C. difficile*. In an embodiment, the first heavy chain variable domain and the first light chain variable domain of the binding protein form a functional binding site for toxin A of *C. difficile* and the second heavy chain variable domain and the second light chain variable domain of the binding protein form a functional binding site for toxin B of *C. difficile*. In an embodiment, the first heavy chain variable domain and the first light chain variable domain of the binding protein form a functional binding site for toxin B of *C. difficile* and the second heavy chain variable domain and the second light chain variable domain of the binding protein form a functional binding site for toxin A of *C. difficile*. In an embodiment, the binding protein comprises an Fc region. In an embodiment, the binding protein neutralizes the toxicity of toxin A and toxin B of *C. difficile*. In various embodiments, the binding protein has an on rate constant (Kon) to toxin A or toxin B selected from at least $10^2\ M^{-1}s^{-1}$; at least $10^3\ M^{-1}s^{-1}$; at least $10^4\ M^{-1}s^{-1}$; at least $10^5\ M^{-1}s^{-1}$; at least $10^6\ M^{-1}s^{-1}$; or at least $10^7\ M^{-1}s^{-1}$, as measured by surface plasmon resonance. In various embodiments, the binding protein has an off rate constant (Koff) to toxin A or toxin B selected from at most $10^{-3}\ s^{-1}$; at most $10^{-4}$ s$^{-1}$; at most $10^{-5}$ s$^{-1}$; or at most $10^{-6}$ s$^{-1}$, as measured by surface plasmon resonance. In various embodiments, the binding protein has a dissociation constant ($K_D$) to toxin A or toxin B selected from at most $10^{-7}$ M; at most $10^{-8}$ M; at most $10^{-9}$ M; at most $10^{-10}$ M; at most $10^{-11}$ M; at most $10^{-12}$ M; or at most $10^{-13}$ M.

In another aspect a composition comprising the binding protein as described above and herein and a pharmaceutically acceptable carrier, excipient, vehicle, or diluent is provided. In an embodiment, the composition further comprises an additional therapeutic agent. In an embodiment, the additional therapeutic agent of the composition is a/an antibiotic, antibacterial, bacteriocide, bacteriostat, or combination thereof. In an embodiment, the additional therapeutic agent of the composition is metronizadole, vancomycin, fidaxomicin, nitazoxanide, rifaximin ramoplanin, or a combination thereof.

In another aspect a hybridoma cell line deposited under ATCC Accession No. PTA-9692, PTA-9693, PTA-9494, or PTA-9888 is provided.

Another aspect provides a method of treating a subject with C. difficile infection or C. difficile-associated disease, comprising administering to the subject at least one composition as described herein. In an embodiment the compositions include one or more the antibodies of the invention, preferably in humanized form. In an embodiment the compositions contain at least one anti-toxin A antibody provided herein in humanized form, or an antigen-binding fragment thereof, and at least one antitoxin B antibody of the invention in humanized form, or an antigen-binding fragment thereof. In various embodiments, one or more additional therapeutic reagents, drugs, compounds, or ingredients may be included in the compositions. In an embodiment the compositions further include a pharmaceutically acceptable carrier, diluent, vehicle, or excipient. In an embodiment the compositions are administered in an amount effective to treat the C. difficile infection or C. difficile-associated disease, for example, C. difficile-associated diarrhea (CDAD). In an embodiment, two compositions are administered to the subject in an amount effective to treat the C. difficile infection or C. difficile-associated disease. In an embodiment, the two compositions are administered at the same time. In an embodiment, the two compositions are administered at different times.

Another aspect provides a method of inhibiting or neutralizing toxicity to a cell by C. difficile toxin A and toxin B, which comprises subjecting the cell to an effective C. difficile toxin A inhibiting or neutralizing dose of an anti-toxin A monoclonal antibody of the invention, or an antigen-binding fragment thereof, and an effective C. difficile toxin B inhibiting or neutralizing dose of an anti-toxin B monoclonal antibody of the invention, or an antigen-binding fragment thereof. In an embodiment, the anti-toxin A antibody and the anti-toxin B antibody are in humanized form. In an embodiment, the anti-toxin A antibody and the anti-toxin B antibody are in chimeric form. In an embodiment, the antibodies or antigen-binding fragments thereof are administered at the same time. In an embodiment, the antibodies or antigen-binding fragments thereof are administered at different times. In an embodiment of the method, the cell is present in a subject and the antibodies or antigen-binding fragments thereof are administered to the subject in amount effective to inhibit or neutralize the C. difficile toxin A and toxin B.

Another aspect provides a method of inhibiting or neutralizing toxicity of a cell by a C. difficile toxin which comprises subjecting the cell to an effective C. difficile toxin inhibiting or neutralizing dose of at least one of the compositions of the invention as described herein. In an embodiment of the method, the cell is subjected to an effective C. difficile toxin inhibiting or neutralizing dose of two compositions, one of which comprises an anti-toxin A antibody or antigen-binding fragment thereof, and one of which comprises an anti-toxin B antibody or antigen-binding fragment thereof. In an embodiment, the antibodies are humanized. In an embodiment, the antibodies are chimeric. In embodiments, the two compositions are administered at the same time or at different times. In an embodiment, the cell is present in a subject and the at least one composition is administered to the subject in amount effective to inhibit or neutralize the C. difficile toxin.

Another aspect provides a method of neutralizing toxins produced by a hypervirulent strain of C. difficile, which comprises administering to a subject in need thereof (i) an antibody or antigen-binding fragment thereof of the invention, wherein the antibody binds and neutralizes toxin A of C. difficile and (ii) an antibody or antigen-binding fragment thereof of the invention, wherein the antibody binds and neutralizes toxin B of C. difficile, in an amount effective to neutralize the toxins produced by the hypervirulent strain. In an embodiment, the antibodies of (i) and (ii) are humanized antibodies. In an embodiment, the antibodies of (i) and (ii) are chimeric antibodies. In embodiments, the antibodies or antigen-binding fragments thereof are administered at the same time or at different times. In an embodiment, the toxins of the hypervirulent strain are toxin A and toxin B. In an embodiment, the hypervirulent strain of C. difficile are one or more of BI/NAP1/027, CCL676, HMC553, Pitt45, CD196, montreal 5, or montreal 7.1. In an embodiment, the anti-oxin A antibody or antigen-binding fragment thereof has a neutralizing activity against toxin A produced by hypervirulent strains of C. difficile as determined by an EC$_{50}$ value of $2.6^{-12}$M to $7.7^{-11}$M or of $7.7^{-12}$M to $4.8^{-8}$M. In an embodiment, the anti-toxin B antibody or antigen-binding fragment thereof has a neutralizing activity against toxin B produced by hypervirulent strains of C. difficile as determined by an EC$_{50}$ value of from $1.1^{-11}$M to $6.5^{-10}$M.

In another aspect a kit comprising an antibody or antigen-binding fragment thereof of the invention and as described herein, particularly in humanized form, and instructions for use is provided. In an embodiment, the antibodies or antigen-binding fragments are contained in the same container in the kit. In an embodiment, the antibodies or antigen-binding fragments are contained in separate containers in the kit. In an embodiment, the kit comprises a linker for conjugating the antibodies or antigen-binding fragments thereof. In an embodiment, the kit comprises an additional therapeutic agent, which may be a/an antibiotic, antibacterial, bacteriocide, or bacteriostat. In an embodiment, the additional therapeutic agent is metronizadole, vancomycin, fidaxomicin, nitazoxanide, rifaximin ramoplanin, or a combination thereof.

In another aspect a monoclonal antibody, or an antigen-binding fragment thereof, particularly in humanized form, which neutralizes toxin A or toxin B of a hypervirulent strain of C. difficile is provided. In an embodiment the monoclonal antibody is designated by ATCC Accession number PTA-9692, PTA-9694, PTA-9888, or PTA-9693 and is produced by a hybridoma cell line deposited under ATCC Accession No. PTA-9692, PTA-9694, PTA-9888, or PTA-9693, respectively. In an embodiment, the antibody produced by the hybridoma cell line deposited under ATCC Accession No. PTA-9692, PTA-9694, PTA-9888, PTA-9693, or PTA-9692 has been humanized or is in chimeric form. In an embodiment, the hypervirulent strain of C. difficile is one or more of BI/NAP1/027, CCL676, HMC553, Pitt45, CD196, montreal 5 and montreal 7.1.

In another aspect a method of treating a subject who is asymptomatic, but who is susceptible to, or at risk of, contracting *C. difficile* infection, which comprises: administering to the subject (i) an anti-*C. difficile* toxin A antibody or antigen-binding fragment thereof provided and as described herein and (ii) an anti-*C. difficile* toxin B antibody or antigen-binding fragment thereof provided and as described herein, in an amount effective to treat the subject is provided. In an embodiment of the method, the subject is hospitalized.

In another aspect a humanized monoclonal antibody generated against toxin A of *C. difficile* is provided. In an embodiment, such an anti-*C. difficile* toxin A antibody is composed of two heavy chain polypeptides, wherein each heavy chain contains a VH region comprising the amino acid sequence as set forth in SEQ ID NO:1 and a human CH region, and two light chain polypeptides, wherein each light chain contains a VL region comprising the amino acid sequence as set forth in SEQ ID NO:3 and a human CL region. In an embodiment, such an anti-*C. difficile* toxin A antibody is composed of two heavy chain polypeptides, wherein each heavy chain contains a VH region comprising the amino acid sequence as set forth in SEQ ID NO:2 and a human CH region, and two light chain polypeptides, wherein each light chain contains a VL region comprising the amino acid sequence as set forth in SEQ ID NO:3 and a human CL region. In an embodiment, such an anti-*C. difficile* toxin A antibody is composed of two heavy chain polypeptides, wherein each heavy chain contains a VH region comprising the amino acid sequence as set forth in SEQ ID NO:1 and a human CH region, and two light chain polypeptides, wherein each light chain contains a VL region comprising the amino acid sequence as set forth in SEQ ID NO:4 and a human CL region. In an embodiment, such an anti-*C. difficile* toxin A antibody is composed of two heavy chain polypeptides, wherein each heavy chain contains a VH region comprising the amino acid sequence as set forth in SEQ ID NO:2 and a human CH region, and two light chain polypeptides, wherein each light chain contains a VL region comprising the amino acid sequence as set forth in SEQ ID NO:4 and a human CL region. In an embodiment, such an anti-*C. difficile* toxin A antibody is composed of two heavy chain polypeptides, wherein each heavy chain contains a VH region comprising the amino acid sequence as set forth in SEQ ID NO:5 and a human CH region, and two light chain polypeptides, wherein each light chain contains a VL region comprising the amino acid sequence as set forth in SEQ ID NO:7 and a human CL region. In an embodiment, such an anti-*C. difficile* toxin A antibody is composed of two heavy chain polypeptides, wherein each heavy chain contains a VH region comprising the amino acid sequence as set forth in SEQ ID NO:6 and a human CH region, and two light chain polypeptides, wherein each light chain contains a VL region comprising the amino acid sequence as set forth in SEQ ID NO:7 and a human CL region.

In another aspect a humanized monoclonal antibody generated against toxin B of *C. difficile* is provided. In an embodiment, such an anti-*C. difficile* toxin B antibody is composed of two heavy chain polypeptides, wherein each heavy chain contains a VH region comprising the amino acid sequence as set forth in SEQ ID NO:8 and a human CH region, and two light chain polypeptides, wherein each light chain contains a VL region comprising the amino acid sequence as set forth in SEQ ID NO:10 and a human CL region. In an embodiment, such an anti-*C. difficile* toxin B antibody is composed of two heavy chain polypeptides, wherein each heavy chain contains a VH region comprising the amino acid sequence as set forth in SEQ ID NO:9 and a human CH region, and two light chain polypeptides, wherein each light chain contains a VL region comprising the amino acid sequence as set forth in SEQ ID NO:10 and a human CL region.

In another aspect a monoclonal antibody, or a fragment thereof, generated against toxin A of *C. difficile*, wherein the antibody is composed of two heavy chain polypeptides, each heavy chain containing a VH region and a human CH region and two light chain polypeptides, each light chain containing a VL region and a human CL region is provided. The nucleic acid sequence (or cDNA) encoding the amino acid sequence of the antibody heavy chain polypeptide of SEQ ID NO: 14 is set forth in SEQ ID NO:15 (FIG. 38B); the nucleic acid sequence (or cDNA) encoding the amino acid sequence of the antibody light chain polypeptide of SEQ ID NO:16 is set forth in SEQ ID NO:17 (FIG. 38A).

In another aspect a monoclonal antibody, or a fragment thereof, generated against toxin A of *C. difficile*, wherein the antibody is composed of two heavy chain polypeptides, each heavy chain containing a VH region and a human CH region and two light chain polypeptides, each light chain containing a VL region and a human CL region is provided. The nucleic acid sequence (or cDNA) encoding the amino acid sequence of the antibody heavy chain polypeptide of SEQ ID NO: 18 is set forth in SEQ ID NO:19 (FIG. 39B); the nucleic acid sequence (or cDNA) encoding the amino acid sequence of the antibody light chain polypeptide of SEQ ID NO:20 is set forth in SEQ ID NO:21 (FIG. 39A).

In another aspect a monoclonal antibody, or a fragment thereof, generated against toxin B of *C. difficile*, wherein the antibody is composed of two heavy chain polypeptides, each heavy chain containing a VH region and a human CH region and two light chain polypeptides, each light chain containing a VL region and a human CL region is provided. The nucleic acid sequence (or cDNA) encoding the amino acid sequence of the antibody heavy chain polypeptide of SEQ ID NO:22 is set forth in SEQ ID NO:23 (FIG. 40B); the nucleic acid sequence (or cDNA) encoding the amino acid sequence of the antibody light chain polypeptide of SEQ ID NO:24 is set forth in SEQ ID NO:25 (FIG. 40A)

In various embodiments directed to any of the foregoing humanized monoclonal antibodies of the invention, the CH region of the monoclonal antibody is selected from IgG1, IgG2a, IgG2b, IgG3, IgG4, IgA, IgE, or IgM. In an embodiment, the CH region is IgG1. In an embodiment, the CL region is selected from the κ or λ isotype. In an embodiment, the CL region is of the κ isotype. In other embodiments, the CDRs, i.e., CDR1, CDR2, and/or CDR3, of the humanized antibodies, or antigen-binding fragments thereof, as described herein, are embraced to bind and/or neutralize toxin A and/or toxin B of *C. difficile* in products and methods according to the invention.

In another aspect an anti-*C. difficile* toxin A antibody, or a fragment thereof, wherein the V region of the L chain comprises a sequence selected from one or more of SEQ ID NO:3, SEQ ID NO:4 and SEQ ID NO:7 is provided. Also provided is an anti-*C. difficile* toxin B antibody, or a fragment thereof, wherein the V region of the L chain comprises a sequence as set forth in SEQ ID NO:10. Also provided is an anti-*C. difficile* toxin A antibody, or a fragment thereof, wherein the V region of the H chain comprises a sequence selected from one or more of SEQ ID NO:1, SEQ ID NO:2, SEQ ID NO:5 and SEQ ID NO:6. Also provided is an anti-*C. difficile* toxin B antibody, or a fragment thereof, wherein the V region of the H chain comprises a sequence selected from one or more of SEQ ID NO:8 or SEQ ID NO:9.

In another aspect an isolated antibody or an antigen-binding fragment thereof, which (i) specifically binds toxin A of *C. difficile* and which cross competes for binding to toxin A of C. difficile with a monoclonal antibody produced by a hybridoma cell line deposited under ATCC Accession No. PTA-9692, or which (ii) specifically binds to a C. difficile toxin A epitope defined by a monoclonal antibody produced by the hybridoma cell line deposited under ATCC Accession No. PTA-9692, wherein the epitope defined by the monoclonal antibody produced by the hybridoma cell line deposited under ATCC Accession No. PTA-9692 comprises a region outside of the receptor binding domain, e.g., the translocation domain, of C. difficile toxin A is provided. In an embodiment, the antibody is in humanized form. In an embodiment, the antibody is in chimeric form.

In another aspect an isolated antibody or an antigen-binding fragment thereof, which (i) specifically binds toxin A of C. difficile and which cross competes for binding to toxin A of C. difficile with a monoclonal antibody produced by a hybridoma cell line deposited under ATCC Accession No. PTA-9694, or which (ii) specifically binds to a C. difficile toxin A epitope defined by a monoclonal antibody produced by the hybridoma cell line deposited under ATCC Accession No. PTA-9694, wherein the epitope defined by the monoclonal antibody produced by the hybridoma cell line deposited under ATCC Accession No. PTA-9694 comprises at least two sites in the receptor binding domain, e.g., C-terminal receptor binding epitopes, of C. difficile toxin A is provided. In an embodiment, the antibody is in humanized form. In an embodiment, the antibody is in chimeric form.

In another aspect an isolated antibody or an antigen-binding fragment thereof, which (i) specifically binds toxin A of C. difficile and which cross competes for binding to toxin A of C. difficile with a monoclonal antibody produced by a hybridoma cell line deposited under ATCC Accession No. PTA-9888, or which (ii) specifically binds to a C. difficile toxin A epitope defined by a monoclonal antibody produced by the hybridoma cell line deposited under ATCC Accession No. PTA-9888, wherein the epitope defined by the monoclonal antibody produced by the hybridoma cell line deposited under ATCC Accession No. PTA-9888 comprises C-terminal receptor binding epitopes of C. difficile toxin A is provided. In an embodiment, the antibody is in humanized form. In an embodiment, the antibody is in chimeric form.

In another aspect an isolated antibody or an antigen-binding fragment thereof, which (i) specifically binds toxin B of C. difficile and which cross competes for binding to toxin B of C. difficile with a monoclonal antibody produced by a hybridoma cell line deposited under ATCC Accession No. PTA-9693, or which (ii) specifically binds to a C. difficile toxin B epitope defined by a monoclonal antibody produced by the hybridoma cell line deposited under ATCC Accession No. PTA-9693, wherein the epitope defined by the monoclonal antibody produced by the hybridoma cell line deposited under ATCC Accession No. PTA-9693 comprises the N-terminal enzyme domain of C. difficile toxin B is provided. In an embodiment, the epitope defined by the monoclonal antibody produced by the hybridoma cell line deposited under ATCC Accession No. PTA-9693 comprises a 63 kDa fragment generated by caspase 1-treatment of toxin B comprising the N-terminal enzyme domain of C. difficile toxin B. In an embodiment, the epitope defined by the monoclonal antibody produced by the hybridoma cell line deposited under ATCC Accession No. PTA-9692 comprises the translocation domain of C. difficile toxin B.

In an embodiment, the epitope defined by the monoclonal antibody produced by the hybridoma cell line deposited under ATCC Accession No. PTA-9692 comprises a 167 kDa fragment generated by caspase 1-treatment of toxin B and a 63 kDa protein which comprises untreated toxin B. In an embodiment, the antibody is in humanized form. In an embodiment, the antibody is in chimeric form.

In another aspect a method of producing a monoclonal antibody which binds and neutralizes toxin A or toxin B of C. difficile, involving immunizing one or more recipient animals with inactive toxoid A at periodic intervals; boosting the animals with increasing amounts of active toxin A or active toxin B at periodic intervals; obtaining hybridoma cells from immune cells of the immunized and boosted animal fused with a suitable immortalized cell line, wherein the hybridoma cells produce and secrete anti-toxin A antibodies which bind and neutralize toxin A of C. difficile or anti-toxin B antibodies which bind and neutralize toxin B of C. difficile is provided. In an embodiment, the anti-C. difficile toxin A-neutralizing monoclonal antibodies and/or the anti-C. difficile toxin B-neutralizing monoclonal antibodies are isolated. In embodiments of the method, the immunizing and boosting steps include an adjuvant. In an embodiment, the adjuvant is Quil A. In other embodiments of the method, the immunizing and boosting steps are performed at periodic intervals of every three weeks. In other embodiments, the recipient animals are immunized with two or three doses of toxoid A, followed by three to five boosts of escalating doses of either active toxin A or active toxin B.

In another aspect, an isolated antibody, or antigen-binding fragment thereof, which inhibits, blocks, or prevents C. difficile toxin A toxicity by inhibiting, blocking, or preventing toxin A internalization and cytocellular toxicity is provided. In an embodiment, the antibody is a monoclonal antibody. In an embodiment, the antibody is a humanized or chimeric antibody. In an embodiment the antibody is PA-39 (ATCC Accession No. PTA-9692) or humanized PA-39. In an embodiment, the antibody is PA-50 (ATCC Accession No. PTA-964) or humanized PA-50. In other embodiments, the antibody competes with PA-39, humanized PA-39, PA-50, or humanized PA-50 for binding to toxin A. In an embodiment, the antibody binds a single site in a region of toxin A outside of the receptor binding domain of toxin A. In an embodiment, the antibody competes with PA-39 or a humanized form thereof by binding a single site in a region of toxin A outside of the receptor binding domain of toxin A. In an embodiment, the antibody binds to at least two sites in the receptor binding domain of toxin A. In an embodiment, the antibody competes with PA-50 or a humanized form thereof by binding to at least two sites in the receptor binding domain of toxin A. In an embodiment, the antibody inhibits toxin A toxicity via a mixed-competitive mechanism of action. In an embodiment, the antibody inhibits toxin A toxicity via a competitive mechanism of action. All of the above embodiments are meant to encompass the antigen-binding fragment of the antibody.

In another aspect, an isolated antibody, or antigen-binding fragment thereof, which inhibits, blocks, or prevents C. difficile toxin B toxicity by binding to an epitopic site in the N-terminal enzymatic region of toxin B is provided. In an embodiment, the antibody is a monoclonal antibody. In an embodiment, the antibody is a humanized or chimeric antibody. In an embodiment the antibody is PA-41 (ATCC Accession No. PTA-9693) or a humanized form of PA-41. In an embodiment, the antibody competes with PA-41 or humanized PA-41 for binding to the N-terminal enzymatic region of toxin B of C. difficile. In an embodiment, the antibody competes with PA-41 or humanized PA-41 for binding to a single site in the N-terminal enzymatic region of toxin B of C. difficile. In an embodiment, the antibody inhibits toxin B toxicity via a mixed-competitive mechanism of action.

Another aspect provides a vaccine or immunogen comprising portions, fragments, or peptides of toxin A and/or toxin B of C. difficile containing the epitopic regions recognized and/or bound by one or more of monoclonal antibody PA-39 (ATCC Accession No. PTA-9692), a humanized form of PA-39, monoclonal antibody PA-50 (ATCC Accession No. PTA-9694), a humanized form of PA-51, monoclonal antibody PA-41 (ATCC Accession No. PTA-9693), a humanized form of PA-41, an antibody that competes for binding of toxin A with monoclonal antibody PA-39 or a humanized form thereof, an antibody that competes for binding of toxin A with monoclonal antibody PA-50 or a humanized form thereof, or an antibody that competes for binding of toxin B with monoclonal antibody PA-41 or a humanized form thereof. In an embodiment, the vaccine or immunogen comprises portions, fragments, or peptides of toxin A and toxin B of C. difficile containing the epitopic regions recognized and/or bound by one or more of monoclonal antibody PA-39 (ATCC Accession No. PTA-9692), a humanized form of PA-39, or an antibody that competes for binding of toxin A and toxin B with monoclonal antibody PA-39 or a humanized form thereof. In an embodiment, the epitope-containing portions, fragments, or peptides of toxin A and/or toxin B of the vaccine or immunogen are derived from the toxin A or toxin B protein by proteolytic cleavage. In an embodiment, the toxin A fragments, portions, or peptides of the vaccine or immunogen are produced by proteolytic cleavage by enterokinase. In an embodiment, the toxin B fragments, portions, or peptides of the vaccine or immunogen are produced by proteolytic cleavage by caspase (caspase 1). In an embodiment, the epitope-containing portions or fragments of the vaccine or immunogen are chemically or recombinantly synthesized peptides of the toxin A or toxin B protein. In an embodiment, the fragments, portions, or peptides of the vaccine or immunogen containing one or more epitopic regions of toxin A and/or toxin B that are recognized and bound by the antibody are derived from one or more of the amino terminus of toxin A; the amino terminus of toxin B; the carboxy terminus of toxin A; the carboxy terminus of toxin B; the receptor binding domain of toxin A; a region outside of the receptor binding domain of toxin A; the receptor binding domain of toxin B; the N-terminal enzymatic region of toxin B; the glucosyltransferase domain of toxin A; the glucosyltransferase domain of toxin B; the proteolytic domain of toxin A; the proteolytic domain of toxin B; the hydrophobic, pore-forming domain of toxin A; or the hydrophobic, pore-forming domain of toxin B. In an embodiment, the epitope-containing fragments or portions of toxin A or toxin B are <300 kDa, ~158-160 kDa, ~100-105 kDa, e.g., 103 kDa, ~90-95 kDa, e.g., 91 kDa, and/or ~63-68 kDa, e.g., 63 kDa or 68 kDa in size. In an embodiment, the epitope-containing fragments or portions of toxin A are ~158-160 kDa; ~90-95 kDa, e.g., 91 kDa, and/or ~63-68 kDa, e.g., 68 kDa in size. In an embodiment, the epitope-containing fragments or portions of toxin B are ~100-105 kDa, e.g., 103 kDa and/or ~63-68 kDa, e.g., 63 kDa in size. In any of the vaccine or immunogen embodiments, the toxin A or toxin B, or fragment, portion or peptide thereof, is that of any of the strains provided herein.

Another aspect provides a method of neutralizing, inhibiting, blocking, reducing, ameliorating, curing, or treating C. difficile infection or a C. difficile-associated disease in a subject in need thereof, comprising administering to the subject an effective amount of the above-described vaccine or immunogen. In an embodiment of the method, a humoral response to toxin A and/or toxin B of C. difficile following administration of the vaccine or immunogen is elicited in the subject, thereby producing anti-toxin A and/or anti-toxin B antibodies that can specifically neutralize, inhibit, block, reduce, ameliorate, cure, or treat C. difficile-associated disease or CDAD, including mild to severe diarrhea and in some cases associated with severe, life threatening complications, such as pseudomembranous colitis, toxic megacolon, bowel perforation, sepsis and death, in the subject. In an embodiment of the method, the antibodies that are elicited via the subject's humoral response include antibodies having specificities and mechanisms of action similar or identical to the mAbs of the invention, or antibodies which compete with the mAbs of the invention in neutralizing toxin A and/or toxin B of C. difficile, or which compete with the mAbs of the invention in the mechanism of action involved in neutralizing toxin A and/or toxin B of C. difficile. In another aspect, a method of neutralizing, inhibiting, or blocking toxin A and/or toxin B activity in or against a cell susceptible to C. difficile infection, comprising contacting the cell with an antibody, or antigen-binding fragment thereof, in accordance with the present invention, wherein the antibody, or antigen-binding fragment thereof, neutralizes, inhibits, or blocks the toxin A and/or toxin B activity in or against the cell by a competitive or a mixed competitive mechanism of action is provided. In an embodiment of the method, the antibody is one or more of a monoclonal antibody, a humanized antibody, or a chimeric antibody. In an embodiment of the method, the cell, e.g., an intestinal epithelial cell, is in a subject and the antibody, or antigen-binding fragment thereof, is administered in an effective amount to the subject. In an embodiment of the method, the toxin is toxin A. In an embodiment of the method, the toxin is toxin B. In an embodiment of the method, the toxin is toxin A and the mechanism of action is a competitive inhibition mechanism of action. In an embodiment of the method, the antibody, or antigen binding fragment thereof, is PA-50 (ATCC Accession No. PTA-9694), a humanized form thereof, or an antibody, or fragment thereof, which competes with PA-50 for neutralizing toxin A activity. In an embodiment of the method, the toxin is toxin A and the mechanism of action is a mixed-competitive inhibition mechanism of action. In an embodiment of the method, the antibody, or antigen binding fragment thereof, is PA-39 (ATCC Accession No. PTA-9692), a humanized form thereof, or an antibody, or fragment thereof, which competes with PA-39 for neutralizing toxin A activity. In an embodiment of the method, the toxin is toxin B and the mechanism of action is a mixed competitive inhibition mechanism of action. In an embodiment, the antibody, or antigen binding fragment thereof, is PA-41 (ATCC Accession No. PTA-9693), a humanized form thereof, or an antibody, or fragment thereof, which competes with PA-41 for neutralizing toxin B activity.

These and other aspects of the invention will be described in further detail in connection with the detailed description of the invention.

BRIEF DESCRIPTION OF THE DRAWINGS

FIG. 3A: binding of PA-38 to toxin A; FIG. 3B: binding of PA-50 to toxin A; FIG. 3C: binding of PA-39 to toxin A; FIG. 3D: binding of PA-39 to toxin B; and FIG. 3E: binding of PA-41 to toxin B. For FIGS. 3F-3H, as above, murine mAbs, i.e., mPA-50, mPA-41, or mPA-39, were covalently linked to a CMS sensor chip by the amine-coupling method. Toxin A (line designated "(red)") or toxin B (line designated "(blue)") at 30 nM was passed over test flow cells (mPA-50, mPA-41, or mPA-39) at a flow rate of 5 µL/min. The results show that mPA-50 selectively binds toxin A (FIG. 3F), and mPA-41 selectively binds toxin B (FIG. 3G). mPA-39 binds preferentially to toxin A, but also demonstrates cross-reactivity to toxin B (FIG. 3H).

FIG. 16A illustrates the survival results of the hamster study described in Example 5C. In this study, hamsters were treated with clindamycin, inoculated with C. difficile (■ infected control, Group 1), and then different groups of animals were treated with vancomycin (♦ 20 mg/kg, Group 2), the combination of murine mAbs PA-39+PA-41 (▲ 50+50 mg/kg, Group 3), murine mAb PA-41 alone (○ 50 mg/kg, Group 4), murine mAb PA-38 alone (∇ 50 mg/kg, Group 5), murine mAb PA-39 alone (□ 50 mg/kg, Group 6), or murine mAb PA-50 alone (◇ 50 mg/kg, Group 7). All animals in the uninfected control (Group 1) survived during the course of the study. FIG. 16B-1 illustrates the animal survival results of the hamster study described in Example 5E. Kaplan-Meier survival curves are shown for animals treated with clindamycin and then inoculated with C. difficile (■, Infected control, Group 2); treated with vancomycin (◇, 20 mg/kg, Group 3); treated with a 1:1 combination of humanized PA-50+PA-41 mAbs ((hPA-50+hPA-41), Δ, 50+50 mg/kg, Group 4); treated with a 1:1 combination of humanized PA-50+PA-41 mAbs ((hPA-50+hPA-41), ○, 20+20 mg/kg, Group 5); treated with a 1:1 combination of comparator mAbs CDA-1+CDB-1 ((CDA-1+CDB-1), ∇, 50+50 mg/kg, Group 6); or treated with a 1:1 combination of comparator mAbs CDA-1+CDB-1 ((CDA-1+CDB-1), □ 20+20 mg/kg, Group 7). FIG. 16B-2 illustrates the weight change results of the hamster study described in Example 5E. Mean (±SD) body weights of animals over time in the different treatment groups described for FIG. 16B-1 compared with uninfected control animals.

FIGS. 18A-18C show SDS-PAGE (A) and Western blot (B, C) detection of C. difficile toxin B fragments using anti-toxin B mAbs. (A): SDS-PAGE analysis of toxin B fragments generated by caspase 1 treatment (same as FIG. 17B); (B): Western blot detection of toxin B fragments using mAb PA-41. (C) Western blot detection of toxin B fragments using murine mAb PA-39.

FIGS. 21A-21C show Coomassie Blue staining (SDS-PAGE), (A), and Western blot (B, C) detection of *C. difficile* toxin A fragments using anti-toxin A murine mAbs. (A): SDS-PAGE analysis of toxin A fragments generated by EK treatment (same as FIG. 20B). (B): Western blot detection of toxin A fragments using mAb PA-50. (C): Western blot detection of toxin A fragments using mAb PA-39. In FIGS. 21B and 21C, the kDa band is ~158 kDa and may be considered to be ~158-160 kDa.

FIGS. 22A-1 and A-2-22F. FIGS. 22A-1 and A-2-22D show the characterization of murine anti-toxin A mAb binding to toxin A of *C. difficile* using a Biacore binding assay. FIG. 22A-1: PA-50 mAb was observed to bind multiple sites on toxin A. FIG. 22A-2: PA-50 mAb was immobilized onto the sensor chip and then sequentially contacted with purified toxin A, additional PA-50 and comparator mAb CDA-1 (WO/2006/121422; US2005/0287150).

FIG. 23A shows the neutralizing activity of murine mAb PA-41 on CHO-K1 cells against supernatants generated from the different *C. difficile* clinical isolate cultures as presented in Example 8, Table 6. Purified mAb PA-41 was serially diluted and then mixed with a supernatant with predefined dilution factor that can cause >90% cell death. The mixtures were incubated for 1 hour at 37° C. and then added to CHO-K1 cells. The cells were incubated for 72 hours, and cell viability was measured using Cell-Titer Blue. FIG. 23B illustrates the neutralizing activity of humanized mAb hPA-41 as well as that of comparator mAb CDB-1 against the 2 *C. difficile* reference strains (VPI 10463 and ATCC 43596) and 6 *C. difficile* BI/027/027 strains (CCL678, HMC553, Pitt 45, CD196, Montreal 5.1 and Montreal 7.1). The neutralization activity of hPA-41 mAb (filled squares) and comparator mAb CDB-1 (filled triangles) on CHO-K1 cells against supernatants from reference strains (VPI 10483 and ATCC 43596) and BI/NAP1/027 strains (CCL678, HMC553, Pitt 45, CD196, Montreal 5.1 and Montreal 7.1) is shown.

FIG. 24A shows the neutralizing activity of murine mAb PA-50 on T-84 cells against supernatants generated from different *C. difficile* clinical isolate cultures as presented in Example 8, Table 6. Purified mAb PA-50 was serially diluted and then mixed with a supernatant with predefined dilution factor that can cause >90% cell death. The mixtures were incubated for 1 hour at 37° C. and then added to T-84 cells. The cells were incubated for 72 hours, and cell viability was measured using Cell-Titer Blue. FIG. 24B shows the results of similar experiments performed using humanized mAb hPA-50 and the comparator mAb CDA-1 on T-84 cells. The neutralization activity of hPA-50 (filled squares) and CDA-1 comparator (filled triangles) on T-84 cells against supernatants generated from six BI/NAP1/027 strains (CCL678, HMC553, Pitt 45, CD196, Montreal 5.1 and Montreal 7.1) is shown. For FIG. 24A: *: N/A: Not Applicable; no toxin A was produced from toxin A−/toxin B+ strains F1470, 8864, CCL13820 and CCL14402; ": Toxin A titer was very low; no measurable cytotoxicity on T-84 using supernatant; ˆ: Not applicable; no toxin A was produced from toxin A−/toxin B+ strains or concentration was too low.

FIGS. 25A and 25B show neutralizing activity of murine mAb PA-39 on T-84 cells against supernatants generated from different *C. difficile* clinical isolate cultures as presented in Example 8, Table 6. mAb PA-39 (hybridoma supernatant) was serially diluted and the dilution factor of each supernatant is shown. FIG. 25B shows the results of similar experiments performed using murine mAb PA-39 and the comparator CDA-1 mAb on T-84 cells. The neutralization activity of PA-39 (filled squares) and comparator CDA-1 mAb (filled triangles) on T-84 cells against supernatants generated from six BI/NAP1/027 strains (CCL678, HMC553, Pitt 45, CD196, Montreal 5.1 and Montreal 7.1) is shown. For FIG. 25A: *: N/A: Not Applicable; no toxin A was produced from toxin A−/toxin B+ strains F1470, 8864, CCL13820 and CCL14402; ": Toxin A titer was very low; no measurable cytotoxcity on T-84 using supernatant; ˆ: Not applicable; no toxin A was produced from toxin A−/toxin B+ strains or concentration was too low. In FIG. 25C, humanized anti-toxin A mAb PA-50 and comparator anti-toxin A mAb CDA-1 were tested for neutralization of cytotoxicity of *C. difficile* culture supernatants against T-84 cells. (Example 8, Table 7). In FIG. 25D, humanized anti-toxin B mAb PA-41 and comparator anti-toxin A mAb CDB-1 were tested for neutralization of cytotoxicity of *C. difficile* culture supernatants against T-84 cells. (Example 8, Table 7).

FIGS. 31A-31H show the results of in vitro neutralization activity and mechanism of action (MOA) studies using the described mAbs. The cell-based assays using CHO-K1 cells and T-84 cells were carried out as described in Examples 1, 3 and 7. FIG. 31A shows that humanized PA-50 (hPA-50) mAb effectively neutralized the toxicity of toxin A (60 ng/mL, TechLab) on T-84 cells compared with the parental murine PA-50 mAb (mPA-50). FIGS. 31B-D show the neutralization activities of anti-toxin A mAbs PA-39 and PA-50 compared with that of comparator anti-toxin A mAb CDA-1. The $EC_{50}$ and maximum percent inhibition values are as presented in Table A of Example 7C. FIGS. 31E and F show the neutralization activity of anti-toxin B mAb PA-41 compared with that of comparator anti-toxin B mAb CDB-1. The $EC_{50}$ and maximum percent inhibition values are as presented in Table B of Example 7C. FIGS. 31G and H show an ELISA method and results for assessing the ability of the anti-toxin A mAbs to block toxin A internalization into cells and for evaluating the activities of these mAbs in preventing toxin A internalization relative to polyclonal goat anti-toxin A antibody control and no antibody control.

FIGS. 32A and 32B depict the amino acid sequences of humanized PA-39 (hPA-39) VH regions, SEQ ID NO:1 and SEQ ID NO:2. Amino acid residues are shown in single letter code. Numbers above the sequences indicate the locations according to Kabat et al. The locations of the CDRs are underlined.

FIGS. 33A and 33B depict the amino acid sequences of humanized PA-39 (hPA-39) VL regions, SEQ ID NO:3 and SEQ ID NO:4. Amino acid residues are shown in single letter code. Numbers above the sequences indicate the locations according to Kabat et al. The locations of the CDRs are underlined.

FIGS. 34A and 34B depict the amino acid sequences of humanized PA-50 (hPA-50) VH regions, SEQ ID NO:5 and SEQ ID NO:6. Amino acid residues are shown in single letter code. Numbers above the sequences indicate the locations according to Kabat et al. The locations of the CDRs are underlined.

FIG. 35 depicts the amino acid sequence of humanized PA-50 VL region, SEQ ID NO:7. Amino acid residues are shown in single letter code. Numbers above the sequences indicate the locations according to Kabat et al. The locations of the CDRs are underlined.

FIGS. 36A and 36B depict the amino acid sequences of humanized PA-41 (hPA-41) VH regions, SEQ ID NO:8 and SEQ ID NO:9. Amino acid residues are shown in single letter code. Numbers above the sequences indicate the locations according to Kabat et al. The locations of the CDRs are underlined.

FIG. 37 depicts the amino acid sequence of humanized PA-41 VL region, SEQ ID NO:10. Amino acid residues are shown in single letter code. Numbers above the sequences indicate the locations according to Kabat et al. The locations of the CDRs are underlined.

FIGS. 38A and 38B show the nucleic acid sequence and encoded amino acid sequence of a humanized anti-C. difficile toxin A monoclonal antibody. FIG. 38A depicts the amino acid sequence of the light chain of the humanized anti-toxin A monoclonal antibody as set forth in SEQ ID NO:16, which is encoded by the nucleic acid sequence as set forth in SEQ ID NO:17. FIG. 38B depicts the amino acid sequence of the heavy chain of the humanized monoclonal antibody as set forth in SEQ ID NO:14, which is encoded by the nucleic acid sequence as set forth in SEQ ID NO:15.

FIGS. 39A and 39B show the nucleic acid sequence and encoded amino acid sequence of a humanized anti-C. difficile toxin A monoclonal antibody. FIG. 39A depicts the amino acid sequence of the light chain of the humanized anti-toxin A monoclonal antibody as set forth in SEQ ID NO:20, which is encoded by the nucleic acid sequence as set forth in SEQ ID NO:21. FIG. 39B depicts the amino acid sequence of the heavy chain of the humanized anti-toxin A monoclonal antibody as set forth in SEQ ID NO:18, which is encoded by the nucleic acid sequence as set forth in SEQ ID NO:19.

FIGS. 40A and 40B show the nucleic acid sequence and encoded amino acid sequence of a humanized anti-C. difficile toxin B monoclonal antibody. FIG. 40A depicts the amino acid sequence of the light chain of the humanized anti-toxin B monoclonal antibody as set forth in SEQ ID NO:24, which is encoded by the nucleic acid sequence as set forth in SEQ ID NO:25. FIG. 40B depicts the amino acid sequence of the heavy chain of the humanized anti-toxin B monoclonal antibody as set forth in SEQ ID NO:22, which is encoded by the nucleic acid sequence as set forth in SEQ ID NO:23.

FIG. 42A depicts the PK results (serum antibody concentration in μg/mL) over 29 days from animals receiving a single dose of purified, humanized, anti-toxin A mAb PA-50 at a concentration of 1 mg/kg (▲) or 5 mg/kg (■) on day 0. FIG. 42B depicts the PK results (serum antibody concentration in μg/mL) over 29 days from animals receiving a single dose of purified, humanized, anti-toxin B mAb PA-41 at a concentration of 1 mg/kg (▲) or 5 mg/kg (■) on day 0.

DETAILED DESCRIPTION OF THE INVENTION

Figure 1A:
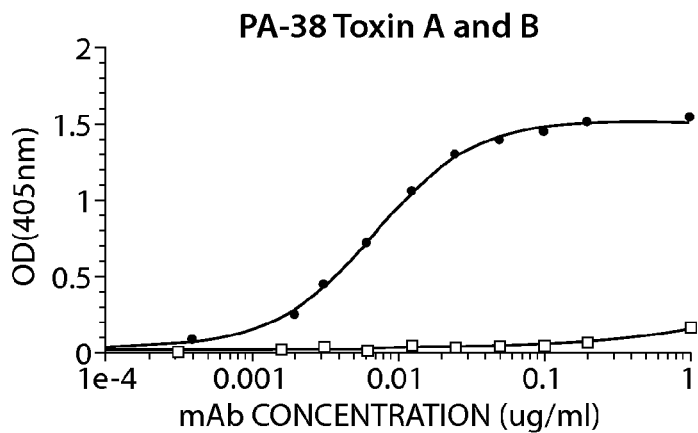
FIGS. 1A-1C demonstrate the specificity of anti-C. difficile toxin mAbs of the invention for toxin A and/or toxin B via ELISA. ELISA plates were coated with toxin A (filled circles) or toxin B (open squares) overnight at 4° C. After the plates were washed and blocked, murine mAb PA-38 (A), PA-39 (B), or PA-41 (C) was titrated and added to the plates. Monoclonal antibody binding was detected with HRP conjugated goat anti-mouse IgG-Fc. OD was measured on a SpectraMax M5 Plate Reader (Molecular Devices).

The present invention encompasses antibodies and antigen-binding fragments thereof that provide non-antibiotic therapies and treatments which block the pathogenic effects of *C. difficile* infection and, preferably, provide time for the colon to heal and/or the normal microflora of the gastrointestinal tract, e.g., colon, bowel, intestine, etc., to become reestablished. The monoclonal antibodies as described herein, antigen-binding fragments thereof, such as humanized or chimeric forms thereof, provide non-antibiotic therapeutics and medicaments both to treat active disease and to prevent recurrent disease so as to allow patients suffering from *C. difficile* infection and CDAD to resolve their disease without relapse to further disease or to more severe disease or symptoms. In an embodiment, antibodies of the invention have therapeutic activity against active disease caused by, or associated with, infection of subjects by *C. difficile*. In an embodiment, antibodies of the invention resolve active disease caused by, or associated with, infection of subjects by *C. difficile*. In an embodiment, antibodies of the invention have therapeutic effects in decreasing the duration and/or severity of active disease caused by, or associated with, infection by *C. difficile* in a subject. In an embodiment, antibodies of the invention or portions or fragments thereof can be provided in combination with antibiotic therapeutics.

Monoclonal antibodies (mAbs) against *C. difficile* toxins A and B have been generated as described herein. The anti-toxin mAbs exhibit potent activity both in in vitro assays and in preclinical animal models of *C. difficile* infection in vivo. More specifically, mAbs of the invention potently and durably protect hamsters from mortality in a relevant and stringent hamster model of *C. difficile* infection.

The antibodies provide non-antibiotic approaches for the treatment of CDAD and may allow the discontinuation of antibiotics and block the pathogenic effects of *C. difficile* toxins, thereby providing time for the colon to heal and the normal bowel microflora to become re-established. The mAbs as described herein can provide therapeutic benefit by their ability to neutralize the toxins of *C. difficile* and may be employed in passive or active strategies to treat patients with multiple recurrences of *C. difficile*. In particular, the mAbs may be utilized for preventing recurrence of infection, for treating severe, active forms of disease, and for treating patients with multiple relapses of *C. difficile*-associated diseases. The mAbs as described herein can provide an effective means to neutralize *C. difficile* toxins A and B so as to prevent, block, or inhibit recurrence of infection, and/or severe and active forms of the disease and multiple relapses.

As used herein, "toxin A" and "toxin B" refer to the cytotoxic enterotoxins produced by the *C. difficile* microorganism. Toxins A and B are the major virulence determinants of *C. difficile*, and toxin-negative strains are nonpathogenic. Toxins A and B are transcribed from a pathogenicity locus that includes the toxin genes, tcdA (toxin A) and tcdB (toxin B), and three regulatory genes, one of which (tcdC) encodes a putative negative regulator of toxin transcription. TcdC protein appears to inhibit toxin transcription during the early, exponential-growth phase of the bacterial life cycle. For toxin B, an autocatalytic cleavage site between leucine$_{543}$ and glycine$_{544}$ has been described. Cleavage results from activation of an aspartyl protease domain by host cytosolic inositol phosphate, and releases the active glucosyltransferase domain.

Provided herein are antibodies and antigen-binding fragments thereof that bind specifically to toxin A and/or toxin B of *C. difficile*, compositions containing one or more of such antibodies or antigen-binding fragments thereof, vectors containing nucleic acid sequences that encode the antibodies or antigen-binding fragments thereof, hybridoma cell lines that produce the antibodies, and methods of using the antibodies or antigen-binding fragments thereof for treatment or prevention of *C. difficile* infection or *C. difficile*-associated disease.

It is to be understood that when the term "antibodies" or "immunoglobulins" is referred to herein in describing the present invention and its various aspects and embodiments, this term is also generally meant to embrace antigen-binding fragments of such antibodies or immunoglobulins, so as to avoid excessive repetition of the associated phrase "antigen-binding fragments" whenever the term "antibodies" or "immunoglobulins" is mentioned. Thus, the present invention emcompasses not only antibodies directed against toxin A and toxin B of *C. difficile*, i.e., toxin A and toxin B antigens, but also fragments of such antibodies which bind the *C. difficile* toxin A and toxin B antigens, as described further herein. In embodiments, such antigen-binding fragments are capable of neutralizing the toxicity of toxin A and/or toxin B in a manner similar to that of the intact antibody.

The antibodies embraced by the invention include isolated antibodies which specifically bind toxin A of *C. difficile* and which competitively inhibit, or cross compete for, the specific binding to toxin A of *C. difficile* of an isolated monoclonal antibody produced by the hybridoma cell line deposited under ATCC Accession No. PTA-9692, PTA-9694, or PTA-9888. The antibodies also include isolated antibodies which specifically bind to toxin A of *C. difficile* and which specifically bind to an epitope on toxin A of *C. difficile* defined by the binding of an isolated monoclonal antibody produced by the hybridoma cell line deposited under ATCC Accession No. PTA-9692, PTA-9694, or PTA-9888. In some embodiments, the epitope resides in the C-terminal receptor binding domain of tcdA. In some of these embodiments, the antibodies competitively inhibit, or cross compete for, the binding of PA-50 to tcdA. In other embodiments, the epitope resides in the translocation domain of tcdA. In some of these embodiments, the antibodies competitively inhibit, or cross compete for, the binding of PA-39 to tcdA. Such isolated antibodies may comprise monoclonal antibodies, polyclonal antibodies, chimeric antibodies, human antibodies, humanized antibodies, and antigen binding fragments or portions thereof.

Experiments employing enzymatic (enterokinase) proteolysis of toxin A to assess the specificity of anti-*C. difficile* toxin A monoclonal antibodies of the invention were performed as described in Example 6. The epitope on toxin A that is recognized and bound by mAb PA-39 lies within a region that is distinct from the receptor-binding domain of toxin A, i.e., outside of the toxin A receptor binding domain, and that is distinct from an epitope bound by a human anti-toxin A antibody reported to bind a C-terminal receptor binding domain of toxin A (7). As described in Examples 6 and 7 herein and shown in FIGS. 22 and 31, Biacore assays support a single binding site on toxin A for PA-39. Western blot detection of enzymatically-digested toxin A demonstrates that PA-39 binds a region on toxin A that is separate from the regions bound by PA-50 and the CDA-1 comparator mAb. The in vitro activity of PA-39 in the toxin potency assay shows shifts in both $EC_{50}$ and the maximum percent inhibition as more toxin A is added to culture, indicating a mixed-competitive mechanism of inhibition for PA-39. ELISA detection of toxin A after protection by 100-fold excess of PA-39 confirmed that inhibition of toxin by PA-39 occurs by preventing toxin internalization and adverse cytocellular toxin effects, e.g., cytotoxicity.

Additionally, as described in Examples 6 and 7 herein and shown in FIGS. 22 and 31, Biacore assays support at least two binding sites on toxin A for PA-50. Western blot detection of enzymatically-digested toxin A demonstrates that PA-50 binds a region on toxin A similar to that bound by comparator mAb CDA-1. The in vitro activity of PA-50 in the toxin potency assay shows a shift in EC50 as more toxin A is added to culture, indicating a competitive mechanism of inhibition for PA-50. ELISA detection of toxin A after protection by 100-fold excess of PA-50 confirmed that inhibition of toxin by PA-50 occurs by preventing toxin internalization and subsequent cytotoxicity.

The antibodies of the invention also include isolated antibodies which specifically bind toxin B of *C. difficile* and which competitively inhibit, or cross compete for, the specific binding to toxin B of *C. difficile* of an isolated monoclonal antibody produced by the hybridoma cell line deposited under ATCC Accession No. PTA-9693 or PTA-9692. The antibodies also include isolated antibodies which specifically bind to toxin B of *C. difficile* and which specifically bind to an epitope on toxin B of *C. difficile* defined by the binding of an isolated monoclonal antibody produced by the hybridoma cell line deposited under ATCC Accession No. PTA-9693 or PTA-9692. In some embodiments, the epitope resides in the N-terminal enzyme domain of tcdB. In some of these embodiments, the antibodies competitively inhibit, or cross compete for, the binding of PA-41 to tcdB. In other embodiments, the epitope resides in the translocation domain, e.g., amino acids 850-1330 of tcdB. In some of these embodiments, the antibodies competitively inhibit, or cross compete for, the binding of PA-39 to tcdB.

Experiments employing enzymatic (caspase 1) proteolysis of toxin B to assess the specificity of anti-*C. difficile* toxin B monoclonal antibodies of the invention were performed as described in Example 6. mAb PA-41 (PTA-9693) was shown to recognize fragments of approximately 103 kDa and 63 kDa, which derive from the N-terminal enzymatic domain of toxin B. N-terminal sequence analysis of the major digest fragments confirmed this analysis. mAb PA-41 was shown to bind a unique epitope within the N-terminal enzymatic domain of toxin B, distinct from a C-terminal receptor binding domain of toxin B bound by a human anti-toxin B antibody (7). As described in Examples 6 and 7 herein and shown in FIGS. 19 and 31E and F, Biacore assays support a single binding site on toxin B for PA-41. Western blot detection of enzymatically-digested toxin B shows that PA-41 binds a different region on toxin B that is different from that bound by comparator mAb CDB-1. The in vitro activity of PA-41 in the toxin potency assay shows shifts in both $EC_{50}$ and the maximum percent inhibition as more toxin B is added to culture, indicating a mixed-competitive mechanism of inhibition PA-41.

Antibodies provided herein include monoclonal antibodies produced by hybridomas that were deposited and given the following Patent Deposit Designations: PTA-9692 (for PA-39), PTA-9693 (for PA-41), PTA-9694 (for PA-50), and PTA-9888 (for PA-38). These hybridomas were deposited pursuant to, and in satisfaction of, the requirements of the Budapest Treaty on the International Recognition of the Deposit of Microorganisms for the Purposes of Patent Procedure with the American Type Culture Collection ("ATCC"), P.O. Box 1549, Manassas, Va. 20108 USA, as an International Depository Authority, on Jan. 6, 2009 (for PTA-9692, PTA-9693, PTA-9694) and on Mar. 24, 2009 (for PTA-9888) and given the aforementioned Patent Deposit Designations. As used herein, both the deposited hybridomas and the monoclonal antibodies produced by the hybridomas may be referred to by the same ATCC Deposit Designations or to the numbers found within the ATCC Deposit Designations. For example, PTA-9888 or 9888 may be used to refer to the deposited hybridoma or to the monoclonal antibody produced by the hybridoma. Accordingly, the names of the monoclonal antibodies described herein may be used interchangeably with the names of the hybridomas that produce them. It will be clear to one of skill in the art when the name is intended to refer to the antibody or to the hybridoma that produces the antibody. The antigen-binding fragments provided herein include the antigen-binding fragments of the aforementioned deposited antibodies.

The antibodies of the invention exhibit a number of beneficial characteristics. For example, the anti-toxin A antibodies neutralize or inhibit the toxicity of toxin A both in vitro and in vivo. In in vitro neutralization studies using IMR-90 cells, humanized PA-39 and humanized PA-41 demonstrated neutralization potencies (i.e., $EC_{50}$ values) of 46 µM against toxin A on cells and 5 µM against toxin B, respectively, on these cells. When compared with values reported in the literature for neutralization by human anti-toxin A and anti-toxin B monoclonal antibodies (WO/2006/121422; US2005/0287150; Babcock et al., Infect. Immun., 2006), (7), the 46 µM $EC_{50}$ neutralization value of hPA-39 appeared to be higher than that reported for human anti-toxin A mAb, and the 5 µM $EC_{50}$ neutralization value of hPA-41 appeared to be higher than that reported for human anti-toxin B mAb. Accordingly, in the studies described herein, humanized anti-*C. difficile* toxin A and anti-*C. difficile* toxin B monoclonal antibodies of the invention, in particular, humanized forms of these monoclonal antibodies, show increased anti-toxin neutralization characteristics compared with those of other anti-toxin antibodies that have been reported.

In one embodiment, an anti-toxin A antibody of the invention neutralizes or inhibits the in vivo toxicity of *C. difficile* toxin A at an effective dose. In another embodiment, the anti-toxin B antibodies neutralize or inhibit the in vivo toxicity of toxin B. In an embodiment, an effective dose of one or more anti-toxin A antibodies of the invention is provided to a *C. difficile*-infected subject. In an embodiment, an effective dose of one or more anti-toxin A antibodies of the invention is provided in combination with an effective dose of one or more anti-toxin B antibodies of the invention to a *C. difficile*-infected subject. In an embodiment, an anti-toxin A antibody of the invention in a 1:1 combination with an anti-toxin B antibody of the invention is provided as an effective dose to a *C. difficile*-infected subject. In an embodiment, an effective dose of an anti-toxin A antibody and an anti-toxin B antibody of the invention may be, for example, a ½:1, 1:1, 2:1, 3:1, 4:1, etc., combination of the antibodies provided to a *C. difficile*-infected subject. In an embodiment, the antibodies are humanized. In an embodiment, the antibodies are included in a composition. Illustratively, an effective dose of the anti-toxin A and/or anti-toxin B antibodies may range from 0.1 µg to 1000 milligrams (mg). The anti-toxin A antibodies and anti-toxin B antibodies or antigen-binding fragments thereof may be administered to a subject in an amount of, for example, 0.1 mg/kg-150 mg/kg; in an amount of 0.5 mg/kg-75 mg/kg; in an amount of 1 mg/kg-100 mg/kg; in an amount of 1 mg/kg-50 mg/kg; in an amount of 2 mg/kg-40 mg/kg; in an amount of 2 mg/kg-50 mg/kg; in an amount of 5 mg/kg-50 mg/kg; in an amount of 5 mg/kg-25 mg/kg; in an amount of 10 mg/kg-40 mg/kg; in an amount of 10 mg/kg-50 mg/kg; in an amount of 10 mg/kg-25 mg/kg; or in an amount of 15 mg/kg-50 mg/kg. In an embodiment, the aforementioned amounts may comprise the varying ratios of anti-toxin A antibody and anti-toxin B antibody provided in combination.

As used herein, "neutralize" refers to the reduction, inhibition, blocking, amelioration, or elimination of adverse effect(s) of the toxin(s) which the antibody(ies) specifically bind. Neutralization of adverse effect(s) of the toxin(s) includes 1) delaying, reducing, inhibiting, or preventing onset or progression of *C. difficile* infection or *C. difficile*-associated diarrhea or disease, 2) increasing survival of a subject as compared to the median survival of subjects who have not been treated with the antibody(ies) and who have *C. difficile* infection or *C. difficile*-associated disease, 3) eliminating one or more symptoms or adverse effects or reducing the severity of one or more symptoms or adverse effects associated with *C. difficile* infection or *C. difficile*-associated diarrhea or disease, 4) allowing for the repopulation of the normal microflora of the gastrointestinal tract of subjects who are or have been infected with *C. difficile,* 5) preventing a recurrence of *C. difficile* infection or *C. difficile*-associated disease in subjects who have been afflicted with *C. difficile* infection or *C. difficile*-associated disease, 6) effecting a cure rate of at least 50%, 55%, 60%, 65%, 70%, 75%, 80%, 85%, 90%, 95%, 97%, 98%, 99%, or 100% in subjects who have *C. difficile* infection or *C. difficile*-associated disease, and/or 7) preventing death due to CDAD or other adverse events associated with *C. difficile* infection.

Anti-*C. difficile* toxin A and toxin B antibodies of the invention may be used to treat a number of species of subjects, including man (humans) and other non-human (mammalian) animals. Subjects treatable in accordance with the invention include human beings, non-human primates, dogs, cats, mice, rats, hamsters, guinea pigs, cows, goats, sheep, pigs, horses, and the like. Human subjects may also be referred to as patients or individuals herein. In particular, subjects include a human patient having a *C. difficile* infection or a *C. difficile*-associated disease. Such human patients include those who are elderly or immune-compromised.

In accordance with the invention, anti-*C. difficile* toxin A and toxin B antibodies can resolve *C. difficile* disease and increase the survival of a subject. In one embodiment, one or more anti-toxin A antibodies and/or one or more anti-toxin B antibodies, when administered to a subject, improve(s) the survival of the subject compared with the median survival of subjects who have not been treated with the antibody(ies) and who have *C. difficile* infection or *C. difficile*-associated disease.

In some embodiments, the dose or amount of the one or more anti-toxin A or anti-toxin B antibodies may range for example from 0.2 µg-250 µg, or from 2 µg-50 µg, or from 5 µg-50 µg, e.g., based on in vivo mouse studies. In some embodiments, the dose or amount of one or more anti-toxin A or anti-toxin B antibodies, and in particular a combination of an anti-toxin A antibody and an anti-toxin B antibody, may range for example from 2 mg/kg-40 mg/kg, 2 mg/kg-50 mg/kg, 5 mg/kg-40 mg/kg, 5 mg/kg-50 mg/kg, 10 mg/kg-40 mg/kg, or 10 mg/kg-50 mg/kg, e.g., based on in vivo hamster studies.

As another example, antibodies of the invention can effect a cure or survival rate of at least 50%, 55%, 60%, 65%, 70%, 75%, 80%, 85%, 90%, 95%, 97%, or 99%. As another example, the antibodies can effect a cure or survival rate of 100%. In one embodiment, one or more anti-toxin A antibodies, when administered to a subject, together with one or more anti-toxin B antibodies, effect a cure or survival rate of 50%, 55%, 60%, 65%, 70%, 75%, 80%, 85%, 90%, 95%, 97%, 99%, or 100%. As used herein, "cure rate" refers to the percentage of subjects that a clinician would determine to no longer have the infection or disease out of a population of subjects with the infection or disease administered one or more antibodies, or one or more compositions thereof, of the invention. "Survival rate", as used herein, refers to the percentage of subjects that survive for a desired period of time out of a population of subjects administered one or more antibodies, or one or more compositions thereof, of the invention. Examples of such desired periods of time are provided elsewhere herein.

Anti-toxin A and anti-toxin B antibodies provided by the invention can allow for the restoration of normal gut flora in a subject infected with *C. difficile*. In this way, such antibodies can resolve disease in patients undergoing treatment. Anti-toxin A and anti-toxin B antibodies of the invention can also demonstrate beneficial in vivo pharmacokinetics. Anti-toxin A and anti-toxin B antibodies of the invention can also provide prolonged or long lasting therapy for a subject who has been infected with *C. difficile*. As used herein, "long lasting" refers to therapy that results in an absence of *C. difficile* infection or *C. difficile*-associated disease one month or more after cessation of treatment. Preferably, the therapy results in an absence of *C. difficile* infection or *C. difficile*-associated disease for two or more months. In some embodiments, therapy with mAbs of the invention results in treating or depressing active *C. difficile* infection and in reducing or diminishing the robustness of infection. In other embodiments, therapy provided by the invention results in an absence of *C. difficile* infection or *C. difficile*-associated disease in a subject for 1, 2, 3, 4, 5, or 6 months. In other embodiments, therapy provided by the invention results in an absence of *C. difficile* infection or *C. difficile*-associated disease in a subject for longer than 6 months. Anti-toxin A and anti-toxin B antibodies of the invention can prevent recurrence of *C. difficile* infection and/or *C. difficile*-associated disease.

The recurrent nature of CDAD is exacerbated by the emergence of hypervirulent BI/NAP1/027 strains that have been found to be resistant to two of the newer antibiotics of last resort, levofloxacin and moxifloxacin. Such strains have triggered outbreaks of increasing frequency across the U.S., Canada, and Western Europe. Hypervirulent strains comprise a group of closely related isolates characterized as North American Pulsed Field Type 1 (NAP1), restriction enzyme analysis type "BI", and PCR Ribotype 027 known collectively as BI/NAP1/027 (5). The hypervirulence of the BI/NAP1/027 strains has been attributed at least in part to increased production of toxins A and B, two virulent factors of CDAD (6). BI/NAP1/027 isolates produce 16-23-fold higher levels of toxins A and B than other strains (6). The apparent fitness of these strains creates the threat of worldwide spread compromising the potential for antibiotic treatment for other diseases, as well as increasing CDAD recurrence rates and severity. Although there are antibiotics under development for the treatment of CDAD, such as nitazoxanide, rifaximin, ramoplanin and fidaxomicin, clinical isolates of *C. difficile* that are resistant to rifaximin have been reported. In a recently completed phase 3 trial (91), fidaxomicin significantly reduced the overall rate of CDAD recurrence compared to vancomycin, but not for the BI/NAP1/027 strains. Outbreaks of hypervirulent BI/NAP1/027strains have led to increases in hospital stays, treatment failures, relapse frequencies and mortality rates (3). The novel mAbs developed and described herein provide new therapies to combat the growing incidence and severity of CDAD.

In an embodiment, the mAbs of the invention are employed in the treatment of infection caused by various strains of *C. difficile*. In an embodiment, the *C. difficile* strains are highly infectious and their toxins are neutralized by the mAbs of the invention. In an embodiment, the toxins of hypervirulent strains of *C. difficile*, including BI/NAP1/027, are neutralized by the mAbs of the invention. In an embodiment, the mAbs of the invention provide therapeutic effects in neutralizing toxins from a broad range of toxigenic clinical isolates, including strains from outpatient isolates. Preferably, the mAbs neutralize the toxins of hypervirulent isolates, such as BI/NAP1/027, and at least 90% or more of other clinically relevant isolates of *C. difficile*. In particular and as illustrated in Example 8 herein, mAbs of the invention have been shown to neutralize significantly the toxicity/activity of nineteen different clinical isolates of *C. difficile*, including BI/NAP1/027 and other hypervirulent *C. difficile* strains, e.g., CCL676, HMC553, Pitt45, CD196, montreal 5 and montreal 7.1. In accordance with the invention, antibodies are provided which neutralize toxin A and toxin B of hypervirulent strains of *C. difficile*, for example without limitation, as determined by an $EC_{50}$ value ranging from $7.7^{-12}$M to $4.8^{-8}$M for anti-toxin A mAbs and an $EC_{50}$ value ranging from $1.1^{-11}$M to $6.5^{-10}$M for an anti-toxin B mAb. In addition, mAbs of the invention are provided for use in neutralizing hypervirulent strains of *C. difficile*, including hospital and non-hospital derived isolates, as treatment for *C. difficile* infection and diseases related thereto.

In other embodiments and by nonlimiting example, mAbs of the invention exhibit an $EC_{50}$ neutralization value in the range of 93 µM-30 nM, or an $EC_{50}$ of 46 µM, for neutralizing toxin A and an $EC_{50}$ value in the range of 4 µM-9.5 µM, or an $EC_{50}$ of 5 µM, for neutralizing toxin B depending on the in vitro cell-based assay employed. As described in Example 3 herein, in an assay comprising CHO-K1 cells in which 8 µg/ml of toxin A was used, anti-toxin A mAbs of the invention exhibited an $EC_{50}$ value of 93 µM. In an assay comprising CHO-K1 cells in which 8 pg/ml of toxin B was used, anti-toxin B mAb of the invention exhibited an $EC_{50}$ value of 9.2 µM. In an assay comprising T-84 cells in which 240 ng/ml of toxin A was used, anti-toxin A mAbs of the invention exhibited $EC_{50}$ values of 146 µM and 175 µM. In a Caco-2 cell-based assay, anti-toxin A mAbs of the invention neutralized toxin A toxicity at $EC_{50}$ levels of 196 µM and 485 µM. In the red blood cell hemagglutination assay in which 8 µg/ml of toxin A was used, anti-toxin A mAbs of the invention had an $EC_{50}$ neutralization value of 1.8 nM and 30 nM for preventing RBC hemagglutination.

The antibodies of the invention can have any one of, a combination of, or all of, the aforementioned features.

As described in the Examples herein, mAbs of the invention demonstrate superior toxin-neutralizing potency both in vitro and in vivo in the best available preclinical models of CDAD. In addition, mAbs of the invention demonstrate uniquely broad and potent neutralization of toxins from numerous BI/NAP1/027 strains. Moreover, such mAbs have demonstrated complete and durable protection from mortality in a highly stringent hamster model of CDAD. These results support the ability of mAbs of the invention to block efficiently and effectively the pathogenic effects of *C. difficile* toxins in a manner that enables the colon to heal, the normal bowel microflora to become re-established, and CDAD disease and/or *C. difficile* infection to be resolved.

In an embodiment, antibodies to toxin A include those that competitively inhibit, or cross compete for, the specific binding to toxin A of *C. difficile* of an isolated monoclonal antibody produced by the hybridoma cell line deposited under ATCC Accession Nos. PTA-9692, PTA-9694, or PTA-9888. Preferred antibodies to toxin B include those that competitively inhibit, or cross compete for, the specific binding to toxin B of *C. difficile* of an isolated monoclonal antibody produced by the hybridoma cell line deposited under ATCC Accession No. PTA-9693 or PTA-9692. In some embodiments, antibodies include those that competitively inhibit, or cross compete for, the specific binding to toxin A of *C. difficile* of an isolated monoclonal antibody produced by the hybridoma cell line deposited under ATCC Accession No. PTA-9692, PTA-9694, or PTA-9888, and competitively inhibit, or cross compete for, the specific binding to toxin B of *C. difficile* of an isolated monoclonal antibody produced by the hybridoma cell line deposited under ATCC Accession No. PTA-9693 or PTA-9692. All embodiments further encompass humanized forms of the above-described antibodies under ATCC Accession Nos. PTA-9692, PTA-9694, PTA-9888, or PTA-9693.

To determine competitive inhibition, or cross competition of binding, a variety of assays known to one of ordinary skill in the art can be employed. For example, cross-competition assays can be used to determine if an antibody competitively inhibits binding to toxin A and/or toxin B by another antibody. Such methods can be cell-based methods employing flow cytometry or solid phase binding analysis. Other assays that evaluate the ability of antibodies to cross-compete for binding toxin A and/or toxin B in solid phase or in solution phase, also can be used. Examples of antibodies or antigen-binding fragments thereof encompassed by the invention include those that competitively inhibit the specific binding by at least about 10%, 20%, 30%, 40%, 50%, 60%, 70%, 80%, 90%, 95%, or 99%. Inhibition can be assessed at various molar ratios or mass ratios; for example, competitive binding experiments can be conducted with a 2-fold, 3-fold, 4-fold, 5-fold, 7-fold, 10-fold or more molar excess of the first antibody over the second antibody.

Other antibodies encompassed by the invention include those that specifically bind to an epitope on toxin A of *C. difficile* defined by the binding of an isolated monoclonal antibody produced by the hybridoma cell line deposited under ATCC Accession No. PTA-9692, PTA-9694, or PTA-9888. Still other antibodies or antigen-binding fragments encompassed by the invention include those that specifically bind to an epitope on toxin B of *C. difficile* defined by the binding of an isolated monoclonal antibody produced by the hybridoma cell line deposited under ATCC Accession No. PTA-9693 or PTA-9692. Still other antibodies or antigen-binding fragments encompassed by the invention include those that specifically bind to an epitope on toxin A of *C. difficile* defined by the binding of an isolated monoclonal antibody produced by the hybridoma cell line deposited under ATCC Accession No. PTA-9692, PTA-9694, or PTA-9888 and specifically bind to an epitope on toxin B of *C. difficile* defined by the binding of an isolated monoclonal antibody produced by the hybridoma cell line deposited under ATCC Accession No. PTA-9693 or PTA-9692.

To determine an epitope, one can use standard epitope mapping methods known in the art. For example, fragments (peptides) of the toxin (preferably synthetic peptides) that bind an antibody can be used to determine whether a candidate antibody or antigen-binding fragment thereof binds the same epitope. For linear epitopes, overlapping peptides of a defined length (e.g., 8 or more amino acids) are synthesized. The peptides preferably are offset by 1 amino acid, such that a series of peptides covering every 8 amino acid fragment of the toxin sequence are prepared. Fewer peptides can be prepared by using larger offsets, e.g., 2 or 3 amino acids. In addition, longer peptides (e.g., 9-, 10- or 11-mers) can be synthesized. Binding of peptides to antibodies can be determined using standard methodologies including surface plasmon resonance (e.g., Biacore) and ELISA assays. For examination of conformational epitopes, which the antibodies provided herein may, in some embodiments, bind, larger peptide fragments can be used. Other methods that use mass spectrometry to define conformational epitopes have been described and can be used (see, e.g., Baerga-Ortiz et al., Protein Science 11:1300-1308, 2002 and references cited therein). Still other methods for epitope determination are provided in standard laboratory reference works, such as Unit 6.8 ("Phage Display Selection and Analysis of B-cell Epitopes") and Unit 9.8 ("Identification of Antigenic Determinants Using Synthetic Peptide Combinatorial Libraries") of Current Protocols in Immunology, Coligan et al., eds., John Wiley & Sons. Epitopes can be confirmed by introducing one or more point mutations or deletions into a known epitope, and then testing binding with one or more antibodies to determine which mutations reduce binding of the antibodies.

The antibodies or antigen-binding fragments provided by the invention may specifically bind toxin A and/or toxin B with sub-nanomolar affinity. The antibodies or antigen-binding fragments may have binding affinities of about $1 \times 10^{-9}$M or less, about $1 \times 10^{-10}$M or less, or about $1 \times 10^{-11}$M or less. In a particular embodiment, the binding affinity is less than about $5 \times 10^{-10}$M.

The antibodies or antigen-binding fragments may have an on rate constant (Kon) to toxin A or toxin B of at least $10^2$ $M^{-1}s^{-1}$; at least $10^3$ $M^{-1}s^{-1}$; at least $10^4$ $M^{-1}s^{-1}$; at least $10^5$ $M^{-1}s^{-1}$; at least $10^6$ $M^{-1}s^{-1}$; or at least $10^7$ $M^{-1}s^{-1}$, as measured by surface plasmon resonance. The antibodies or antigen-binding fragments may have an off rate constant (Koff) to toxin A or toxin B of at most $10^{-3}$ $s^{-1}$; at most $10^{-4}$ $s^{-1}$; at most $10^{-5}$ $s^{-1}$; or at most $10^{-6}$ $s^{-1}$, as measured by surface plasmon resonance. The antibodies or antigen-binding fragments may have a dissociation constant ($K_D$) to toxin A or toxin B of at most $10^{-7}$ M; at most $10^{-8}$ M; at most $10^{-9}$ M; at most $10^{-10}$ M; at most $10^{-11}$ M; at most $10^{-12}$ M; or at most $10^{-13}$M.

As used herein, the terms "antibody" or "immunoglobulin" include glycoproteins comprising at least two heavy (H) chain polypeptides and two light (L) chain polypeptides interconnected by disulfide bonds. Each heavy chain is comprised of a heavy chain variable region (abbreviated herein as HCVR or $V_H$) and a heavy chain constant region ($C_H$). The heavy chain constant region is comprised of three domains, CH1, CH2 and CH3. Each light chain is comprised of a light chain variable region (abbreviated herein as LCVR or $V_L$) and a light chain constant region ($C_L$). The light chain constant region is comprised of one domain, $C_L$. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. Together, the variable regions of the heavy and light chain polypeptides contain or form a binding domain that interacts with/binds an antigen. The constant regions of the antibodies may mediate the binding of the immunoglobulin to host tissues or factors, including various cells of the immune system (e.g., effector cells) and the first component (C1q) of the classical complement system.

The invention further provides other forms of antibodies, such as single chain antibodies, recombinantly produced antibodies, bispecific, heterospecific, or multimeric antibodies, diabodies, etc., as further described herein.

The term "antigen-binding fragment" of an antibody as used herein, refers to one or more portions of an antibody that retain the ability to specifically bind to an antigen (e.g., toxin A, toxin B, toxin A and toxin B, etc.) or to epitopic regions of an antigen. It has been shown that the antigen-binding function of an antibody can be performed by fragments of a full-length antibody. In an embodiment, the monoclonal antibody fragments function in a manner similar to the intact counterpart monoclonal antibodies. In an embodiment, the monoclonal antibody fragments cross-react with the intact counterpart monoclonal antibodies. In an embodiment, the monoclonal antibody fragments can be used interchangeably with the intact counterpart monoclonal antibodies. Examples of binding fragments encompassed within the term "antigen-binding fragment" of an antibody include (i) a Fab fragment, a monovalent fragment consisting of the $V_L$, $V_H$, $C_L$, and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546) which consists of a $V_H$ domain; and (vi) an isolated complementarity determining region (CDR). Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference, as well as by other techniques known to those having skill in the art. The fragments are screened for activity or utility in the same manner as are intact antibodies.

In an embodiment, Fab fragments of mAbs of the invention were generated and tested for their neutralization activity in cell-based assays, as described in Example 10 herein. Thus, antibody fragments, such as Fab fragments, of the mAbs of the invention may also be utilized to bind and neutralize toxin A and/or toxin B of C. difficile.

An "isolated antibody", as used herein, is intended to refer to an antibody which is substantially free of other antibodies having different antigenic specificities (e.g., an isolated antibody that specifically binds to toxin A is substantially free of antibodies that specifically bind antigens other than toxin A). An isolated antibody that specifically binds to an epitope, isoform or variant of toxin A or toxin B, however, generally has cross-reactivity to other related antigens, e.g., from other C. difficile strains. In addition, an isolated antibody that specifically binds to an epitope, isoform, or variant of toxin A may also specifically bind toxin B, and an isolated antibody that specifically binds to an epitope, isoform, or variant of toxin B may also specifically bind toxin A. In some embodiments, however, the isolated antibody or antigen-binding fragment thereof that specifically binds to an epitope, isoform, or variant of toxin A does not also specifically bind toxin B. In still other embodiments, the isolated antibody or antigen-binding fragment thereof that specifically binds to an epitope, isoform, or variant of toxin B does not also specifically bind toxin A. Moreover, an isolated antibody may be substantially free of other cellular material and/or chemicals. Antibodies which are substantially free of other antibodies having different antigenic specificities, or other materials and/or chemicals and/or proteins may be isolated and/or purified antibodies. Antibodies may be purified by methods commonly performed by those having skill in the art, e.g., affinity chromatography, Protein A chromatography, and the like. As used herein, "specific binding" refers to antibody binding to a predetermined or cognate antigen. Typically, the antibody binds with an affinity that is at least two-fold greater than its affinity for binding to a non-specific antigen (e.g., BSA, casein) other than the predetermined antigen or a closely-related antigen. In an embodiment, an antibody of the invention may bind a linear epitope of the target antigen, e.g., toxin A and/or toxin B. In an embodiment, an antibody of the invention may bind a conformational epitope of the target antigen, e.g., toxin A and/or toxin B.

The isolated antibodies of the invention encompass various antibody (immunoglobulin) heavy and light chain isotypes, such as the heavy chain classes or isotypes IgG1, IgG2, IgG3, IgG4, IgM, IgA1, IgA2, IgAsec, IgD, IgE, and subtypes thereof, e.g., IgG2a, IgG2b; and the light chain isotypes κ and λ, and subtypes thereof. In one embodiment, the isolated antibodies are of the IgG2a or IgG1 κ isotype. As used herein, "isotype" refers to the antibody class (e.g., IgM or IgG1 or λ1) that is encoded by heavy and light chain constant region genes. The antibodies or antigen-binding fragments thereof can be full length or can include only an antigen-binding fragment, such as the antibody constant and/or variable domain of IgG1, IgG2, IgG3, IgG4, IgM, IgA1, IgA2, IgAsec, IgD, or IgE, or can consist of a Fab fragment, a F(ab')$_2$ fragment, and a Fv fragment.

The antibodies of the present invention can be polyclonal, monoclonal, or a mixture of polyclonal and monoclonal antibodies. The antibodies can be produced by a variety of techniques well known in the art. Procedures for raising polyclonal antibodies are well known. As a nonlimiting example, polyclonal antibodies are raised by administering toxin A and/or toxin B protein subcutaneously to New Zealand white rabbits which have first been bled to obtain pre-immune serum. The toxin A and/or toxin B can be injected at a total volume of 100 µl per site at six different sites, typically with one or more adjuvants. The rabbits are then bled two weeks after the first injection and periodically boosted with the same antigen three times every six weeks. A sample of serum is collected 10 days after each boost. Polyclonal antibodies are recovered from the serum, preferably by affinity chromatography using toxin A and/or toxin B to capture the antibody. This and other procedures for raising polyclonal antibodies are described in Harlow, E. and Lane, D., Eds., Antibodies: A Laboratory Manual (1988), Cold Spring Harbor Laboratory Press, Cold Spring Harbor, N.Y., the contents of which are hereby incorporated by reference.

Monoclonal antibody production may be effected by techniques which are also well known in the art. The term "monoclonal antibody", as used herein, refers to a preparation of antibody molecules of single molecular composition. A monoclonal antibody displays a single binding specificity and affinity for a particular epitope of a given antigen or immunogen. The process of monoclonal antibody production involves obtaining immune somatic cells with the potential for producing antibody, in particular B lymphocytes, which have been previously immunized with the antigen of interest either in vivo or in vitro or both, and that are suitable for fusion with a B-cell myeloma line. Monoclonal antibodies can be produced using immune cells and myeloma cells from different species, such as murine and human cells and cell lines, or for example, in mouse strains which have been genetically engineered to harbor a human immune system, as further described below.

Although monoclonal antibodies directed against toxin A and toxin B have been typically produced by immunizing animals with toxoids (inactive forms of the toxin A and toxin B) and/or with inactive fragments of these toxins, mAbs of the present invention were generated by designing and employing a new immunization strategy. In accordance with the invention, the mAbs described herein and deposited were produced by immunizing animals with toxoid, followed by boosting the animals with the active (non toxoid) form of toxin A and/or toxin B (see Example 1 herein). Boosting with the active form of toxin A or toxin B served to identify those immunized animals that had developed uniquely protective antibodies by virtue of the novel immunization scheme. Without wishing to be bound by theory, the active toxin A and/or toxin B boosting regimen was more highly immunogenic in recipient animals. Those animals that tolerated the increasing boosting doses of active toxin A or toxin B, which are typically lethal to naïve animals, produced highly effective neutralizing antibodies, which protected these animals and contributed to their survival despite their having received active toxin. The production of hybridomas from the animals that mounted an effective immune response against toxin A or toxin B yielded highly potent anti-toxin A and anti-toxin B monoclonal antibodies, which provide a high level of protection both in vitro and in vivo. In producing antibodies, including polyclonal and monoclonal antibodies, adjuvants may be employed. Nonlimiting examples of adjuvants that are suitable for use include incomplete Freund's adjuvant, aluminum phosphate, aluminum hydroxide, Ribi (i.e., monophosphoryl lipid A, trehalose dimycolate, *Mycobacterium* cell wall skeleton, and TWEEN® 80, with 2% squalene), saponins, Quil A, or alum. A cytotoxic T lymphocyte (CTL) response can be primed by conjugating toxins (or fragments, inactive derivatives or analogs thereof) to lipids, such as, for example, tri-palmitoyl-S-glycerylcysteinyl-seryl-serine.

In other embodiments, additional immunization methods can be utilized for generating monoclonal antibodies directed against toxin A and/or toxin B. For example, in vivo immunization of animals (e.g., mice) can be carried out with the desired type and amount of protein or polypeptide, e.g., toxoid or toxin. Such immunizations are repeated as necessary at intervals of up to several weeks to obtain a sufficient titer of antibodies. Once immunized, animals can be used as a source of antibody-producing lymphocytes. Following the last antigen boost, the animals are sacrificed and spleen cells removed. Mouse lymphocytes give a higher percentage of stable fusions with the mouse myeloma lines described herein. Of these, the BALB/c mouse strain is suitable. However, other mouse strains, rabbit, hamster, sheep, goat and frog may also be used as hosts for preparing antibody-producing cells. See; Goding (in Monoclonal Antibodies: Principles and Practice, 2d ed., pp. 60-61, Orlando, Fla., Academic Press, 1986). In particular, mouse strains that have human immunoglobulin genes inserted in the genome (and which cannot produce mouse immunoglobulins) can be used. Examples include the HumAb mouse strains produced by Medarex (now Bristol Myers Squibb)/GenPharm International, and the XenoMouse strains produced by Abgenix. Such mice produce fully human immunoglobulin molecules in response to immunization.

Those antibody-producing cells that are in the dividing plasmablast stage fuse preferentially. Somatic cells may be obtained from, for example, the lymph nodes, spleens, and peripheral blood of antigen-primed animals, and the lymphatic cells of choice depend to a large extent on their empirical usefulness in the particular fusion system. The antibody-secreting lymphocytes are then fused with (mouse) B cell myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, subcloned and grown either in vivo (as ascites) or in vitro to produce large quantities of antibody. Descriptions of hybridoma methodology and technology may be found in Kohler and Milstein, *Nature* 256:495 (1975) or Harlow, E. and Lane, D., Eds., Antibodies: A Laboratory Manual (1988), Cold Spring Harbor Laboratory Press, Cold Spring Harbor, N.Y., which are hereby incorporated by reference.

Alternatively, human somatic cells capable of producing antibody, specifically B lymphocytes, are suitable for fusion with myeloma cell lines. While B lymphocytes from biopsied spleens, tonsils or lymph nodes of an individual may be used, the more easily accessible peripheral blood B lymphocytes (PBLs) are preferred. In addition, human B cells may be directly immortalized by the Epstein-Barr virus (Cole et al., 1995, Monoclonal Antibodies and Cancer Therapy, Alan R. Liss, Inc., pp. 77-96). Although somatic cell hybridization procedures are preferred, in principle, other techniques for producing monoclonal antibodies can be employed, such as viral or oncogenic transformation of B lymphocytes.

Myeloma cell lines suited for use in hybridoma-producing fusion procedures preferably are non-antibody-producing, have high fusion efficiency, and enzyme deficiencies that render them incapable of growing in certain selective media that support the growth of the desired hybridomas. Examples of such myeloma cell lines that may be used for the production of fused cell lines include P3-X63/Ag8, X63-Ag8.653, NS1/1.Ag 4.1, Sp2/0-Ag14, FO, NSO/U, MPC-11, MPC11-X45-GTG 1.7, 5194/5XX0 Bul, derived from mice; R210.RCY3, Y3-Ag 1.2.3, IR983F and 4B210 derived from rats; and U-266, GM1500-GRG2, LICR-LON-HMy2, UC729-6, derived from humans (Goding, in Monoclonal Antibodies: Principles and Practice, 2d ed., pp. 65-66, Orlando, Fla., Academic Press, 1986; Campbell, in Monoclonal Antibody Technology, Laboratory Techniques in Biochemistry and Molecular Biology Vol. 13, Burden and Von Knippenberg, eds. pp. 75-83, Amsterdam, Elsevier, 1984).

Fusion with mammalian myeloma cells or other fusion partners capable of replicating indefinitely in cell culture is effected by standard and well-known techniques, for example, by using polyethylene glycol ("PEG") or other fusing agents (See Kohler and Milstein, *Eur. J. Immunol.* 6:511 (1976), which is hereby incorporated by reference).

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created, or isolated by any other means that involves splicing of immunoglobulin gene sequences to other DNA sequences.

In yet other embodiments, the antibodies can be chimeric or humanized antibodies. As used herein, the term "chimeric antibody" refers to an antibody that combines a murine immunoglobulin (Ig) variable or hypervariable regions with a human Ig constant region or constant and variable framework regions. In some embodiments, the chimeric antibody comprises the variable region of any of the deposited antibodies provided herein and a human constant region. In some embodiments, the human constant region is an human IgG constant region, such as an human IgG1 constant region. The chimeric antibodies can be produced by the method provided below in the Examples or by any method known to those of skill in the art. As used herein, the term "humanized antibody" refers to an antibody that retains substantially only the antigen-binding CDRs from the parent antibody, e.g., murine monoclonal antibody, in association with human framework regions (see, e.g., Waldmann, 1991, *Science* 252:1657). Such chimeric or humanized antibodies, which retain the binding specificity of the murine antibody, but have human Ig constant/framework regions, are expected to have reduced immunogenicity when administered in vivo. Therefore, the chimeric and humanized antibodies preferably retain the toxin-neutralizing activities of the monoclonal antibodies provided and are suitable for repeat dosing (e.g., in humans). One of ordinary skill in the art can use known methods (e.g., in vitro cell-based assays) for comparing the activity of the humanized antibodies to the deposited monoclonal antibodies provided herein and for determining whether or not the humanized antibodies treat and/or prevent relapse of an established *C. difficile* infection. One of ordinary skill in the art can also use the methods described herein including the hamster model of *C. difficile* infection described below.

The sequences of the humanized mAbs can be designed by the following illustrative, non-limiting method. First, the framework amino acid residues important for the CDR structure are identified. In parallel, human $V_H$ and $V_L$ sequences having high homology to the murine $V_H$ and $V_L$, respectively, are selected from among known human immunoglobulin (germline) sequences. CDR sequences from the murine mAb, together with framework amino acid residues important for maintaining the structure of the CDRs, are grafted into the selected human framework sequences. In addition, human framework amino acid residues that are found to be atypical in the corresponding V region subgroup are substituted with the typical residues to reduce potential immunogenicity of the resulting humanized mAb. These humanized $V_H$ and $V_L$ regions are cloned into the expression vectors, e.g., pCON Gamma1 and pCON kappa (Lonza Biologics, Berkshire, UK), respectively. These vectors encode the constant region(s) of the human immunoglobulin heavy and light chain genes. 293T cells can be transiently transfected with these expression vectors using the Effectene system (Qiagen, Valencia, Calif.). Cell supernatants containing secreted chimeric mAb can be collected following transfection, e.g., after three days, and purified using Protein A chromatography. Other expression vectors and host cells may be used to recombinantly produce the described antibodies, as understood by those having skill in the art.

Other methods for humanizing antibodies or antigen-binding fragments are well known in the art and include the methods provided in, for example, U.S. Pat. Nos. 5,585,089; 5,693,761; 5,693,762; and 6,180,370. The methods for performing the humanization provided in these patents are incorporated herein by reference in their entirety. Antibodies or antigen-binding fragments humanized according to the methods provided in these patents are also provided herein.

In an embodiment, a humanized anti-*C. difficile* toxin A mAb (hmAb) of the invention encompasses an immunoglobulin protein, or a fragment thereof, which is composed of (i) two heavy (H) chain polypeptides, wherein each H chain contains a VH region comprising the amino acid sequence as set forth in SEQ ID NO:1 and a human CH region, e.g., an IgG1 C region, and (ii) two light (L) chain polypeptides, wherein each L chain contains a VL region comprising the amino acid sequence as set forth in SEQ ID NO:3 and a human CL region, e.g., a κ chain C region. In an embodiment, a humanized anti-*C. difficile* toxin A mAb of the invention encompasses an immunoglobulin protein, or a fragment thereof, which is composed of (i) two heavy (H) chain polypeptides, wherein each H chain contains a VH region comprising the amino acid sequence as set forth in SEQ ID NO:2 and a human CH region, e.g., an IgG1 C region, and (ii) two light (L) chain polypeptides, wherein each L chain contains a VL region comprising the amino acid sequence as set forth in SEQ ID NO:3 and a human CL region, e.g., a κ chain C region. In an embodiment, a humanized anti-*C. difficile* toxin A mAb of the invention encompasses an immunoglobulin protein which is composed of (i) two heavy (H) chain polypeptides, wherein each H chain contains a VH region comprising the amino acid sequence as set forth in SEQ ID NO:1 and a human CH region, e.g., an IgG1 C region, and (ii) two light (L) chain polypeptides, wherein each L chain contains a VL region comprising the amino acid sequence as set forth in SEQ ID NO:4 and a human CL region, e.g., a κ chain C region. In an embodiment, a humanized anti-*C. difficile* toxin A mAb of the invention encompasses an immunoglobulin protein which is composed of (i) two heavy (H) chain polypeptides, wherein each H chain contains a VH region comprising the amino acid sequence as set forth in SEQ ID NO:2 and a human CH region, e.g., an IgG1 C region, and (ii) two light (L) chain polypeptides, wherein each L chain contains a VL region comprising the amino acid sequence as set forth in SEQ ID NO:4 and a human CL region, e.g., a κ chain C region. Such humanized anti-*C. difficile* toxin A mAbs embrace a hPA-39 mAb of the invention.

In an embodiment, a humanized anti-*C. difficile* toxin A mAb of the invention encompasses an immunoglobulin protein which is composed of (i) two heavy (H) chain polypeptides, wherein each H chain contains a VH region comprising the amino acid sequence as set forth in SEQ ID NO:5 and a human CH region, e.g., a IgG1 C region, and (ii) two light (L) chain polypeptides, wherein each L chain contains a VL region comprising the amino acid sequence as set forth in SEQ ID NO:7 and a human CL region, e.g., a κ chain C region. In an embodiment, a humanized anti-*C. difficile* toxin A mAb of the invention encompasses an immunoglobulin protein which is composed of (i) two heavy (H) chain polypeptides, wherein each H chain contains a VH region comprising the amino acid sequence as set forth in SEQ ID NO:6 and a human CH region, e.g., an IgG1 C region, and (ii) two light (L) chain polypeptides, wherein each L chain contains a VL region comprising the amino acid sequence as set forth in SEQ ID NO:7 and a human CL region, e.g., a κ chain C region. Such humanized anti-*C. difficile* toxin A mAbs embrace a hPA-50 mAb of the invention.

In an embodiment, a humanized anti-*C. difficile* toxin B mAb of the invention encompasses an immunoglobulin protein which is composed of (i) two heavy (H) chain polypeptides, wherein each H chain contains a VH region comprising the amino acid sequence as set forth in SEQ ID NO:8 and a human CH region, e.g., an IgG1 C region, and (ii) two light (L) chain polypeptides, wherein each L chain contains a VL region comprising the amino acid sequence as set forth in SEQ ID NO:10 and a human CL region, e.g., a κ chain C region. In an embodiment, a humanized anti-*C. difficile* toxin B mAb of the invention encompasses an immunoglobulin protein which is composed of (i) two heavy (H) chain polypeptides, wherein each H chain contains a VH region comprising the amino acid sequence as set forth in SEQ ID NO:9 and a human CH region, e.g., an IgG1 C region, and (ii) two light (L) chain polypeptides, wherein each L chain contains a VL region comprising the amino acid sequence as set forth in SEQ ID NO:10 and a human CL region, e.g., a κ chain C region. Such humanized anti-*C. difficile* toxin B mAbs embrace a hPA-41 mAb of the invention.

The L chain and H chain C regions of the above-described humanized antibodies of the invention may comprise the human K L chain C region (CL) and human IgG1 H chain C region (CH) having sequences contained in Genbank Accession No. NW_001838785 and in Genbank Accession No. NW_001838121, respectively. In other embodiments, the humanized antibodies comprise a human H chain C region selected from the IgG2a, IgG2b, IgG3, or IgG4 isotypes.

In an illustrative embodiment, the invention embraces a monoclonal antibody, or a fragment thereof, generated against toxin A of *C. difficile*, wherein the antibody is composed of two heavy chain polypeptides, each heavy chain containing a VH region and a human CH region and two light chain polypeptides, each light chain containing a VL region and a human CL region. The nucleic acid sequence (or cDNA) encoding the consecutive amino acid sequence of the heavy chain polypeptide of SEQ ID NO: 14 is set forth in SEQ ID NO:15, (FIG. 38B); the nucleic acid sequence (or cDNA) encoding the consecutive amino acid sequence of the light chain polypeptide of SEQ ID NO:16 is set forth in SEQ ID NO:17 (FIG. 38A).

In an illustrative embodiment, the invention embraces a monoclonal antibody, or a fragment thereof, generated against toxin A of *C. difficile*, wherein the antibody is composed of two heavy chain polypeptides, each heavy chain containing a VH region and a human CH region and two light chain polypeptides, each light chain containing a VL region and a human CL region. The nucleic acid sequence (or cDNA) encoding the consecutive amino acid sequence of the heavy chain polypeptide of SEQ ID NO: 18 is set forth in SEQ ID NO:19, (FIG. 39B); the nucleic acid sequence (or cDNA) encoding the consecutive amino acid sequence of the light chain polypeptide of SEQ ID NO:20 is set forth in SEQ ID NO:21 (FIG. 39A).

In an illustrative embodiment, the invention embraces a monoclonal antibody, or a fragment thereof, generated against toxin B of *C. difficile*, wherein the antibody is composed of two heavy chain polypeptides, each heavy chain containing a VH region and a human CH region and two light chain polypeptides, each light chain containing a VL region and a human CL region. The nucleic acid sequence (or cDNA) encoding the consecutive amino acid sequence of the heavy chain polypeptide of SEQ ID NO:22 is set forth in SEQ ID NO:23 (FIG. 40B); the nucleic acid sequence (or cDNA) encoding the consecutive amino acid sequence of the light chain polypeptide of SEQ ID NO:24 is set forth in SEQ ID NO:25 (FIG. 40A).

Also encompassed by the invention are portions or fragments of the above-described anti-*C. difficile* toxin A and anti-toxin B humanized antibodies. Such portions or fragments include the complementarity determining regions (CDRs) of the V regions of both the H and L chain polypeptides, as may be conventionally determined by those having skill in the art; F(ab) fragments, F(ab') fragments, F(ab')2 fragments, Fc fragments, Fd fragments, and the like. In an embodiment portions or fragments of the humanized antibodies containing V regions, or functional portions thereof, will optimally bind to the respective toxin and neutralize the activity of the toxin. In an embodiment such functional portions or fragments of the humanized antibodies optimally neutralize toxin activity at a level similar to, if not better than, that of the complete humanized antibody.

In accordance with the invention molecularly cloned, humanized mAbs directed against toxins A or B of *C. difficile* are provided. Such humanized mAbs were isolated and characterized as described in Example 9, Sections D and E hereinbelow. In an embodiment, the light chain constant region (CL) of each of the humanized antibodies is of the kappa (κ) class. In an embodiment, the heavy chain constant region (CH) of each of the humanized antibodies is of the IgG1 isotype. In other embodiments, the CH region of the humanized antibodies is of the IgG2a, IgG2b, IgG3, IgG4, IgA, IgE, IgA, or IgM isotype. The humanized mAbs containing unique variable (V) regions were found to bind and neutralize the activity of either toxin A or toxin B of *C. difficile*. The VL and VH regions of the humanized mAbs may form a part of a complete immunoglobulin (Ig) or antibody molecule, or they may be used as portions or fragments of the antibody, in particular, portions or fragments having binding and/or neutralizing activity. Nonlimiting examples of antibody fragments include Fab, F(ab)$_2$ and F(ab'), or F(ab')$_2$ fragments. Embodiments of the invention are directed to anti-*C. difficile* toxin A humanized mAbs, or fragments thereof, having activity against toxin A of *C. difficile*, wherein the V region of the L chain is selected from one or more of SEQ ID NO:3, SEQ ID NO:4 and SEQ ID NO:7. In an embodiment, the invention is directed to the CDRs, namely, CDR1, CDR2, and/or CDR3, in the VH and VL regions of the described antibodies. Embodiments of the invention are directed to anti-*C. difficile* toxin B humanized mAbs, or fragments thereof, having activity against toxin B of *C. difficile*, wherein the V region of the L chain is set forth in SEQ ID NO:10. Embodiments of the invention are directed to anti-*C. difficile* toxin A humanized mAbs, or fragments thereof, having activity against toxin A of *C. difficile*, wherein the V region of the H chain is selected from one or more of SEQ ID NO:1, SEQ ID NO:2, SEQ ID NO:5 and SEQ ID NO:6. Embodiments of the invention are directed to anti-*C. difficile* toxin B humanized mAbs, or fragments thereof, having activity against toxin B of *C. difficile*, wherein the V region of the H chain is selected from one or more of SEQ ID NO:8 or SEQ ID NO:9. In an embodiment, the invention is directed to the CDRs, namely, CDR1, CDR2, and/or CDR3, in the VH and VL regions of the described antibodies.

In other embodiments, the invention encompasses nucleic acids which encode antigen-binding portions, CDRs, or variable (V) regions of the anti-*C. difficile* toxin A and/or anti-toxin B antibodies of the invention. In various embodiments, the portions, CDRs, or V regions are derived from PA-38, PA-39, PA-41, or PA-50, or humanized versions thereof, as described herein. In further embodiments, the invention encompasses the amino acid sequences of the antigen-binding portions, CDRs, or V regions that are encoded by the respective nucleic acids.

According to another embodiment, the monoclonal antibodies of the present invention can be modified to be in the form of a bispecific antibody, a bifunctional antibody, a multispecific antibody, or a heterofunctional antibody. Nonlimiting examples of bispecific and heterospecific antibodies and procedures for making such antibodies may be found in a number of illustrative publications, for example, UA20090060910, WO2009/058383, WO2009/030734, WO2007/093630, U.S. Pat. No. 6,071,517, WO2008/024188, UA20070071675, U.S. Pat. Nos. 7,442,778, 7,235, 641, 5,932,448 and 5,292,668. The term "bispecific antibody" is intended to include any agent, e.g., a protein, peptide, or protein or peptide complex, which has two different binding specificities and which binds to or interacts with (a) toxin A of *C. difficile* and (b) toxin B of *C. difficile*. In one embodiment, the bispecific antibody comprises PA-39 or PA-50 or an antigen-binding fragment thereof and PA-41, or an antigen-binding fragment thereof. In an embodiment, the bispecific antibody comprises a chimeric or humanized form of PA-39 or PA-50, or an antigen-binding fragment thereof and PA-41, or an antigen-binding fragment thereof. Accordingly, a bispecific antibody comprising PA-39 and PA-41, or chimeric or humanized forms thereof, or an antigen-binding fragment thereof, would bind both toxin A and toxin B of *C. difficile*. Similarly, a bispecific antibody comprising PA-50 and PA-41, or chimeric or humanized forms thereof, or an antigen-binding fragment thereof, would bind both toxin A and toxin B of *C. difficile*. The term "multispecific antibody" is intended to include any agent, e.g., a protein, peptide, or protein or peptide complex, which has more than two different binding specificities and which binds to or interacts with (a) toxin A of *C. difficile*, (b) toxin B of *C. difficile*, and (c) at least one other component. Accordingly, the invention includes, but is not limited to, bispecific, trispecific, tetraspecific, and other multispecific antibodies. In one embodiment, the antibodies or antigen-binding fragments of the bispecific or multispecific antibodies are humanized.

The term "bispecific antibodies" further includes diabodies. Diabodies provide therapeutic antibodies having dual specificity and being capable of targeting multiple different epitopes with a single molecule. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen-binding sites (see e.g., Bolliger, P., et al. (1993) *Proc. Natl. Acad. Sci. USA* 90:6444-6448; Poljak, R. J., et al. (1994) *Structure* 2:1121-1123). The two antigen-binding regions of the bispecific antibody are either chemically linked or is expressed by a cell genetically engineered to produce the bispecific antibody. (See generally, Fanger et al., 1995 *Drug News & Perspec.* 8(3):133-137). In an embodiment an effective amount of a bispecific antibody can be administered to a subject with *C. difficile* infection and/or a *C. difficile*-associated disease, and the bispecific antibody neutralizes the toxicity of toxin A and toxin B in the subject.

In certain embodiments, the antibodies may be human antibodies. The term "human antibody", as used herein, is intended to include antibodies having variable and constant Ig regions derived from human germline immunoglobulin sequences. The human antibodies may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences (referred to herein as "humanized antibodies"). Human antibodies directed against toxin A and/or toxin B can be generated using transgenic mice genetically modified and bred to express components of the human immune system rather than the mouse system.

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150, 584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XenoMouse (Abgenix), HumAb mice (Medarex/GenPharm)), monoclonal antibodies are prepared according to standard hybridoma technology. These monoclonal antibodies have human immunoglobulin amino acid sequences and, therefore, will not provoke human anti-mouse antibody (HAMA) responses when administered to humans.

Those of skill in the art will appreciate that provided herein are also the nucleic acids and polynucleotides that encode the described antibodies or antigen-binding fragments thereof. It will also be appreciated that provided herein are nucleic acids and polynucleotides that comprise a sequence encoding the antibodies or antigen-binding fragments thereof. Vectors and plasmids engineered to contain and/or express antibody-encoding nucleic acids and polynucleotides are, therefore, provided by the invention. As used herein, a "coding region" refers to a region of a nucleotide sequence that encodes a polypeptide sequence; the coding region can include a region coding for a portion of a protein that is later cleaved off, such as a signal peptide. In some instances, the nucleotide and amino acid sequences may include sequences that encode or that are signal peptides. The invention embraces each of these sequences with, or without, the portion of the sequence that encodes or is a signal peptide.

The antibodies provided herein can be cloned using the following method, as well as other methods known to those of ordinary skill in the art. As a nonlimiting example, total RNA is generated from hybridoma calls, and cDNA is reverse transcribed using an oligo-dT primer. RNase H can be used to remove RNA to make single-stranded cDNA. Spin column purification can be used to remove free nucleotides. Then, a 3' poly-dG tail can be added with terminal transferase. PCR amplification can be performed using an oligo-dC primer plus a degenerate primer to the constant region. Approximately, 40 cycles can be performed for robust heavy chain amplification. Direct sequencing of the PCR products can then be performed.

In certain embodiments, the antibody or antigen-binding fragment thereof is encoded by a nucleic acid molecule that is highly homologous to the foregoing nucleic acid molecules. The homologous nucleic acid molecule can comprise a nucleotide sequence that is at least about 90% identical to the nucleotide sequence provided herein. The homologous nucleic acid molecule can comprise a nucleotide sequence is at least about 95% identical, at least about 97% identical, at least about 98% identical, or at least about 99% identical to the nucleotide sequence provided herein. The homology can be calculated using various, publicly available software tools well known to one of ordinary skill in the art. Exemplary tools include the BLAST system available from the website of the National Center for Biotechnology Information (NCBI) at the National Institutes of Health.

One method of identifying highly homologous nucleotide sequences is via nucleic acid hybridization. Also provided herein are antibodies having the toxin A and/or toxin B binding properties and other functional properties described herein, which are encoded by nucleic acid molecules that hybridize under high stringency conditions to the nucleic acid molecules encoding the antibodies of the invention. Identification of related sequences can also be achieved using polymerase chain reaction (PCR) and other amplification techniques suitable for cloning related nucleic acid sequences. For such techniques, PCR primers are typically selected to amplify portions of a nucleic acid sequence of interest, such as a CDR.

The term "high stringency conditions" as used herein refers to parameters with which the art is familiar. Nucleic acid hybridization parameters may be found in references that compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. One nonlimiting example of high-stringency conditions is hybridization at 65° C. in hybridization buffer (3.5×SSC, 0.02% Ficoll, 0.02% polyvinyl pyrrolidone, 0.02% Bovine Serum Albumin, 2.5 mM $NaH_2PO_4$ (pH7), 0.5% SDS, 2 mM EDTA). SSC is 0.15M sodium chloride/0.015M sodium citrate, pH7; SDS is sodium dodecyl sulphate; and EDTA is ethylenediaminetetracetic acid. After hybridization, a membrane upon which the nucleic acid is transferred is washed, for example, in 2×SSC at room temperature and then at 0.1-0.5×SSC/0.1×SDS at temperatures up to 68° C.

Provided herein are vectors (e.g., expression vectors) or plasmids comprising the nucleic acid molecules described, in addition to other nucleic acid sequences, e.g., ORI, promoter, enhancer, termination sequences, required for protein, polypeptide, or peptide expression. The vectors can be used to transform or transfect host cells for producing the antibodies or antigen-binding fragments thereof with the binding specificity and/or characteristics of the antibodies or antigen-binding fragments described herein. In one embodiment, the vectors can comprise an isolated nucleic acid molecule encoding the heavy chain or portion thereof of the antibodies and antigen-binding fragments provided. In another embodiment, the vectors can comprise the nucleic acid sequences encoding the light chain or portion thereof. In a further embodiment, the vectors of the invention may comprise a sequence for a heavy chain or a portion thereof and a sequence of a light chain or portion thereof. In a further embodiment, plasmids are given which produce the antibodies or antigen binding fragments described herein.

Modified versions of the antibodies of the invention are also provided. Modifications to an antibody or antigen-binding fragment thereof are typically made to the nucleic acid which encodes the antibody or antigen-binding fragment thereof, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the antibody or antigen-binding fragment amino acid sequence. Modifications further embrace coupling or joining of the antibody to another agent, such as a cytotoxic agent, drug, or therapeutic.

Modified polypeptides include polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a polypeptide by eliminating proteolysis by proteases in an expression system (e.g., dibasic amino acid residues in yeast expression systems in which KEX2 protease activity is present). Additionally, one or more amino acids can be changed, particularly in the Ig constant region, to prevent proteolytic degration of the antibody by enzymes following certain routes of administration, e.g., oral administration, as described for example, in WO2006/071877, published 6 Jul. 2006.

Modifications conveniently are prepared by altering a nucleic acid molecule that encodes the polypeptide. Mutations of a nucleic acid which encode a polypeptide preferably preserve the amino acid reading frame of the coding sequence, and preferably do not create regions in the nucleic acid which are likely to hybridize to form secondary structures, such a hairpins or loops, which can be deleterious to expression of the modified polypeptide.

Modifications can be made to any of the antibodies or antigen-binding fragments thereof by selecting an amino acid substitution, or by random mutagenesis of a selected site in a nucleic acid which encodes the polypeptide. Modified polypeptides then can be expressed and tested for one or more activities to determine which mutation provides a modified polypeptide with the desired properties. Further mutations can be made to modified polypeptides (or to non-modified polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a sequence or cDNA clone to enhance expression of the polypeptide. The activity of modified polypeptides can be tested by cloning the gene encoding the modified polypeptide into an expression vector, introducing the vector into an appropriate host cell, expressing the modified polypeptide, and testing for a functional capability of the polypeptides as disclosed herein. The foregoing procedures are well known to one of ordinary skill in the art.

The skilled artisan will also realize that conservative amino acid substitutions may be made in polypeptides to provide functionally equivalent polypeptides. As used herein, a "conservative amino acid substitution" refers to an amino acid substitution which does not alter the relative charge or size characteristics of the protein in which the amino acid substitution is made. Modified polypeptides can be prepared according to methods for altering a polypeptide sequence as known to one of ordinary skill in the art, such as can be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Conservative substitutions of amino acids include substitutions made among amino acids within the following exemplary groups: (a) M, I, L, V; (b) F, Y, W; (c) K, R, H; (d) A, G; (e) S, T; (f) Q, N; and (g) E, D.

Conservative amino-acid substitutions in polypeptides typically are made by alteration of a nucleic acid encoding a polypeptide. Such substitutions can be made by a variety of methods known to one of ordinary skill in the art. For example, amino acid substitutions may be made by PCR-directed mutation, site-directed mutagenesis, or by chemical synthesis of a gene encoding a polypeptide. Where amino acid substitutions are made to a small fragment of a polypeptide, the substitutions can be made by directly synthesizing the peptide. The activity of functionally equivalent fragments of polypeptides can be tested by cloning the gene encoding the altered polypeptide into a bacterial or mammalian expression vector, introducing the vector into an appropriate host cell, expressing the altered polypeptide, and testing for a functional capability of the polypeptides as disclosed herein.

An anti-toxin antibody, or antigen-binding portion thereof, of the invention can be derivatized or linked to another functional molecule, for example, another peptide or protein. Additionally, an antibody or antibody portion can be functionally linked, e.g., by chemical coupling, genetic fusion, noncovalent association, etc., to one or more other molecular entities, such as another antibody, a detectable agent, a cytotoxic agent, a therapeutic agent, a pharmaceutical agent, and/or or a protein or peptide that can mediate association with another molecule, for example, a streptavidin core region or a polyhistidine tag.

A derivatized protein or antibody may be produced by crosslinking or coupling two or more proteins or antibodies of the same or different types. Suitable crosslinkers or coupling agents include those that are heterobifunctional, having two distinct reactive groups separated by an appropriate spacer (e.g., m-maleimidobenzoyl-N-hydroxysuccinimide ester) or homobifunctional (e.g., disuccinimidyl suberate), and commercially available (Pierce Chemical Company, Rockford, Ill.). An anti-toxin antibody or antigen-binding fragment thereof of the invention may be conjugated to another molecular entity, such as a label. Detectable agents or labels with which a protein can be derivatized or labeled include fluorescent compounds, enzymes, prosthetic groups (e.g., streptavidin/biotin and avidin/biotin), chemiluminescent materials, bioluminescent materials, chemical entities and radioactive materials. Examples of detectable fluorescent compounds include fluorescein, fluorescein isothiocyanate (FITC), rhodamine and phycoerythrin. A protein or antibody can also be derivatized with detectable enzymes, such as alkaline phosphatase (AP), horseradish peroxidase, beta-galactosidase, acetylcholinesterase, glucose oxidase, etc. Such enzymatically derivatized proteins or antibodies become detectable upon addition of a specific substrate of the enzyme so as to produce a detectable reaction product. Proteins derivatized with a prosthetic group, such as biotin, can be detected by indirect measurement of avidin or streptavidin binding.

Labeled proteins and antibodies may be used as diagnostic and/or experimental agents or reagents to isolate a known or predetermined antigen by standard techniques, such as affinity chromatography or immunoprecipitation, or to detect a known or predetermined antigen so as to determine protein levels in tissue as part of a clinical testing procedure, e.g., to monitor the efficacy of a given treatment regimen. In an embodiment, the antigen to be detected may be a toxin in a cellular lysate or in a patient sample.

In a particular embodiment, the antibodies or antigen-binding fragments of the invention are used in combination, e.g., as a pharmaceutical composition comprising two or more different antibodies or antigen-binding fragments thereof (e.g., one or more directed against toxin A and one or more directed against toxin B, two or more directed against toxin A, or two or more directed against toxin B, etc.). Combinations of antibodies or antigen-binding fragments thereof can be combined in a single therapy (i.e., administered simultaneously) to achieve a desired therapeutic effect. Alternatively, the antibodies or antigen-binding fragments thereof can be administered separately (i.e., at different times). It follows, therefore, that the antibodies or antigen-binding fragments thereof can be stored together or separately. The antibodies or antigen-binding fragments thereof can be stored in an aqueous medium or as a lyophilized form, which can be reconstituted prior to use.

In another embodiment, compositions comprising one or more isolated antibodies or an antigen-binding fragment thereof are provided. Also provided are compositions comprising a combination of one or more of the aforementioned antibodies or antigen-binding fragments thereof. Also provided are compositions, each containing one or more of the aforementioned antibodies or antigen-binding fragments thereof, which compositions are intended for use in combination. Such compositions may include a physiologically or pharmaceutically acceptable carrier, excipient, vehicle, or diluent. The physiologically or pharmaceutically acceptable carrier, excipient, vehicle, or diluent can be mixed with the isolated antibody or antigen-binding fragment thereof. In an embodiment, the compositions include a combination of multiple (e.g., two or more) isolated antibodies or antigen-binding fragments thereof. In an embodiment, one or more of the antibodies or antigen-binding fragments thereof of the composition specifically bind toxin A of *C. difficile* and neutralize its toxic effects, while one or more of the antibodies or antigen-binding fragments thereof specifically bind toxin B of *C. difficile* and neutralize its toxic effects. In one embodiment, both the one or more of the antibodies or antigen-binding fragments thereof that specifically bind toxin A of *C. difficile* and neutralize its toxic effects and the one or more that specifically bind toxin B of *C. difficile* and neutralizes its toxic effects are humanized.

In a particular embodiment, the composition comprises a combination of one anti-toxin A antibody or antigen-binding fragment thereof as described herein and one anti-toxin B antibody or antigen-binding fragment thereof as described herein. In such a composition, the anti-toxin A antibody and the anti-toxin B antibody may be present in equal amounts or ratios, e.g., 1:1. Alternatively, in such a composition, the anti-toxin A antibody and the anti-toxin B antibody may be present in different amounts or ratios, such as ½:1; 2:1; 3:1; 4:1, etc. In an embodiment, the antibodies of the composition are humanized. In one embodiment, the composition comprises a combination of mAb PTA-9888, an antigen-binding fragment thereof, or a humanized form thereof, and mAb 9693, an antigen-binding fragment thereof, or a humanized form thereof. In an embodiment, the composition comprises a combination of mAb PTA-9694, an antigen-binding fragment thereof, or a humanized form thereof, and mAb 9693, an antigen-binding fragment thereof, or a humanized form thereof. In an embodiment, the composition comprises a combination of any one of the following: Mab PTA-9692, an antigen-binding fragment thereof, or a humanized form thereof and mAb 9693, an antigen-binding fragment thereof, or a humanized form thereof; or mAb PTA-9888, an antigen-binding fragment thereof, or a humanized form thereof and mAb 9692, an antigen-binding fragment thereof, or a humanized form thereof; or mAb PTA-9694, an antigen-binding fragment thereof, or a humanized form thereof and mAb 9692, an antigen-binding fragment thereof, or a humanized form thereof.

Pharmaceutical compositions also can be administered in combination therapy, i.e., combined with other therapeutic agents. For example, the combination therapy can include a composition comprising one or more antibodies or antigen-binding fragments thereof as provided herein with at least one other conventional therapy. Such additional therapeutic agents include antibiotic therapeutics and non-antibiotic therapeutics. Additional therapeutic agents include *C. difficile* toxoid vaccine, ampicillin/amoxicillin, vancomycin, metronidazole, fidaxomicin, linezolid, nitazoxanide, rifaximin, ramoplanin, difimicin (also called PAR-101 or OPT-80), clindamycin, cephalosporins (such as second and third generation cephalosporins), fluoroquinolones (such as gatifloxacin or moxifloxacin), macrolides (e.g., erythromycin, clarithromycin, azithromycin), penicillins, aminoglycosides, trimethoprim-sulfamethoxazole, chloramphenicol, tetracycline, imipenem, and meropenem. Additional therapeutics also include antibiotics, antibacterial agents, bacteriocides, or bacteriostats. In an embodiment, the additional therapeutic agent may be a small molecule or chemical compound of low molecular weight, which targets *C. difficile* and/or its toxins. In an embodiment, the additional therapeutic agent is OPT-80. Non-antibiotic therapeutics include tolevamer, a high-molecular-weight anionic polymer that binds toxins A and B via non-specific charge mechanisms.

As an alternative, it is envisioned that the antibodies or antigen-binding fragments thereof of the invention may be used in combination with other antibodies or antigen-binding fragments thereof. Other additional therapeutic agents include normal pooled immunoglobulin, intravenous immunoglobulin, or polyclonal anti-toxin A and anti-toxin B immunoglobulins in sera. Other antibodies include human mAbs directed against toxin A or toxin B of *C. difficile*, as described and reported in the published literature (e.g., WO/2006/121422; US2005/0287150).

Also encompassed herein, is a method which involves using the antibodies or antigen-binding fragments thereof of the invention for treatment or prophylaxis, i.e., to treat, resolve, ameliorate, eradicate, prevent, or delay *C. difficile* infection or *C. difficile*-associated disease, pathology, or development or progression thereof. CDAD typically is precipitated by the disruption of the colonic flora through the use of antibiotics such as clindamycin, cephalosporins, and fluoroquinolones. This perturbation in the colonic microenvironment, along with exposure to *C. difficile* spores, leads to colonization in afflicted individuals. Approximately one-third of all patients who become colonized develop CDAD, which can result in severe diarrhea, perforation of the colon, colectomy and death. Methods, therefore, are provided whereby a subject is administered one or more antibodies of the invention, or a composition as described herein to treat *C. difficile* infection or CDAD.

As used herein, to "treat" refers to any benefit to a subject with *C. difficile* infection or *C. difficile*-associated disease conferred through the administration of the antibodies or a composition or combination of compositions provided herein. For example and without limitation, such a benefit can be the elimination of one or more symptoms or adverse effects, or a reduction in, or amelioration of, the severity of the one or more symptoms or adverse effects that result from the infection or disease; a delay, halt, or reversal in the progression of the infection or disease; a recolonization, resurgence, or repopulation of the normal and natural microflora of the gastrointestinal tract, colon, bowel, etc., or the cure of the infection or disease (i.e., a clinician would evaluate the subject and determine that the subject no longer has the infection or disease). Symptoms or adverse effects associated with *C. difficile* infection include dehydration, diarrhea, cramping, kidney failure, bowel perforation, toxic megacolon, which can lead to rupture of the colon, and death. The compositions provided can be used to reduce, diminish, ameliorate, or eliminate any or all of the symptoms or adverse effects provided herein.

As used herein, a "*C. difficile* infection" refers to an infection that results from the presence of *C. difficile* in the intestinal flora where it was not previously present or a change in the presence of *C. difficile* in the intestinal flora (e.g., an increase in the total amount of *C. difficile* relative to one or more other bacteria, etc.), which gives rise or may give rise to adverse effect(s) and/or an increase in the level of toxins A and/or B in the intestine or other organs and tissues comprising the gastrointestinal tract. Typically, CDAD results from the acquisition and proliferation of *C. difficile* in the gut. In vivo, toxins A and B demonstrate different pathological profiles with potential synergy in causing disease. In rabbits and mice, for example, toxin A is an enterotoxin that induces diarrhea, while toxin B does not elicit a fluid response in this species. However, toxin B is more potently cytotoxic in vitro. Toxin A-negative, toxin B-positive (A− B+) strains of *C. difficile* have been increasingly reported. A−/B+ strains fail to produce toxin A due to deletion of the repetitive domain of the tcdA gene, yet are still capable of causing clinical disease. In contrast, there are to date no reports of toxin A-positive, toxin B-negative (A+/B−) strains in humans.

*C. difficile* infection commonly manifests as mild-to-moderate diarrhea, occasionally with abdominal cramping. Pseudomembranes, which are adherent yellowish-white plaques on the intestinal mucosa, are occasionally observed. In rare cases, patients with *C. difficile* infection can present with an acute abdomen and fulminant life-threatening colitis, which results from a disruption of the normal bacterial flora of the colon, colonization with *C. difficile* and release of toxins that cause mucosal inflammation and damage. Antibiotic therapy is the key factor that alters the colonic flora. While normal gut flora resists colonization and overgrowth with *C. difficile*, antibiotic use, which suppresses the normal flora, allows *C. difficile* bacteria to proliferate. *C. difficile* is present in 2-3% of healthy adults and in as many as 70% of healthy infants. In one of its aspects, the mAbs of the present invention are utilized for the treatment of subjects who are asymptomatic, but who are susceptible to, or at risk of, contracting *C. difficile* infection and becoming afflicted with its associated diseases. Such subjects may be hospitalized or may be outside of a hospital setting.

The chief risk factor for *C. difficile*-related disease is prior exposure to antibiotics. The most common antibiotics implicated in *C. difficile* colitis include cephalosporins (especially second and third generation), ampicillin/amoxicillin and clindamycin. Less commonly implicated antibiotics are the macrolides (i.e., erythromycin, clarithromycin, azithromycin) and other penicillins. Compounds or other agents which are occasionally reported to cause the disease include aminoglycosides, fluoroquinolones, trimethoprim-sulfamethoxazole, metronidazole, chloramphenicol, tetracycline, imipenem, and meropenem. Even brief exposure to any single antibiotic can cause *C difficile* colitis, particularly if normal intestinal flora are adversely affected or killed. A prolonged antibiotic course, or the use of two or more antibiotics, increases the risk of disease. Antibiotics traditionally used to treat *C. difficile* colitis have been shown to cause disease. Other risk factors associated with infection by *C. difficile* include advanced age (>65 years); weakened immune system; recent hospitalization (particularly sharing a hospital room with an infected patient, intensive care unit stays and prolonged hospital stays); living in a nursing home, hospice, or other longterm care facility; abdominal surgery; chronic colon disease, (e.g., inflammatory bowel disease (IBD) or colorectal cancer); taking prescription or over the counter antacids which may reduce stomach acid and allow *C. difficile* to pass more easily into the intestine; and a previous *C. difficile* infection. More factors associated with *C. difficile* disease include antineoplastic agents, principally methotrexate, hemolytic-uremic syndrome, malignancies, intestinal ischemia, renal failure, necrotizing enterocolitis, Hirschsprung disease, IBD and nonsurgical gastrointestinal procedures, including nasogastric tubes. The subjects that can be administered the compositions provided herein include any of the subjects described that are at risk for *C. difficile* infection.

While most patients with *C. difficile* colitis recover without specific therapy, symptoms may be prolonged and debilitating. *C. difficile*-associated diarrhea can be a serious condition with a mortality rate of up to 25% in elderly patients who are frail. Reports that focus on more seriously ill patients indicate mortality rates of 10-30%. *C. difficile* infection is more common in elderly people, and old age may promote susceptibility to colonization and disease. While infants and young children frequently harbor *C. difficile* and its toxins, clinical infection is uncommon. Cross-infection by *C. difficile* is common in neonatal units, but neonates do not seem to develop *C. difficile* associated diarrhea.

Provided herein are a number of methods using the humanized antibodies of the invention and/or the compositions provided herein. For example, a method for treating a subject who has *C. difficile* infection or disease, exhibits any of the symptoms or the adverse effects provided herein, or has any of diseases provided herein is provided. In one embodiment, the method reduces, diminishes, or ameliorates the severity of disease associated with *C. difficile* infection or *C. difficile-associate* disease in a subject. As another example, a method of treating a subject who is afflicted with *C. difficile*-associated diarrhea is provided.

Also provided is a method of neutralizing toxin A and/or toxin B of *C. difficile* in a subject. As an example, a method of neutralizing combined systemic toxin A and toxin B of *C. difficile* is provided. In one embodiment, combined systemic toxin A and toxin B of *C. difficile* are neutralized by administering both a humanized anti-toxin A antibody or antigen-binding fragment thereof and a humanized anti-toxin B antibody or antigen-binding fragment thereof, or a composition comprising these antibodies. In another aspect, the combined systemic toxin A and toxin B of *C. difficile* are neutralized through the administration of an antibody or antigen-binding fragment thereof that specifically binds both toxin A and toxin B, or a composition comprising the antibody (e.g., in humanized form). In some embodiments, the humanized antibodies or compositions are administered in conjunction with another therapeutic agent which targets *C. difficile*.

As another embodiment, a method of restoring normal gastrointestinal flora in a subject infected with *C. difficile*, thereby effectively treating infection caused by *C. difficile* and/or and its toxins, is also provided. As yet another embodiment, a method of reducing the susceptibility of a subject to *C. difficile* infection or *C. difficile*-associated disease is also provided. As another embodiment, a method of preventing *C. difficile* infection or *C. difficile*-associated disease in a subject is provided.

In the aforementioned methods, the subject is administered one or more of the antibodies or the compositions provided herein (e.g., a composition comprising a monoclonal antibody or an antigen-binding fragment thereof directed against *C. difficile* toxin A and a composition comprising a monoclonal antibody or antigen-binding fragment directed against *C. difficile* toxin B). The compositions can be administered to the subject at the same time or at different times. The compositions can be administered to the subject as a mixture in a composition comprising a pharmaceutically acceptable carrier, vehicle, or excipient, and optionally another antibiotic, non-antibiotic, drug or therapeutic effective against *C. difficile* and/or its enterotoxins.

A humanized anti-toxin A monoclonal antibody or antigen-binding fragment thereof and/or a humanized anti-toxin B monoclonal antibody or antigen-binding fragment thereof, or a pharmaceutically acceptable composition comprising the humanized antibodies or antigen-binding fragments thereof, separately or together, can be used in any of the described methods according to the invention.

As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. Preferably, the carrier is suitable for oral, intravenous, intraperitoneal, intramuscular, subcutaneous, parenteral, spinal or epidermal administration (e.g., by injection or infusion). Depending on the route of administration, the active compound, i.e., antibody may be coated in a material to protect the compound from the action of acids and other natural conditions that may inactivate the compound.

When administered, the pharmaceutical preparations of the invention are applied in pharmaceutically-acceptable amounts and in pharmaceutically-acceptable compositions. The term "pharmaceutically acceptable" means a non-toxic, physiologically acceptable material that does not interfere with the effectiveness of the biological activity of the active ingredients. Such preparations may routinely contain salts, buffering agents, preservatives, compatible carriers, and optionally other therapeutic agents, such as supplementary immune potentiating agents, including adjuvants, chemokines and cytokines. When used in medicine, the salts should be pharmaceutically acceptable, but non-pharmaceutically acceptable salts may conveniently be used to prepare pharmaceutically-acceptable salts thereof and are not excluded from the scope of the invention.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, ethylenediamine acetate (EDTA), with or without a counterion, such as sodium or calcium, procaine and the like.

Any of the compositions of the invention may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being admixed with the molecules of the compositions provided, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; and parabens.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Anti-toxin A and anti-toxin B antibodies of the invention, or portions thereof, can be provided according to dosage regimens that may be adjusted to provide the optimum desired response, such as a therapeutic or prophylactic response, in an individual subject. Illustratively, a single bolus may be administered, several divided doses may be administered over time, or the dose may be reduced or increased proportionally, as may be indicated by a particular therapeutic situation. Parenteral compositions may be packaged or prepared in unit dosage form for ease of administration and uniformity of dosage. Unit dosage form refers to physically discrete units provided as unitary dosages for the subjects to be treated, wherein each unit contains a predetermined quantity of active compound calculated to produce the desired therapeutic effect in association with the required pharmaceutical carrier, vehicle, excipient, or diluent. The specification for the unit dosage forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Compositions suitable for parenteral administration conveniently comprise a sterile aqueous or non-aqueous preparation, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intraperitoneal, intravenous, intramuscular, etc. administration can be found in *Remington's Pharmaceutical Sciences*, Mack Publishing Co., Easton, Pa.

The active components can be prepared with carriers that will protect the components against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The antibody and compositions of the invention as therapeutics can be administered by any conventional route, including injection or by gradual infusion over time. The administration route may, as nonlimiting examples, be oral, intravenous, subcutaneous, intraperitoneal, intramuscular, intrathecal, intracavity, retroorbital, vaginal, rectal, inhalation, aspiration, dermal, via suppository, or transdermal.

The antibodies and compositions of the invention are administered in effective amounts or doses. An "effective amount" is that amount of an antibody or antigen-binding fragment thereof or composition(s) as provided herein that alone, or together with further doses, or other therapeutic agent(s), produce the desired response, e.g., treats, ameliorates, eradicates, resolves, or prevents *C. difficile* infection, diarrhea, or a *C. difficile*-associated disease in a subject. This may involve only slowing the progression of the infection, diarrhea, or disease for a sustained period, e.g., longer than one week, two weeks, three weeks, one month, two months, three months, or more than three months. However, such effective amounts optimally treat or halt the progression of the infection, diarrhea, or disease permanently. This can be monitored by routine methods. The desired response to treatment of the disease or condition also can be delaying the onset or even preventing the onset of the infection or disease.

Effective amounts will depend, of course, on the particular infection or disease being treated, the severity of the infection or disease, the individual patient parameters including age, physical condition, size, and weight, the duration of the treatment, the nature of concurrent therapy (if any), the specific route of administration and like factors within the knowledge and expertise of the health practitioner. These factors are well known to those of ordinary skill in the art and can be addressed with no more than routine testing or experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The pharmaceutical compositions used in the foregoing methods preferably are sterile and contain an effective amount of one or more antibodies or antigen-binding fragments provided herein for producing the desired response in a unit of weight or volume suitable for administration to a patient. The response can, for example, be measured by determining the physiological effects of the composition, such as decrease of disease symptoms. Other assays will be known to one of ordinary skill in the art and can be employed for measuring the level of the response.

The doses or amounts of the compositions administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses or amounts can range from about 1 µg/kg to about 100,000 µg/kg. Nonlimiting examples of dose ranges constituting a therapeutically or prophylactically effective amount of an antibody, antibody portion, or composition of the invention include 0.1 mg/kg-100 mg/kg; 0.1 mg/kg-60 mg/kg; of 0.5 mg/kg-75 mg/kg; 0.5 mg/kg-25 mg/kg; 0.75 mg/kg-40 mg/kg; 1 mg/kg-50 mg/kg; or 1 mg/kg-5 mg/kg. It will be appreciated that for any particular individual, patient, or subject, specific doses and dosage regimens should be adjusted over time according to individual need and the professional judgment of the skilled practitioner who is administering or supervising the administration of the antibodies and/or compositions. Such dose ranges are exemplary only and are not intended to limit scope or practice of the invention. Based upon the composition, the dose can be delivered continuously, such as by continuous pump, or at periodic intervals. Desired time intervals of multiple doses of a particular composition can be determined without undue experimentation by one skilled in the art. Other protocols for the administration of the compositions will be known to one of ordinary skill in the art, in which the dose amount, schedule of administration, sites of administration, mode of administration and the like vary from the foregoing.

Administration of the compositions to mammals other than humans, e.g., for testing purposes or veterinary therapeutic purposes, is carried out under substantially the same conditions as described above.

Also provided herein are kits comprising antibodies of the invention or compositions comprising antibodies of the invention, and instructions for use. The kits can further contain at least one additional reagent, such as an additional therapeutic agent, or one or more additional antibodies or antigen-binding fragments as provided herein (e.g., an antibody or antigen-binding fragment thereof to toxin A when the first antibody or antigen-binding fragment thereof in the kit is an antibody or antigen-binding fragment thereof to toxin B, and vice versa).

The components of the kits can be packaged either in aqueous medium or in lyophilized form. When the antibodies or antigen-binding fragments thereof are used in the kits in the form of conjugates (e.g., a bispecific antibody conjugate), the components of such conjugates can be supplied either in fully conjugated form, in the form of intermediates, or as separate moieties to be conjugated by the user or the kit in accordance with the provided instructions for use.

A kit may comprise a carrier being compartmentalized to receive in close confinement therein one or more container means, or series of container means, such as test tubes, vials, flasks, bottles, syringes, or the like. A first container means or series of container means may contain one or more antibodies or antigen-binding fragments thereof. A second container means or series of container means may contain one or more antibodies or antigen-binding fragments thereof, wherein the antibodies or antigen-binding fragments thereof are different from those in the first container means, or some other additional therapeutic agent. The kits provided herein can further include a third container that contains a molecule to link the antibodies or antigen-binding fragments contained in the first and second containers.

As used herein with respect to polypeptides, proteins or fragments thereof, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature, or from in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be naturally associated in living systems, i.e. isolated from other naturally-occurring proteins.

Methods for evaluating a candidate agent for efficacy in the treatment of *C. difficile* infection or *C. difficile*-associated disease are also provided. Such methods may comprise the steps of treating a subject with an agent that increases the risk of *C. difficile* infection or *C. difficile*-associated disease in the subject, inoculating the subject with *C. difficile*, treating the subject with the candidate agent, and evaluating the efficacy of treatment with the candidate agent. As used herein, an "agent that increases the risk of C. difficile infection or C. difficile-associated disease" is any agent that is thought to promote the onset or progression of C. difficile infection or C. difficile-associated disease. Such an agent can be an antibiotic or non-antibiotic agent. For example, the agent can be any of the antibiotics described herein. Illustratively, such an antibiotic may be clindamycin metronizadole, vancomycin, fidaxomicin, nitazoxanide, rifaximin ramoplanin, or a combination thereof.

In these methods, the candidate agent can be administered to the subject prior to or after inoculation with C. difficile. The candidate agent can be any agent that is thought to have the potential for treating or preventing C. difficile infection or C. difficile-associated disease. The candidate agents, which can be an antibiotic or a non-antibiotic, include antibodies or antigen-binding fragments thereof that specifically bind toxin A and/or toxin B of C. difficile. These methods include any of the in vitro and in vivo methods described in the Examples hereinbelow.

The ultimate goal of CDAD treatment is to discontinue all antibiotics and allow restoration of the normal bowel microflora. In accordance with the invention, anti-toxin A and B mAbs described herein can provide non-antibiotic therapies designed to block the pathogenic effects of C. difficile toxins, allow the discontinuation of antibiotics and thereby provide time for the colon to heal and the normal bowel microflora to become re-established. Monoclonal antibodies of the invention have demonstrated complete and durable (>37 days) protection in a stringent hamster model of CDAD. Based on their exceptional characteristics and properties, anti-C. difficile toxin A and toxin B mAbs of the invention provide new treatment options and medicaments for patients poorly served by existing therapies, including those individuals afflicted with the severest cases of disease.

The present invention further encompasses a vaccine or immunogen comprising portions, fragments, or peptides of toxin A and/or toxin B of C. difficile containing the epitopic regions recognized and/or bound by one or more of monoclonal antibody PA-39 (ATCC Accession No. PTA-9692), a humanized form of PA-39, monoclonal antibody PA-50 (ATCC Accession No. PTA-9694), a humanized form of PA-50, monoclonal antibody PA-41 (ATCC Accession No. PTA-9693), a humanized form of PA-41, an antibody that competes for binding of toxin A with monoclonal antibody PA-39 or a humanized form thereof, an antibody that competes for binding of toxin A with monoclonal antibody PA-50 or a humanized form thereof, or an antibody that competes for binding of toxin B with monoclonal antibody PA-41 or a humanized form thereof. In an embodiment, the vaccine or immunogen comprises portions, fragments, or peptides of toxin A and toxin B of C. difficile containing the epitopic regions recognized and/or bound by one or more of monoclonal antibody PA-39 (ATCC Accession No. PTA-9692), a humanized form of PA-39, or an antibody that competes for binding of toxin A and toxin B with monoclonal antibody PA-39 or a humanized form thereof. In an embodiment, the epitope-containing portions, fragments, or peptides of toxin A and/or toxin B of the vaccine or immunogen are derived from the toxin A or toxin B protein by proteolytic cleavage. In an embodiment, the toxin A fragments, portions, or peptides of the vaccine or immunogen are produced by proteolytic cleavage by enterokinase. In an embodiment, the toxin B fragments, portions, or peptides of the vaccine or immunogen are produced by proteolytic cleavage by caspase (caspase 1). In an embodiment, the epitope-containing portions or fragments of the vaccine or immunogen are chemically or recombinantly synthesized peptides of the toxin A or toxin B protein. In an embodiment, the fragments, portions, or peptides of the vaccine or immunogen containing one or more epitopic regions of toxin A and/or toxin B that are recognized and bound by the antibody are derived from one or more of the amino terminus of toxin A; the amino terminus of toxin B; the carboxy terminus of toxin A; the carboxy terminus of toxin B; the receptor binding domain of toxin A; a region outside of the receptor binding domain of toxin A; the N-terminal enzymatic region of toxin B; the glucosyltransferase domain of toxin A; the glucosyltransferase domain of toxin B; the proteolytic domain of toxin A; the proteolytic domain of toxin B; the hydrophobic, pore-forming domain of toxin A; or the hydrophobic, pore-forming domain of toxin B.

In some embodiments, the fragments containing one or more epitopic regions recognized and bound by the antibodies are derived from the amino terminus of toxin A or toxin B. In some embodiments, the fragments containing one or more epitopic regions recognized and bound by the antibodies are derived from the carboxy terminus of toxin A or toxin B. In some embodiments, the fragments containing one or more epitopic regions recognized and bound by the antibodies are derived from the glucosyltransferase domain of toxin A or toxin B. In some embodiments, the fragments containing one or more epitopic regions recognized and bound by the antibodies are derived from the proteolytic domain of toxin A or toxin B. In some embodiments, the fragments containing one or more epitopic regions recognized and bound by the antibodies are derived from the hydrophobic, pore-forming domain of toxin A or toxin B. In some embodiments, the fragments containing one or more epitopic regions recognized and bound by the antibodies are derived from the receptor binding domain of toxin A. In some embodiments, the fragments containing one or more epitopic regions recognized and bound by the antibodies are derived from the receptor binding domain of toxin B. In some embodiments, the fragments containing one or more epitopic regions recognized and bound by the antibodies are derived from a region outside of the receptor binding domain of toxin A. In some embodiments, the fragments containing one or more epitopic regions recognized and bound by the antibodies are derived from the N-terminal enzymatic region of toxin B. In an embodiment, the epitope-containing fragments or portions of toxin A and/or toxin B are <300 kDa in size. In other embodiments, the epitope-containing fragments or portions of toxin A and/or toxin B are ~158-160 kDa, ~100-105 kDa, e.g., 103 kDa, ~90-95 kDa, e.g., 91 kDa, and/or ~63-68 kDa, e.g., 63 kDa or 68 kDa in size. In other embodiments, the epitope-containing fragments or portions of toxin A are ~158-160 kDa; ~90-95 kDa, e.g., 91 kDa, and/or ~63-68 kDa, e.g., 68 kDa in size. In other embodiments, the epitope-containing fragments or portions of toxin B are ~100-105 kDa, e.g., 103 kDa, and/or ~63-68 kDa, e.g., 63 kDa in size.

Such portions, fragments, or peptides of the toxins, when administered in the form of a vaccine or immunogen to a subject infected with C. difficile or afflicted with C. difficile-associated disease, may elicit a humoral response in the subject, i.e., antibodies having specificities for toxin A and/or toxin B, thereby allowing the subject to mount an immune response against the toxins and to neutralize, block, reduce, ameliorate, cure, or treat the C. difficile-associated disease, infection, or CDAD in the subject. Accordingly, another embodiment provides a method of neutralizing, blocking, reducing, ameliorating, curing, or treating C. difficile infection or a C. difficile-associated disease in a subject in need thereof, comprising administering to the subject an effective amount of the above-described vaccine or immunogen. In an embodiment, the subject elicits a humoral response to toxin A and/or toxin B of *C. difficile*, thereby neutralizing, blocking, reducing, ameliorating, curing, or treating *C. difficile*-associated disease, infection, or CDAD in the subject. In another embodiment, the subject elicits a cellular immune response to toxin A and/or toxin B of *C. difficile*. In another embodiment, the subject elicits both a humoral and a cellular immune response to toxin A and/or toxin B of *C. difficile*.

In another embodiment, the invention encompasses a method of neutralizing, inhibiting, or blocking toxin A and/or toxin B activity in or against a cell susceptible to *C. difficile* infection, comprising contacting the cell with an antibody, or antigen-binding fragment thereof, in accordance with the present invention, wherein the antibody, or antigen-binding fragment thereof, neutralizes, inhibits, or blocks the toxin A and/or toxin B activity in or against the cell by a competitive or a mixed competitive mechanism of action. In an embodiment, the antibody is one or more of a monoclonal antibody, a humanized antibody, or a chimeric antibody. In an embodiment, the cell is in a subject and the antibody, or antigen-binding fragment thereof, is administered in an effective amount to the subject. In an embodiment, the cell is within the gastrointestinal tract, e.g., an intestinal epithelial cell, of the subject. In an embodiment, the toxin is toxin A. In an embodiment, the toxin is toxin B. In an embodiment, the toxin is toxin A and the antibody's mechanism of action is a competitive inhibition mechanism of action. In an embodiment, the toxin is toxin A and the antibody, or antigen binding fragment thereof, is PA-50 (ATCC Accession No. PTA-9694), a humanized form thereof, or an antibody, or fragment thereof, which competes with PA-50 for neutralizing toxin A activity. In an embodiment, the toxin is toxin A and the antibody's mechanism of action is a mixed-competitive inhibition mechanism of action. In an embodiment, toxin is toxin A and the antibody, or antigen binding fragment thereof, is PA-39 (ATCC Accession No. PTA-9692), a humanized form thereof, or an antibody, or fragment thereof, which competes with PA-39 for neutralizing toxin A activity. In an embodiment, the toxin is toxin B and the antibody's mechanism of action is a mixed competitive inhibition mechanism of action. In an embodiment, the toxin is toxin B and the antibody, or antigen binding fragment thereof, is PA-41 (ATCC Accession No. PTA-9693), a humanized form thereof, or an antibody, or fragment thereof, which competes with PA-41 for neutralizing toxin B activity.

As used herein, the term "competitive inhibitor" of toxin refers to a toxin neutralization inhibitor, e.g., an antibody, agent, or small molecule or chemical entity, that displays a rightward $EC_{50}$ shift in the neutralization curve, without a change in the maximal percent neutralization as the concentration of toxin increases in the culture. Thus, a competitive inhibitor is typically able to overcome the toxin's cytotoxic effect by addition of more inhibitor. The term "non-competitive inhibitor" of a toxin refers to a toxin neutralization inhibitor that displays a decrease in the maximal percent neutralization without a change in concentration, producing a half-maximal response ($EC_{50}$) as the concentration of toxin increases in the culture. Thus, a non-competitive inhibitor is typically unable to overcome completely the toxin's cytotoxic effect by addition of more inhibitor. The term "mixed-competitive inhibitor" of toxin refers to a toxin neutralization inhibitor that displays some degree of both competitive and non-competitive inhibition as the concentration of toxin increases in the culture. For example, a mixed-competitive inhibitor of toxin may bind to toxin and exert its effect by blocking the binding of toxin to a cell, as well as by blocking other cytotoxic effects of the toxin; thereby exerting a mixed-competitive mechanism of action.

EXAMPLES

Example 1

Generation of Neutralizing Monoclonal Antibodies Against *C. difficile* Toxin A and/or Toxin B A. Immunogen Preparation Neutralizing monoclonal antibodies directed against toxin A and/or toxin B of *C. difficile* were generated by immunizing mice with *C. difficile* toxin A toxoid (inactive form of toxin) and with active forms of toxin A and/or toxin B. The murine mAbs (PA-38: anti-toxin A mAb, ATCC #PTA-9888; PA-39: anti-toxin A and B mAb, ATCC #PTA-9692; PA-41: anti-toxin B mAb ATCC #PTA-9693; and PA-50: anti-toxin A mAb, ATCC #PTA-9694) were generated by immunizing animals with toxoid A followed by immunizations with the active form of toxin A and/or toxin B. Toxin A toxoid, toxin A, toxin B (List Biological Laboratories Inc., Campbell, Calif.) and toxin A (Techlab Inc., Blacksburg, Va.) were stored at 4° C. until use. The toxins and toxoid were derived from strain VPI 10463, a commonly used reference strain of *C. difficile*. Quil A adjuvant (Accurate Chemical, Westbury, N.Y.) was added to the required volume of toxoid or toxin and mixed. The mixture was prepared within 60 minutes of immunizations and stored on ice until ready to immunize. For the final boost prior to fusion, the required toxin was diluted in PBS and stored on ice until used for immunization.

B. Immunization and Fusion

Thirty female BALB/c mice (Charles River Labs, Wilmington, Mass.) received two immunizing doses (for PA-50) or three immunizing doses (for PA-38, PA-39, and PA-41) of toxin A toxoid (10 μg) subcutaneously at three week intervals prior to receiving boosting immunizations with increasing doses of active toxin A or active toxin B, also at three week intervals. For PA-38, one mouse received a boosting immunization every three weeks for a total of three boosts with toxin A (List Biological Laboratories Inc.), each boost escalating in dose from 500 ng to 2 μg, and a final boost of toxin A (8 μg) three days prior to splenectomy. For PA-39 and PA-41, two mice received either three or five boosting immunizations, respectively, every three weeks with toxin B, each boost escalating in dose from 2 μg to 12.5 μg, and a final boost of toxin B (20 μg) three days prior to splenectomy. For PA-50, one mouse received a boosting immunization every three weeks for a total of four boosts with toxin A (Techlab Inc.), each boost escalating in dose from 20 ng to 2.5 μg, and a final boost of toxin A (10 μg) three days prior to splenectomy. The immunizing and boosting doses of toxoid and toxin, respectively, were administered in conjunction with adjuvant, e.g., Quil A (10 μg). Boosting with the active form of toxin A or toxin B served to identify animals that may have developed protective antibodies. Sera from the immunized animals were serially diluted and tested for neutralization of toxin A cytotoxic effect on CHO-K1 cells as described below. Animals with the highest titer of neutralizing antibodies were chosen for fusions and boosted with toxin without adjuvant.

Following boosting, the animals were sacrificed, and isolated splenocytes were fused with the Sp2/0 cell line, using standard methods. Hybridomas were suspended in selection medium, RPMI-1640, 10% FBS, 10% BM Condimed-H1 (Roche Applied Science, Indianapolis, Ind.) and beta mercaptoethanol (for PA-38 and PA-39) or Hybridoma-SFM and 10% FBS (for PA-41 and PA-50) which contained 100 μM hypoxanthine, 1 μg/ml azaserine and 16 μM thymidine for selective pressure. The hybridomas were plated into 96 well flat bottom tissue culture plates (BD Biosciences, San Jose, Calif.). The plates were incubated at 37° C. for 3 days, followed by addition of HT growth medium (the selection media without azaserine). Incubation continued for an additional 4-7 days prior to screening the hybridoma supernatants for neutralizing activity.

In the primary screen for PA-38, 608 hybridoma supernatants were tested for the ability to neutralize the cytotoxic effect of toxin A (List Laboratories) on CHO-K1 cells (ATCC#CCL-61, Manassas, Va.). In the primary screen for PA-39 and PA-41, 2416 hybridoma supernatants were tested for the ability to neutralize the cytotoxic effect of toxin B (List Laboratories) on CHO-K1 cells. In the primary screen for PA-50, 1440 hybridoma supernatants were tested for the ability to neutralize the cytotoxic effect of toxin A (Techlab Inc.) on T-84 cells. A second assay examined inhibition of toxin-mediated agglutination of rabbit erythrocytes. From the screening procedure, four mAbs, which were designated PA-38 (anti-toxin A), PA-39 (anti-toxin A/B), PA-50 (anti-toxin A) and PA-41 (anti-toxin B) and which effectively inhibited or neutralized the *C. difficile* toxins in the screening assays, were isolated. Hybridoma cell lines that produced these mAbs were cloned twice by limiting dilution to generate clonal cell lines. The PA-38, PA-39, PA-41, and PA-50 mAbs were determined to be isotype IgG2a,κ, IgG1,κ, IgG1,κ, and IgG1,κ, respectively, using IsoStrip Mouse Monoclonal Antibody Isotyping Kit (Roche Applied Science, Indianapolis, Ind.). The mAb-producing hybridoma cell lines are designated by the same name as the mAbs that they produce.

C. Screening: Neutralization of Toxin A or B Cytotoxic Effect on Cells

Hybridoma supernatants were screened for the ability to neutralize the cytotoxic effect of toxin A or toxin B on cells. A high throughput method was developed to process thousands of hybridoma supernatants at one time. The cytotoxicity assay used either CHO-K1 cells (for PA-38, PA-39 and PA-41) or T-84 cells (for PA-50). The cells were added to assay plates (96 well, white opaque wall, clear flat bottom plates; Perkin Elmer, Waltham, Mass.) using the Biomek FX robotic system (Beckman Coulter, Brea, Calif.). The assay plates were incubated for 4 hours at 37 C to allow the cells to attach to the wells. For the T-84 assay, toxin A was diluted to 240 ng/ml. For the CHO-K1 assay, toxin A was diluted to 2 μlg/ml or toxin B was diluted to 6 ng/ml. Diluted toxin was added to reagent dilution plates (96 well round bottom plates; BD, Franklin Lakes, N.J.) manually in a Biosafety Cabinet (BSC). Hybridoma supernatants were harvested manually and added to the wells of the reagent dilution plates using the Biomek FX system. The supernatant and toxin mixture was incubated at 37 C for 1 hour and added to assay plates containing the cells using the Biomek FX system. After incubating at 37 C for 72 hours, 20 μL/well CELLTITER-BLUE (Promega, Madison, Wis.) was added to each well. Plates were incubated for an additional 4hours and then read on a SpectraMax M5 Plate Reader (Molecular Devices, Sunnyvale, Calif.) using an excitation wavelength of 560 nm and an emission wavelength of 590 nm. Cell survival was compared in untreated and toxin treated cultures. Percent cell survival was plotted over concentration.

D. Production of Murine mAbs of the Invention

In vivo and in vitro production methods were used to obtain isolated and/or purified mAbs of the invention. For in vivo production of murine mAbs, ascites fluid was prepared by injecting the appropriate hybridoma cell line into the peritoneal cavity of pristane-primed BALB/c mice. The mAb was purified to >95% homogeneity by precipitation with ammonium sulfate followed by protein A chromatography. The purified antibodies were resuspended in phosphate buffered saline (PBS).

For small scale (<100 mg) in vitro production, murine mAbs were purified from hybridoma supernatants grown in culture. Hybridomas were cultured in Hybridoma-SFM (Invitrogen) and 10% FBS. Cell lines were passaged and expanded in T-150 flasks three times weekly to ensure that cell concentration did not exceed $2\times10^6$ cells/ml. Supernatants containing PA-39 (IgG1,κ), PA-41 (IgG1,κ), and PA-50 (IgG1,κ) were clarified by centrifugation at 2000 rpm for 10 minutes and filtered. Clarified material was diluted into a final concentration of running buffer (60 mM glycine/3 M NaCl, pH 8.5) and loaded onto a protein A column equilibrated with running buffer. After washing the column, the PA-39 or PA-41 mAbs were eluted with 0.1 sodium acetate, pH 5.5, and neutralized to pH 7.0. Supernatants containing PA-38 (IgG2a,κ) were clarified by centrifugation at 2000 rpm for 10 minutes and filtered. Clarified material was adjusted to a final concentration of 25 mM sodium phosphate buffer/100 mM NaCl, pH 7.0 and loaded onto a protein A column equilibrated with 50 mM sodium phosphate buffer/0.5 M NaCl. The column was washed; PA-38 mAb was eluted with 0.1 M sodium acetate, pH 3.0, and the eluted antibody was neutralized to pH 7.0.

For in vitro production of large (>100 mg) mAb quantities, hybridomas were inoculated into a WAVE Bioreactor (GE Healthcare, Piscataway, N.J.) with an initial density of $2\times10^5$ cells/ml of Hybridoma-SFM with 5% Ultra Low IgG FBS. Cell count and viability were monitored daily. By about day 6 or 7 when antibody production had plateaued, the culture was terminated. The culture was clarified and was then concentrated 10-20 fold by tangential flow filtration. The antibody was loaded on a protein A column equilibrated with 60 mM glycine 3 M NaCl at pH 8.5. The column was washed with the same buffer and the antibody was eluted with 50 mM acetate, pH 3.5. The pooled antibody was neutralized to pH 7.4 with 1 M Tris, concentrated to 10 mg/mL, and diafiltered into PBS. Purified mAbs were sterile filtered and stored at −80° C.

Example 2

Specificity and Affinity of Anti-*C difficile* Toxin A and/or Toxin B mAbs of the Invention to Toxin A and/or Toxin B A. ELISA to Determine mAb Specificity for Toxin A and/or Toxin B ELISA plates (BD Biosciences) were coated with 50 ng/well of toxin A (List Laboratories) or 25 ng/well of toxin B (List Laboratories) overnight at 4 C After washing plates with PBS− (PBS without calcium or magnesium, 0.05% TWEEN 20), wells were blocked with 200 μl of blocking buffer (PBS without calcium or magnesium, 0.1% Tween 20, 2.5% non-fat milk) for one hour at 37 C The wash step was repeated, and hybridoma supernatants or purified mAb were added for one hour at 37 C The plate was washed and incubated for one hour at 37 C with goat anti-mouse IgG-Fc, horseradish peroxidase (HRP)-conjugated (Jackson Immunoresearch, West Grove, Pa.). The plate was developed with ABTS peroxidase substrate system (KPL, Gaithersburg, Md.), with ABTS peroxidase stop solution (KPL), and read on a SpectraMax plate reader (Molecular Devices) at 405 nm.

Figure 1B:
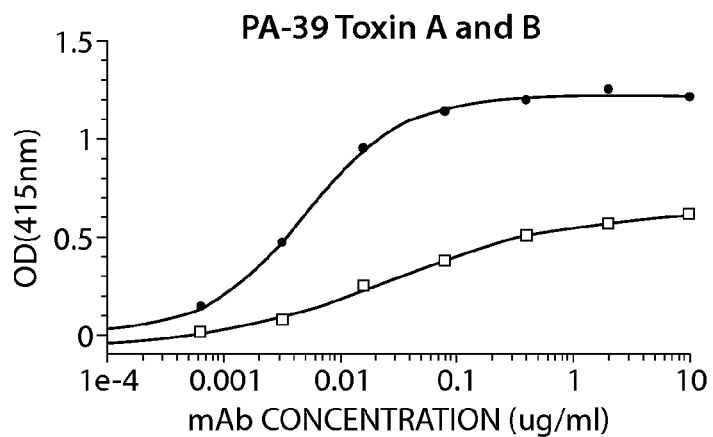
Figure 1C:
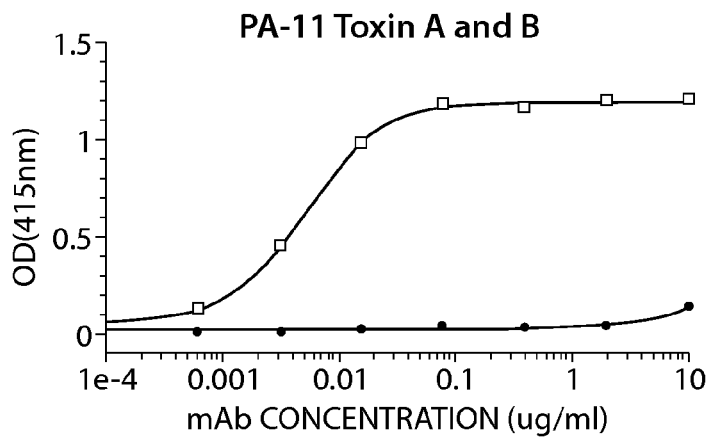
Figure 2A:
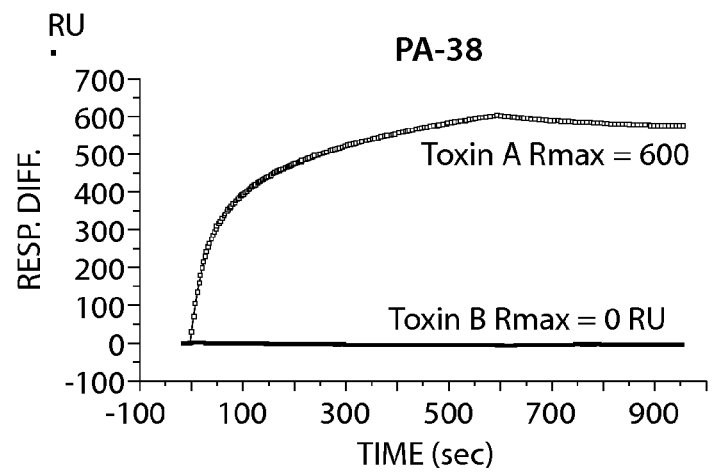
FIGS. 2A-2D provide results from Biacore binding characterization assays using murine mAbs PA-38, PA-39, PA-41 and PA-50. Binding specificity was determined using a Biacore 3000 instrument (GE Healthcare). The mAbs (PA-38 (2A), PA-39 (2B), PA-50 (2C), PA-41 (2D), or nonspecific mAb as control) were covalently immobilized onto the CM5 sensor chip (GE Healthcare) surface at approximately 10,000 resonance units (RU) according to the manufacturer's instructions for amine coupling. Binding experiments were performed at 25° C. in PBS. Purified toxin A or toxin B (List Biological Laboratories) at 30 nM was passed over control (nonspecific mAb) and test flow cells at a flow rate of 5 µL/min with an association phase (600 s for PA-38, PA-39 and PA-41; and 300 s for PA-50) and a dissociation phase (300 s for PA-38, PA-39 and PA-41; and 600 s for PA-50). Graphs are presented in RU over time.
Figure 2B:
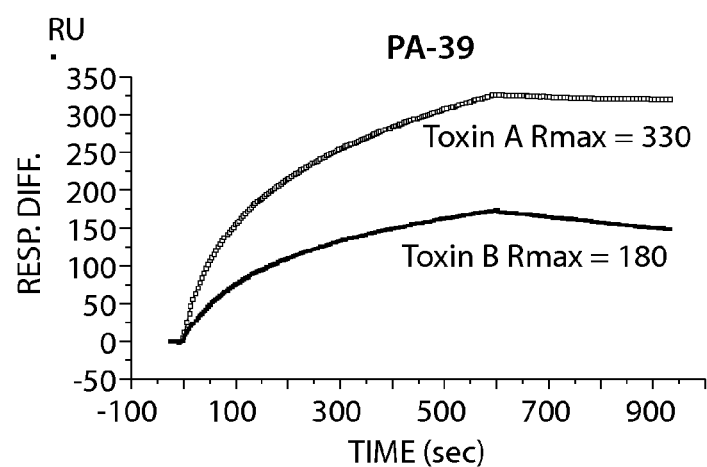
Figure 2C:
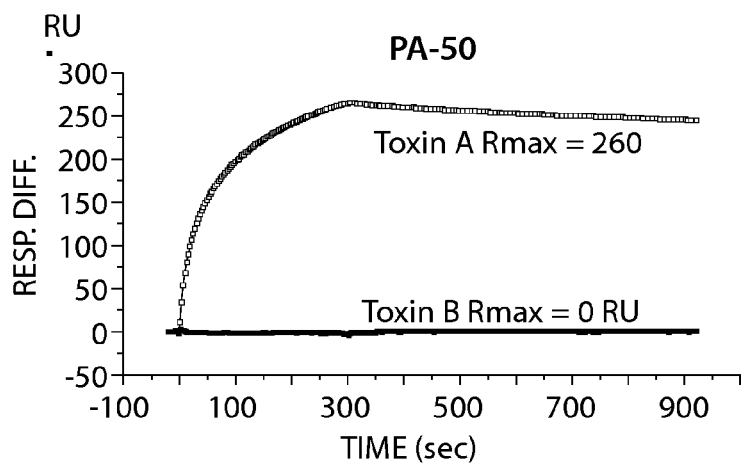
Figure 2D:
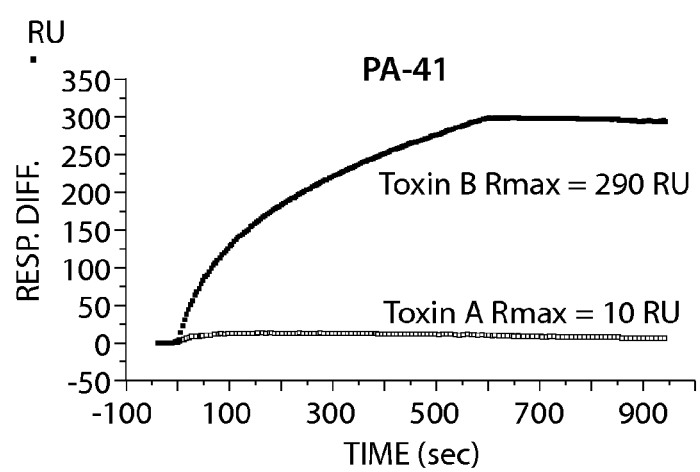
Figure 3A:
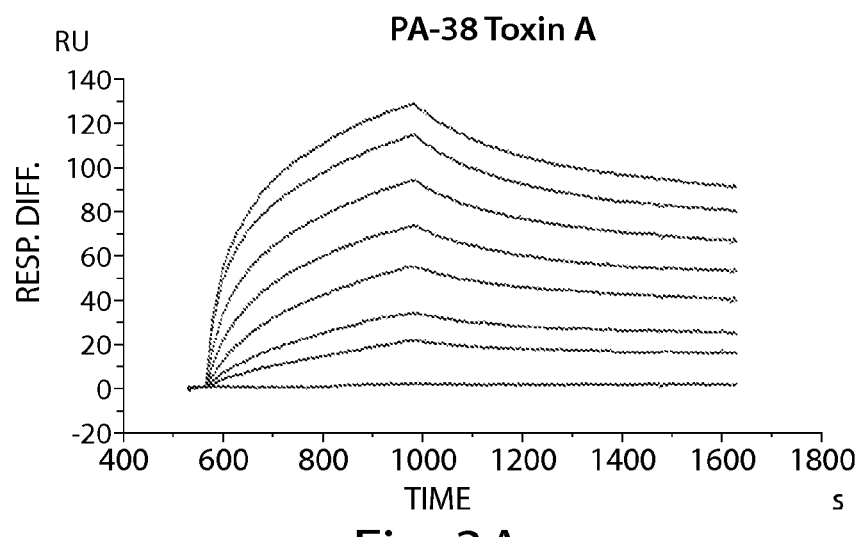
FIGS. 3A-3E and 3F-3H show the results of antibody-toxin binding kinetics as determined by Biacore. For FIGS. 3A-3E, murine mAbs were captured using a CM5 sensor chip prepared with Biacore's mouse antibody capture kit. Toxin was then passed through the flow cells at varying concentrations (0.4-100 nM, two-fold escalation) at a flow rate of 30 µL/min. All mAb concentrations were tested in duplicate and the chip surface was regenerated after each run using the conditions specified in the kit. The changes in RU were recorded and analyzed using the Bia Evaluation Software 1:1 (Langmuir) binding model which calculated the $K_D$ of the mAb for the toxin.
Figure 3B:
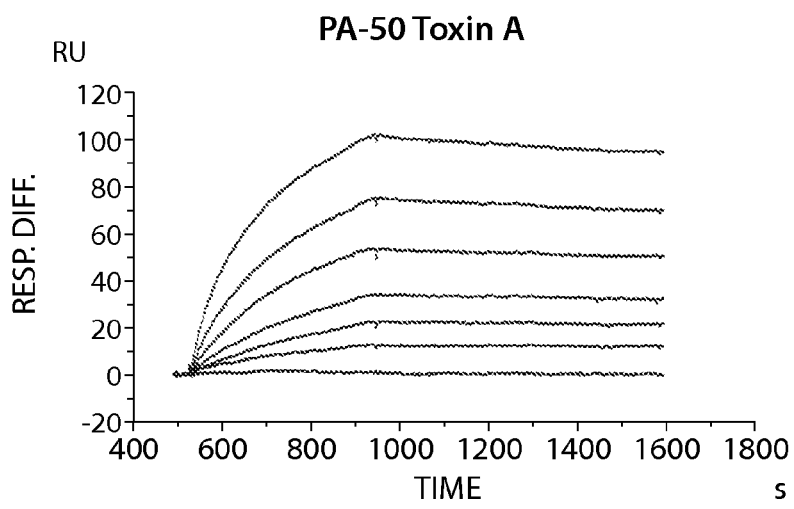
Figure 3C:
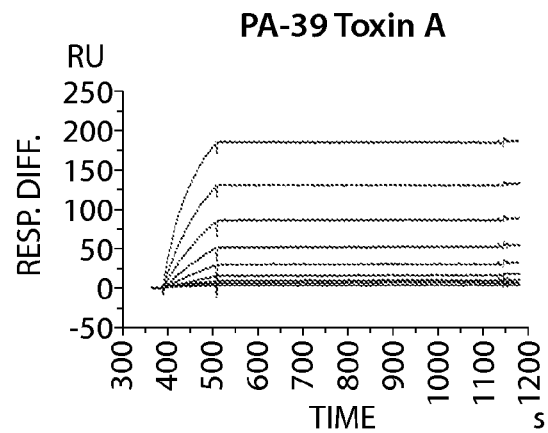
Figure 3D:
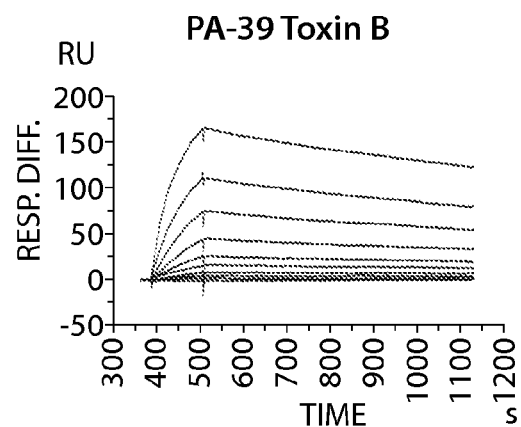
Figure 3E:
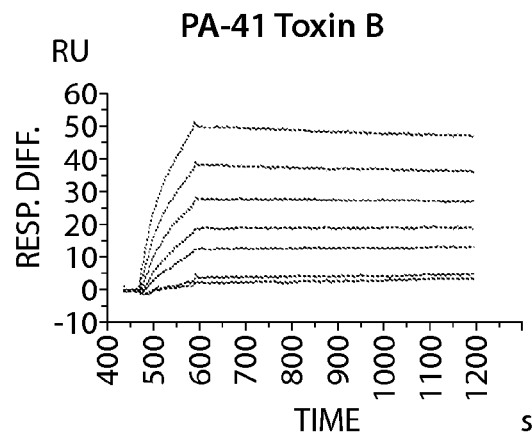
Figure 3F:
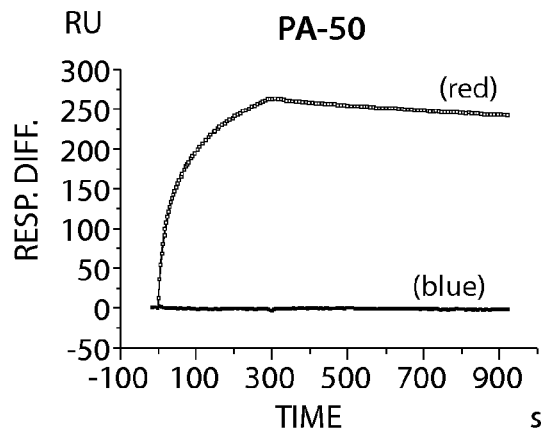
Figure 3G:
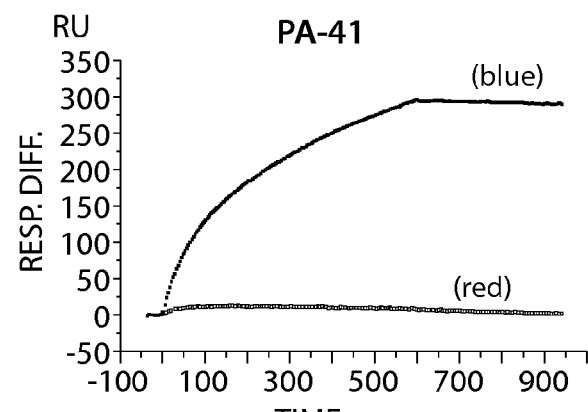
Figure 3H:
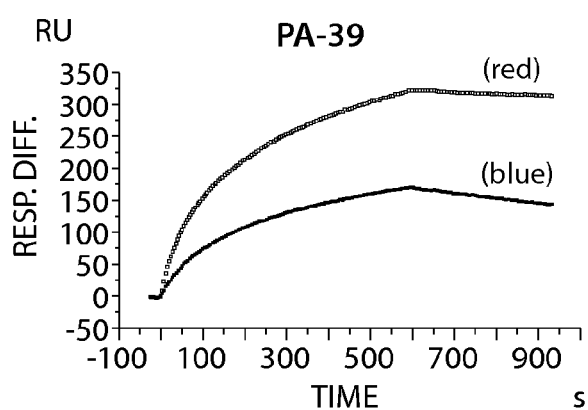

Titration data are shown in FIGS. 1A-C. FIG. 1A demonstrates that PA-38 binds to toxin A and not to toxin B. FIG. 1B demonstrates that PA-39 can bind to both toxin A and toxin B. FIG. 1C demonstrates that PA-41 binds to toxin B and not to toxin A.

B. Reactivity of mAbs to Toxin A and B in Biacore

A Biacore 3000 instrument (GE Healthcare) was used to determine the binding specificity of mAbs of the invention to toxin A and/or toxin B. MAbs were immobilized at approximately 10,000 resonance units (RU) to CM5 sensor chips (GE Healthcare) according to the manufacturer's instructions for amine coupling. A reference surface of isotype-matched antibody of irrelevant specificity (Southern Biotech) was used as a control. Binding experiments were performed at 25° C. in HEPES-based HPS-EP buffer (GE Healthcare). Purified toxin A or toxin B (30 nM; List Biological Laboratories) was passed over control and test flow cells at a rate of 5 μL/min. Where indicated, additional mAb (100 nM) was then passed over the flow cell at 5 μL/min to examine multivalent or competitive binding.

As shown in FIGS. 2A-D, mAb PA-38 (FIG. 2A) and mAb PA-50 (FIG. 2C) specifically bound to toxin A; mAb PA-41 (FIG. 2D) specifically bound to toxin B; and mAb PA-39 (FIG. 2B) bound preferentially to toxin A, but also demonstrated binding to toxin B. Results from these data are consistent with the ELISA data (FIGS. 1A-C) and demonstrate the binding specificities of mAbs of the invention to toxin A and/or toxin B.

C. Binding Affinity

Biacore analysis was also used to determine the binding avidity of mAbs of the invention to their respective toxins. The mAb was captured using a CM5 sensor chip prepared with Biacore's mouse antibody capture kit. Toxin was then passed through the flow cells at varying concentrations (0.4-100 nM, two-fold escalation). All toxin concentrations were tested in duplicate and the chip surface was regenerated after each run using the conditions specified in the kits. The changes in RU were recorded and analyzed using Bia Evaluation Software 1:1 (Langmuir) binding model which calculated the $K_D$ of the mAb for the toxin. The association and dissociation data and the fitting are illustrated in FIGS. 3A-E.

The $K_D$ of the mAbs for toxin A was determined by Biacore analysis to be 1.0 nM for PA-38, 0.16 nM for PA-39, and 0.16 nM for PA-50. The $K_D$ of the mAbs for toxin B was determined to be 2.4 nM for PA-39 and 0.59 nM for PA-41. These results demonstrated that mAbs of the invention bound toxin A and/or toxin B with nanomolar and subnanomolar affinities.

Example 3

In vitro Cell-based Neutralization Assays

Cell-based cytotoxicity assays employing either CHO-K1 cells or T-84 cells were used to evaluate neutralization activities of the described anti-toxin A and anti-toxin B mAbs.

A. Neutralization of Toxin A Cytotoxic Effect on CHO-K1 Cells

Figure 4:
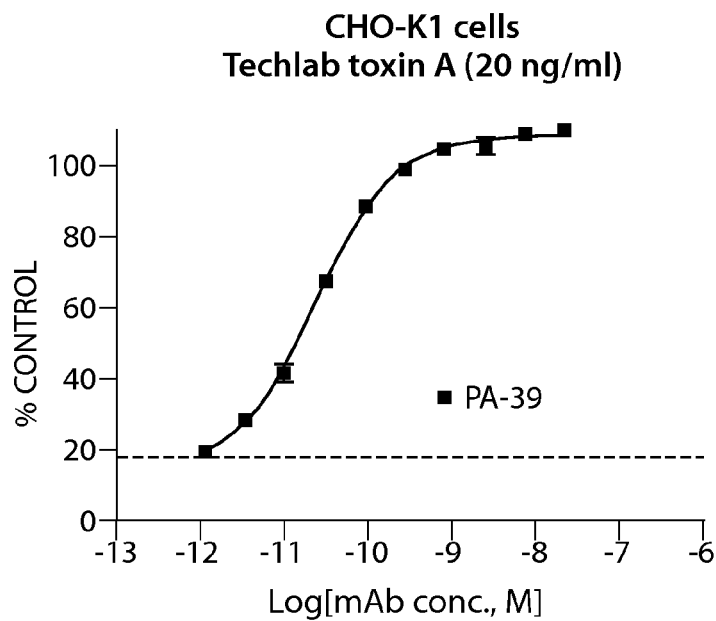
FIG. 4 demonstrates the in vitro neutralization activity of toxin A activity using purified murine mAb PA-39 on CHO-K1 cells. For cytotoxicity measurements, toxin A was incubated with varying concentrations of PA-39 for 1 hour at 37 C (Example 3A). The mA-toxin mixtures were then added to CHO-K1 cells plated in 96-well plates at 2,000 cells/well and incubated for 72 hours. Cell survival was compared in treated and untreated cultures and the concentration of mAbs required for 50% neutralization of cytotoxicity ($EC_{50}$) was calculated. Cell viability was determined via CELLTITER-BLUE; raw data were normalized to untreated control wells. The values were plotted using Prism and curves were calculated using a sigmoidal dose response (variable slope) model. The curve was then used to determine mAb $EC_{50}$. The data points represent the average of three wells on the same plate.

CHO-K1 cells were seeded (2,000 cells in 50 μL/well) in assay plates (96 well, white opaque wall, clear flat bottom plates (Perkin Elmer)). Cells were allowed to attach for 4 hours prior to treatment. Equal volumes (35 μL) of 2 μg/mL toxin A (List Biological Laboratories) and serially diluted mAbs were mixed in reagent dilution plates (96-well round bottom plates (Falcon)) for 1 hour at 37 C, and then 50 μl of the mixture was added to each well of the plates. After incubating for 72 hours, 20 μL/well CELLTITER-BLUE (Promega) was added to each well. Plates were incubated for an additional 4 hours, then read on a SpectraMax M5 Plate Reader (Molecular Devices) using an excitation wavelength of 560 nm and an emission wavelength of 590 nm. Cell survival was compared in untreated and toxin treated cultures. Percent cell survival was plotted over concentration of mAb Inhibition data were fit to non-linear regression, sigmoidal dose-response curve using GraphPad Prism software, and the concentration of mAb required for 50% neutralization of cytotoxicity ($EC_{50}$) was calculated. As shown in FIG. 4, mAb PA-39 fully neutralized toxin A activity on CHO-K1 cells with an $EC_{50}$ of 93 pM.

B. Neutralization of Toxin B Cytotoxic Effect on CHO-K1 Cells

Figure 5:
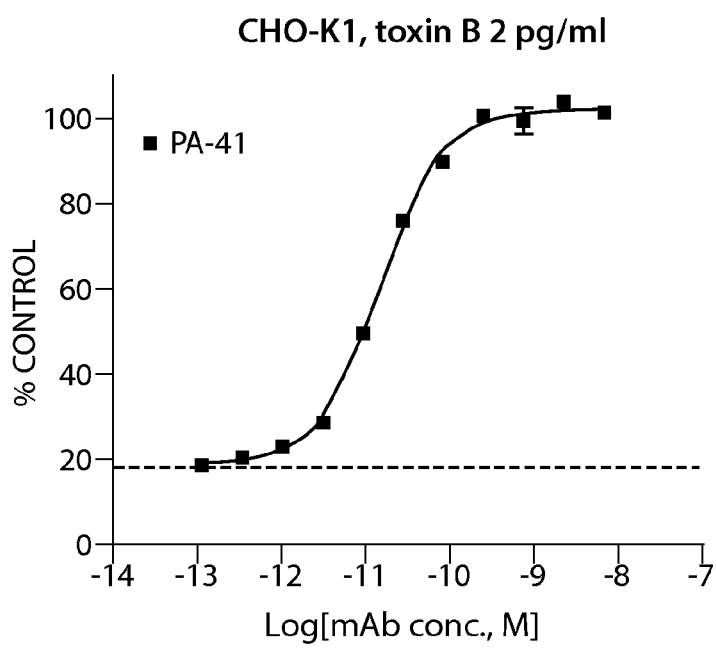
FIG. 5 demonstrates the in vitro neutralization activity of toxin B activity using purified murine mAb PA-41 on CHO-K1 cells. For cytotoxicity measurements, toxin B was incubated with varying concentrations of PA-41 for 1 hour at 37 C (Example 3B). The mAb-toxin mixtures were then added to CHO-K1 cells plated in 96-well plates at 2,000 cells/well and incubated for 72 hours. Cell survival was compared in treated and untreated cultures and the concentration of mAbs required for 50% neutralization of cytotoxicity ($EC_{50}$) was calculated. Cell viability was determined via CELLTITER-BLUE; raw data were normalized to untreated control wells. The values were plotted using Prism and curves were calculated using a sigmoidal dose response (variable slope) model. The curve was then used to determine mAB $EC_{50}$. The data points represent the average of three wells on the same plate.

A CHO-K1 cytotoxicity assay was used to evaluate the neutralization activity of anti-toxin B specific mAbs. Similar to the evaluation of anti-toxin A mAbs, toxin B (8 pg/mL, TechLab) was incubated for 1 hr at 37 C with serially diluted mAbs prior to addition to CHO-K1 (2,000 cells/well) in a 96-well plate. After 72 hours, 20 μL/well CELLTITER-BLUE (Promega) was added to each well. Plates were incubated for an additional 4 hours, and then read on a SpectraMax M5 Plate Reader (Molecular Devices) using an excitation wavelength of 560 nm and an emission wavelength of 590 nm. Cell viability was determined using CELLTITER-BLUE; cell survival was compared between treated and untreated cultures. Inhibition data were fit to non-linear regression, sigmoidal dose-response curve using GraphPad Prism software, and the concentration of mAb required for 50% neutralization of cytotoxicity ($EC_{50}$) was 20 calculated. As shown in FIG. 5, PA-41 demonstrated a high degree of activity (an $EC_{50}$ of 9.2 pM) in neutralizing toxin B cytotoxicity on CHO-K1 cells.

Although mAb PA-39 demonstrated binding to toxin B based on ELISA and Biacore analyses, this mAb did not have in vitro activity against toxin B in CHO-K1 and other cell-based assays. Antibodies that bind to both toxin A and toxin B but have no functional activity in neutralizing toxin A or toxin B in in vitro cell-based assays have been reported (46, 92 and 93). The present invention encompasses a novel mAb having the dual ability to bind both toxin A and toxin B and also to neutralize the cytotoxicity of a *C. difficile* toxin, i.e., toxin A.

C. Neutralization of Toxin A Cytotoxic Effect on T-84 Cells

Figure 6:
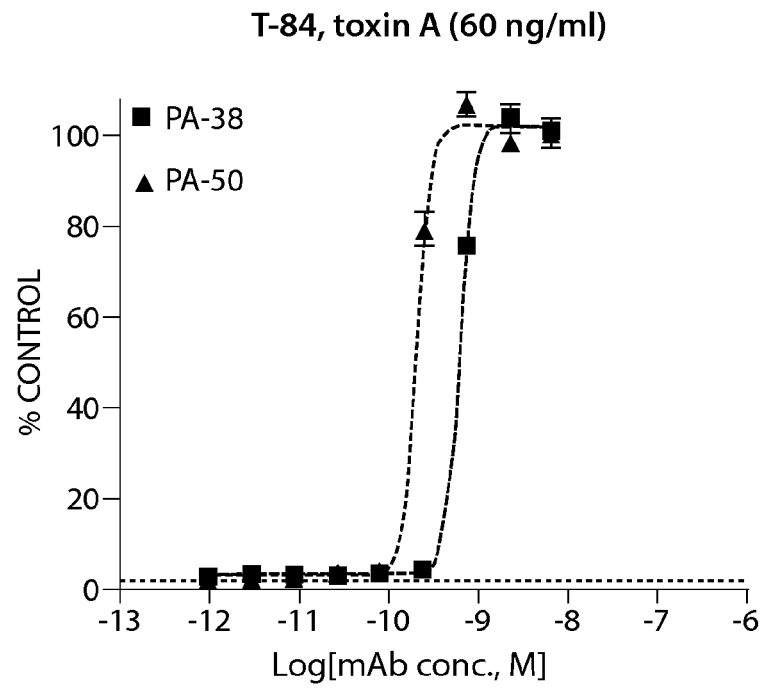
FIG. 6 demonstrates the in vitro neutralization activity of toxin A activity using purified murine mAbs PA-38 and PA-50 on T-84 cells. (Example 3C). T-84 cells were seeded (15,000 cells/well) in 96 well plates and treated with a combination of titrated mAb (PA-38 (■) or PA-50 (▲)) and toxin A (60 ng/ml). After incubation (72 hours), cell survival was compared in treated and untreated cultures and the concentration of mAbs required for 50% neutralization of cytotoxicity ($EC_{50}$) was calculated. Cell viability was determined via CELLTITER-BLUE; raw data were normalized to untreated control wells. The values were plotted using Prism and curves were calculated using a sigmoidal dose response (variable slope) model. The curve was then used to determine mAb $EC_{50}$. The data points represent the average of three wells on the same plate.

A T-84 cytotoxicity assay was used to evaluate the neutralization activity of the described anti-toxin A mAbs. T-84 cells were seeded (15,000 cells in 50 μL/well) in assay plates (96 well, white opaque wall, clear flat bottom plates (Perkin Elmer)). Cells were allowed to attach for 4 hours prior to treatment. Equal volumes (35 μL) of 240 ng/mL toxin A (Techlab) and serially diluted mAbs were mixed in reagent dilution plates (96-well round bottom plates (Falcon)) for 1 hour at 37 C, and then 50 μl of mixture was added to each well of the assay plates. After incubating for 72 hours, 20 μl/well CELLTITER-BLUE (Promega) was added to each well. Plates were incubated for an additional 4 hours, then read on a SpectraMax M5 Plate Reader (Molecular Devices) using an excitation wavelength of 560 nm and an emission wavelength of 590 nm. Cell survival was compared in untreated and toxin treated cultures. Inhibition data were fit to non-linear regression, sigmoidal dose-response curve using GraphPad Prism software, and the concentration of mAb required for 50% neutralization of cytotoxicity ($EC_{50}$) was calculated. As shown in FIG. 6, mAbs PA-38 and PA-50 fully neutralized toxin A activity on T-84 cells with an $EC_{50}$ of 175 pM and 146 pM, respectively. In the T-84 cell assay, mAb PA-39 demonstrated minimal activity against toxin A and PA-41 was not active.

D. Rabbit Red Blood Cell (RBC) Hemagglutination

Figure 7:
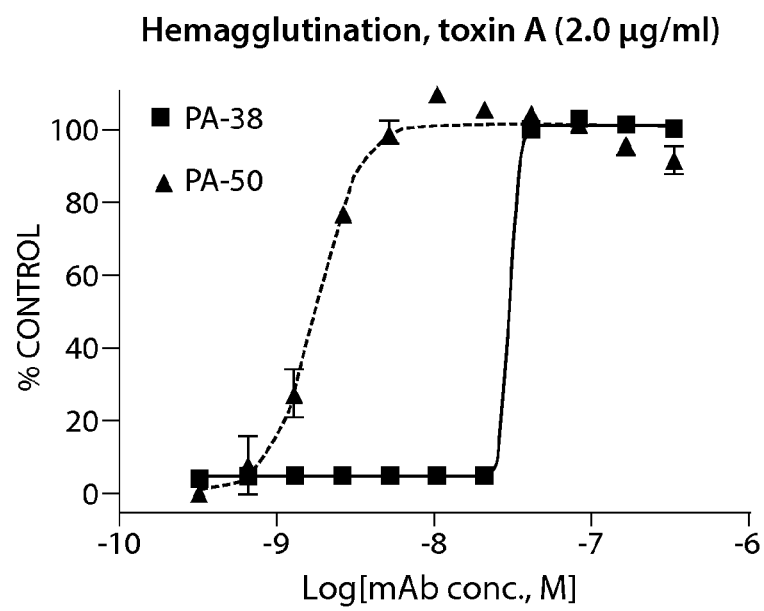
FIG. 7 demonstrates the results of testing murine mAbs PA-38 (■) or PA-50 (▲) for their ability to block or prevent toxin A induced hemagglutination of rabbit red blood cells (RBCs). Toxin A (2 µg/ml) was combined with various dilutions of PA-38 or PA-50 and the mixture was added to plates containing 50 µL rabbit erythrocytes. Plates were incubated at 4° C. for 4 hours. Hemagglutination was quantified as color intensity using ImageQuant 400 (GE Healthcare) dot array analysis. The data were rendered as % control, with 100% representing no hemagglutination. The data points represent the average of three wells assayed on the same plate.

The ability of mAbs of the invention to block the binding of toxin A to cellular receptors was assessed using a hemagglutination assay. For this assay, equal volumes (30 μL/well) of toxin A (8 μg/mL; TechLab) and serially-diluted mAbs were mixed in reagent dilution plates (96-well round bottom plates (Falcon)) for 1 hour at 4° C. Rabbit red blood cells (RBC), (Colorado Serum Co., Denver, Colo.) were washed with PBS three times and resuspended in PBS. 60 µL of a 1% RBC suspension were added into the wells of 96-well plates containing the toxin A-mAb mixture, and the plates were incubated at 4° C. for 4 hours. Free toxin A causes hemagglutination of RBC. Accordingly, the addition of anti-toxin A mAb that binds to toxin A is expected to prevent hemagglutination. The extent of hemagglutination was determined using an ImageQuant 400 instrument; complete hemagglutination yielded a stronger signal compared with RBC in suspension. $EC_{50}$ values were calculated from the inhibition data using GraphPad Prism non-linear regression, sigmoidal dose-response curve fitting. As shown in FIG. 7, mAb PA-38 (filled squares) and mAb PA-50 (filled triangles) fully neutralized toxin A activity on RBC with an $EC_{50}$ of 30 nM and 1.8 nM, respectively. PA-38 and PA-50 appear to neutralize toxin A by blocking the binding of toxin A to its receptor. mAbs PA-39 and PA-41 were found to be inactive in the assay.

E. Caco-2 Monolayer Assay

Figure 8:
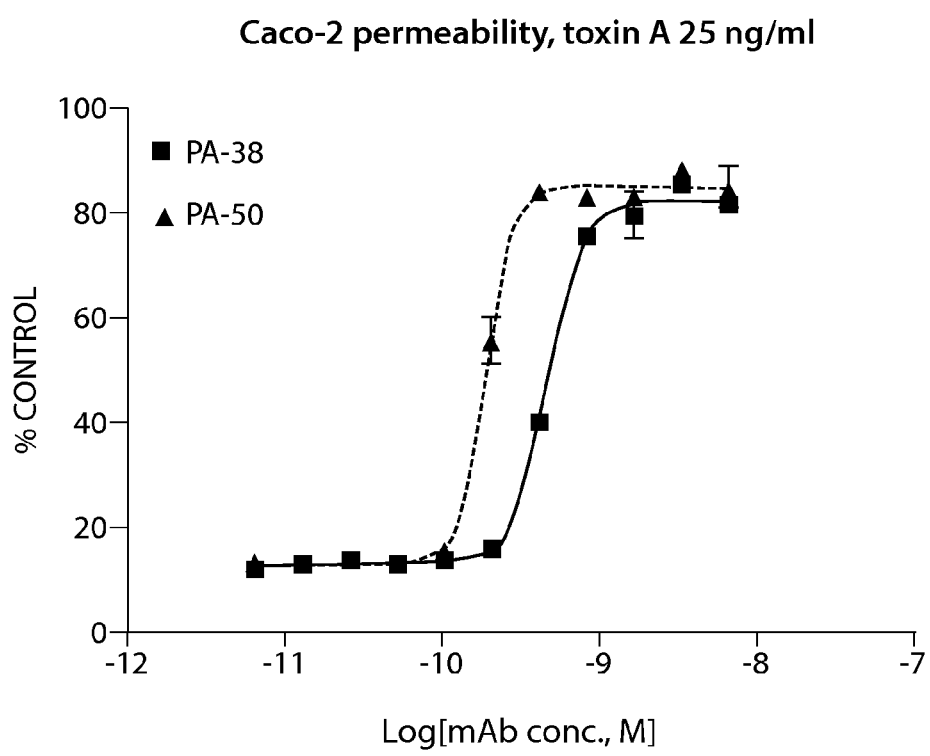
FIG. 8 demonstrates the activity of anti-*C. difficile* toxin mAbs of the invention in preventing disruption of a Caco-2 cell monolayer by toxin A. Caco-2 cells were seeded (25,000 cells/well) in the upper chamber of a 96-well Multiscreen Caco-2 Assay plate (Millipore). After an incubation of 10-14 days, the formation of a tight monolayer was confirmed by measuring transepithelial electrical resistance (TEER) using an epithelial voltohmmeter (World Precision Instruments). After the integrity of the monolayer was established and determined, toxin A (25 ng/mL) and serially-diluted murine mAbs (PA-38 (■) or PA-50 (▲)) were added to the upper chamber of the assay plate. The plates were incubated for 18-24 hours, and the TEER value was measured using the voltohmmeter. Monolayer integrity was compared in untreated and toxin treated wells. Inhibition data were fit to a non-linear regression, sigmoidal dose-response curve using GraphPad Prism software in order to determine the concentration of mAb required for 50% toxin inhibition ($EC_{50}$).

Caco-2 cells were seeded (25,000 cells in 75 µL/well) in the upper chamber of 96-well Multiscreen Caco-2 plates (Millipore Billerica, Mass.) with 250 µL of media added to the lower chamber. Cells were allowed to grow for 10 days with regular changes of medium every 3-4 days. After an incubation of 10-14 days, the formation of a tight monolayer was confirmed by measuring transepithelial electrical resistance (TEER) using an epithelial voltohmmeter (model: EVOMX, World Precision Instruments, Sarasota, Fla.). After the integrity of the monolayer was established and determined, equal volumes (60 µl) of toxin A (at 50 ng/ml) and serially-diluted mAb were mixed for 1 hour at 37° C. and then were added to the upper chamber of the assay plate. The plates were incubated for 18-24 hours, and then the TEER value was measured using the voltohmmeter. Monolayer integrity was compared in untreated and toxin treated wells. As shown in FIG. 8, inhibition data were fit to a non-linear regression, sigmoidal dose-response curve using GraphPad Prism software to determine the concentration of mAb required for 50% neutralization ($EC_{50}$). mAbs PA-38 and PA-50 neutralized the disruption of Caco-2 monolayers by toxin A with an $EC_{50}$ of 485 µM and 196 µM, respectively. The other mAbs were found to be inactive in this assay.

While not wishing to be bound by theory, the cell-based, in vitro results demonstrate that PA-38 and PA-50 appear to represent one class of anti-toxin A mAbs, while PA-39 represents another class of anti-toxin A mAbs. mAbs PA-38 and PA-50 appear to bind a toxin A epitope important for receptor binding; mAb PA-39 appears to bind toxin in a manner that more directly blocks the cytotoxic effects of toxin A in vitro.

Example 4

Evaluation of the in vivo Efficacy of Anti-*C. difficile* Toxin A and Toxin B mAbs of the Invention in Mice An in vivo mouse model was used to measure the ability of the mAbs described herein to neutralize circulating *C. difficile* toxins in an animal. The in vivo neutralizing activities of mAbs PA-38, PA-39, PA-41, or PA-50, administered alone or in combinations, were tested against the effects of combined, systemic *C. difficile* toxin A and toxin B (Techlab) in test animals.

Female Swiss Webster 4-6 mice/group (age: ~6-8 weeks at start of study; Charles River Laboratories) were used in the experiments. The mice were acclimated in the facility for a minimum of 4 days, and the health of the animals was checked before use. Animal experiments were conducted under IACUC approved protocol.

Initial experiments were performed to determine the toxicity of toxin A and toxin B in mice. Animals were dosed at 0, 20, 100, 500, 2500 ng toxin/animal intraperitoneally (i.p.) and a dose that was lethal to animals was selected for use in subsequent antibody neutralization experiments. The control mice injected with PBS were unaffected. A dose of 100 ng of toxin A (TechLab) was selected for the neutralization experiments, as it was the lowest dose level found to be lethal to 100% of the mice within 24 hours after the injection. Similarly, a dose of 100 ng of toxin B (TechLab) was selected for neutralization experiments, as it was the lowest dose level found to be lethal to 100% of the mice within 24 hours after the injection.

To evaluate the neutralization activity of the anti-toxin mAbs, a single injection of each mAb at different dose levels was administered i.p. to the mice (5 per group) on Day 0, followed by i.p. administration of 100 ng/200 µl of toxin A or toxin B on Day 1. Animals were observed daily for three days and then weekly for up to 21 days following toxin administration. Survival of animals was the primary endpoint of the study.

For the neutralization experiments, all doses of antibody were formulated in PBS without calcium or magnesium (PBS–, Invitrogen, Carlsbad, Calif.). A single injection of mAb PA-38, PA-39, PA-41, or PA-50 at different dose levels was administered i.p. (200 µl/dose/animal) to mice at Day 0, followed by toxin injection (i.p. at a site different from the antibody injection site) on Day 1. The health status of the animals was monitored daily for the first 3-4 days and then twice weekly for up to 21 days following toxin administration. Cage-side observations of the animals (e.g., hunched posturing, matted fur, inactive) were recorded, as well as survival.

Figure 9A:
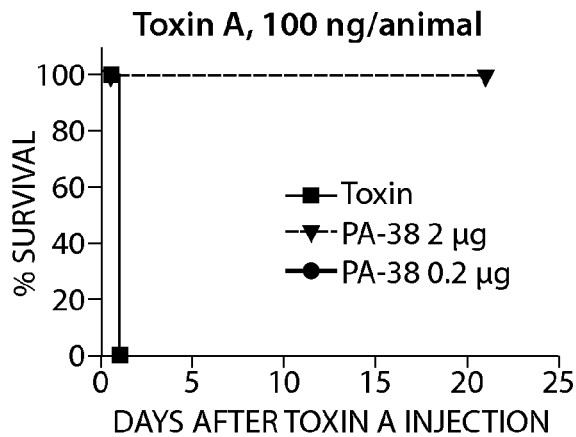
FIGS. 9A-9C demonstrate the ability of the anti-toxin A mAbs PA-38 (9A) and PA-50 (9B) to neutralize toxin A activity in vivo. Female Swiss Webster mice (6-8-weeks old, 5 mice/group) were injected (i.p.) with murine mAb PA-38 or murine mAb PA-50 in the amounts indicated, or with PBS (200 µl) on Day 0. The neutralization activity of a comparator anti-toxin A monoclonal antibody, referred to herein as CDA-1, was evaluated in the antibody amounts indicated (9C). The anti-toxin A comparator mAb CDA-1 was produced by synthesizing (DNA2.0) nucleic acids encoding heavy and light chain variable regions of 3D8 (WO2006/121422 and US2005/0287150), which were cloned into full-length human IgG1 expression vectors (pCON-gamma1 and pCON-kappa). The CDA-1 comparator mAb was expressed and produced in CHO-KSV1 cells and purified as described in the Examples section herein. The mice were then injected with 100 ng of toxin A (200 µl) on Day 1 and monitored daily for the first 72 hours and weekly thereafter. The results show that both the PA-38 and PA-50 mAbs are able to fully inhibit toxin A-associated toxicity after a single dose of 2 µg of mAb/animal, while the comparator CDA-1 mAb (5 µg/animal) failed to fully inhibit *C. difficile* toxin A-associated toxicity.
Figure 9B:
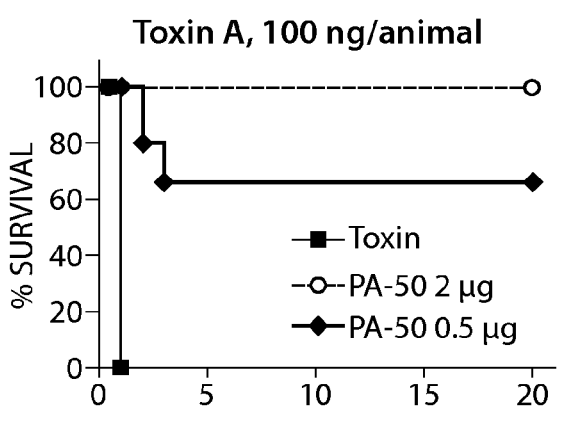
Figure 9C:
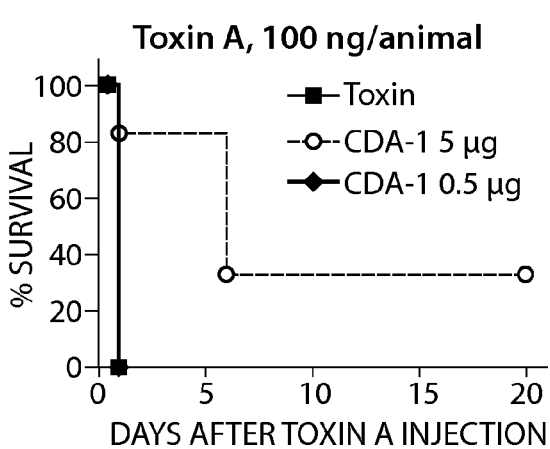
Figure 10:
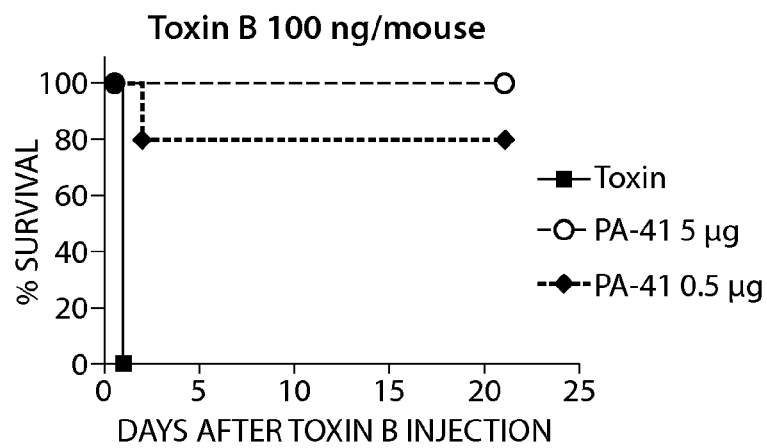
FIG. 10 demonstrates the ability of mAb PA-41 to neutralize toxin B activity in vivo. Female Swiss Webster mice (6-8-weeks old, 5 mice/group) were injected (i.p.) with either murine mAb PA-41 in the amounts indicated or with PBS (200 µl) on Day 0. The mice were then injected with 100 ng of toxin B (200 µl) on Day 1 and monitored daily for the first 72 hours and weekly thereafter. The results of this experiment show that the PA-41 mAb completely inhibits C. difficile toxin B-associated toxicity after a single dose of 5 µg of mAb/animal. A similar experiment was performed using a comparator anti-toxin B monoclonal antibody, referred to as CDB-1 comparator mAb herein. The anti-toxin B comparator mAb CDB-1 was produced by synthesizing (DNA2.0) nucleic acids encoding heavy and light chain variable regions of 124 (WO2006/121422 and US2005/0287150), which were cloned into full-length human IgG1 expression vectors (pCON-gamma1 and pCON-kappa). The CDB-1 comparator mAb was expressed and produced in CHO-KSV1 cells and purified as described in the Examples section herein. The results of these experiments showed no toxin B neutralization activity by the comparator CDB-1 mAb, even in an amount of 250 µg.

Different dose levels of PA-38 (0.2 µg to 250 µg per animal) and PA-50 (0.2 µg to 100 µg per animal) were evaluated. In this model, PA-38 and PA-50 were found to neutralize a 100 ng dose of toxin A and enabled 100% survival at dose levels as low as 2 µg of mAb per animal as shown in FIGS. 9A and B. By contrast, a comparator human anti-toxin A monoclonal antibody (WO/2006/121422 and US2005/0287150), referred to herein as CDA-1 comparator mAb, at 5 µg per animal, did not protect animals from toxin-related death as did mAbs of the invention (FIG. 9C). Doses of PA-41 ranging from 0.5 µg to 250 µg were evaluated, and a single dose of 5 µg of mAb per animal was found to neutralize completely a 100 ng dose of toxin B toxicity in animals as shown in FIG. 10. MAb PA-39 (100 µg per animal) was not observed to provide a delay of toxin-related death of the mice for either toxin A or B.

Figure 11:
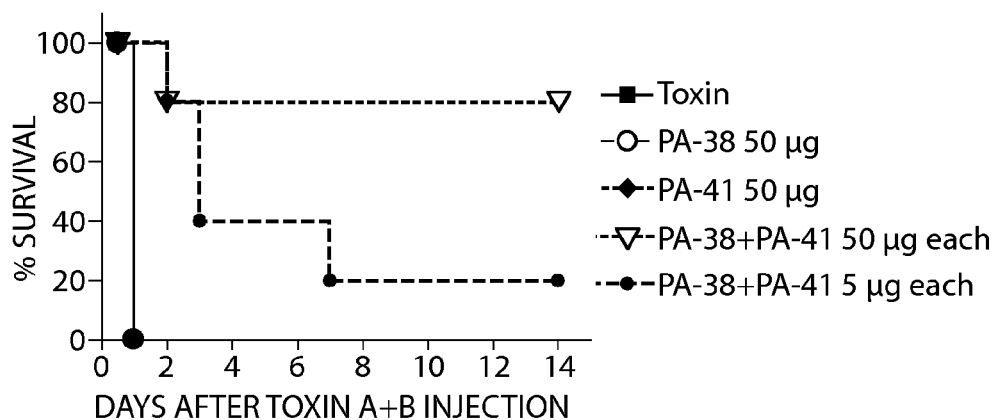
FIG. 11 demonstrates the ability of a combination of murine mAbs PA-38 and PA-41 (PA-38+PA-41) of the invention to neutralize toxin A and toxin B activity in vivo. Female Swiss Webster mice (6-8-weeks old, 5 mice/group) were injected (i.p.) with the PA-38+PA-41 mAb combination or with PBS (200 µl) on Day 0. The mice were then injected with 100 ng of a combination of toxin A and toxin B (200 µl) on Day 1 and were monitored daily for the first 72 hours and weekly thereafter. The plots for toxin, PA-38 alone (open circles) and PA-41 alone (filled diamonds) overlap in the graph. The results show that neither the PA-38 mAb (open circles) nor the PA-41 mAb (filled diamonds) alone was sufficient to inhibit the effects of both toxins and did not protect animals against C. difficile infection. In contrast, the combination of PA-38 and PA-41 (PA-38+PA-41) at 50 µg each (open, inverted triangles) was able to protect the infected animals and to prevent toxin-related death in 4 out of 5 test animals. The combination of PA-38 and PA-41 (PA-38+PA-41) at 5 µg each (filled circles) provided some protection against toxicity of C. difficile toxin A and toxin B in infected test animals.

After the neutralization activity of individual antibodies against toxin A (PA-38, PA-50) or against toxin B (PA-41) was clearly demonstrated in vivo, an experiment was conducted to test the combination of mAbs (PA-38+PA-41) at dose levels of 5 and 50 µg of each mAb against a combined lethal dose of toxins (100 ng of toxin A and 100 ng of toxin B) in the same in vivo mouse model. In addition, the individual monoclonal antibodies were included as controls. As shown in FIG. 11, a combination of PA-38 and PA-41 mAbs showed protection from the toxin combination at both 50 µg/animal (4 of 5 survived) and 5 µg/animal (1 of 5 survived) compared with the activity of each mAb alone (all animals died within 24 hours of toxin administration).

Example 5

Evaluation of Anti-*C. difficile* Toxin A and Toxin B mAbs of the Invention in the *C. difficile*-associated Diarrhea (CDAD) Model in Golden Syrian Hamsters The CDAD model in hamsters reproduces the key aspects of CDAD disease in humans. Upon treatment with antibiotics, normal colonic flora is eradicated and the hamsters become readily susceptible to infection by *C. difficile*. Infection results in severe diarrhea, pseudomembranous colitis and death. The hamster CDAD model was utilized to evaluate the potential efficacy of mAbs of the invention to prevent disease and death associated with challenge of animals from live *C. difficile* bacteria. These experiments were conducted under IACUC approved protocols.

A. Pharmacokinetic Analysis

Before conducting the efficacy study in the hamster model using hamsters infected with live *C. difficile* microorganisms, a pharmacokinetic study was performed in normal, uninfected hamsters. Golden Syrian hamsters (Harlan) were injected intraperitoneally with 0.2 mg/animal, or 1 mg/animal of purified mAb PA-38 or mAb PA-41. Blood samples were collected by retro-orbital or cardiac puncture (terminal) bleeding techniques at 0.125, 0.25, 1, 2, 4, 7, 10, 14, and 21 days. The blood samples were centrifuged at 8000 rpm for 10 minutes to obtain sera.

The mAb concentration in the sera was determined via ELISA. Ninety-six well ELISA plates (BD Biosciences) were coated overnight with toxin A (Techlab) or toxin B (Techlab) at 250 ng/well at 4 C. Plates were washed three times with PBS/0.05% TWEEN-20® (PBS-T) and blocked with 200 µl of blocking buffer (PBS without calcium or magnesium, 0.1% TWEEN 20®, 2.5% non-fat milk) for one hour at room temperature. The antibody reference standard (purified mAb PA-38 or mAb PA-41) was diluted in 1% pooled naive hamster serum to generate a standard curve with a range of 0.3-1000 ng/ml. Diluted test samples and standards were incubated for one hour at room temperature.

Figure 12A:
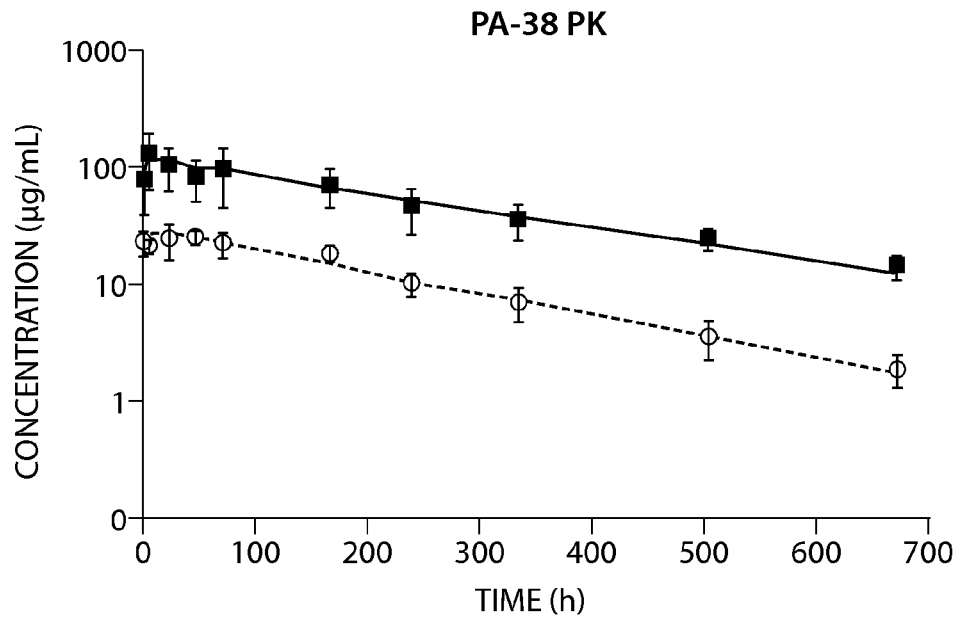
FIGS. 12A and 12B demonstrate pharmacokinetic (PK) results in hamsters for murine mAbs PA-38 and PA-41. Hamsters were dosed i.p. with 2 mg/kg (○) or 10 mg/kg (■) of mAb PA-38 (12A) or PA41 (12B). Animals were bled at set intervals and serum was analyzed using an ELISA with toxin coated plates and goat anti-mouse IgG, HRP conjugated for detection. The resulting curves illustrate the dose dependent response in the 2 mg/kg and 10/mg/kg cohorts for each antibody. WinNonLin analysis was performed on each curve. Both monoclonal antibodies have a terminal half life of greater than 6 days.
Figure 12B:
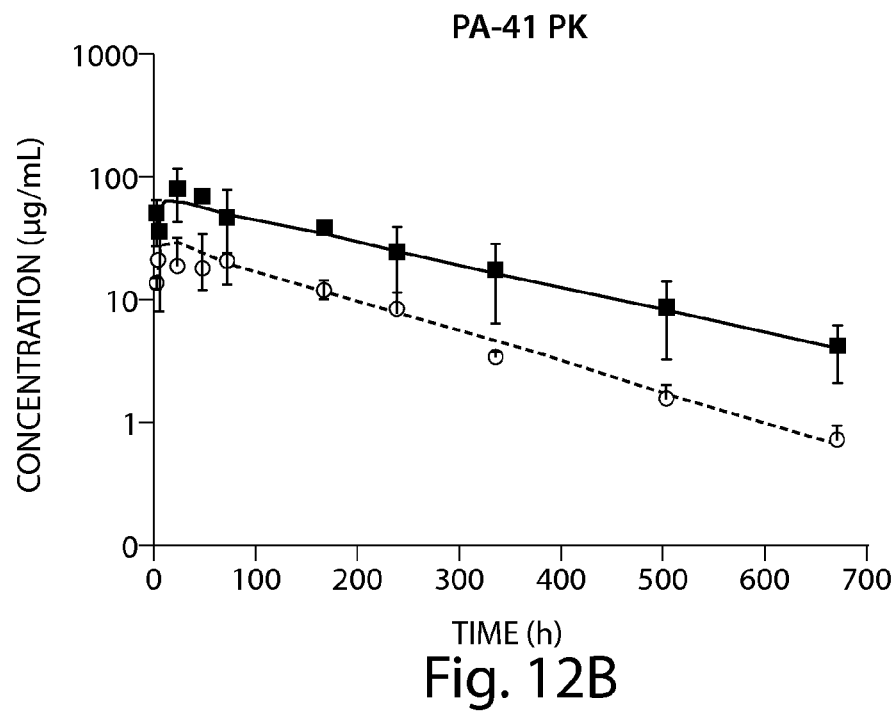

Plates were washed (as above) and incubated for one hour at room temperature with HRP-conjugated goat anti-mouse IgG, Fcγ specific (Jackson Immunoresearch). Plates were developed with ABTS peroxidase substrate system (KPL), stopped with ABTS peroxidase stop solution (KPL) and read on a SpectraMax plate reader (Molecular Devices) at 405 nm. mAb concentration in each hamster at different time points was calculated using the standard curves. Approximately 10% of the samples did not have antibody titer, probably due to missed injection or no absorption; these samples were not included in the PK parameter calculation. Noncompartmental pharmacokinetic analysis was performed using WinNonLin, Version 4.0 (Pharsight Corp., Mountain View, Calif.) and the data are illustrated in Table 1 and in FIGS. 12A and B. As indicated, Cmax and area under curve (AUC) were dose dependent. Each of the antibodies demonstrated a terminal half life of greater than 6 days, which ensured antibody retention in the efficacy studies described hereinbelow.

TABLE 1

PK parameters of mAbs in hamsters

| mAb | $AUC_{INF}$_obs (day * µg/ml) | Tmax (day) | Cmax (µg/ml) | Half-life$_\lambda$ (day) | Rsq |
|---|---|---|---|---|---|
| PA-38 2 mg/kg | 303.8 | 2.00 | 25.2 | 7.4 | 0.999 |
| PA-38 10 mg/kg | 1522.6 | 0.25 | 128.0 | 10.6 | 0.988 |
| PA-41 2 mg/kg | 202.2 | 0.25 | 20.5 | 6.2 | 1.000 |
| PA-41 10 mg/kg | 696.7 | 1.00 | 78.1 | 6.8 | 1.000 |

B. Evaluation of Anti-*C. difficile* Toxin A and Toxin B mAbs of the Invention, in Combination, in the *C. difficile*-associated Diarrhea (CDAD) Model in Golden Syrian Hamsters An efficacy experiment was performed to evaluate the murine anti-toxin A and anti-toxin B mAbs of the invention for their ability to affect the survivability of infected animals in an in vivo model of *C. difficile*-associated diarrhea in hamsters. Golden Syrian male hamsters (~90 g) (Crl:LVG(SYR)), (Charles River Laboratories, Inc., Kingston, N.Y.) were pretreated with a single subcutaneous dose of clindamycin (Sigma, St. Louis, formulated in PBS at 5 mg/mL) at 50 mg/kg to disrupt the normal colonic flora. On the following day, hamsters in the relevant test groups received an oral dose ($1 \times 10^7$ CFU in 0.5 mL) of a suspension of *C. difficile* (ATCC 43596 strain). Strain 43596 has been previously used in hamster models for evaluating neutralizing antibodies. Animals were weighed weekly and monitored daily for health status and survival.

The test antibodies comprised combinations of the murine mAbs of the invention, i.e., a combination of mAbs PA-38 and PA-41 or a combination of mAbs PA-39 and PA-41. Goat anti-*C. difficile* toxin A and toxin B polyclonal antibodies (Techlab) were included as a positive control. The mAbs and control reagents were administered as described in Table 2.

TABLE 2

Treatment groups in the hamster efficacy study.

| Grp | Treatment | Dose (mg/kg) | Route | Schedule | No. hamsters |
|---|---|---|---|---|---|
| 1 | Uninfected | NA* | NA | NA | 4 |
| 2 | Uninfected + clindamycin | NA | NA | NA | 4 |
| 3 | Infected control | NA | NA | NA | 8 |
| 4 | Vancomycin | 20 | PO | BID X 5 days | 8 |
| 5 | Goat polyclonal Abs | 1 mL/hamster | IP | Q2d X 4 | 8 |
| 6 | PA-38 + PA-41 | 50, 50 | IP | Q2d X 4 | 8 |
| 7 | PA-39 + PA-41 | 50, 40 | IP | Q2d X 4 | 8 |

*Not applicable

The hamsters in Group 1 received no treatment throughout the study. The hamsters in Groups 2-7 were pretreated with a single subcutaneous dose of clindamycin phosphate at 50 mg/kg (Day −1). The hamsters in Groups 5-7 were dosed with the polyclonal goat antibodies (Group 5) or with the mAb combinations (Groups 6 and 7) as set forth in Table 2 by i.p. administration immediately after the clindamycin treatment. After 24 hours, each hamster in Groups 3-7 was inoculated with 0.5 mL of the appropriate suspension of *C. difficile* ATCC 43596 ($10^6$-$10^7$ CFU/mL) via oral gavage (day 0). Following the initial treatment with antibodies on Day −1, the subsequent three treatments for these groups were administered every other day, once per day, on days 1, 3 and 5. Vancomycin (20 mg/kg BID) was administered via oral gavage to the animals in Group 4 twice daily, approximately 6 hours apart on Days 1-5. The administration of vancomycin (Group 4 animals) began approximately 20-24 hours after the animals had been inoculated with *C. difficile*.

Figure 13:
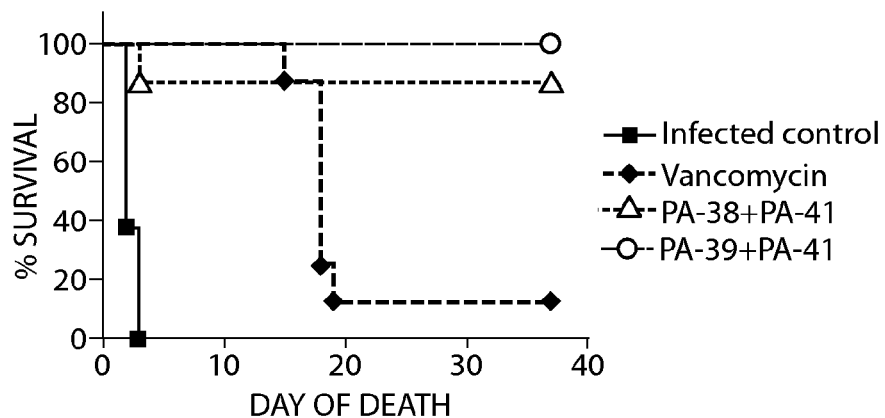
FIG. 13 illustrates the survival results of the hamster study described in Example 5B. In this study, hamsters were treated with clindamycin, inoculated with C. difficile (■ infected control, Group 3), and then treated with vancomycin (♦ 20 mg/kg, Group 4), a combination of murine mAbs PA-38+PA-41 (Δ 50, 50 mg/kg, Group 6), or a combination of mAbs PA-39+PA-41 (○ 50, 40 mg/kg, Group 7). All animals in the uninfected control (Group 1) and goat polyclonal Abs treated control (group 5) survived. The animals treated with a combination of anti-toxin A and anti-toxin B mAbs of the invention survived and were protected against C. difficile toxicity for the duration of the study.
Figure 15A:
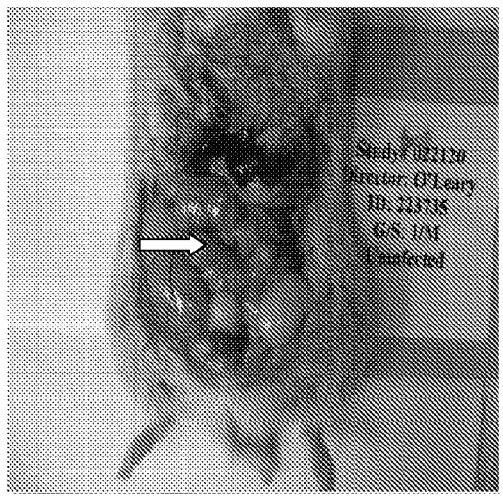
FIGS. 15A-15D depict postmortem necropsy results from the hamster study described in Example 5B. Representative animals from each of the relevant groups of the study were evaluated: (A) Group 1, uninfected control; (B) Group 3, infected control; (C) Group 6, PA-38+PA-41 murine mAb combination-treated group; and (D) Group 7, PA-39+PA-41 murine mAb combination-treated group. The arrows indicate the cecum of each hamster. The cecum was noticeably red and inflamed in the infected control Group 3 (B). By contrast, the ceca of the hamsters in Group 6 (C) and Group 7 (D) were similar to the ceca in the healthy, uninfected control animals of Group 1 (A).
Figure 15B:
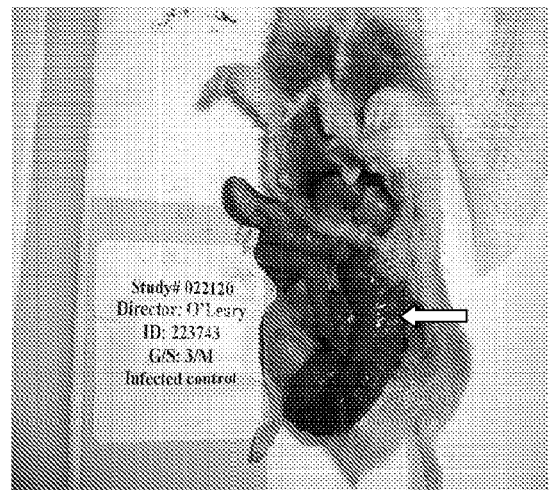
Figure 15C:
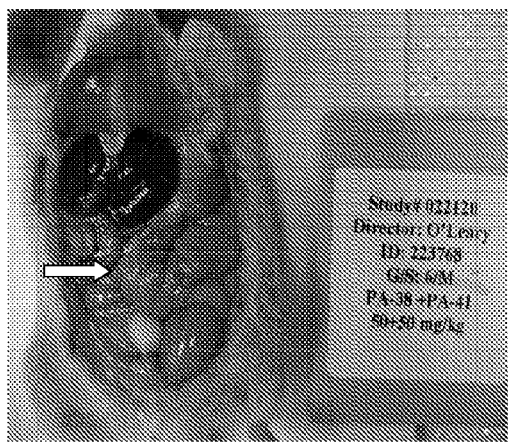
Figure 15D:
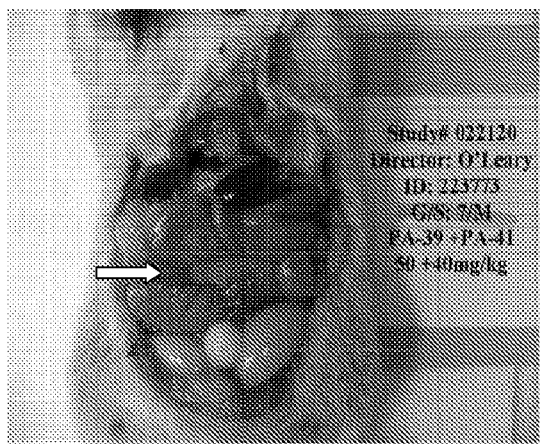

Survival results for the mAb-treated and control groups are illustrated in FIG. 13. A summary of hamster mortality for all groups is presented in Table 3. All hamsters infected with *C difficile* without any treatment (infected control, Group 3) were found dead on Day 2 or Day 3 of the study. In the vancomycin-treated group (Group 4), seven of eight hamsters were found dead between Days 15 and 19. As is typically observed in this model, most (88%) of the vancomycin-treated hamsters relapsed and died from *C. difficile* infection within two weeks after discontinuation of therapy. In contrast, all hamsters treated with the combination of mAbs PA-39+PA-41 (Group 7), and 7 out of 8 hamsters treated with the combination of mAbs PA-38+PA-41 (Group 6), survived to the end of the study (37 days post-infection). In addition, at the end of the study, all animals in the group treated with goat polyclonal antibodies (Group 5) were alive. All surviving hamsters had normal GI tracts at the postmortem necropsy (see FIGS. 15A, C and D).

TABLE 3

Mortality rate and day of hamster death in each group

| Grp | Treatment | No of animals | % mortality | 2 | 3 | 5 | 7 | 15 | 18 | 19 | 37 |
|---|---|---|---|---|---|---|---|---|---|---|---|
| 1 | Uninfected | 4 | 0 | | | | | | | | |
| 2 | Uninfected + Clindamycin | 4 | 50 | | | | | 1 | 1 | | |
| 3 | Infected control | 8 | 100 | 5 | 3 | | | | | | |
| 4 | Vancomycin | 8 | 88 | | | | | | 1 | 5 | 1 |
| 5 | Goat polyclonal Abs | 8 | 0 | | | | | | | | |
| 6 | PA-38 + PA-41 | 8 | 13 | | | | | 1 | | | |
| 7 | PA-39 + PA-41 | 8 | 0 | | | | | | | | |

These results indicate that the combination of mAbs PA-39 and PA-41 and the combination of mAbs PA-38 and PA-41 effectively and durably protected the hamsters from severe disease, both initially and from subsequent relapse of disease. The duration of benefit from mAb treatment (37 days) significantly exceeded the window (two weeks) for establishing *C. difficile* infection following treatment with clindamycin in the hamster model.

Figure 14:
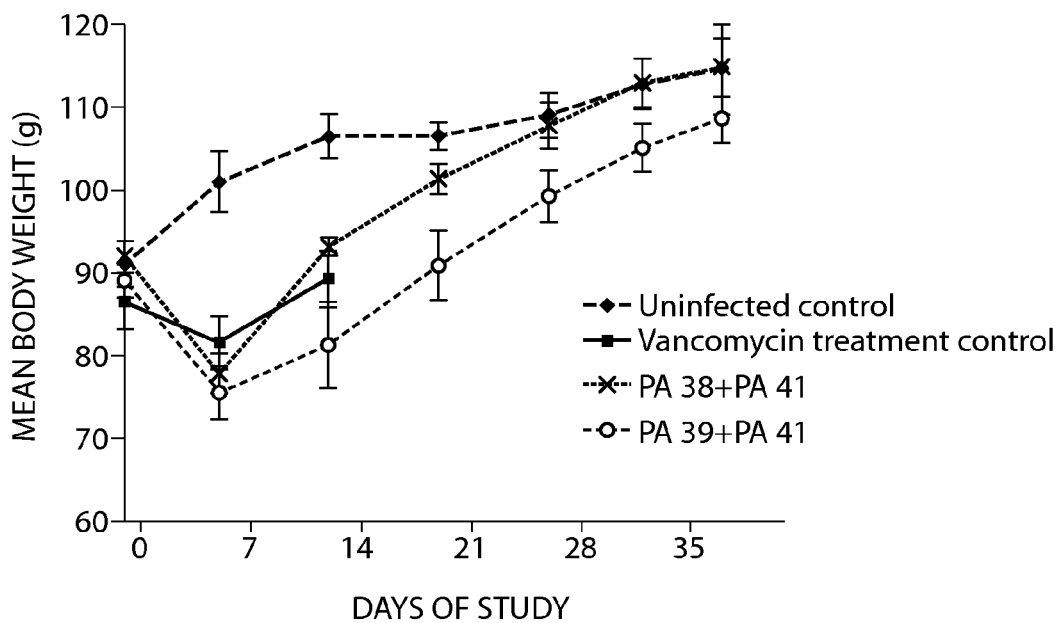
FIG. 14 shows the mean body weight (in grams) of hamsters from the study described in Example 5B. The animal treatment groups are as follows: uninfected control (♦, Group 1); vancomycin-treated control (■, Group 4); PA-38+PA-41 murine mAb combination-treated group (x, Group 6), or PA-39+PA-41 murine mAb combination-treated group (●, Group 7). Animals in the infected control group (Group 3) did not survive for 5 days; therefore, a post-infection body weight measurement could not be made for Group 3.

The body weights of animals in the polyclonal- and mAb-treated groups and in the control groups are illustrated in FIG. 14. Hamsters in the uninfected control group (Group 1) gained weight steadily, ranging from 13-29 g over the course of the study. All infected control animals died prior to the first post-inoculation weight measurement. The mean body weights of the animals treated with vancomycin, goat polyclonal antibodies, the PA-38+PA-41 mAb combination, and the PA-39+PA-41 mAb combination declined significantly during the first week after infection. Thereafter, the mean body weights in the mAb-treated groups, as well as in the polyclonal antibody-treated group, steadily increased and were similar to those of the uninfected control by the end of the study, indicating that there was no overt toxicity.

Overall in this hamster study, it was demonstrated that combinations of mAbs of the invention effectively and durably protected hamsters from mortality in a relevant and stringent hamster model of *C. difficile* infection. These findings support a mechanism by which mAb combinations protected the animals from *C. difficile* disease for a time long enough to allow outgrowth and repopulation of the normal gut flora in the mAb-treated animals compared with uninfected animals (FIGS. 15A-D). Thus, mAbs of the invention provided therapeutic protection to the infected animals and effected resolution of *C. difficile*-associated disease, restoration to gastrointestinal health and survival.

C. Evaluation of Individual Anti-*C. difficile* Toxin A and/or Toxin B mAbs of the Invention in the *C. difficile*-associated Diarrhea (CDAD) Model in Golden Syrian Hamsters An additional study in hamsters was conducted to evaluate the efficacy of individual murine mAbs of the invention administered to infected animals compared with that of the mAbs administered in combination. The treatment groups for this study are presented in Table 4.

TABLE 4

Hamster efficacy study of individual mAbs compared with a mAb combination

| Grp | Treatment | Dose (mg/kg) | Route | Schedule | No. hamsters |
|---|---|---|---|---|---|
| 1 | Infected control | NA[1] | NA | NA | 7 |
| 2 | Vancomycin | 20 | PO | BID X 5 days | 7 |
| 3 | PA-39 + PA-41 | 50, 50 | IP | Q2d X 4 | 7 |
| 4 | PA-41 | 50 | IP | Q2d X 4 | 7 |
| 5 | PA-38 | 50 | IP | Q2d X 4 | 7 |
| 6 | PA-39 | 50 | IP | Q2d X 4 | 7 |
| 7 | PA-50 | 50 | IP | Q2d X 4 | 7 |

[1]Not applicable

In this study, the hamsters in Groups 1-7 were pretreated with a single subcutaneous dose of clindamycin phosphate at 50 mg/kg (day −1). Animals in groups 3-7 were dosed with mAbs by i.p. administration immediately after the clindamycin treatment. After 24 hours, each hamster in Groups 1-7 was inoculated with 0.5 mL of the suspension of *C. difficile* via oral gavage (day 0), as described in Section B, supra. The test mAb treatments were administered to the animals in Groups 3-7 in a single dose on days 1, 3, and 5. Vancomycin was administered to animals twice daily on days 1-5 (Group 2). The hamsters were observed twice daily for viability. Body weights were recorded once per week. A necropsy was performed on animals that were found dead or that were euthanized during the study. At the end of the study (40 days post inoculation), a terminal necropsy was performed on all remaining hamsters.

Figure 16A:
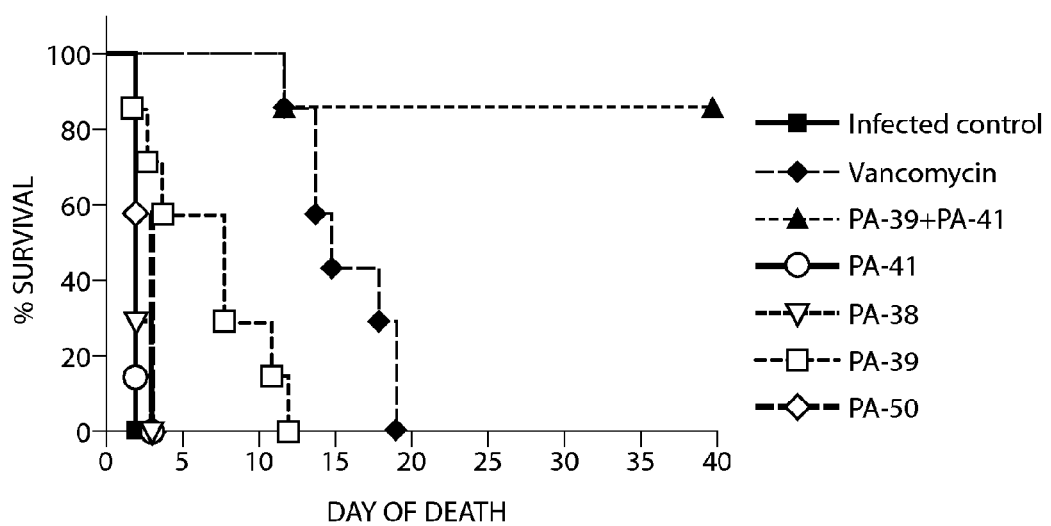
FIGS. 16A and 16B-1 and B-2.

Survival of mAb-treated and control animal groups is depicted in FIG. 16A, and the day of death for the hamsters in all groups is summarized in Table 5.

TABLE 5

Mortality data and day of death

| Grp | Treatment | No. hamsters | % mortality | 2 | 3 | 4 | 8 | 11 | 12 | 14 | 15 | 18 | 19 | 40 |
|---|---|---|---|---|---|---|---|---|---|---|---|---|---|---|
| 1 | Infected control | 7 | 100 | 7 | | | | | | | | | | |
| 2 | Vancomycin | 7 | 100 | | | | | | 1 | 2 | 1 | 1 | 2 | |
| 3 | PA-39 + PA-41 | 7 | 14 | | | | | | | 1 | | | | |
| 4 | PA-41 | 7 | 100 | 6 | 1 | | | | | | | | | |
| 5 | PA-38 | 7 | 100 | 5 | 2 | | | | | | | | | |
| 6 | PA-39 | 7 | 100 | 1 | 1 | 1 | 2 | 1 | | 1 | | | | |
| 7 | PA-50 | 7 | 100 | 3 | 4 | | | | | | | | | |

In the infected control group (Group 1), all seven hamsters were found dead on day 2. All of these hamsters had inflamed GI tracts at the postmortem examination. In the vancomycin-treated group (Group 2), all seven of the hamsters died between days 12 and 19 of the study. The timing of these deaths was similar to the timing that has been observed previously with vancomycin treatment in this model. The postmortem examination indicated that all of the hamsters had inflamed GI tracts indicative of C. difficile infection.

The PA-39+PA-41 mAb combination treatment (Group 3) was very effective in protecting infected hamsters in this study. Six of the seven hamsters in Group 3 survived to the end of the study. One hamster was found dead on day 12 of the study. The postmortem examination indicated that this hamster had an inflamed GI tract typical of C. difficile infection.

Among the single antibody treatments (Groups 4-7), mAb PA-39 alone (Group 6) exhibited some protective activity in treated animals. Hamsters in this group were found dead on days 2 through 12. In the groups treated with the individual mAbs, PA-41 (Group 4), PA-38 (Group 5), or PA-50 (Group 7), the hamsters were found dead on days 2 and 3. At terminal necropsy, all of the hamsters in these groups had inflamed GI tracts, which is indicative of C. difficile infection. In contrast, all of the treated hamsters that survived had normal GI tracts. The results of this study indicate that treatment with the mAb combination of PA-39+PA-41 successfully protected the hamsters from developing disease for over one month after cessation of treatment, and are the same as those obtained in the above-described study of Example 5B in which eight out of eight hamsters treated with the combination of the PA-39+PA-41 survived C. difficile infection. In this study, mAb PA-39 as a single mAb treatment exhibited some activity in protecting C. difficile-infected hamsters from C. difficile disease.

D. Determination of Antibody Concentrations from Terminal Blood and Evaluation of Existing of C. difficile in Terminal Hamster Ceca Samples Blood was collected from animals that were found moribund during the study. At the end of the study, blood was also collected from all animals that remained alive. The blood samples were processed to collect serum, unless noted otherwise below. Processed samples were frozen at <−70° C. for possible further analysis.

Following the in vivo efficacy hamster studies described above, the presence of mAbs was examined in terminal bleeds taken from animals in the studies. For the mAb combination study described in Example 5B, eight of the Group 7 animals, which had received a dosage (Q2d×4) of a combination of mAb PA-39 (50 mg/kg)+mAb PA-41 (40 mg/kg) were terminally bled on day 37 of the study. In serum collected from this terminal bleed, PA-39 was detected at a level of 3.3±3.4 µg/mL, and PA-41 was detected at a level of 2.4±1.7 µg/mL. For the individual mAb study described in Example 5C, six of the Group 3 animals, which had received a dosage (Q2d×4) of a combination of mAb PA-39 (50 mg/kg)+mAb PA-41 (50 mg/kg) were terminally bled on day 40 of the study and the blood sample was processed to obtain the plasma. In plasma collected from this terminal bleed, PA-39 was detected at a level of 1.8±1.4 µg/mL, and PA-41 was detected at a level of 3.4±3.2 µg/mL. The limit of detection of antibody in these analyses was 1.6 ng/mL. Thus, detectable levels of mAbs were measured in the animals over several weeks' time. This supports a mode of action in which these mAbs provide a therapeutic benefit over the course of a treatment regimen and after the last doses of the mAbs are administered.

At terminal necropsy from group 3 in Example 5C, the cecum of each hamster was exposed and each appeared normal. No inflammation or redness was observed and the contents of the ceca were relatively firm in consistency. The wall of each cecum was cut open with a sterile, disposable scalpel. A new scalpel was used for each hamster to avoid cross-contamination. A small amount of feces was removed from the cecum with a sterile swab and placed in a sterile test tube. A 10-µL inoculating loop was used to collect a sample of the feces from the tube and to streak the sample across an agar plate containing CCFA with horse blood medium (Remel, Lot 735065), which is selective for C. difficile. The plates were placed in an anaerobic box and incubated for 48 hours at 37° C. One plate was streaked with C. difficile ATCC 43596 from the stock culture and incubated along with the fecal streaks for colony comparison. Colonies resembling C. difficile were observed on the plates from all six of the hamsters. The results of these experiments indicate that while the surviving animals treated with mAbs of the invention still harbored C. difficile, their normal flora had repopulated so as to restore the normal gut microbial equilibrium, which contributed to their overall survival.

E. Evaluation of Anti-C. difficile Toxin A and/or Toxin B Humanized mAbs of the Invention and Comparator Anti-toxin A and Anti-toxin B mAbs in the C. difficile-associated Diarrhea (CDAD) Model in Golden Syrian Hamsters A further study in hamsters was conducted to evaluate the in vivo efficacy of a combination of the humanized anti-toxin A and anti-toxin B mAbs of the invention compared with that of a combination of human anti-toxin A comparator mAb, CDA-1, and human anti-toxin B comparator mAb, CDB-1, when the respective antibody combinations were administered to C. difficile-infected animals. The treatment groups for this study are presented in Table 5A.

TABLE 5A

Treatment groups in the hamster comparative efficacy study.

| Group | Treatment | Dose (mg/kg) | Route | Schedule | No. hamsters |
|---|---|---|---|---|---|
| 1 | Uninfected control | NA[1] | NA | NA | 4 |
| 2 | Infected control | NA | NA | NA | 8 |
| 3 | Vancomycin | 20 | BID | BID X 5 days | 8 |
| 4 | hPA-41 + hPA-50 | 50, 50 | IP | Q2d X 4 | 10 |
| 5 | hPA-41 + hPA-50 | 20, 20 | IP | Q2d X 4 | 10 |
| 6 | CDA-1 + CDB-1 | 50, 50 | IP | Q2d X 4 | 10 |
| 7 | CDA-1 + CDB-1 | 20, 20 | IP | Q2d X 4 | 10 |

[1]Not applicable

The test antibodies comprised combinations of the humanized mAbs of the invention, i.e., a combination of humanized anti-toxin A mAb PA-50 and humanized anti-toxin B mAb PA-41 (hPA-41+hPA-50), or a combination of comparator human anti-toxin A mAb referred to as CDA-1 comparator mAb and comparator human anti-toxin B mAb referred to as CDB-1 comparator mAb (CDA-1+CDB-1) in the amounts indicated in Table 5A. The comparator mAbs were synthesized (DNA2.0) based on the published heavy and light chain regions of 3D8 and 124, (WO2006/121422 and US2005/0287150), cloned into full-length IgG1 expression vectors (pCON-gamma and pCON-kappa), expressed in CHO-KSV1 cells and purified using methods described herein. The mAb combinations and control treatments were administered as described in Table 5A.

The treatment methods were essentially as described for Part B of this Example, supra. Briefly, Golden Syrian hamsters (Charles River Laboratories, Stone Ridge, N.Y., 50 days old) were utilized in this Example 5E study. The hamsters in the control Group 1 were uninfected (and untreated). The animals in Groups 2-7 were pretreated with a single subcutaneous dose of clindamycin phosphate at 50 mg/kg to disrupt the normal colonic flora (Day −1). The Groups 4-7 animals were dosed by IP administration immediately after the clindamycin treatment. After 24 hours, each animal in Groups 2-7 was inoculated with 0.5 mL of *C. difficile* (ATCC 43596, strain 545) suspension via oral gavage (Day 0), (i.e., oral dose). Additional administrations of the test treatments were given to the animals in Groups 4-7 in a single dose on Days 1, 3 and 5. Vancomycin was administered to the animals of Group 3 twice daily, approximately 6 hours apart, on Days 1-5. Animals were weighed weekly and monitored daily for health status and survival for 39 days. Necropsy was performed at termination, and cecal titers of *C. difficile* microorganisms were determined following anaerobic culture at 37° C. for 48 hours in selective medium. The limit of detection was 20 CFU/g cecum contents. This study and the above-described hamster studies were carried out at Ricerca Biosciences (Concord, Ohio) in accordance with Institutional Animal Care and Use Committee guidelines.

Figures 1, 16B:
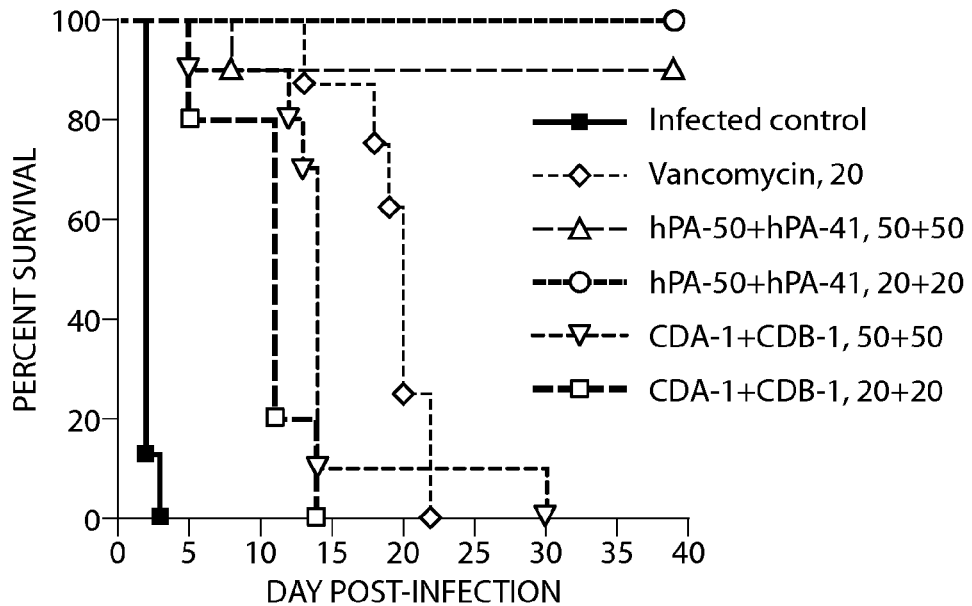

Survival results for the mAb-treated and control groups are illustrated in FIG. 16B-1. Mortality data for the study are presented in Table 5B below. A summary of hamster survival is presented in Table 5C below.

TABLE 5B

Mortality data and day of hamster death in each group

| Grp | Treatment | No of animals | % mortality | \<br>2 | Day of study | | | 11 to 14 | 18 to 20 | 22 | ... 30 |
|---|---|---|---|---|---|---|---|---|---|---|---|
| | | | | | 3 | 5 | 8 | | | | |
| 1 | Uninfected control | 4 | 0 | | | | | | | | |
| 2 | Infected control | 8 | 100 | 7 | 1 | | | | | | |
| 3 | Vancomycin | 8 | 100 | | | | | 1 | 5 | 2 | |
| 4 | hPA-50 + hPA-41 50, 50 mg/kg | 10 | 10 | | | | 1 | | | | |
| 5 | hPA-50 + hPA-41 20, 20 mg/kg | 10 | 0 | | | | | | | | |
| 6 | Comparator CDA-1 + CDB-1 50, 50 mg/kg | 10 | 100 | | | 1 | 8 | | | | 1 |
| 7 | Comparator CDA-1 + CDB-1 20, 20 mg/kg | 10 | 100 | | | 2 | 8 | | | | |

As observed in Table 5B, all 4 uninfected control hamsters (Group 1) survived to the end of the study. All infected control (Group 2) animals died on days 2 and 3. In the vancomycin-treated group (Group 3), all of the study animals died between days 13 and 22. For the hPA-50+hPA-41 (50, 50 mg/kg) Group 4, nine out of ten animals survived to the end of the study. One hamster of this group was found moribund on Day 8, with red discoloration of the GI tract, while the remaining nine surviving animals in this group had normal GI tracts. All ten hamsters in Group 5 survived to the end of the study with normal GI tracts. In the comparator mAb groups, nine of ten animals dosed with 50 mg/kg (Group 6), died between days 5 and 14; one animal died by day 28 of the study. All ten of the hamsters treated with 20 mg/kg of the comparator mAb combination (Group 7) died between days 5 and 14 of the study.

TABLE 5C

Median and overall survival of animals treated with humanized mAbs of the invention and comparator mAbs

| Group/Treatment | Dose (mg/kg) | Median Survival (Days) | Day 40 Survival (%) |
|---|---|---|---|
| Group 1 Uninfected | NA* | 40 | 100 |
| Group 2 Infected | NA* | 2 | 0 |
| Group 3 Vancomycin | 20 | 20 | 0 |
| Group 4 hPA-50 + hPA-41 | 50, 50 | NA | 90 |
| Group 5 hPA-50 + hPA-41 | 20, 20 | NA | 100 |
| Group 6 CDA-1 + CDB-1 | 50, 50 | 14 | 0 |
| Group 7 CDA-1 + CDB-1 | 20, 20 | 11 | 0 |

*Not Applicable

As observed in Table 5C, all four of the animals in the uninfected control Group 1 survived to the end of the study (40 days). All hamsters infected with *C difficile* without any treatment (infected control, Group 2) had a median survival of 2 days; no animals in this group survived at the end of the study. In the vancomycin-treated group (Group 3), the median survival was 20 days, with no surviving animals by day 40. Both of the hPA-50+hPA-41 mAb combination treatments were effective in protecting infected animals in this study (Groups 4 and 5). All (100%) of the hamsters treated with the combination of humanized mAbs PA-50+PA-41 (20 mg/kg each; Group 5), and 90% of the hamsters treated with the combination of humanized mAbs PA-50+PA-41 (50 mg/kg each; Group 4), survived to the end of the study (40 days post-infection). All surviving hamsters had essentially normal GI tracts at the postmortem necropsy. In contrast, the median survival of animals receiving a combination of the comparator anti-toxin A and anti-toxin B mAbs was similar for both doses of comparator mAbs; all animals died in the two groups treated with the comparator mAb combinations. Specifically, for animals receiving the CDA-1+CDB-1 (50 mg/kg each; Group 6) combination, the median survival was 14 days, while for animals receiving the CDA-1+CDB-1 (20 mg/kg each; Group 7) combination, the median survival was 11 days.

Figures 2, 16B:
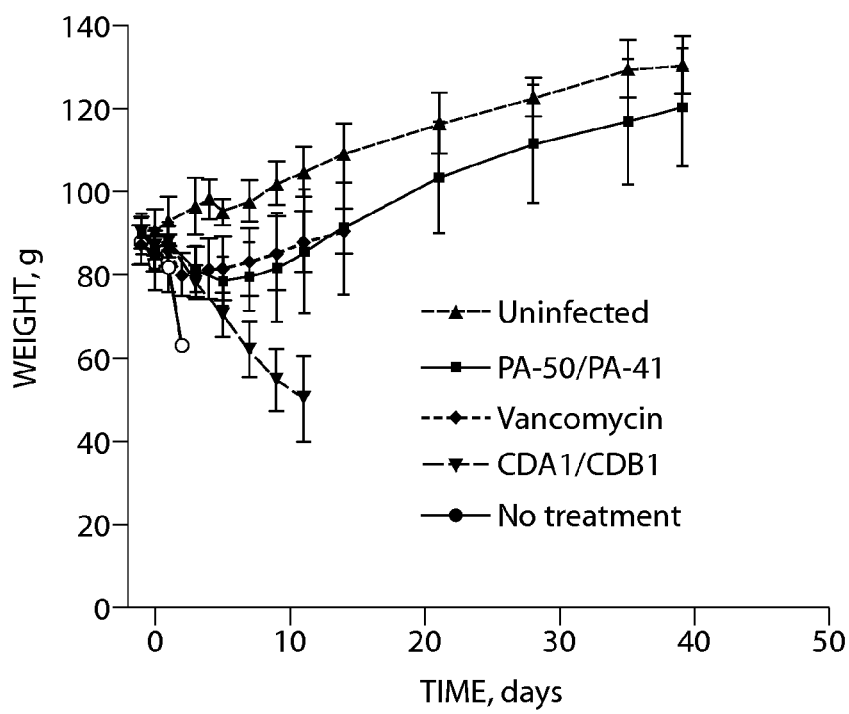

Additional evaluations in the study included body weight measurements, gross necropsy and cecal titer of *C. difficile* microorganisms at the termination of the study. Mean body weights of animals treated with vancomycin or the combination of PA-50/PA-41 decreased during the first week post-infection and then rebounded (FIG. 16B-2). By day 39, the mean body weight of animals treated with the PA-50/PA-41 combination was similar to that of healthy, uninfected animals that were housed in parallel (P>0.05). The mean body weights of animals treated with the combination of the comparator CDA1/CDB1 comparator antibodies declined steadily during the study.

At day 39, the gastrointestinal tracts of the 19 surviving animals treated with the PA-50/PA-41 combination appeared similar to those of uninfected animals; and cecal titers of *C. difficile* were either undetectable (<1.3 $\log_{10}$ CFU, n=11), or low (4.15±0.76 $\log_{10}$ CFU, n=8). In contrast, inflamed gastrointestinal tracts were observed in some or all of the animals in the other treatment groups at the time of death. *C. difficile* was detected in 4 of 4 untreated animals (mean CFU=8.96±0.59 $\log_{10}$, P<0.0001 relative to PA-50/PA-41)

and 4 of 4 vancomycin-treated animals (mean CFU=6.01±0.93 log$_{10}$, P<0.017 relative to PA-50/PA-41) for which cecal analyses were performed. Most hamsters treated with CDA1/CDB1 comparator antibody combination had little to no cecum contents, which precluded quantitative analysis of *C. difficile* titers.

For statistical analysis in this study and the above studies, neutralization data were fit to a four-parameter logistic equation using GraphPad Prism (v. 4.0 GraphPad Software, San Diego, Calif.). Two-sided t tests or log-rank tests were used for comparison of means or survival data, respectively.

The results of the study indicate that treatment of *C. difficile*-infected animals with the combination of the humanized mAbs PA-50 and PA-41 at both dose levels effectively and durably protected the hamsters from severe disease, both initially and from subsequent relapse of disease. The duration of benefit from humanized mAb combination treatment (40 days) significantly improved the long-term survival of animals compared with treatment with vancomycin or comparator anti-toxin A and anti-toxin B mAbs as controls.

As evidenced by the in vivo animal studies, combination treatment with a combination of humanized PA-50/PA-41 mAbs was highly efficacious against *C. difficile* infection in the well established Golden Syrian hamster model for CDI and therapy. A short course of treatment with PA-50/PA-41 resulted in 95% survival at 39 days post-infection, compared with 0% survival for animals that had received no treatment, standard antibiotic therapy, or comparator mAbs. At 39 days post-infection, animals treated with PA-50/PA-41 had normal weights and no obvious gastrointestinal lesions. *C. difficile* could not be recovered from most animals, reflecting a >7-log$_{10}$ clearance relative to untreated animals. One likely explanation for these findings is that mAb-mediated neutralization of toxins in the absence of antibiotics allowed a protective microbial flora to become re-established in the gastrointestinal tracts of the animals.

Either toxin A or toxin B alone has been reported to be able to cause fatal disease in the hamster model of CDI, and mAbs to both toxins are generally required for maximum treatment efficacy. In the studies described supra, murine mAbs PA-50 and PA-41 showed no survival benefit when used individually at 50 mg/kg doses in the hamster model, thus underscoring the requirement for combination treatment.

Overall in this hamster study, similar to the findings described supra utilizing murine mAb combinations, it was demonstrated that combinations of humanized mAbs of the invention effectively and durably protected hamsters from mortality in the rigorous hamster model of *C. difficile* infection. Without wishing to be bound by theory, these findings support a mechanism of action by which the humanized mAb combinations protected the animals from *C. difficile* disease, and/or allowed the animals to mount a response against the *C. difficile* infection, for a time long enough to allow outgrowth and repopulation of the normal gut flora in the humanized mAb-treated animals, thus affording therapeutic protection to the infected animals, effective resolution of *C. difficile*-associated disease and restoration to gastrointestinal health and survival.

Example 6

Binding of mAbs to Regions of Toxin A and Toxin B of *C. difficile*

Experiments were conducted to determine the epitope regions of *C. difficile* toxin A and toxin B to which mAbs of the invention bind. Both toxin A and toxin B produced by *C. difficile* are approximately 300 kDa and share considerable sequence and structural homology. Both have a C-terminal receptor-binding domain that contains clostridial repetitive oligopeptides (CROPs), a central hydrophobic domain that is believed cause pore formation and mediate the insertion of the toxin into the membrane of the endosome and a proteolytic domain that cleaves the N-terminal enzymatic domain, thereby allowing the glucosyltransferase to enter the cytosol. Nucleic acid sequences encoding the toxins of *C. difficile*, as well as other *C. difficile* proteins, have been published and are also accessible in the National Center for Biotechnology Information (NCBI) database (i.e., www.ncbi.nlm.nih.gov). For example, for *C. difficile* strain VPI 10463, DNA sequences encoding toxin A and toxin B may be found under NCBI Accession No. x92982; in addition, NCBI Accession No. NC_009089, region 795842-803975 provides the DNA sequence for toxin A from the *C. difficile* 630 chromosome complete genome sequence, while NCBI Accession No. NC_009089, region 787393-794493 provides the DNA sequence encoding toxin B from the *C. difficile* 630 chromosome sequence.

A. Antibody Binding Domain Mapping of *C. difficile* Toxin B

Figure 17A:
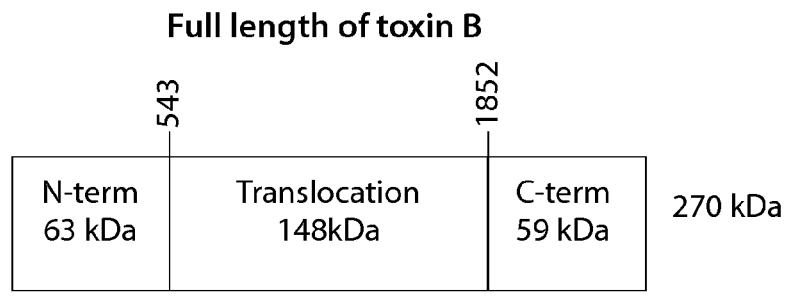
FIGS. 17A-17C show caspase 1 treatment of C. difficile toxin B. (A): Full length C. difficile toxin B and its domains. (B): 3-8% Tris-Acetate SDS-PAGE (reducing) analysis of toxin B (TcdB) and caspase 1-treated toxin B. Four toxin fragments were observed: 193, 167, 103 and 63 kDa. (C): The possible fragments generated following caspase 1 treatment of toxin B.
Figure 17B:
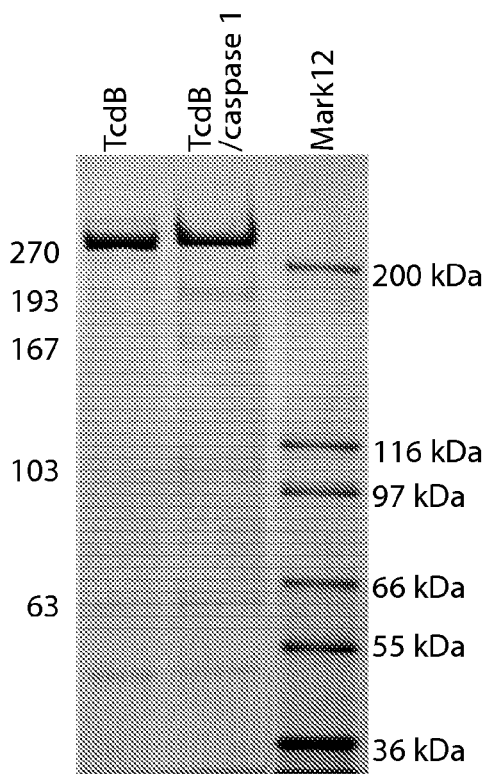
Figure 17C:
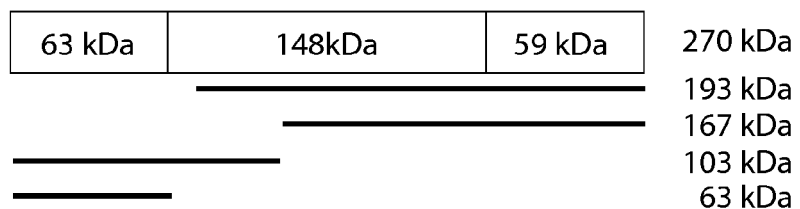

Full length *C. difficile* toxin B consists of three major domains: an N-terminal enzyme domain processing glucosyltransferase (GT) activity (63 kDa) and a C-terminal cell receptor binding (59 kDa), which are on either end of a putative translocation domain (148 kDa) (FIGS. 17A and C). Several toxin B fragments were generated through enzymatic cleavage of the full length toxin B using the enzyme caspase 1 (FIG. 17C). Following treatment of toxin B with capase 1 (enzyme/toxin ratio ~1 U/µg toxin) at 37° C. for 96 hours, four major fragments were produced, including two C-terminal containing fragments (193 and 167 kDa) and two N-terminal containing fragments (103 and 63 kDa) as detected via SDS-PAGE (FIG. 17B). Other smaller fragments, such as 26 and 14 kDa, also appear to be generated, but are not detectable in 3-8% Tris-Acetate gel analysis.

SDS-PAGE and Western blot analyses were performed on toxin B that was untreated or treated with caspase 1 (FIGS. 18A-C). mAb PA-41 recognized both the 103 kDa and the 63 kDa fragments of caspase 1-treated toxin B (right lane in FIG. 18B), thus indicating that the PA-41 binds to the N-terminal enzyme domain of toxin B. N-terminal sequencing analysis confirmed that PA-41 binds to the 63 kDa N-terminal enzyme domain of toxin B. It is interesting to note that a 63 kDa band in the untreated toxin B (left lane, FIG. 18B) was not recognized by PA-41, which suggests that two fragments with the same molecular weight (63 kDa) in the lanes appear to be different proteins.

MAb PA-39 bound the 167 kDa fragment of caspase 1-treated toxin B (FIG. 18C, right lane), as well as a 63 kDa protein in the untreated toxin B preparation (FIG. 18C, left lane), thus suggesting that PA-39 binds an epitope in the translocation domain of toxin B. Thus, based on the results of SDS-PAGE/Western blot analyses of caspase 1-treated *C. difficile* toxin B, mAbs PA-41 and PA-39 were observed to interact differently with toxin B. While mAb PA-41 was found to bind an epitope in the N-terminal enzymatic domain of toxin B, mAb PA-39 was found to bind an epitope in the translocation domain of the toxin (amino acids 850-1330). These findings were also confirmed by SDS-PAGE/Western blot analyses of toxin B fragments using enterokinase digestion.

Figure 19A:
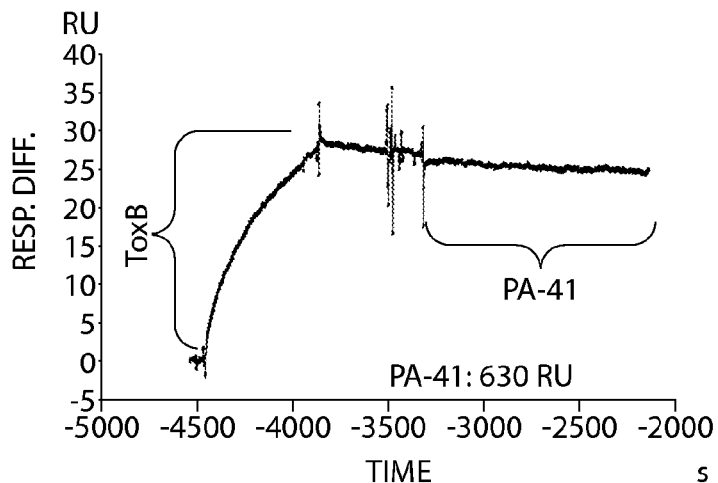
FIGS. 19A-19E show the characterization of anti-C. difficile toxin murine mAbs by Biacore binding. Competitive binding of the anti-toxin mAbs was assessed. (A): mAb PA-41 binds a single epitope on toxin B. (B): mAb PA-39 binds a single epitope on toxin A. (C): mAbs PA-39 and PA-41 bind to different epitopes on toxin B. The binding of mAb PA-41 to toxin B is epitopically different from the binding of the comparator CDB-1 anti-toxin B antibody to toxin B. (D) mPA-41 immobilized on the CM5 chip captures toxin B, but is not able to bind additional mA-41, thus indicating that there is only one binding epitope of mPA-41. The addition of comparator mAb CDB-1 yielded an increased signal, demonstrating that mPA-41 and comparator mAb CDB-1 bind different epitopes on toxin B. (E) Western blot analysis utilizing toxin B, either untreated or treated with caspase 1, demonstrating that mPA-41 and comparator mAb CDB-1 have different binding patterns and bind different epitopes on toxin B.
Figure 19B:
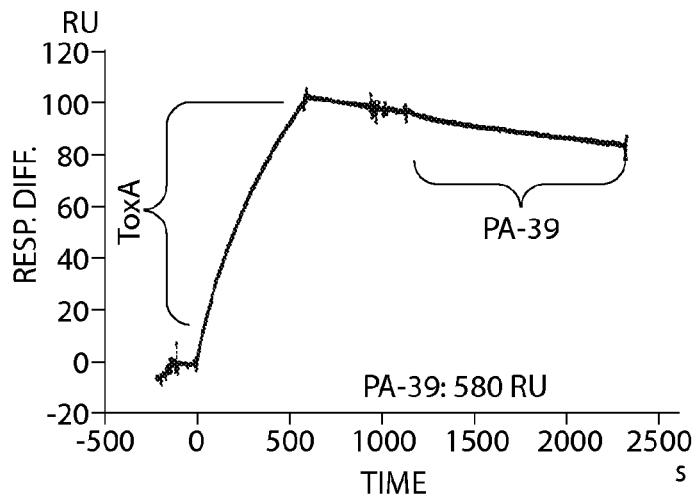
Figure 19C:
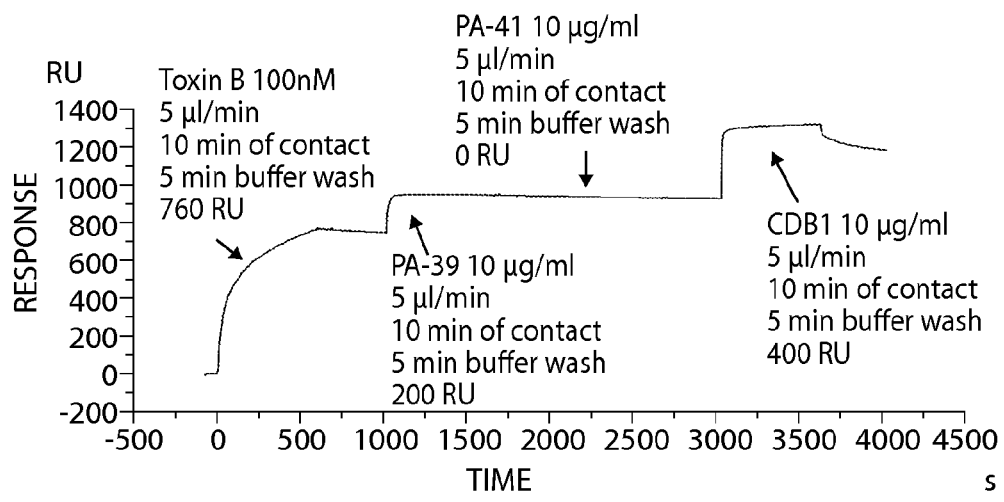
Figure 19D:
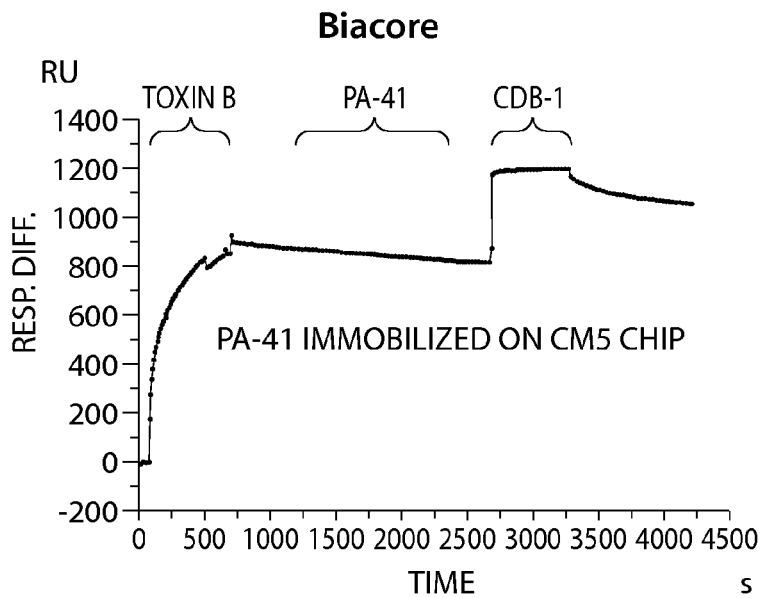
Figure 19E:
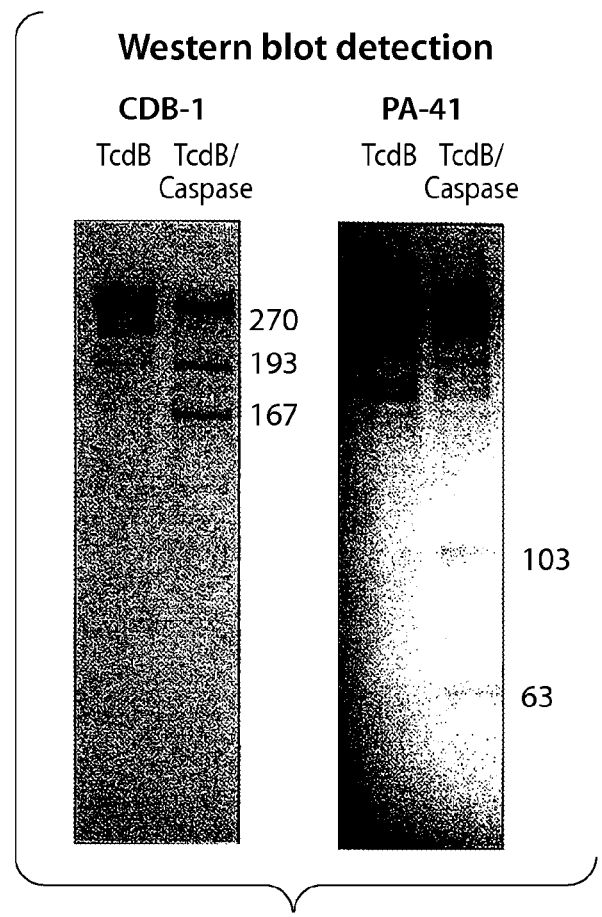

Competitive binding of the anti-toxin B mAbs to toxin B was also performed using Biacore. As seen in FIGS. 19A-E, mAbs PA-39 and PA-41 bind different epitopic regions of toxin B. Murine mAbs PA-39 and PA-41 were observed to bind to a single site or epitope on toxin B; these mAbs were not found to bind to the C-terminal cell receptor binding (CRB) domain. For murine PA-41, the affinity for binding toxin B was 0.59 mM. Additionally, the site on toxin B bound by PA-41 did not block binding of comparator anti-toxin B mAb CDB-1 (WO/2006/121422; US2005/0287150), (FIG. 19D). These findings are in agreement with the results from the Western blot analyses. As observed in FIGS. 19C and E, the comparator anti-toxin B mAb CDB-1 binds toxin B at epitopes different from those of mAbs PA-39 and PA-41.

B. Antibody Binding Domain Mapping of *C. difficile* Toxin A

Figure 20A:
FIGS. 20A-20C show *C. difficile* toxin A cleavage using enterokinase (EK). (A): Full length *C. difficile* toxin A and its domains. (B): 3-8% Tris-Acetate SDS-PAGE (reducing) analysis of toxin A (TcdA) and EK-treated toxin A. (C): The possible fragments generated following EK treatment of toxin A at 25° C. for 48 hours.

Full length toxin A of *C. difficile* has a molecular weight of 310 kDa (FIG. 20A) and contains three major domains: an N-terminal enzyme processing domain having glucosyltransferase (GT) activity (~63 kDa) and a C-terminal CRB domain (~101 kDa), which are at either end of a hydrophobic domain (~144 kDa).

Figure 20B:
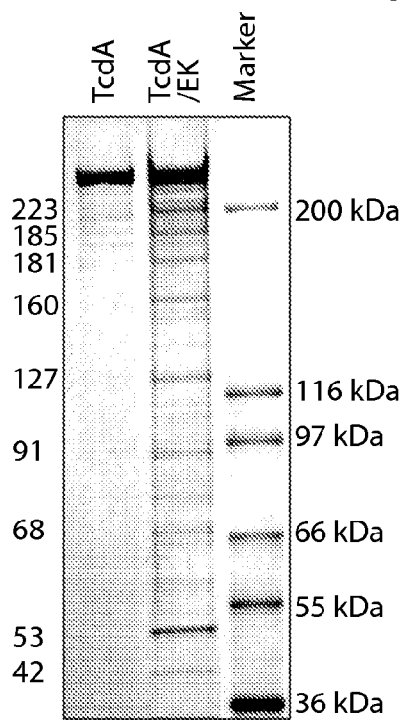
Figure 20C:
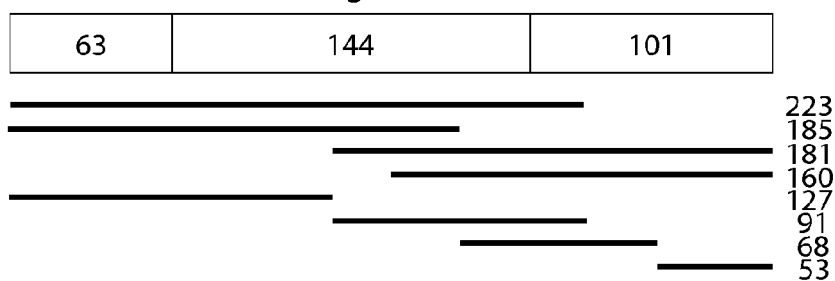

Several toxin A fragments were generated through enzymatic cleavage of the full length toxin using the enzyme enterokinase (EK). Following treatment of toxin A with enterokinase (enzyme/toxin ratio: about 3 mU/μg toxin) at 25° C. for 48 hours, nine major fragments were produced, including four C-terminal fragments (~223, ~158-160, ~91, and ~68 kDa) and three N-terminal fragments (~195, ~181, and ~127 kDa). Smaller fragments (~53 and ~42 kDa) were also observed. (FIGS. 20 B and C).

Figures 1, 22A:
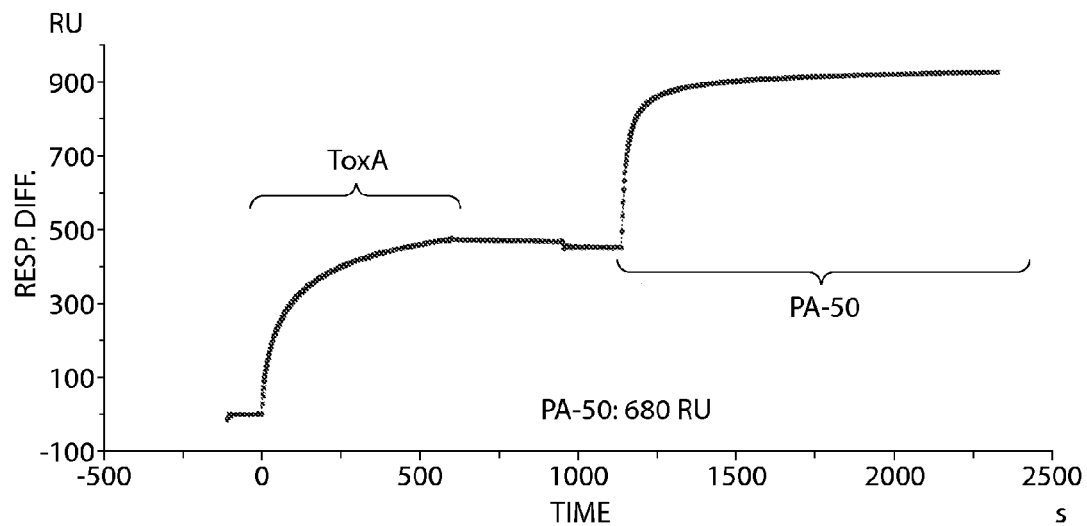
Figures 2, 22A:
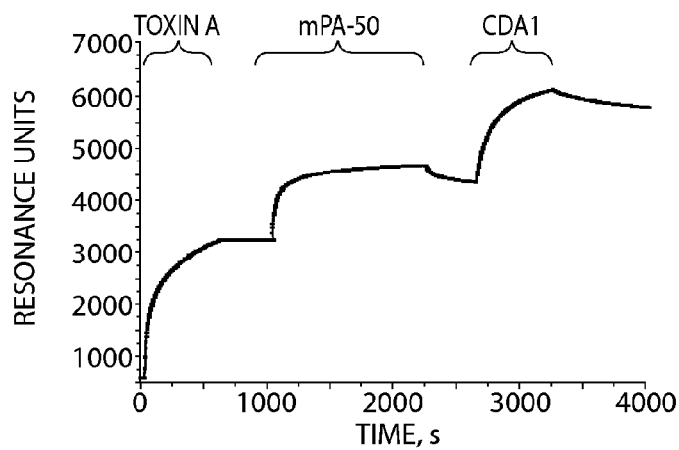
Figure 22B:
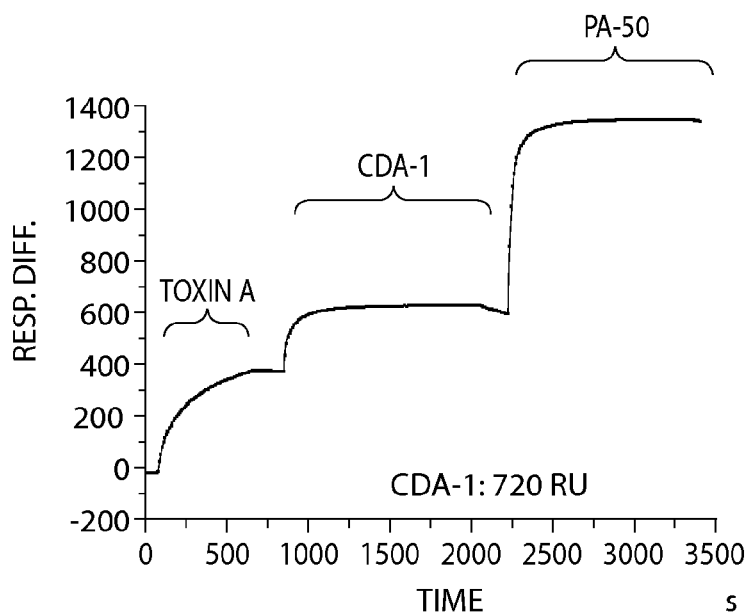
FIG. 22B: toxin A captured by comparator mAb CDA-1 on the Biacore chip further binds additional CDA-1 and PA-50 mAb, showing the differences in toxin A epitopes bound by the antibodies.
Figure 22C:
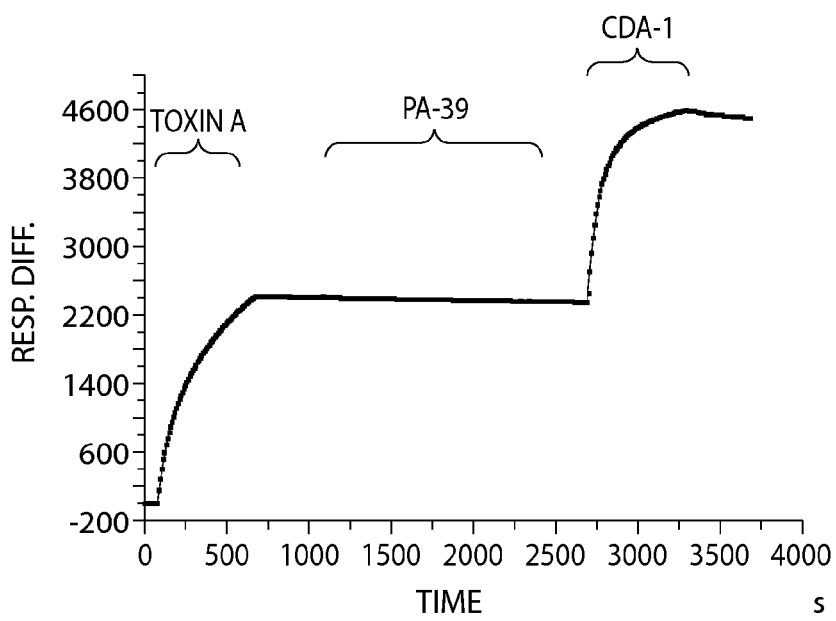
FIG. 22C: the PA-39 mAb binding epitope on toxin A is different from the comparator mAb CDA-1 binding epitope on toxin A.
Figure 22D:
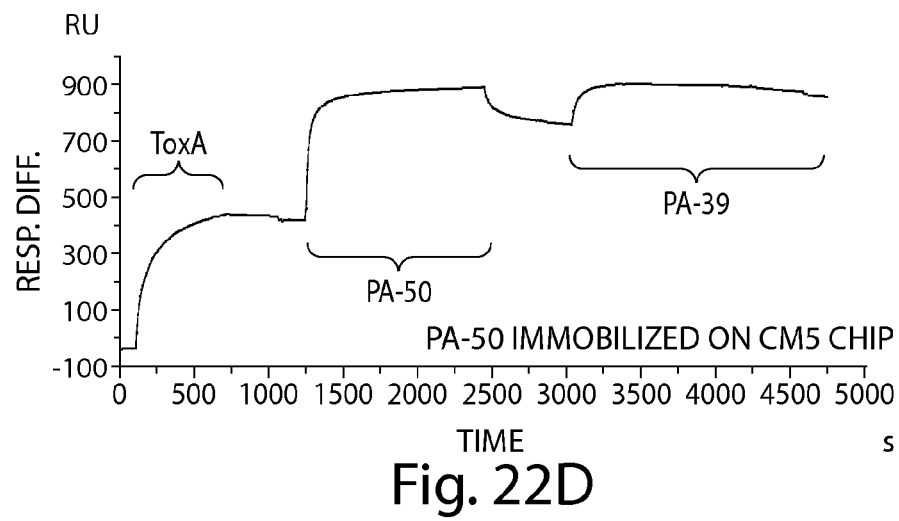
FIG. 22D: competitive binding of murine mAbs PA-50 and PA-39 to toxin A was performed using Biacore. MAb PA-50 immobilized on the CMS chip captures toxin A, which can bind additional mPA-50 and also mPA-39, demonstrating that there are multiple copies of the mPA-50 epitope on toxin A and that mPA-50 and mPA-39 bind to disparate epitopes on toxin A.
Figures 22E, 22F:
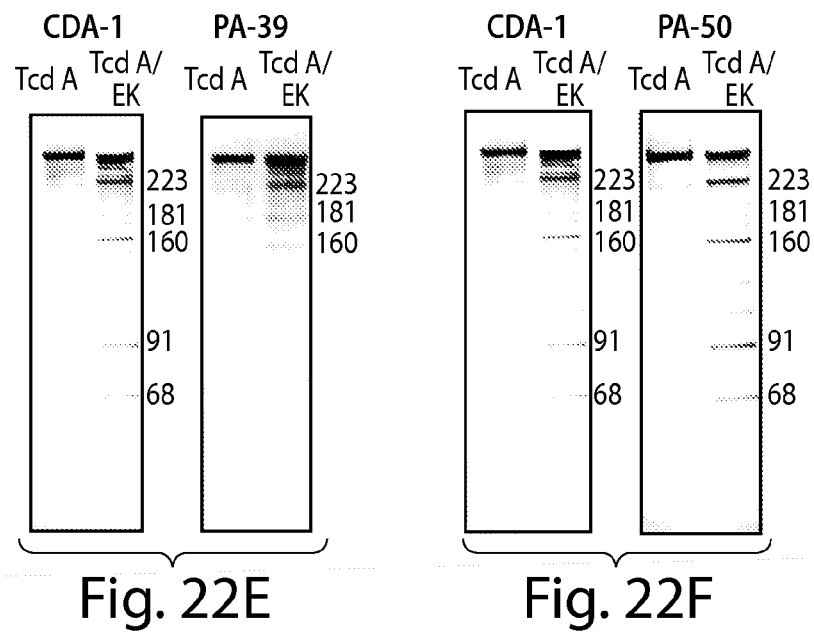
FIGS. 22E and 22F: The Biacore results were confirmed by Western Blot analysis utilizing toxin A that was untreated or treated with the enzyme enterokinase (EK). (E): mPA-39 and comparator mAb CDA-1 show different binding patterns to EK-treated toxin A (Lane: TcdA/EK), thus indicating different binding domains and epitopes on toxin A. (F): mPA-50 and comparator mAb CDA-1 bind to the same domain of toxin A, but to different epitopes.

SDS-PAGE and Western blot analyses were performed on toxin A that was untreated or treated with enterokinase (FIGS. 21A-C). Full length toxin A and its fragments having molecular weights of ~223, ~158-160, ~91, and ~68 kDa were recognized by mAb PA-50 (FIG. 21B); N-terminal sequencing confirmed that the 68 kDa fragment contains part of the C-terminal receptor binding (CRB) domain. The binding pattern of mAb PA-50 suggests that the mAb binds to C-terminal containing fragments of toxin A. Taken together, the results indicate that mAb PA-50 binds to C-terminal receptor-binding epitopes on toxin A. mAb PA-39 bound C-terminal containing fragments (~223 and ~158-160 kDa), as well as an ~181 kDa N-terminal containing fragment (FIG. 21C), thus indicating that mAb PA-39 binds an epitope in a region outside of the receptor binding domain of toxin A. Multiple binding sites (at least two binding sites) were also identified in a mAb PA-50 and toxin A interaction study using a Biacore assay (FIG. 22A-1). In comparison studies using Biacore analysis, immobilized murine PA-50 specifically bound toxin A with an affinity of 0.16 nM. It was also found that after being captured onto the sensor chip by murine mAb PA-50, toxin A was able to bind additional PA-50 and, subsequently, comparator anti-toxin A mAb CDA-1 (WO/2006/121422; US2005/0287150), (FIG. 22A-2). Additionally, toxin A captured by comparator anti-toxin A mAb CDA-1 on the Biacore chip further bound additional CDA-1 and PA-50 mAb, indicating that comparator mAb CDA-1 binds to multiple repeats on toxin A, which are different from the PA-50 mAb binding epitopes on toxin A (FIG. 22B). Thus, as determined from these results, the PA-50 mAb epitope is present in multiple copies on toxin A and does not overlap with the epitope for CDA-1. Further, the PA-39 mAb bound epitope(s) on toxin A different from the toxin A epitope(s) bound by the comparator CDA-1 mAb (FIG. 22C). MAbs PA-39 and PA-50 were found to bind different epitopes on toxin A (FIG. 22D). Western blot analysis showed that PA-39 and comparator mAb CDA-1 have different binding patterns to EK-treated toxin A, thus indicating different binding domains and different epitopes on toxin A (FIG. 22E). Western blot analysis showed that PA-50 and comparator mAb CDA-1 bind to the same domain of EK-treated toxin A (FIG. 22F), but to different epitopes (FIG. 22B).

As described in A and B of this Example, the binding sites for the murine mAbs PA-50 and PA-41 were localized to specific regions of the toxins by limited proteolysis of the toxins followed by Western blotting. Murine mAb PA-50 recognized full-length toxin A and several enterokinase cleavage products, including a large 223 kDa fragment and carboxy-terminal fragments of 68, 91 and 160 kDa in size (FIG. 22F). N-terminal sequencing confirmed that the 68 kDa fragment corresponds to the carboxy-terminal domain of toxin A. The same fragments were recognized by CDA-1 comparator mAb. Murine mAb PA-41 bound full-length toxin B as well as the 63 and 103 kDa amino-terminal fragments generated by caspase-1 digestion (FIG. 18B), while CDB-1 comparator mAb recognized a distinct set of caspase-1 cleavage products. N-terminal sequencing confirmed that the 63 kDa fragment corresponds to the amino-terminal domain of toxin B. Collectively, the data indicate that mPA-50 binds multiple sites within the receptor-binding domain of toxin A, and mPA-41 binds a single site within the enzymatic domain of toxin B.

Example 7

Anti-*C. difficile* Toxin A and Toxin B mAbs

Mechanism of Action Studies

A. In vitro Cell-based Assays Used for Mechanism of Action Studies

To evaluate the mechanism of action of the anti-toxin mAbs, in vitro assays were performed using different concentrations of toxin A or toxin B. These assays utilized either CHO-K1 or T-84 cells, as described in Example 3 supra.

Briefly, the CHO-K1 assay was used to evaluate the neutralization potency of anti-toxin A and anti-toxin B mAbs (PA-39 and PA-41). CHO-K1 cells were seeded (2,000 cells/well) in 96-well plates. Cells were allowed to attach for 4 hours prior to treatment. Different concentrations (60, 30, 15, or 6 ng/mL) of *C. difficile* toxin (strain VPI 10463) were incubated with serially-diluted mAbs, mixed in 96-well round bottom plates for 1 hr at 37 C and the mixtures were then added to the cell culture plates. After incubation for 72 hrs, 20 μL/well CELLTITER-BLUE was added; the mixtures were incubated for an additional 4 hours; and the percent cell survival compared to controls was measured.

The T-84 cytotoxicity assay was also used to evaluate the neutralization potency of anti-toxin A mAbs. T-84 cells (human colon carcinoma cell line) were seeded (15,000 cells/well) in 96-well plates. Cells were allowed to attach for 4 hours prior to treatment. Different concentrations (240, 120, 60, or 30 ng/mL) of *C. difficile* toxin (strain VPI 10463) were incubated with serially-diluted mAbs, mixed in 96-well round bottom plates for 1 h at 37 C and the mixtures were then added to the cell culture plates. After incubation for 72 hrs, 20 μL/well CELLTITER-BLUE was added; the mixtures were incubated for an additional 4 hours; and the percent cell survival compared to controls was measured.

Figure 31A:
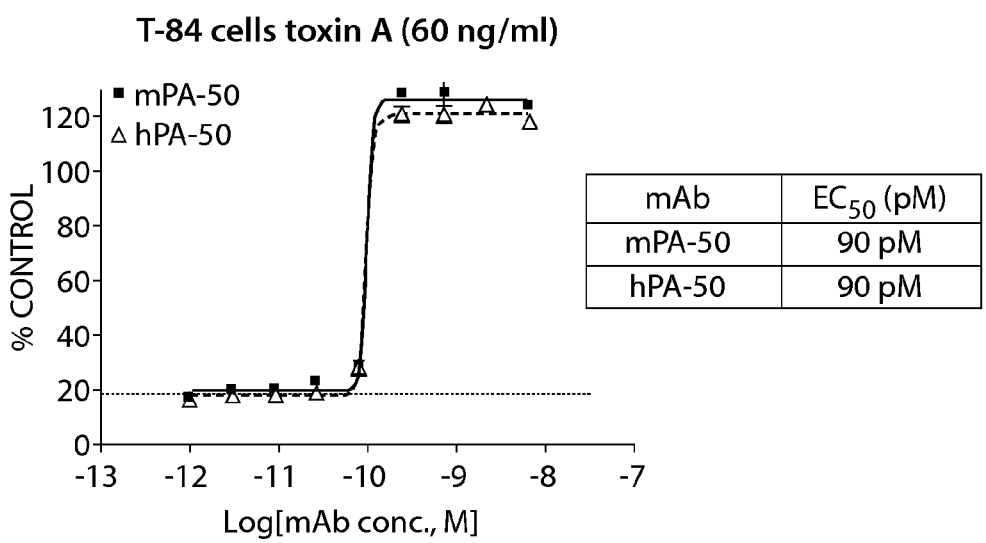
Figure 31E:
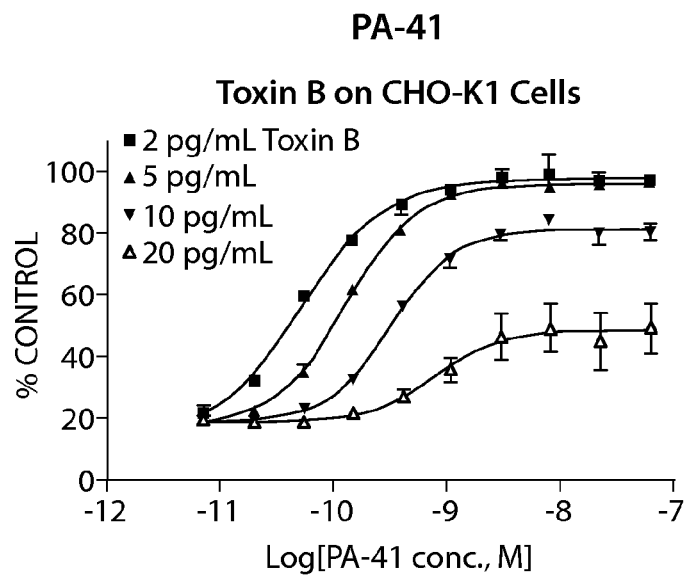
Figure 31F:
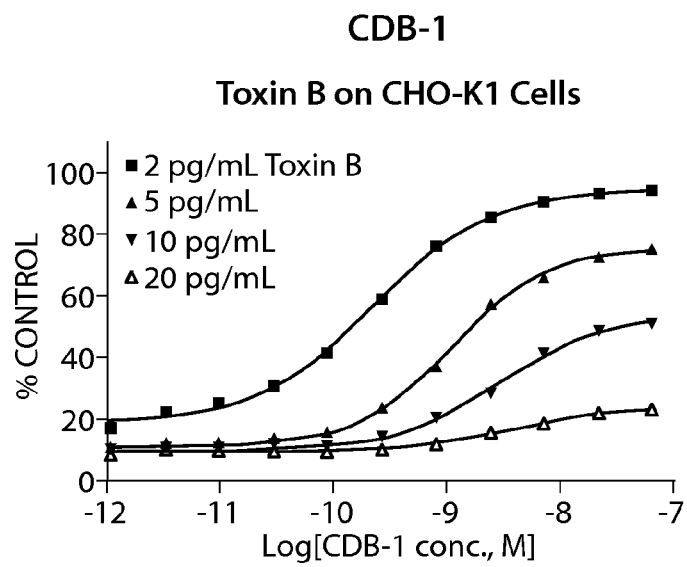
Figure 31G:
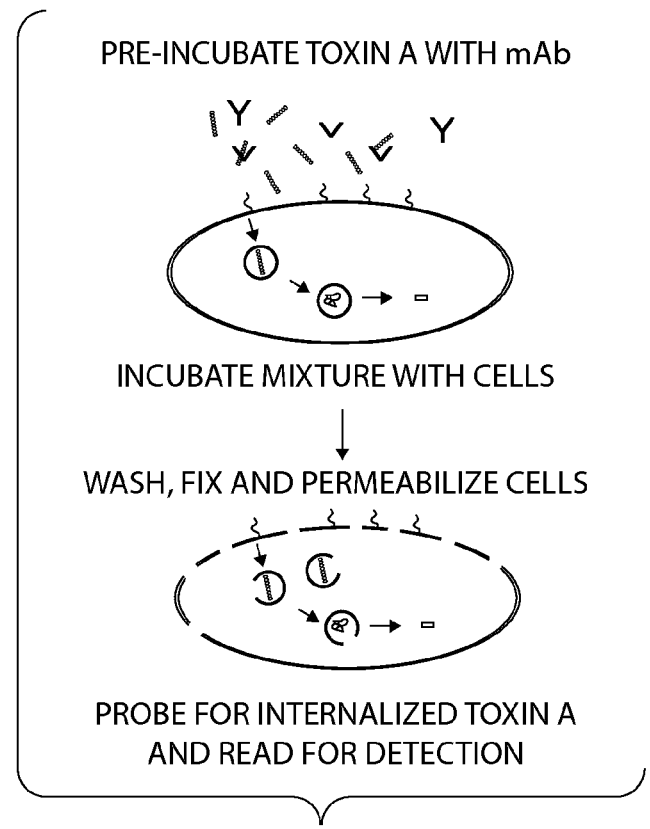
Figure 31H:
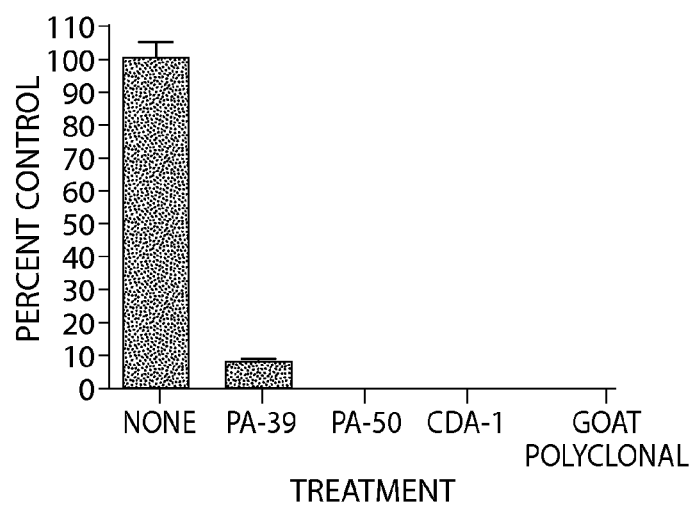

B. ELISA Showing that Anti-toxin A mAbs Prevent Internalization of Toxin A into Cells In an experiment designed to further assess anti-*C. difficile* toxin mAb mechanism of action, each test antibody (PA-39, PA-50, comparator anti-toxin A mAb CDA-1 and an anti-toxin A goat polyclonal antibody control) was mixed and incubated for 1 hour at 100× its $EC_{90}$ value with a $CC_{90}$ concentration of toxin A for Vero cells to insure complete neutralization at a highly cytotoxic concentration of toxin A. The mixture was then incubated with Vero cells at 37° C. for 15 minutes. The cells were then washed with PBS, fixed and permeabilized. An anti-toxin A, horse radish peroxidase (HRP)-labeled antibody (PA-38), which does not compete for binding with the tested antibodies, was used to probe for internalized toxin A and detected using chemiluminescence. (FIG. 31G). In this assay, only toxin A that has bound and been internalized into the cell would be detected by the probe, thus yielding a chemiluminescent signal based on an HRP chemiluminescent reaction. The chemiluminescent detection uses an enzyme to catalyze a reaction the catalyzed oxidation of luminol by peroxide) between the HRP enzyme and its substrate in the presence of peroxide that results in the generation of visible light, Oxidized luminol emits light as it decays to its ground state. Once the substrate is catalyzed by HRP, the light signal is quantified by a luminometer (Analyst GT).

C. Results of Neutralization Activity and MOA Studies

Anti-toxin A mAbs

In the cellular cytotoxicity assay used to evaluate neutralization activity and mechanism of action for the anti-toxin A antibodies, toxin A was added in increasing concentrations to cells, as described supra in Section A of this Example. The results of these experiments in which toxin A neutralization by the anti-toxin A mAbs PA-39, PA-50 and comparator mAb CDA-1 was assessed are shown in FIGS. 31B-D and in the below Table A.

TABLE A

Toxin A potency experiment results and maximum percent inhibition

| mAb | [Toxin A] (ng/mL) | [EC$_{50}$]* (nM) | Maximum Percent Inhibition |
|---|---|---|---|
| PA-39 | 60 | 0.340 | 69 |
|  | 30 | 0.080 | 86 |
|  | 15 | 0.003 | 96 |
|  | 6 | 0.002 | 97 |
| PA-50 | 240 | 0.91 | 105 |
|  | 120 | 0.54 | 100 |
|  | 60 | 0.27 | 114 |
|  | 30 | 0.10 | 118 |
| CDA-1 Comparator mAb | 240 | 9.0 | 52 |
|  | 120 | 6.6 | 74 |
|  | 60 | 5.1 | 103 |
|  | 30 | 2.0 | 110 |

*EC$_{50}$ was calculated as 50% maximum percent inhibition in cases where the curves did not reach 100% of control.

As seen from the data presented in Table A, the in vitro activity of mAb PA-39 in the toxin potency assay shows shifts in both EC$_{50}$ and the maximum percent inhibition as more toxin A is added to the culture, indicating a mixed-competitive mechanism of inhibition for PA-39. ELISA detection of toxin A after protection by 100-fold excess of PA-39 confirmed that inhibition of toxin by PA-39 occurs by preventing toxin internalization and cytocellular toxin effect. The in vitro activity of mAb PA-50 in the toxin potency assay shows a shift in EC$_{50}$ as more toxin A is added to the culture, indicating a competitive mechanism of inhibition for PA-50. ELISA detection of toxin A after protection by 100-fold excess of PA-50 confirmed that inhibition of toxin by PA-50 occurs by preventing toxin internalization.

Anti-toxin B mAbs

In the cellular cytotoxicity assay used to evaluate neutralization potency and mechanism of action for the anti-toxin B antibodies, toxin B was added in increasing concentrations to cells, as described in Section A of this Example. The results of the potency experiments in which toxin B neutralization by the anti-toxin B mAbs PA-41 and comparator mAb CDB-1 was assessed are shown in FIGS. 31E and F and in the below Table B. As seen from the data presented in the Table, the in vitro activity of PA-41 in the toxin potency assay shows shifts in both EC50 and the maximum percent inhibition as more toxin B is added to culture, indicating a mixed-competitive mechanism of inhibition PA-41.

TABLE B

Toxin B potency experiment results and maximum percent inhibition

| mAb | [Toxin B] (pg/mL) | [EC$_{50}$]* (nM) | Maximum Percent Inhibition |
|---|---|---|---|
| PA-41 | 20 | 0.82 | 49 |
|  | 10 | 0.33 | 80 |
|  | 5 | 0.13 | 96 |
|  | 2 | 0.05 | 96 |
| CDB-1 Comparator mAb | 20 | 4.1 | 23 |
|  | 10 | 3.0 | 51 |
|  | 5 | 1.1 | 75 |
|  | 2 | 0.2 | 95 |

*EC$_{50}$ was calculated as 50% maximum percent inhibition in cases where the curves did not reach 100% of control.

Based on the above-described assays in this Example, an inhibitor that has the capacity to neutralize completely increasing concentrations of toxin A or toxin B simply by the addition of greater concentrations of inhibitor would display a shift in EC$_{50}$ as more antibody binds and neutralizes the higher concentrations of toxin and thus would be considered to be a competitive inhibitor. An inhibitor that is unable to overcome the toxic effects of increasing concentrations of toxin would display a lowered maximal percent effect at higher concentrations of inhibitor, but would not display a shift in EC$_{50}$ and thus would be considered to be a non-competitive inhibitor. Further, an inhibitor that displays both a shift in EC$_{50}$ and a lowered maximal percent effect as a result of increasing concentrations of inhibitor at higher concentrations of toxin would be considered to be a mixed-competitive inhibitor. To some degree, the evaluation of the mechanism of action using cellular cytotoxicity assays must be performed under consideration of the error involved in assay repeatability and the background cytotoxicity observed in control wells containing no inhibitor, which affects the plateau of the maximal percent inhibition. Consequently, a slight rightward shift in the EC$_{50}$ values may be observed as toxin concentrations are increased due to these effects.

In accordance with the foregoing, for toxin A neutralization and MOA, the PA-39 mAb is considered a mixed-competitive inhibitor due to the shift in EC$_{50}$ and lowered plateau observed for the PA-39 cytotoxicity curves (FIG. 31B), as well as in the lowered maximal percent effect calculated in Table A. These data are supported by the ELISA results (FIG. 31H), which show a degree of cytotoxic effect at high concentrations of PA-39, thus indicating that at least some of PA-39's MOA occurs intracellularly, The PA-50 mAb is observed to be a competitive inhibitor as evidenced by the rightward shift in EC$_{50}$ values observed in the cytotoxicity assay curves (FIG. 31C) and by the data presented in Table A showing minimal change in maximal percent inhibition. These data are supported by the ELISA results (FIG. 31H), which show complete inhibition of toxin A binding and internalization at high concentrations of PA-50.

Figure 23A:
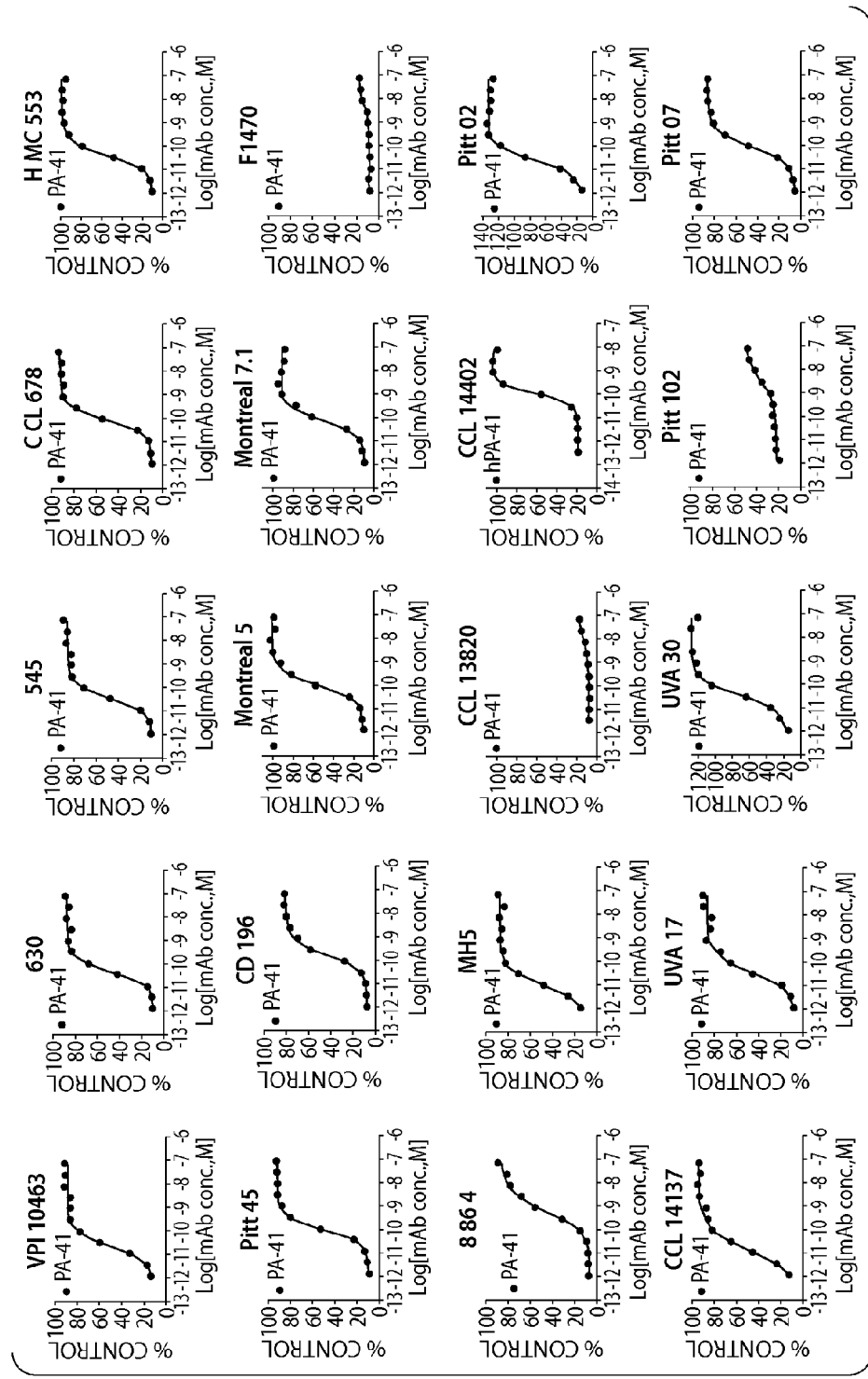
FIGS. 23A and 23B demonstrate the neutralizing activity of PA-41 in vitro against a diverse panel of twenty *C. difficile* toxigenic clinical isolates, including 6 BI/NAP1/027 isolates, 3 reference strains (VPI 10463, ATCC 43596, and 630), 2 toxin A-negative/toxin B-positive (toxA−/toxB+) isolates, 3 outpatient isolates, and 6 other common clinical isolates.
Figure 23B:
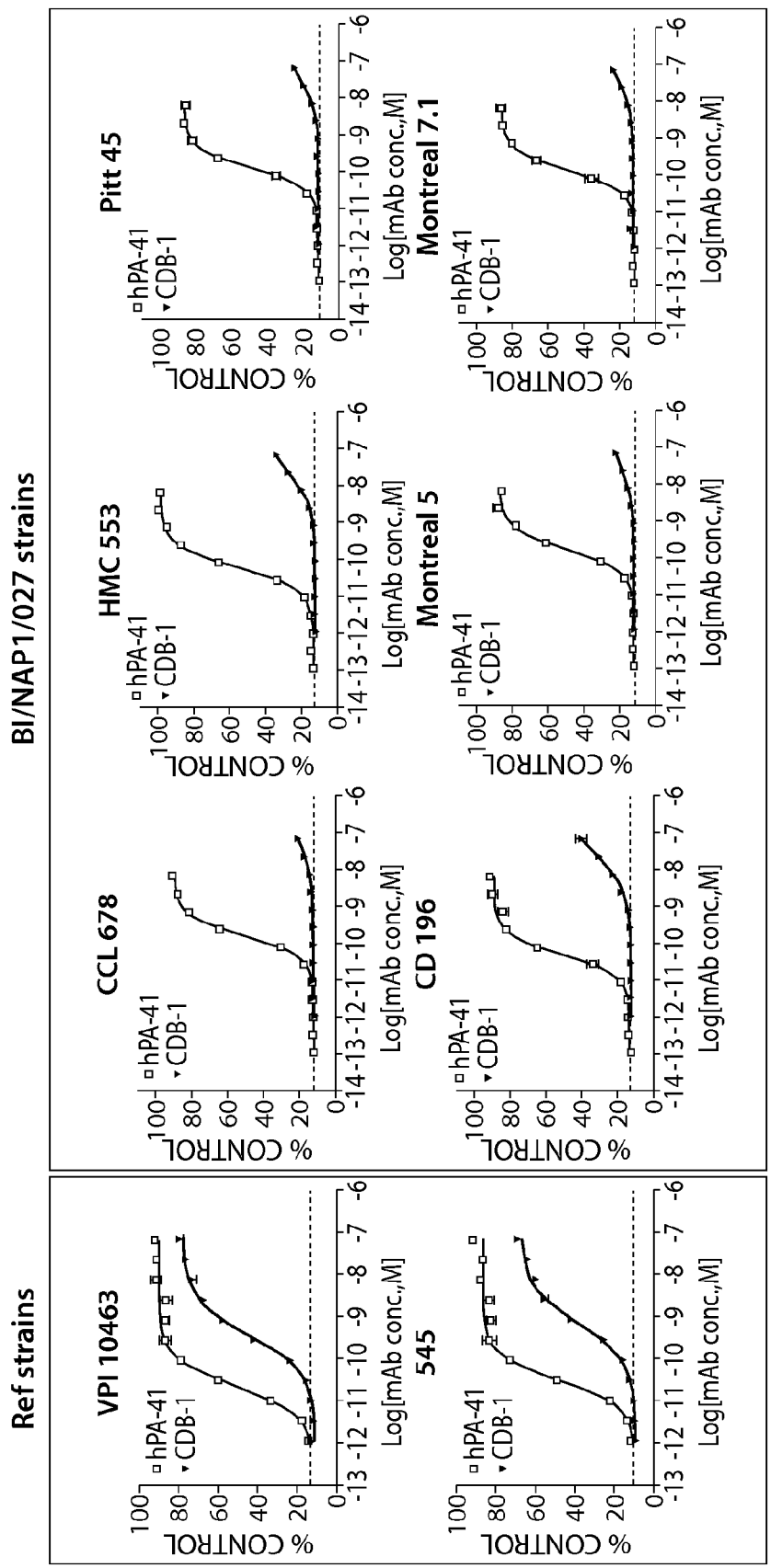

As observed in FIG. 31D, comparator mAb CDA-1 shows a minimal shift in $EC_{50}$, but considerable lowering of the maximal percent effect as toxin is increased. When the results shown in FIG. 31D are considered with the data presented in Table A, the CDA-1 comparator mAb demonstrates a non-competitive mechanism of action, as all of its activity is observed outside of the cell. Steric hindrance of toxin binding and cellular internalization are likely to be responsible for yielding the data plots in FIG. 31D, thereby supporting a non-competitive MOA for the CDA-1 comparator mAb.

In accordance with the foregoing for toxin B neutralization and MOA, the PA-41 mAb is considered to exhibit a mixed-competitive mechanism of action due to the rightward shift of $EC_{50}$ values and the lowered maximal percent effect observed both in FIG. 31E and in the data presented in Table B.

The results observed for mAb PA-41 are in contrast to those observed for comparator mAb CDB-1, which displays a lowered maximal percent effect, but a lesser degree of $EC_{50}$ shift, In this case, the mechanism of action for the activity of the comparator mAb against toxin B is less clear, particularly in view of the error considerations mentioned above.

Example 8

Testing mAbs of the Invention Against a Panel of *C. difficile* Isolates or Strains, Including Hypervirulent Isolates or Strains To evaluate the ability of *C. difficile* anti-toxin A and anti-B mAbs of the invention to neutralize toxins from a broad range of relevant isolates of *C. difficile*, the neutralization activity of the mAbs was tested against a collection of twenty toxigenic, clinical *C. difficile* isolates or strains, including hypervirulent BI/NAP1/027 isolates. Since *C. difficile* exhibits considerable interstrain heterogeneity in the genes encoding toxins A and B, these studies were undertaken to examine the breadth of toxin neutralization by the described mAbs, and in particular, mAbs PA-50 and PA-41.

A panel of toxigenic, clinical *C. difficile* isolates (Table 6) was selected for geographic and genetic diversity based on toxinotype, ribotype and restriction endonuclease analyses from an international collection of *C. difficile* isolates or strains maintained at TechLab (Blacksburg, Va.).

As categorized in Table 6, the strains of *C. difficile* include 3 reference strains (VPI 10463 (ATCC 43255), 630 (ATCC BAA-1382) and 545 (ATCC 43596), six hospital-derived BI/NAP1/027 strains (CCL678, HMC553, Pitt45, CD196, 5, 7.1), two toxin A−/toxin B+ (tcdA-tcdB+) strains (F1470, 8864), three outpatient isolates (MH5, CCL13820 and CCL14402) and other frequent clinical isolates (Pitt2, CCL14137, UVA17, UVA30/TL42, Pitt102, Pitt7). Additionally, isolates 13 (CCL13820) and 19 (Pitt 102), which are categorized as an "outpatient isolate" and a "frequent clinical isolate (other than Ribotype 027)", respectively, in Table 6 are also toxA−/toxB+ strains. Culture supernatants containing these *C. difficile* toxins were produced at TechLab, filter-sterilized and stored at 4° C. The presence of the toxins in the culture supernatants was confirmed using the *C. difficile* Toxin/Antitoxin Kit (TechLab) and cytotoxicity assay.

The cytotoxic activity of each toxin-containing culture supernatant for CHO-K1 cells (used to determine toxin B activity of culture supernatants) and T-84 cells (used to determine toxin A activity of culture supernatants) was assessed by treating cells with titrated culture supernatants.

TABLE 6

*C difficile* isolates/strains used for generating supernatants

| No | Strain | Category | Ribo type | Toxino type | REA type | Year | Location |
|---|---|---|---|---|---|---|---|
| 1 | VPI 10463 ATCC 43255 | A + B + reference | 003 | 0 | Not known | ~1975 | USA |
| 2 | 630 ATCC BAA-1382 | strains | Not known | Not known | Not known | 1982 | Switzerland |
| 3 | 545 ATCC 43596 | | Not known | Not known | Not known | Not known | Louvain, Belgium |
| 4 | CCL 678 | Ribotype | 027 | III | BI | 2007 | Virginia, USA |
| 5 | HMC553 | 027 | | | | 2008 | Pennsylvania, USA |
| 6 | Pitt 45 | (hospital | | | | 2001-2002 | Pennsylvania, USA |
| 7 | Cd 196 | isolates) | | | | 1988 | Paris, France |
| 8 | 5 | | | | | 2004 | Quebec, Canada |
| 9 | 7.1 | | | | | 2004 | Quebec, Canada |
| 10 | F1470 | $tcdA^-tcdB^+$ | 017 | VIII | CF1 | 1990 | Louvain, Belgium |
| 11 | 8864 CCUG 20309 | strains | 036 | X | CY1 | 1986 | Birmingham, England |
| 12 | MH 5 | Outpatient | 001 | Not known | Not known | 2008 | Virginia, USA |
| 13 | CCL13820 | isolates | 017 | VIII | CF | 2008 | Virginia, USA |
| 14 | CCL 14402 | | 027 | III | BI | 2008 | Virginia, USA |
| 15 | Pitt 2 | Frequent | 001 | Not known | J | 2001-2002 | Pennsylvania, USA |
| 16 | CCL 14137 | clinical | 001 | Not known | J | 2008 | Virginia, USA |
| 17 | UVA17 | isolates | 002 | Not known | G | 2006-2007 | Virginia, USA |
| 18 | UVA30/TL42 | (other than | 014 | Not known | Y | 2006-2007 | Virginia, USA |
| 19 | Pitt 102 | Ribotype | 017 | VIII | CF | 2001-2002 | Pennsylvania, USA |
| 20 | Pitt 7 | 027) | 078 | V | BK | 2001-2002 | Pennsylvania, USA |

To test the neutralizing activities of mAbs of the invention, toxin-containing culture supernatants were used at the maximum dilution that resulted in ≥95% loss in cell viability. Toxin supernatants were premixed with various concentrations of the mAbs for lh and then added to cells for incubation at 37 C for 72 h. Cell viability was measured using CELLTI TER-BLUE (Promega). The percent survival of treated wells was compared to that of untreated control wells and graphed to calculate in vitro neutralization activities ($EC_{50}$) of the mAbs. In a first series of experiments, FIG. 23A shows the activity of mAb PA-41 in neutralizing the toxin-containing supernatants using CHO-K1 cells. PA-41 potently ($EC_{50}$ range from $1.1^{-11}$M to $6.5^{-10}$M) neutralized supernatants of all toxigenic strains of C. difficile, including all hypervirulent strains, with the exception of three toxinA−/toxin B+strains. It has been reported that there are significant sequence differences in the enzymatic domains of toxin A/toxin B+ from conventional strains of C. difficile. Because PA-41 binds to the enzymatic domain of toxin B, the sequence diversity in this domain may explain the less effective neutralizing activity of PA-41 against toxin B from the two toxin A−/toxin B+ strains. Experiments were also conducted to evaluate the activity of both hPA-41 and comparator human anti-toxin B mAb CDB-1, (WO/20061121422; US2005/0287150), against hypervirulent strains of C. difficile in the CHO-K1 cell line. In these studies, it was observed that hPA-41 showed significant neutralization activity against the supernatants from all 6 5 BI/NAP1/027 strains, while the comparator mAb CDB-1 showed minimal activity (FIG. 23B). Also in these studies, the neutralization activity of hPA-41 mAb was seen to be >1,000-fold greater than that of the comparator mAb CDB-1 in neutralizing toxicity of the BI/NAP1/027 strains. The neutralization activity of hPA-41 and CDB-1 comparator mAb for the 2 reference strains (VPI 10463 and ATCC 43596) and 6 BI/027/027 strains (CCL678, HMC553, Pitt 45, CD196, Montreal5.1 and Montreal 7.1) is illustrated in FIG. 23B. In these studies hPA-41 was found to be inactive against three Ribotype 017 isolates (Table 6) which are toxin A−/B+, although the hPA-41 anti-toxin B mAb exhibited significantly greater neutralization activity than the comparator mAb against other strains in the panel.

Figure 24A:
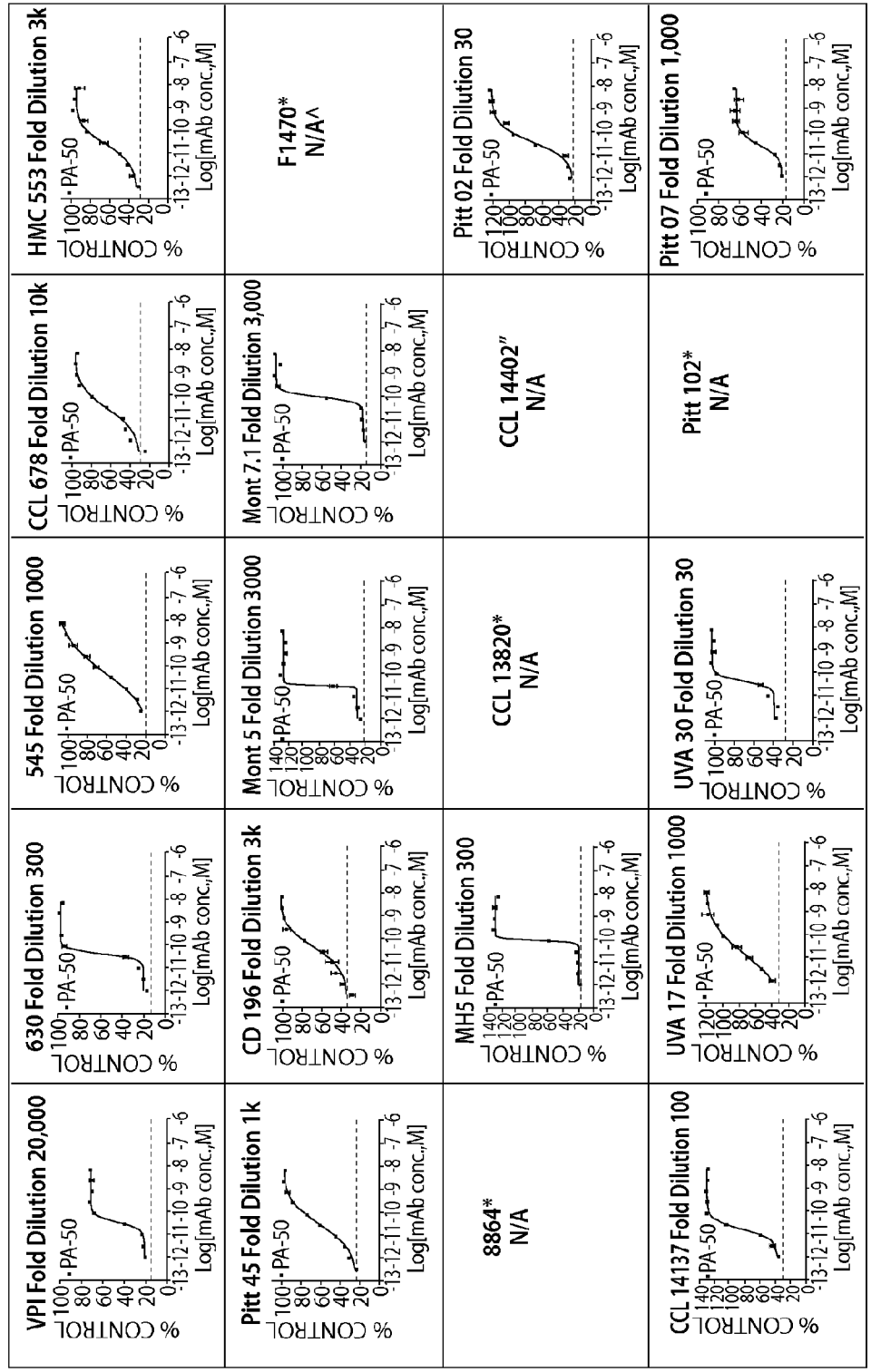
FIGS. 24A and 24B demonstrate the neutralizing activity of mAb PA-50 in vitro against the *C. difficile* toxigenic clinical isolates described for FIGS. 23A and B.
Figure 24B:
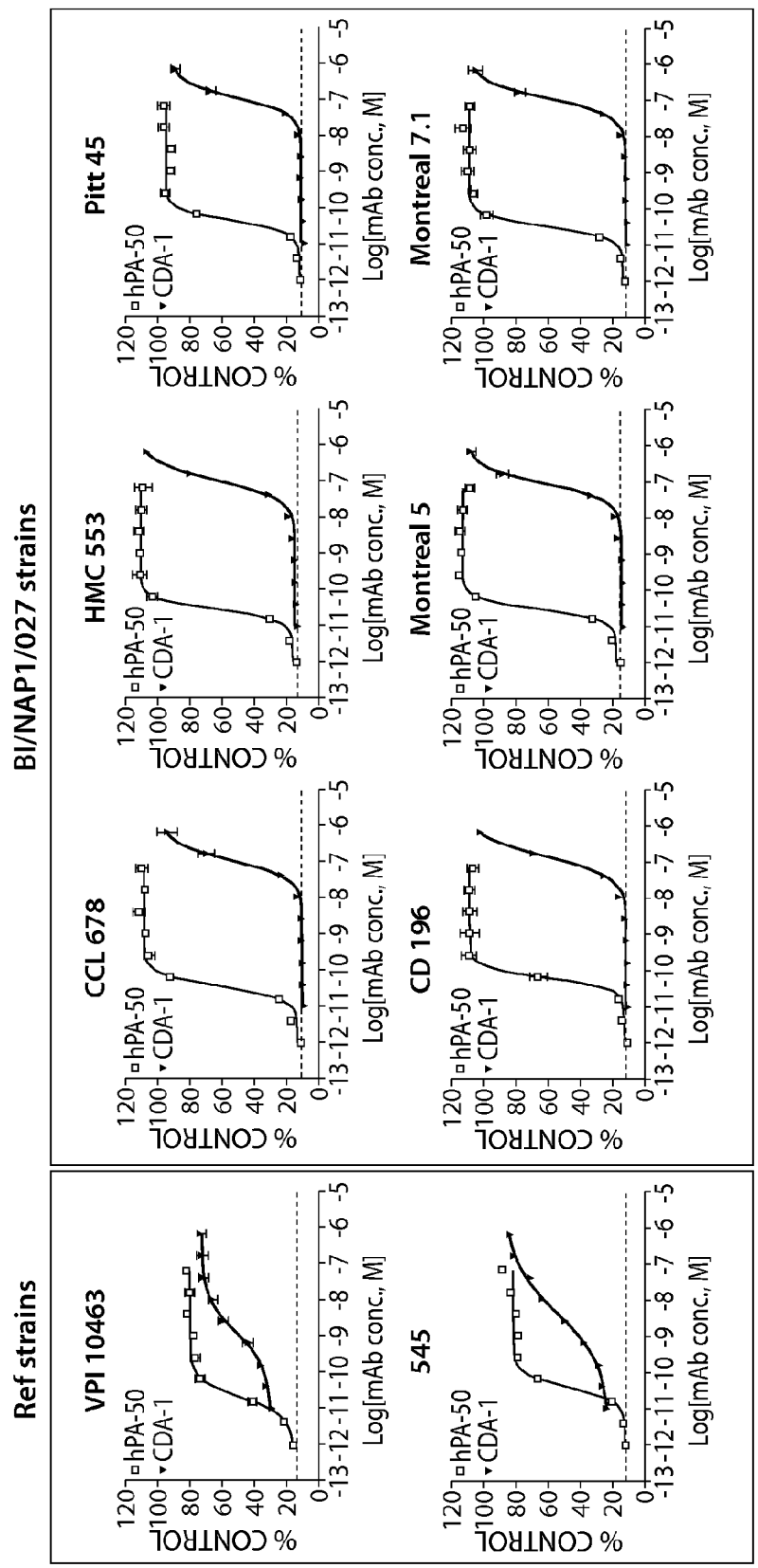
Figure 25A:
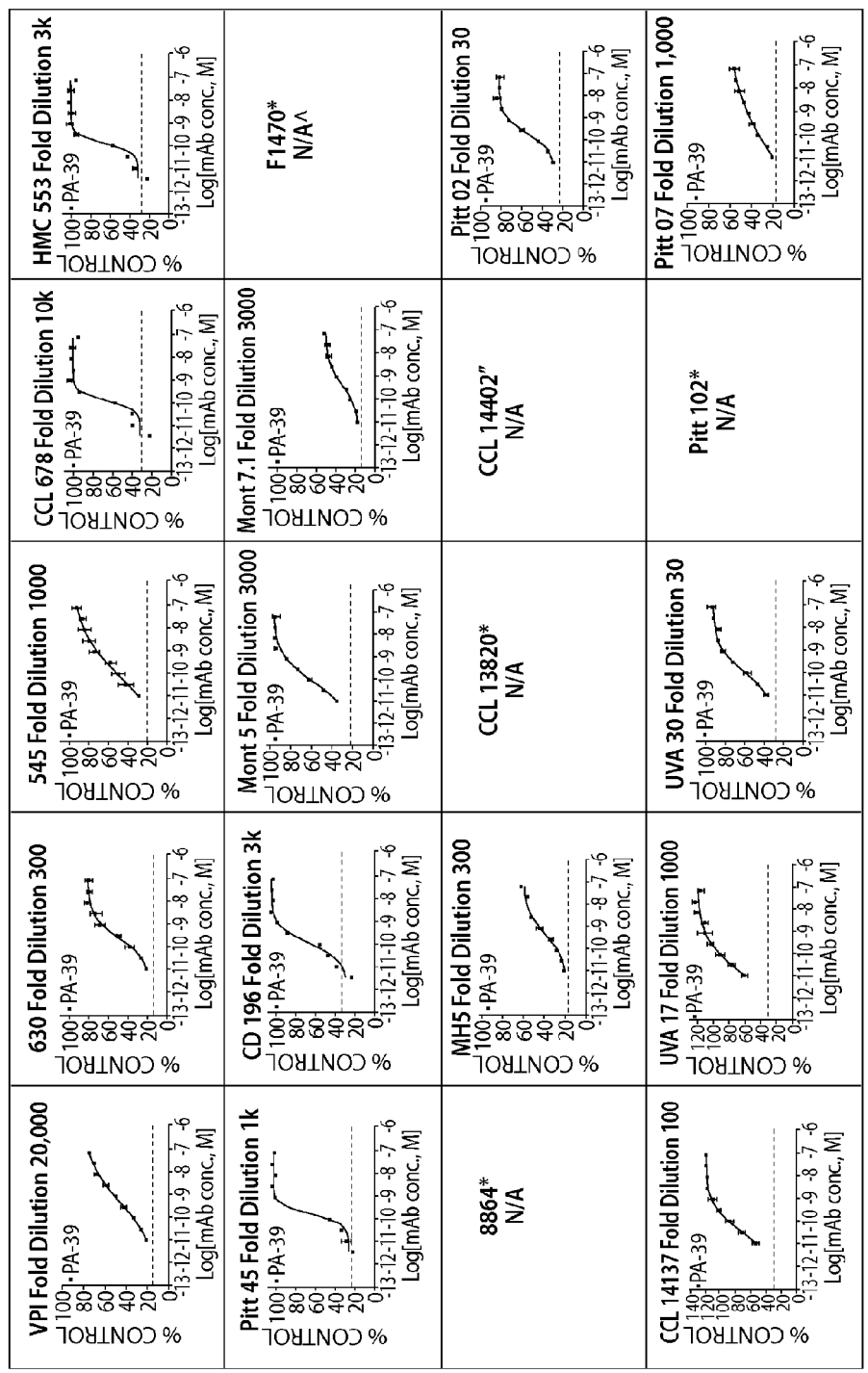
FIGS. 25A-25D demonstrate neutralization of toxins produced by diverse strains of *C. difficile*.
Figure 25B:
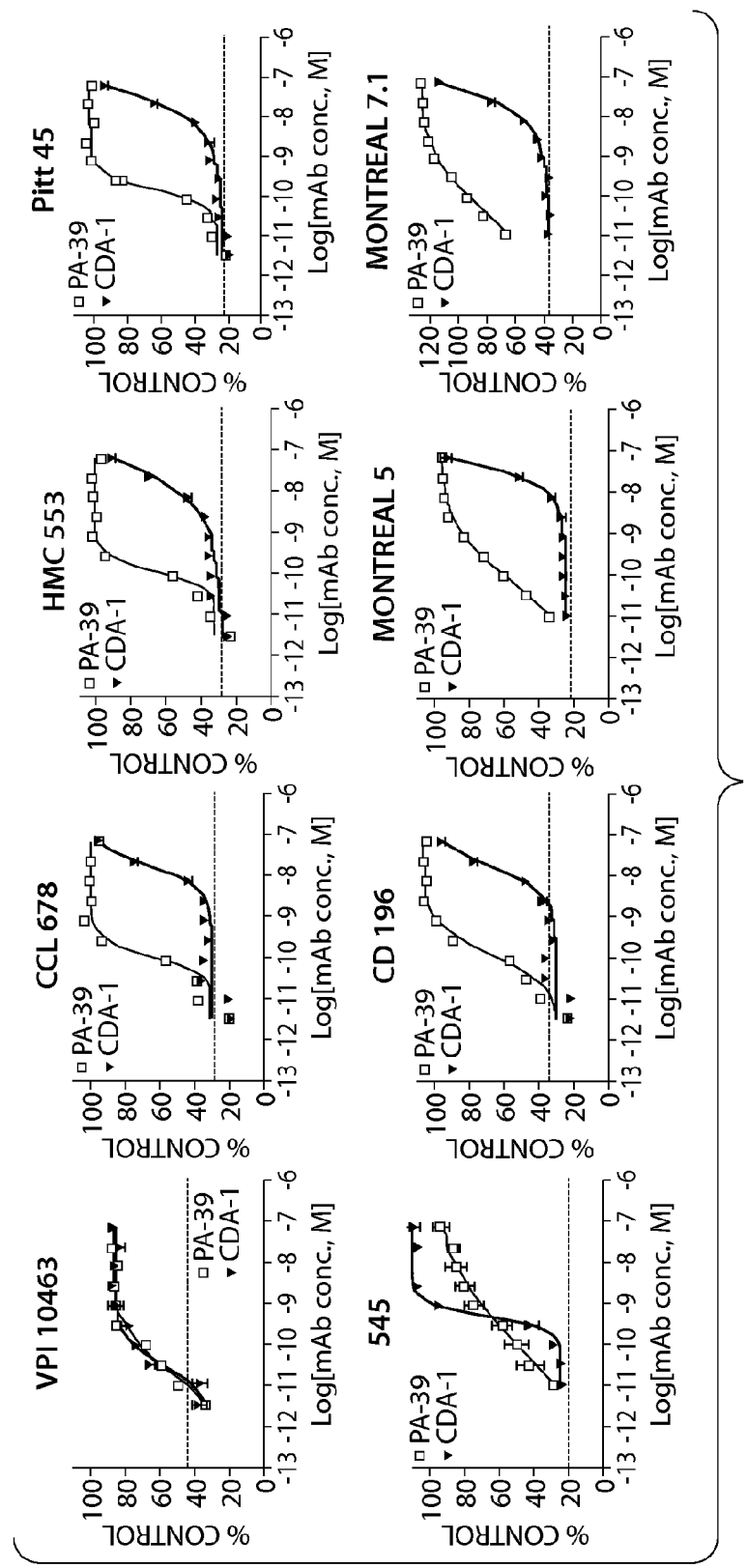

The activity of mAb PA-50 in neutralizing toxin A-containing supernatants of C. difficile cultures using T-84 cells ranged from $2.6^{-12}$M to $7.7^{-11}$M as shown in FIG. 24A. PA-50 fully neutralized supernatants from all available strains which produce toxin A, including hypervirulent strains. PA-50 did not neutralize the four toxin A−/toxin B+ strains (F1470, 8864, CCL 13820, CCL 14402), since these strains do not produce any toxin A. hPA-50 was also significantly more effective in neutralizing the activity of the remaining strains in the panel. In other comparative studies, it was found that the neutralization activity of hPA-50 against all 6 BI/NAP1/027 strains of toxin-A producing C. difficile was >100-fold greater than that of the comparator mAb CDA-1 (WO/2006/121422; US2005/0287150), (FIG. 24B). hPA-50 also showed greater neutralization activity than the comparator mAb CDA-1 against C. difficile toxin A-producing reference strains VPI 10463 and 545. Similarly, mAb PA-39 neutralized toxin A in supernatants of C. difficile cultures with $EC_{50}$ values ranging from $7.7^{-12}$M to $4.8^{-8}$M, as shown in (FIG. 25A). As seen for mAb PA-50, the four toxin A−/toxin B+ strains were not neutralized by PA-39. Moreover, results of comparative studies demonstrated that the neutralization activity of mAb PA-39 against all 6 BI/NAP1/027 strains was >100-fold greater than that of the comparator human anti-toxin A mAb CDA-1; PA-39 also showed significantly more neutralizing activity against the remaining strains in the panel (FIG. 25B). It is noted that one toxin strain, CCL 14402, did not reduce the viability of T-84 cells sufficiently enough to allow an accurate measurement of mAb neutralization activity in the assay.

In these studies, the CHO-K1 cell line, hPA-41 showed high levels of neutralization activity against the supernatants from all 6 BI/NAP1/027 strains, while the comparator mAb CDB-1 showed minimal activity. Humanized PA-41 was seen to have a neutralization activity >1,000-fold greater than that of comparator mAb CDB-1 in neutralizing the hypervirulent BI/NAP1/027 strains of C. difficile. The neutralization activities of hPA-41 and CDB-1 in these studies against the 2 reference strains (VPI 10463 and ATCC 43596) and 6 BI/027/027 strains (CCL678, HMC553, Pitt 45, CD196, Montreal 5.1 and Montreal 7.1) are illustrated in FIG. 23B. Similarly, hPA-41 showed significantly higher neutralization activity in these studies compared with comparator mAb CDB-1 against the other strains in the panel, with the exception of three Ribotype 017 isolates, which are toxin A−/B+. Similar experiments were performed to assess the neutralization activity of hPA-39 and that of comparator human anti-toxin A mAb CDA-1 on T-84 cells. The results showed that neutralization of all 6 BI/NAP1/027 strains by hPA-39 was >100-fold greater than that of comparator mAb CDA-1 (FIG. 25B). Humanized PA-39 also showed significantly higher neutralization activity in the studies than comparator mAb CDA-1 against the remaining strains in the panel. Thus, the hPA-41 and hPA-39 mAbs displayed high levels of anti-C. difficile hypervirulant strain neutralization activities against all strains tested. This indicates that the epitopes recognized by these humanized mAbs are highly conserved across diverse strains.

Similar to Table 6, Table 7 presents the results of the above-described in vitro C. difficile toxin neutralization experiments, showing the panel of toxigenic C. difficile strains isolated from North America and Europe and the resulting $EC_{50}$ values generated by the humanized anti-toxin mAbs and comparator mAbs CDA-1 and CDB-1. The panel includes ribotypes 001, 002, 003, 012, 014, 017, 027 and 078 in approximate proportion to the rates observed clinically (94, 95), with the exception of ribotype 017 tcdA⁻tcdB⁺ strains, which are over-represented in the panel. Supernatants from tcdA⁻tcdB⁺ strains were used as tools to identify cells that were refractory to killing by supernatants containing toxin B alone, and thus would be suitable for examining cytotoxicity mediated by toxin A. VPI 10463 was included in the panel and allowed the comparison of results obtained with purified and unpurified toxins.

Figure 25C:
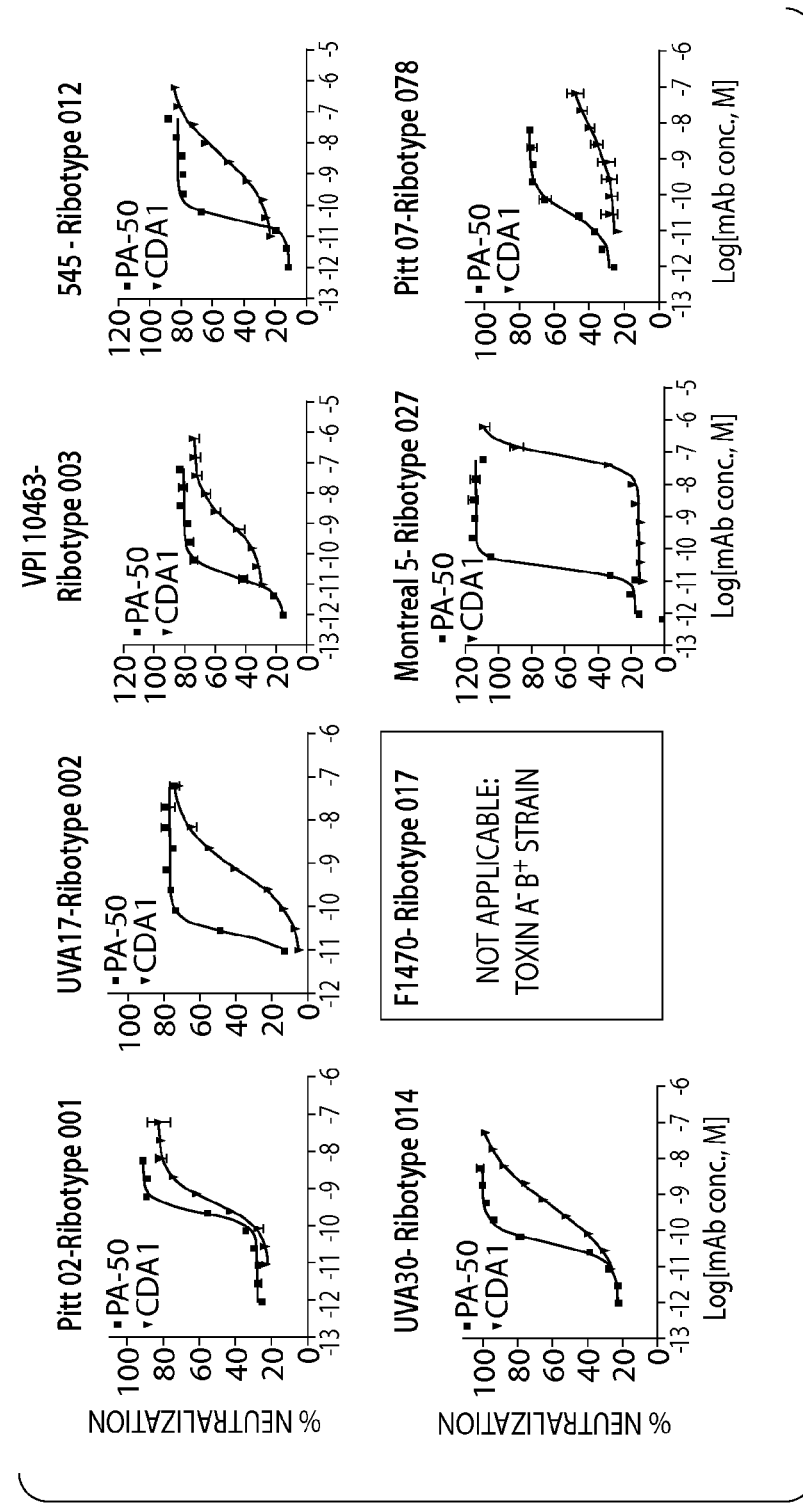

In these studies, humanized mAb PA-50 neutralized toxin A in a strain-independent manner. The median $EC_{50}$ value was 32 μM (range: 20 to 127 μM, Table 7), and steep dose-response curves were observed with Hill slopes that typically were greater than two (FIG. 25C). PA-50 was more active than CDA1 against each of the test isolates. The greatest difference in potency was observed for the hypervirulent 027 strains, for which PA-50 was approximately 1,000-fold more potent than CDA1 (P=0.0002), and for a ribotype 078 strain included in the panel.

Figure 25D:
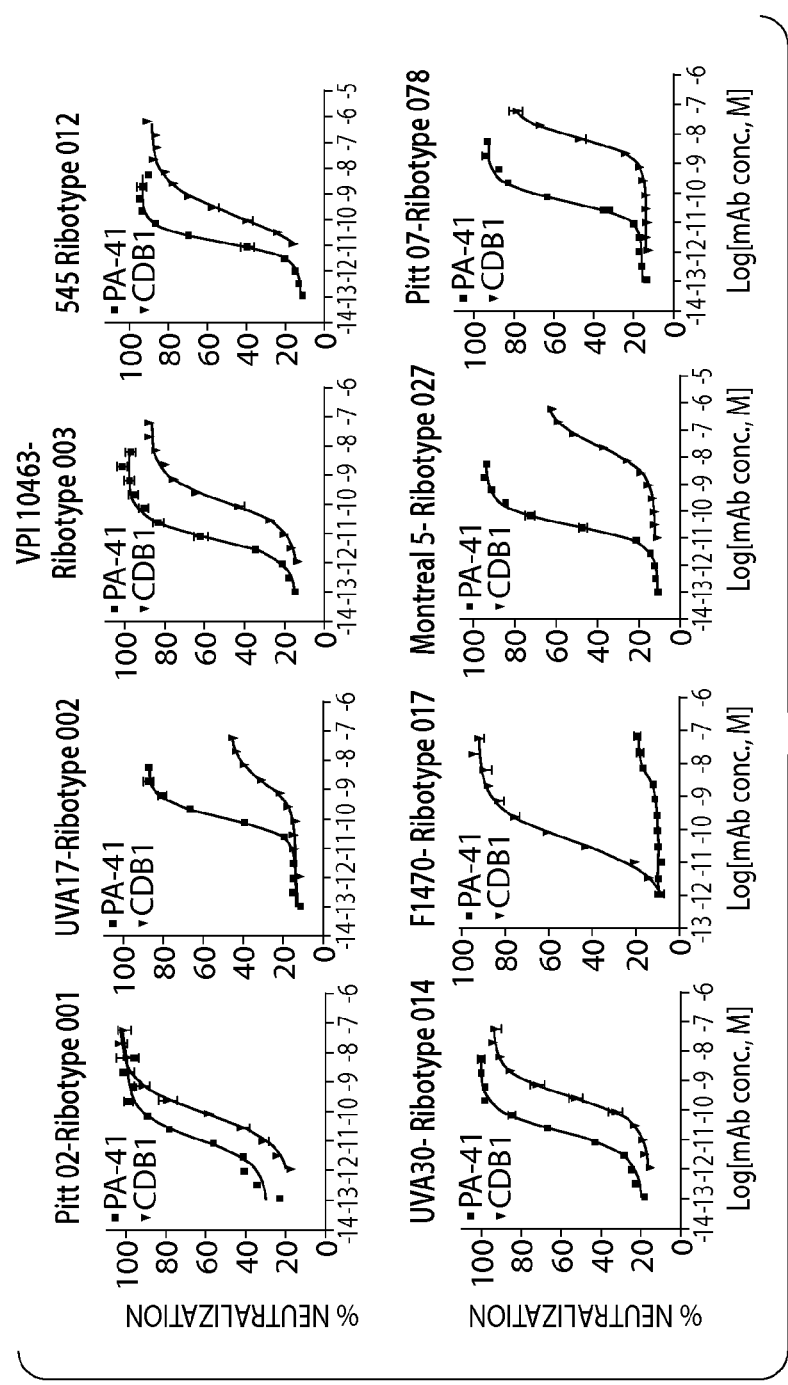

Humanized mAb PA-41 potently inhibited each of the tcdA⁺tcdB⁺ strains with a median $EC_{50}$ value of 23 μM (range: 7.7 to 129 μM, Table 7), and essentially complete neutralization was observed at higher concentrations (FIG. 25D). PA-41 was generally more effective than CDB1 against tcdA⁺tcdB⁺ strains and was approximately 500-fold more potent against the hypervirulent 027 strains (P=0.003). CDB1, but not PA-41, was effective in neutralizing toxin B from ribotype 017 tcdA⁻tcdB⁺ strains. Finally, PA-41 and PA-50 exhibited similar activities against crude and purified forms of toxin from the reference strain VPI 10463 (Table 7 and FIGS. 25C and 25D).

TABLE 7

Neutralization of toxins from diverse C. difficile strains in vitro

| | | $EC_{50}$, pM | | | |
|---|---|---|---|---|---|
| | | anti-toxin A mAbs | | anti-toxin B mAbs | |
| Ribotype | Strain | PA-50 | CDA1 | PA-41 | CDB1 |
| 001 | CCL14137 | 39 | 611 | '09.7 | 129 |
| 001 | MH5 | 127 | 384 | 18 | 73 |
| 001 | Pitt 2 | 27 | 247 | 13 | 92 |
| 002 | UVA17 | 26 | 825 | 129 | 671 |
| 003 | VPI 10463 | 20 | 1271 | 7.7 | 136 |
| 012 | 545 | 38 | 4552 | 15 | 153 |
| 012 | 630 | 54 | 1019 | 111 | 1782 |
| 014 | UVA30/TL42 | 51 | 625 | 21 | 324 |
| 017 | CCL13820 | N/A | N/A | >$10^5$ | 72 |
| 017 | F1470 | N/A | N/A | >$10^5$ | 46 |
| 017 | Pitt 102 | N/A | N/A | >$10^5$ | 8.1 |
| 027 | CCL678 | 29 | 58,950 | 77 | >$10^5$ |
| 027 | CCL14402 | ND | ND | 19 | 4,678 |
| 027 | CD196 | 61 | 132,600 | 16 | 9,812 |
| 027 | HMC553 | 29 | 109,000 | 24 | 14,730 |
| 027 | Montreal 5 | 29 | 87,090 | 36 | 25,810 |
| 027 | Montreal 7.1 | 31 | 109,400 | 29 | 16,800 |
| 027 | Pitt 45 | 43 | 108,100 | 29 | 26,510 |
| 078 | Pitt 07 | 32 | >$10^5$ | 59 | 8,415 |

As shown in this Example, humanized mAbs PA-50 and PA-41 showed a high level of neutralization activity against C. difficile toxins A and B, respectively, from genetically diverse strains representative of the current CDI epidemic. The breadth of activity of these mAbs is notable in light of the genotypic and phenotypic variation within the toxins. In particular, PA-50 and PA-41 neutralized toxins produced by the hypervirulent, antibiotic resistant 027 strains with picomolar activity, while the comparator mAbs were observed to have nanomolar activity. This result may reflect the reduced binding of CDA-1 to toxin A from 027 strains as previously reported (90). Toxin B from 027 strains exhibits marked sequence divergence relative to other C. difficile strains. The sequence differences concentrate within the carboxy-terminal receptor-binding domain and are associated with increased cytotoxicity in vitro. However, such sequence divergence did not affect the neutralizing activity of PA-41, which binds an epitope within the amino-terminal domain of toxin B. PA-50 and PA-41 neutralized all six 027 strains in the panel with picomolar potencies, including strain CD196 that predates the recent rise in 027 prevalence. Overall, the findings indicate that the epitopes for PA-50 and PA-41 are broadly conserved through the 027 lineage.

CDI is typically caused by strains of C. difficile that produce both toxins A and B. However, tcdA⁻tcdB⁺ strains also have been linked with disease. Clinically relevant tcdA⁻tcdB⁺ strains are predominantly ribotype 017. Ribotype 017 strains have been reported to exhibit reduced pathogenicity in hamsters and encode an atypical tcdB whose amino-terminal region bears 70-80% sequence identity with both tcdB from VPI 10463 and lethal toxin (tcsL) from C. sordellii. Phenotypically, ribotype 017 tcdB has hybrid characteristics and exhibits the receptor-binding properties and glucosylating specificities of typical tcdB and tcsL toxins, respectively. The atypical amino-terminal region of 017 tcdB provides a likely explanation for why this toxin was not neutralized by PA-41 in this study. Although 017 strains can be regionally prevalent and cause local outbreaks of CDI, overall they were determined to comprise <2% of the strains encountered in recent international phase 3 clinical studies of investigational therapies for treating CDI (94, 95).

Example 9

Generation of Chimeric mAbs

Chimeric monoclonal antibodies that comprise the variable region of the parent mouse mAb and the constant region of human IgG1 were produced and characterized. Chimeric mAbs were generated to ensure that murine variable regions having the correct anti-toxin activity and binding specificity were cloned and that construction of the murine variable regions with a human constant region did not significantly alter the binding and neutralization properties of each cloned mAb. Chimeric mAbs typically exhibit the same binding activity as the parent mouse mAbs.

MAbs PA-38, PA-39, PA-41 and PA-50 all contain kappa light chains. To generate the chimeric mAbs, the nucleic acid sequences encoding the variable regions of the heavy and light chains were inserted into suitable expression vectors, such as, but not limited to, pCON Gamma1 and pCON kappa, respectively (Lonza Biologics, Berkshire, UK). Suitable plasmids encode either the constant region of the human kappa light chain or the constant region of the human IgG1 heavy chain. For chimeric mAb production, the variable region of the heavy chain of each mAb was cloned into the pCON gamma1 plasmid. The complete heavy chain gene was subcloned into the plasmid containing the light chain gene to create a single plasmid that encoded both the heavy and light chain genes. 293F cells were transiently transfected with this expression vector using Effectene (Qiagen, Valencia, Calif.) according to the manufacturer's suggested protocol. Cell supernatant containing secreted chimeric mAb was collected seven days following transfection and purified using Protein A chromatography. The potencies and activities of the chimeric mAb(s) were compared with those of the murine mAbs in cytotoxicity and hemagglutination assays.

In accordance with the above procedure, chimeric mAbs (cPA-39 and cPA-41) were generated based on the parental mouse PA-39 and PA-41 mAbs. The concentrations of these chimeric mAbs in crude cell supernatants ranged from about 2-11 μg/mL. In particular, crude supernatant from a transfected 293F cell culture producing cPA-39 contained 10.6 μg/mL of the chimeric mAb, while crude supernatants from several transfected 293F cell cultures producing cPA-41 contained from 9.6-10.9 μg/mL of the chimeric mAb.

Figure 26:
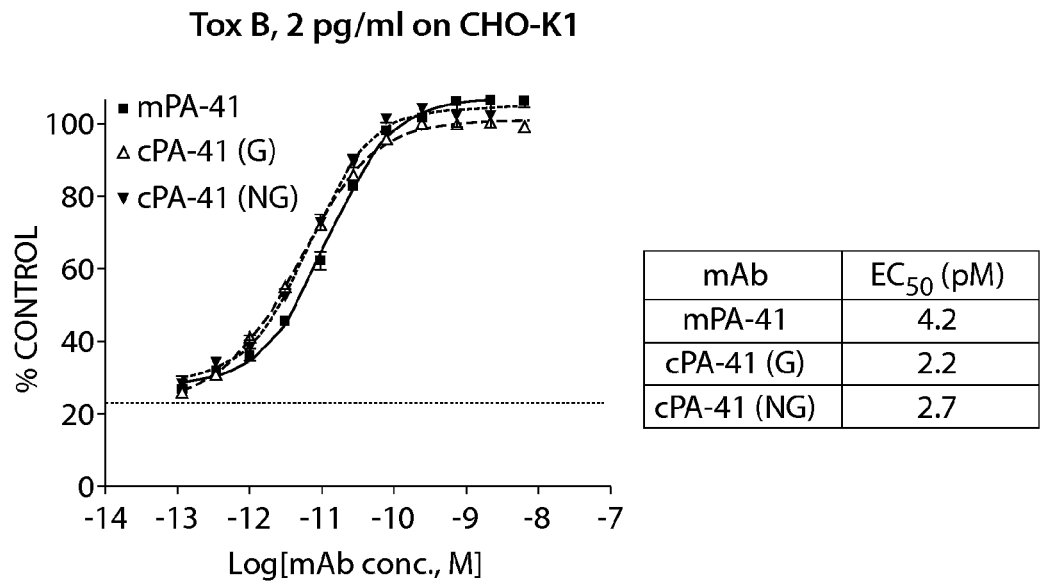
FIG. 26 shows that the chimeric mAb PA-41 (cPA-41 mAb) effectively neutralizes the toxicity of *C. difficile* toxin B on CHO-K1 compared to the counterpart murine mAb PA-41. Two chimeric PA-41 mAbs were generated; one which had a glycosylation site removed in the VL region, designated as cPA-41(NG), and one which had no glycosylation site removal, designated as cPA-41(G) in the figure. Both cPA-41 (NG) and cPA-41(G) showed similar neutralization levels for toxin B (2 pg/mL, TechLab) on CHO-K1 cells, and both chimeric mAbs neutralized toxin B at a level similar to that of the parent murine mAb (mPA-41).
Figure 27:
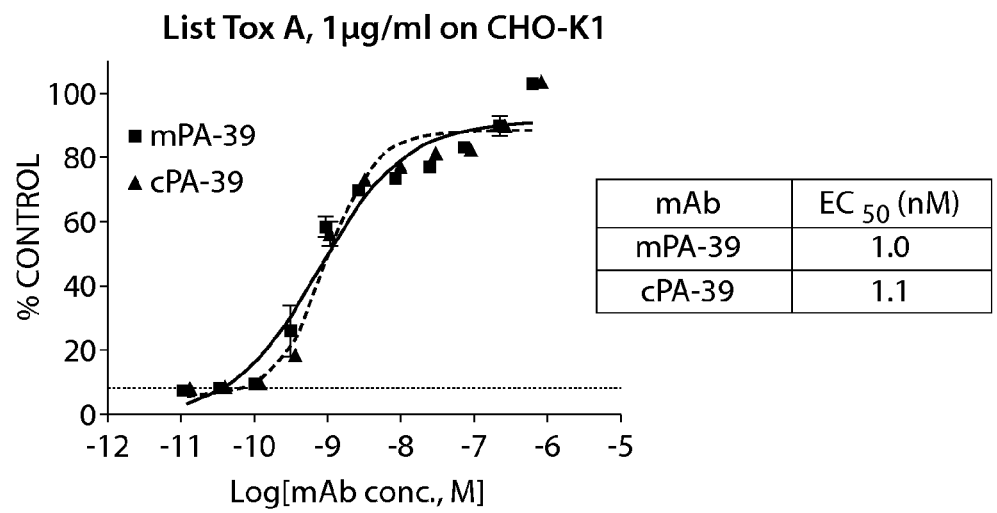
FIG. 27 shows that chimeric PA-39 (cPA-39) mAb effectively neutralizes the toxicity of C. difficile toxin A (1 μg/mL, Listlab) on CHO-K1 cells compared with the parent murine PA-39 (mPA-39) mAb.
Figure 28:
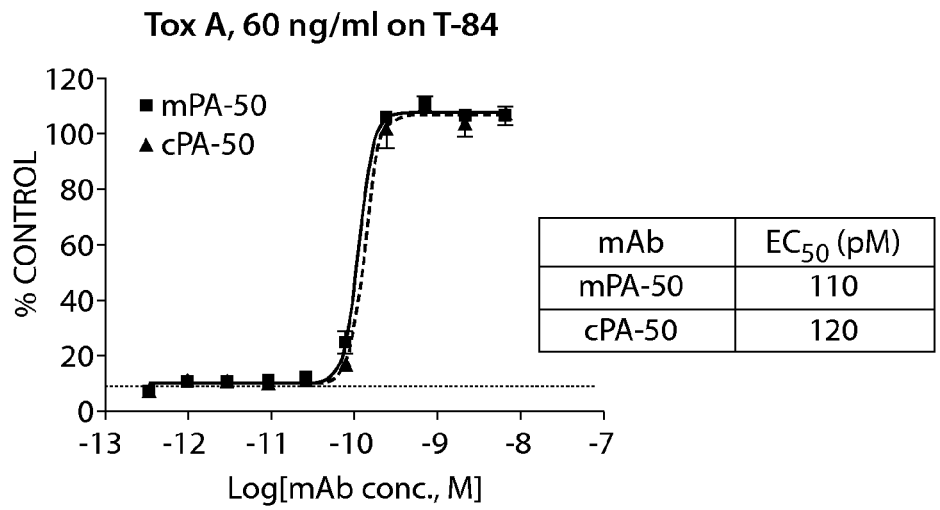
FIG. 28 shows that chimeric PA-50 (cPA-50) mAb effectively neutralizes the toxicity of C. difficile toxin A (60 ng/mL, TechLab) on T-84 cells compared with the parent murine PA-50 (mPA-50) mAb.

The chimeric mAbs were compared with their respective parental mouse mAbs for the ability to neutralize C. difficile toxins in vitro by conducting cytotoxicity assays (cPA-39: CHO-K1 cells, cPA-41: CHO-K1cells and cPA-50: T-84 cells) as previously described (Example 3). All chimeric mAbs were found to be equally effective when compared to their murine parental mAb as shown in FIG. 26 (PA-41), FIG. 27 (PA-39) and FIG. 28 (PA-50). These results demonstrate the success of chimerization and the production of functional chimeric mAbs having toxin neutralization potencies equivalent to those of the parental mouse mAbs.

Example 10

Humanization of Murine mAb(s) and Testing of the Humanized mAbs of the Invention for Toxin Neutralization Potency in vitro Humanized mAbs have been generated by methods known in the art. Examples and descriptions of various humanized mAbs include, for example, Zenapax (65,66) Synagis (67-69), Herceptin (70-72), Mylotarg (73,74), Xolair (75-77), Raptiva (78-80), Avastin (81,82), and Tysabri (83). Humanized monoclonal antibodies that are effective in minimizing immunogenicity can be generated, such that mAb activity in humans is not adversely affected. (84-87). Preferably, the humanized mAbs demonstrate toxin-neutralizing activity that is within two-fold of the parent mouse mAbs. Further, humanized mAbs optimally demonstrate potent efficacy in the hamster model of *C. difficile* infection.

Established methods of complementarity-determining region (CDR) grafting were used to generate humanized forms of the murine anti-toxin A and/or anti-toxin B mAbs as described herein. The humanized mAb(s) were compared with the parent mouse mAb(s) for toxin-neutralizing activity in vitro and in vivo. In accordance with the invention, the humanized mAb(s) can retain the anti-toxin activity of the parent murine mAb(s) and can be suitable for repeat dosing in humans.

A. Molecular Cloning of the Heavy and Light Chain Genes of the Murine mAbs

Established methods were used for the cloning of antibody genes. (88) Briefly, total RNA was purified from $1 \times 10^7$ hybridoma cells using TRIzol reagent (Invitrogen) according to the manufacturer's suggested protocol. 5 µg of total RNA was reverse transcribed using SuperScript II Reverse Transcriptase (Invitrogen) utilizing an oligo-dT primer. The resulting cDNA was treated with RNAse H to remove the RNA template and was then purified using a QIAquick PCR purification kit (Qiagen) to remove free nucleotides and primers. Next, a tail of guanidine nucleotides was added to the 3' end of the cDNA using the enzyme terminal transferase (NEB) in the presence of dGTP according to the manufacturer's suggested protocol. The resulting tailed cDNA was then subjected to PCR using one primer that annealed to the constant region of either the heavy or light chain and one universal primer that annealed to the guanosine tail on the cDNA. For both the heavy and light chains, the universal primer 5'TATATCTAGAATTCCCCCCCCCCCCCCCC3' SEQ ID NO:11 was used. To amplify the light chain, the primer 5' TATAGAGCTCAAGCTTGGATGGTGGGAA-GATGGATACAGTTGGTGC3' (SEQ ID NO:12) was used, while the heavy chain was amplified using the primer 5' TATAGAGCTCAAGCTTCCAGTGGATAGAC(CAT) GATGGGG(GC)TGT(TC)GTTTT GGC3' (SEQ ID NO: 13), where the sequences in parentheses indicate base degeneracies. The resulting PCR-amplified DNA was purified using a QIAquick PCR purification kit (Qiagen) and sequenced. The PCR reactions were performed and sequenced in triplicate to ensure that no errors were introduced during the amplification of the approximately 500 base pair DNA fragments.

B. Humanization of the mAb Variable Regions

To produce the sequences of the humanized mAbs, the framework amino acid residues important for the CDR structure were first identified. In parallel, human $V_H$ and $V_L$ sequences having high homology to the murine $V_H$ and $V_L$, respectively, were selected from among known human immunoglobulin sequences. CDR sequences from the murine mAb, together with any framework amino acid residues important for maintaining the structure of the CDRs, if necessary, were grafted into the selected human framework sequences. In addition, human framework amino acid residues that were found to be atypical in the corresponding V region subgroup were substituted with the typical residues in an effort to reduce potential immunogenicity of the resulting humanized mAb. These humanized $V_H$ and $V_L$ regions were cloned into expression vectors, such as, but not limited to, pCON Gamma1 and pCON kappa (Lonza Biologics, Berkshire, UK), respectively. These vectors encode the constant region(s) of the human immunoglobulin heavy and light chain genes. 293F cells were transiently transfected with these expression vectors using the Effectene system (Qiagen, Valencia, Calif.). Cell supernatants containing secreted humanized mAb were collected seven days following transfection and purified using Protein A chromatography.

C. Generation of Cloned, Stable CHO Cells Expressing Humanized mAbs

The generation of stable CHO cells/cell lines allows for the production of sufficient quantities of mAbs to test in both in vitro cell assays, and in the *C. difficile*-associated diarrhea (CDAD) model in golden Syrian hamsters. As but one example, CHO K1 SV cells can be used from Lonza Biologics (Berkshire, UK) using a glutamine synthetase selection and amplification system (GS) to generate stably transfected CHO cells. The Lonza GS system typically yields high-production CHO cell lines which can produce sizable quantities of the humanized mAbs.

CHO K1 SV cells were expanded in CD CHO cell culture medium (Invitrogen) supplemented with 1× glutamine (Invitrogen) and 1×H/T Supplement (Invitrogen). $1 \times 10^7$ viable cells were electroporated at 290 V, infinite resistance and 960 uF with 40 µg of linearized plasmid DNA resuspended in 100 µl of sterile TE buffer. The cells were transferred to a T-150 flask containing 50 ml of complete CD CHO medium and incubated for approximately 48 hours at 37° C. and 8.0% $CO_2$. The cells were centrifuged and resuspended to a final density of $3.3 \times 10^5$ cells/ml in GS selection medium (CD CHO+1×GS Supplement (JRH Biosciences)+1×H/T Supplement) containing MSX (Sigma) at 100 µM, plated out at 5000 viable cells/well in 96 well plates (Corning) and incubated for approximately 3-4 weeks until primary cell colonies (clones of transfected cells) began to appear. Approximately 300 cell colonies (clones) were sampled for recombinant mAb production by carefully removing 20 µl of supernatant and performing a ELISA assay in a 96-well format. Briefly, 96-well plates were coated with a capture antibody (goat anti-human antibody) and then supernatants from cloned CHO transfectants (diluted 1:800) were added to allow binding to the capture antibody bound to the plate wells. After washing, a secondary antibody (goat anti-human antibody conjugated to alkaline phosphatase) was added to the plate and allowed to bind to the human antibody in the sample before being washed to remove non-specific binding. The plate was then assayed for alkaline phosphatase activity using a 1-Step PNPP kit (Thermo, Rockford, Ill.) to identify the clones producing the greatest amount of secreted antibody. Clones producing high amounts of mAb were expanded in CD CHO cell culture medium supplemented with 1× glutamine and 1×H/T Supplement. Cell supernatants containing secreted humanized mAb were collected and purified using Protein A. The clones exhibiting the best production were subcloned by limiting dilution and scaled up to produce gram quantities of recombinant, humanized, monoclonal antibody.

D. Humanized mAbs hPA-39, hPA-41 and hPA-50

The molecularly cloned, humanized mAbs were isolated as described above and characterized (see Section E below). The light (L) chain constant (CL) region of each of the humanized antibodies is of the kappa (κ) class; the heavy (H) chain constant region (CH) of each of the humanized antibodies is of the IgG1 isotype. The humanized mAbs containing unique variable (V) regions were found to bind and neutralize the activity of either toxin A or toxin B of *C. difficile*. The V regions of the L and H chains of the humanized mAbs may form a part of a complete immunoglobulin (Ig) or antibody molecule composed of two H chain polypeptides and two L chain polypeptides, typically linked by disulfide bonding, or they may be discrete portions or fragments of the antibody, in particular, antibody portions or fragments that bind toxin A and/or toxin B and/or that neutralize toxin activity. Nonlimiting examples of suitable V-region-containing immunoglobulin fragments or portions include F(ab), F(ab'), or F(ab')$_2$ fragments.

Humanized anti-*C. difficile* toxin A and toxin B mAbs were produced according to the above-described procedures. The humanization process yielded several anti-*C. difficile* toxin A humanized mAbs (hmAbs) that bound toxin A and neutralized toxin A activity on susceptible cells. Examples of such hmAbs include humanized anti-*C. difficile* toxin A mAb comprising a H chain polypeptide sequence comprising a VH region of SEQ ID NO:1 (FIG. 32A) and a human IgG1 C region and a L chain polypeptide sequence comprising a VL region of SEQ ID NO:3 (FIG. 33A) and a human κ C region; anti-*C. difficile* toxin A hmAb comprising a H chain polypeptide sequence comprising a VH region of SEQ ID NO:2 (FIG. 32B) and a human IgG1 C region and a L chain polypeptide sequence comprising a VL region of SEQ ID NO:3 (FIG. 33A) and a human κ C region; anti-*C. difficile* toxin A hmAb comprising a H chain polypeptide sequence comprising a VH region of SEQ ID NO:1 (FIG. 32A) and a human IgG1 C region and a L chain polypeptide comprising a VL region of SEQ ID NO:4 (FIG. 33B) and a human κ C region; and anti-*C. difficile* toxin A hmAb comprising a H chain polypeptide sequence comprising a VH region of SEQ ID NO:2 (FIG. 32B) and a human IgG1 C region and a L chain polypeptide sequence comprising a VL region of SEQ ID NO:4 (FIG. 33B) and a human κ C region. Such humanized anti-*C. difficile* toxin A mAbs embrace a PA-39 hmAb (hPA-39) of the invention. Complete hPA-39 immunoglobulin having two L chains and two H chains can be produced in a host cell which co-expresses and secretes a hPA-39 H chain polypeptide composed of a VH region of the invention (e.g., SEQ ID NO:1; SEQ ID NO:2) and a suitable CH region, e.g., of the IgG1 isotype, such as is contained within Genbank Accession No. NW_001838121, and a hPA-39 L chain polypeptide composed of a hPA-39 VL region of the invention (e.g., SEQ ID NO:3; SEQ ID NO:4), and a suitable CL region, e.g., of the κ subtype, such as is contained within GenBank Accession No. NW_001838785.

Other examples of humanized anti-*C. difficile* toxin A mAbs of the invention include humanized anti-*C. difficile* toxin A mAb comprising a H chain polypeptide sequence comprising a VH region of SEQ ID NO:5 (FIG. 34A) and a human IgG1 C region and a L chain polypeptide sequence comprising a VL region of SEQ ID NO:7 (FIG. 35) and a human κ C region; and humanized anti-*C. difficile* toxin A mAb comprising a H chain polypeptide sequence comprising a VH region of SEQ ID NO:6 (FIG. 34B) and a human IgG1 C region and a L chain polypeptide sequence comprising a VL region of SEQ ID NO:7 (FIG. 35) and a human κ C region. Such humanized anti-*C. difficile* toxin A mAbs embrace a humanized PA-50 (hPA-50) mAb of the invention. Complete hPA-50 immunoglobulin having two L chains and two H chains can be produced in a suitable host cell which co-expresses and secretes a hPA-50 H chain polypeptide composed of a VH region of the invention (e.g., SEQ ID NO:5; SEQ ID NO:6) and a suitable CH region, e.g., of the IgG1 isotype, such as is contained within Genbank Accession No. NW_001838121, and a hPA-50 L chain polypeptide composed of a VL region of the invention (SEQ ID NO:7) and a CL region, e.g., of the κ subtype, such as is contained within GenBank Accession No. NW_001838785.

The humanization process further yielded anti-*C. difficile* toxin B humanized mAbs that bound toxin B and neutralized toxin B activity on susceptible cells in vitro. Examples of such hmAbs include humanized anti-*C. difficile* toxin B mAb comprising a H chain polypeptide sequence comprising a VH region of SEQ ID NO:8 (FIG. 36A) and a human IgG1 C region and a L chain polypeptide sequence comprising a VL region of SEQ ID NO:10 (FIG. 37) and a human κ C region; and humanized anti-*C. difficile* toxin B mAb comprising a H chain polypeptide sequence comprising a VH region of SEQ ID NO:9 (FIG. 36B) and a human IgG1 C region and a L chain polypeptide sequence comprising a VL region of SEQ ID NO:10 (FIG. 37) and a human κ C region. Such humanized anti-*C. difficile* toxin B mAbs embrace a humanized PA-41 (hPA-41) mAb of the invention. Complete hPA-41 immunoglobulin having two L chains and two H chains can be produced in a suitable host cell which co-expresses and secretes a hPA-41 H chain polypeptide composed of a hPA-41 VH region of the invention (e.g., SEQ ID NO:8; SEQ ID NO:9) and a suitable CH region, e.g., of the IgG1 isotype, such as is contained within Genbank Accession No. NW_001838121, and a hPA-41 L chain polypeptide composed of a hPA-41 VL region of the invention (e.g., SEQ ID NO:10) and a CL region, e.g., of the κ subtype, such as is contained within GenBank Accession No. NW_001838785.

In addition, humanized, cloned mAbs (hmAbs) were produced which bind toxin A or toxin B of *C. difficile* and strongly neutralize toxin activity. Anti-*C. difficile* toxin A hmAb PA-50 is composed of two heavy chain polypeptides, each heavy chain containing a VH region and a human CH region and two light chain polypeptides, each light chain containing a VL region and a human CL region. The nucleic acid sequence (or cDNA) encoding the amino acid sequence of the hPA-50 heavy chain polypeptide of SEQ ID NO: 14 is set forth in SEQ ID NO:15, (FIG. 38B); the nucleic acid sequence (or cDNA) encoding the amino acid sequence of the hPA-50 light chain polypeptide of SEQ ID NO:16 is set forth in SEQ ID NO:17. (FIG. 38A). Anti-*C. difficile* toxin A hmAb PA-39 is composed of two heavy chain polypeptides, each heavy chain containing a VH region and a human CH region and two light chain polypeptides, each light chain containing a VL region and a human CL region. The nucleic acid sequence (or cDNA) encoding the amino acid sequence of the hPA-39 heavy chain polypeptide of SEQ ID NO: 18 is set forth in SEQ ID NO:19, (FIG. 39B); the nucleic acid sequence (or cDNA) encoding the amino acid sequence of the hPA-39 light chain polypeptide of SEQ ID NO:20 is set forth in SEQ ID NO:21 (FIG. 39A). Anti-*C. difficile* toxin B hmAb PA-41 is composed of two heavy chain polypeptides, each heavy chain containing a VH region and a human CH region and two light chain polypeptides, each light chain containing a VL region and a human CL region. The nucleic acid sequence (or cDNA) encoding the amino acid sequence of the hPA-41 heavy chain polypeptide of SEQ ID NO:22 is set forth in SEQ ID NO:23 (FIG. 40B); the nucleic acid sequence (or cDNA) encoding the amino acid sequence of the hPA-41 light chain polypeptide of SEQ ID NO:24 is set forth in SEQ ID NO:25 (FIG. 40A).

The monoclonal antibodies CDA-1 and CDB1 (7, 89) were prepared for use as comparator mAbs. DNA sequences encoding the Ig heavy and light chain variable regions of 3D8 and 124 (WO2006/121422 and US2005/0287150) were synthesized (DNA2.0) and cloned into vectors pCON-gamma1 and pCON-kappa. Full-length IgG1,κ mAbs were expressed in stably transfected CHO-K1SV cells and purified as described above. When tested for binding affinity to toxins A and B by Biacore, inhibition of toxin-mediated cytopathic effects, and hemagglutination according to published methods (7), the CDA1 and CDB1 preparations exhibited the expected levels of activity.

E. In Vitro Characterization of the Humanized mAbs

Figure 29:
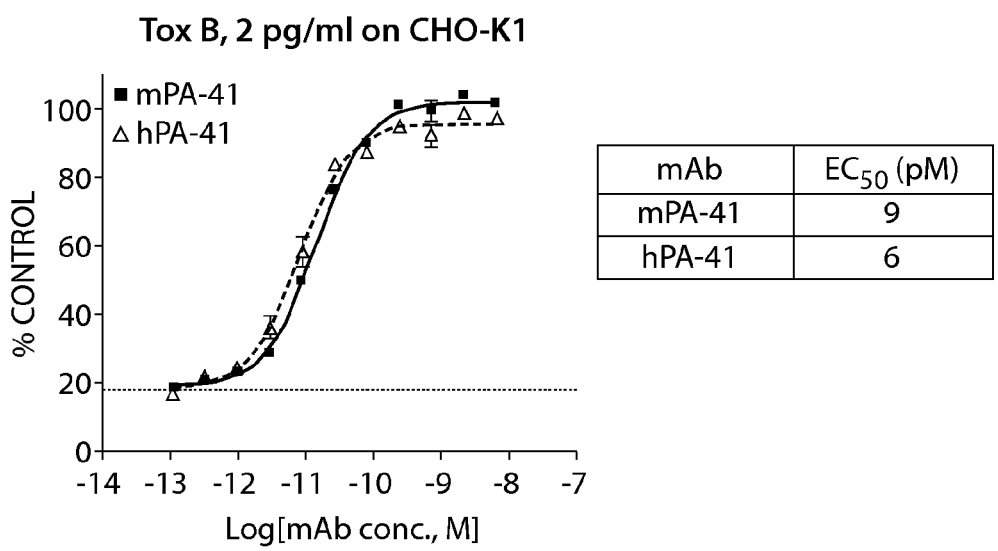
FIG. 29 shows the in vitro neutralization activity of murine PA-41 (mPA-41) and humanized PA-41 (hPA-41) mAbs against C. difficile toxin B. Percent cell survival compared with controls was measured using CellTiter Blue. hPA-41 mAb effectively neutralizes the toxicity of toxin B (2 pg/mL, Techlab) on CHO-K1 cells with an $EC_{50}$ of 6 μM and was virtually equipotent to the parental murine monoclonal antibody (mPA-41).
Figure 30:
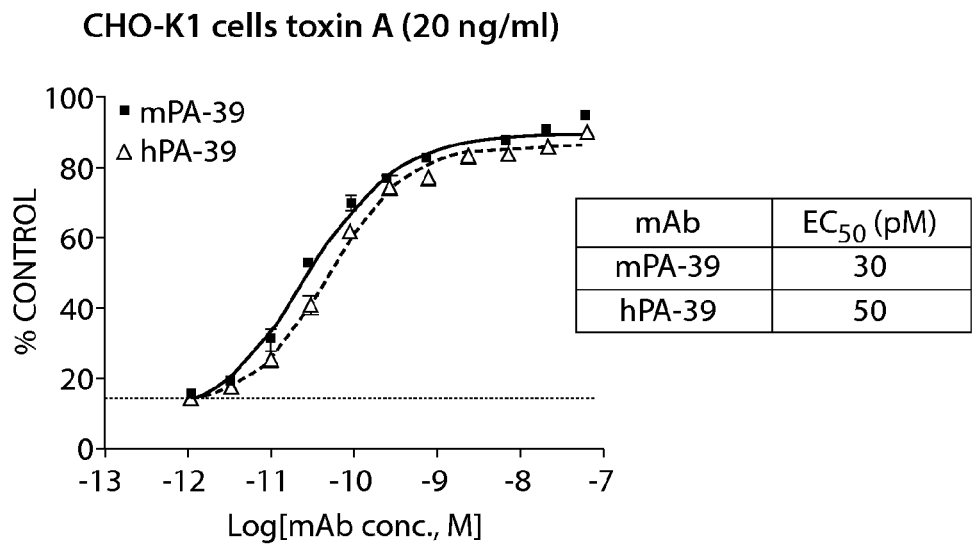
FIG. 30 shows the in vitro neutralization activity of murine PA-39 (mPA-39) and humanized PA-39 (hPA-39) mAbs against C. difficile toxin A. hPA-39 mAb effectively neutralizes the toxicity of toxin A (20 ng/mL, TechLab) on CHO-K1 cells with an $EC_{50}$ of 50 μM and was virtually equipotent to the parental murine monoclonal antibody (mPA-39).

*C. difficile* toxin neutralization experiments were carried out in vitro to compare the functional activity of the humanized mAbs to that of the parental mouse mAbs. As shown in FIG. 29, humanized PA-41 (hPA-41) mAb potently neutralized cytotoxicity of toxin B ($EC_{50}$ of 6 µM) compared with an $EC_{50}$ of 9 µM for the murine PA-41 mAb (mPA-41). Similarly, humanized PA-39 mAb (hPA-39) and humanized PA-50 mAb (hPA-50) were found to be equally potent when compared with their murine parental mAbs in neutralizing toxin A using CHO-K1 cells or T-84 cells, respectively, as shown in FIG. 30 for hPA-39 and in FIG. 31 for hPA-50. These results demonstrate that the parental murine mAbs were successfully humanized and that the humanized mAbs were functional and effective.

Of the anti-*C. difficile* toxin mAbs examined in these studies, PA-50 exhibited a distinct dose-response neutralization curve with Hill coefficients that typically were greater than two, indicating cooperative inhibition. Cooperative interactions are common in nature and often are characterized by steep dose-response curves and Hill coefficients of >1. Drugs that display cooperative activity have been associated with enhanced clinical activity in treating viral infections. In addition, PA-50 binds toxin A in a multivalent fashion, a condition that is often necessary, but not sufficient for cooperativity.

Example 11

Generation of Fab Fragments of the Murine Anti-toxin mAbs of the Invention

A. Preparation of Fab Fragments

Fab fragmentation was performed using a Mouse IgG1 Fab and F(ab')2 Preparation Kit (Pierce) according to manufacturer's instructions and reagents supplied with the kit. The same protocol for fragmentation was used for all mAbs; PA-39, PA-41, and PA-50. Briefly, immobilized ficin slurry (750 µl) was washed with digestion buffer (75 mM cysteine, pH 5.6) before approximately 3 mg of mAb was added and the mixture was incubated at 37° C. for four hours with constant end-over-end rotation. Once digestion was completed, the slurry was centrifuged and the digest product was collected. The slurry was washed three times with Protein A binding buffer and the wash material was added to the completed digest. The NAb Protein A column was equilibrated with Protein A binding buffer and the digested antibody sample was added. The column and sample were incubated at room temperature for 10 minutes. The column was centrifuged at 1000 g for one minute to collect the flow through which contained the Fab fragments. The column was washed three times with Protein A binding buffer. The flow through was collected, buffer-exchanged into PBS– and concentrated.

B. SDS-PAGE of Fab Fragments

Samples were analyzed via SDS-PAGE using the Novex gel system (Invitrogen) and all reagents listed below were from Invitrogen unless noted otherwise. Samples were mixed with NuPage sample buffer and reduced with DTT. Reduced and non-reduced samples were incubated at 100° C. for 10 minutes. After loading samples (4 µg) into a 4-12% Bis Tris NuPage gel, electrophoresis was performed with MOPS running buffer at 180V for 60 minutes. After electrophoresis, the gel was incubated with fixative (40% methanol, 10% acetic acid) for 20 minutes, rinsed with water, and stained with Simply Blue Stain overnight with constant rotation.

C. In vitro Characterization of Fabs

Figure 41A:
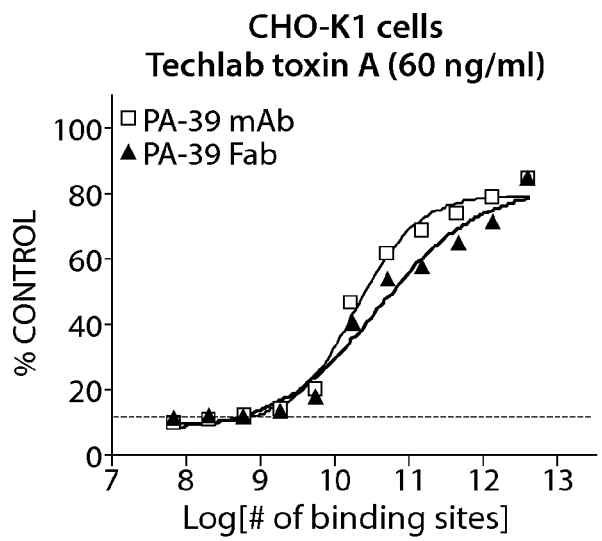
FIGS. 41A-41C demonstrate the in vitro neutralization activity against C. difficile toxin A or toxin B of Fab fragments of murine mAbs compared with the potency of the counterpart whole antibodies. (A): murine mAb PA-39 and PA-39 Fab neutralization activity on CHO-K1 cells; toxin A (Techlab, 60 ng/ml); (B): murine mAb PA-41 and PA-41 Fab neutralization activity on CHO-K1 cells; toxin B (Techlab, 2 pg/ml); (C): murine mAb PA-50 and PA-50 Fab neutralization activity on T-84 cells; toxin A (Techlab, 60 ng/ml).
Figure 41B:
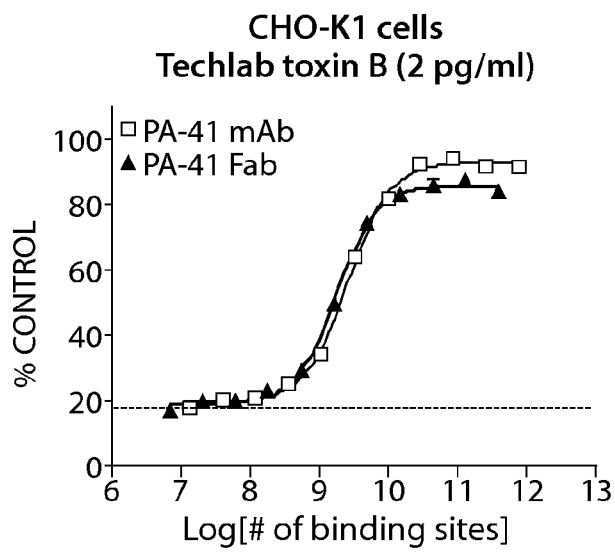
Figure 41C:
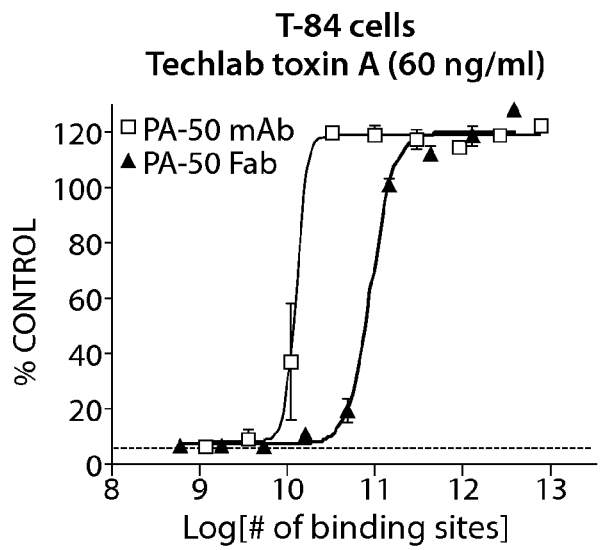

In vitro *C. difficile* toxin neutralization experiments were carried out to compare the functional activity of the Fabs (▲) to that of the whole mAbs (■) based on number of binding sites. The PA-39 Fab strongly neutralized toxin A cytotoxicity on CHO-K1 cells compared with whole PA-39 ($EC_{50}$ of 880 µM and $EC_{50}$ of 200 µM, respectively), (FIG. 41A). The PA-41 Fab was found to be equally potent to the whole PA-41 in neutralizing toxin B activity on CHO-K1 cells ($EC_{50}$ of 88 µM and $EC_{50}$ of 80 µM, respectively), (FIG. 41B). The PA-50 Fab had an $EC_{50}$ value of 1.8 nM compared with an $EC_{50}$ value of 100 µM of the whole PA-50 mAb in neutralizing toxin A on T-84 cells (FIG. 41C).

Example 12

Immunohistochemistry Analysis of the Humanized Anti-*C. difficile* Toxin mAbs on Human Tissue Specimens The value of immunohistochemistry (IHC) in studying the expression of a given antigen is that it allows for the evaluation of micro-anatomical detail and heterogeneity in normal and tumor tissues. IHC is advantageous over other methods of analysis because it can directly localize proteins to individual cell types. Gene expression differences in normal and tumor tissue can be detected while simultaneously noting the changes in cell number and composition. Limitations of this technique include possible false-negative results due to low levels of expression of the molecule under study, as well as false-positive results (cross-reactivity) due to antibody-binding to similar epitopes or those epitopes shared by other antigens. To address these limitations, this study was carried out at the lowest possible concentration of each of the antibodies that showed strong, specific staining on positive toxin-specific injected mouse control specimens.

Humanized mAbs PA-41 and PA-50 were biotinylated to determine an immunohistochemical binding pattern in a selection of frozen human tissues, which included adrenal, bladder, bone marrow, breast, cerebellum, cerebral cortex, cervix, colon, esophagus, eye, fallopian tube, heart, ileum, jejunum, kidney, liver, lung, lymph node, muscle, ovary, peripheral nerve, pancreas, parathyroid, pituitary, placenta, prostate, skin, small intestine, spinal cord, spleen, stomach, testis, thymus, thyroid, ureter, uterus and white blood cells. One tissue each of the foregoing 37 different human tissue types was stained with each antibody. Working IHC assays were developed for both antibodies. An irrelevant human IgG1,κ isotype control antibody was included for all samples.

For tissue preparation, frozen specimens embedded in OCT Compound (Optimal Cutting Temperature embedding compound; Sakura, Torrance, Calif.) were sectioned at 5 microns and placed onto positively charged glass slides. The IHC staining methods and conditions for each antibody and tissue specimen were developed, tested and optimized. A direct biotinylated IHC procedure was performed using freshly-cut frozen unfixed tissue sections. Slides were removed from the cryostat, allowed to air-dry for 10 minutes at room temperature, fixed in 95% ethanol for 5 minutes at room temperature and then washed in three sequential baths of Tris Buffered Saline/0.1% TWEEN-20 wash buffer (TBST; DakoCytomation) for 3 minutes. All subsequent washes were performed in this manner. Endogenous peroxidase activity was blocked with a 5 minute incubation of ready-to-use Peroxidase Block at room temperature. After a buffer wash, endogenous biotin activity was then blocked with 15 minute incubations each of avidin followed by biotin with each step followed by buffer washes. For PA-41, slides were then incubated with Background Sniper protein blocking reagent for 10 minutes at room temperature with no buffer wash to follow. Slides were incubated with the test article or negative control reagent (1.25 11 g/ml for PA-41 and 10 11 g/ml for PA-50) for 30 minutes at room temperature. The PA-50 primary antibody was diluted at 1:350 in Dako Diluent while the PA-41 primary antibody was diluted at 1:3520 in Dako diluent with proline (250 mM, 0.576 g, Genzyme, CA) and histidine (15 mM, 0.046 g, Genzyme, CA) added to 20 ml of diluent (pH 7.7). Following washes in TBST, ABC detection reagent (1:50 in TBST) was applied to the tissue sections for both antibody assays and incubated for 30 minutes at room temperature followed by buffer washes. The immunoreaction was visualized by incubating with a 3,3'-diaminobenzidine tetrahydrochloride (DAB) solution for 5 minutes at room temperature. The slides were rinsed with deionized (DI) water 3 times for 30-60 seconds each, counterstained with a modified Mayers hematoxylin (DakoCytomation), blued in 0.2% ammonia, dehydrated through graded alcohols, cleared in xylene, and coverslipped. The interpretation of stained slides was performed by microscopic examination. In general, a morphologic review of the tissue on the slide after antibody staining determined whether an adequate amount of tissue was present, and whether the designated normal tissue elements were appropriately represented. Samples failing to meet the above standards were rejected from the analysis by the study pathologist.

The scoring system included a semi-quantitative analysis of staining intensity. The staining intensity of the test article was judged relative to the intensity of the tissue control slide containing an adjacent section stained with a negative control antibody. Staining of the section labeled with the negative reagent control was considered "background" staining. A score of "0" indicated no staining relative to background; "1+" indicated weak staining; "2+" indicated moderate staining; and "3+" indicated strong staining. In keeping with standard pathology practice, staining intensity was reported at the highest level of intensity observed in all tissue elements.

The results of the IHC analysis for both the humanized PA-50 and the PA-41 mAbs were that no positive staining (0%) was exhibited in any of the human tissue specimens tested. Consistent strong staining (e.g., 3+) was indicated in the toxin-injected mouse leg muscle control tissues (Toxin A for PA-50 and Toxin B for PA-41) throughout the study. For PA-50, no true positive staining was seen for any tissue sample. (i.e., 100% of cells showed 0% staining). For PA-41, no true positive staining was exhibited in the 37 human tissues tested, however, weak (1+) positive staining was seen as a highest staining intensity in normal liver (due to lipochrome pigment), normal lung (pulmonary macrophages with a foreign body) and normal muscle (reaction consistent with artifact staining). Such weak staining values for PA-41 were deemed to be inconsequential relative to all controls and in view of minimal staining variation within the assay.

Example 13

Pharmacokinetic Analysis of the Humanized Anti-C. Difficile Toxin mAbs in Non-human Primates A pharmacokinetic (PK) study in non-naïve Cynomolgus monkeys was conducted utilizing the purified, humanized mAbs PA-41 or mAb PA-50. In this study, male, non-naïve, Cynomolgus monkeys (Macaca fascicularis) were injected intravenously with 1 mg/kg/animal or 5 mg/kg/animal of purified humanized mAb PA-41 or mAb PA-50. The study was performed in accordance with Institutional Animal Care and Use Committee (IACUC) policies and procedures.

Table 8 presents the PK study format, showing that each mAb (at a 10 mg/kg concentration) was administered intravenously at two dose levels to non-naïve animals.

TABLE 8

Humanized mAb PK study in Non-human primates

| Group | Treatment | Route | Dose Level (mg/kg/day) | Concentration (mg/kg) | Dose Volume (mL/kg/day) | No. of Monkeys (male) |
|---|---|---|---|---|---|---|
| 1 | PA-41 | IV | 1 | 10 | 0.1 | 3 |
| 2 | PA-41 | IV | 5 | 10 | 0.5 | 3 |
| 3 | PA-50 | IV | 1 | 10 | 0.1 | 3 |
| 4 | PA-50 | IV | 5 | 10 | 0.5 | 3 |

The animals received a single intravenous injection of study antibody at initiation of the study. Thereafter, blood samples were obtained by venipuncture of peripheral vessels from each animal at 14 individual time points within 29 days (i.e., pre-dose; at 0.5, 2, 6, 12 and 24 hours on Day 1 (post-dose); and on Days 3, 4, 7, 9, 12, 15, 22 and 29). The blood samples were collected into serum separator tubes and maintained on wet ice until coagulation. After coagulation, the blood samples were centrifuged at 1800 g for 15 minutes at 4° C. to obtain sera. Serum samples were stored at −70° C. until use.

The mAb concentration in the sera was determined via ELISA. Ninety-six well ELISA plates (Thermo Fisher Scientific, Rochester, N.Y.) were coated overnight with toxin A (Techlab) or toxin B (Techlab) at 100 ng/well at 4 C. Plates were washed three times with PBS/0.05% TWEEN-20® (PBS-T) and blocked with 200 µl of blocking buffer (PBS without calcium or magnesium, 0.1% TWEEN 20®, 1% casein) for one hour at room temperature. The antibody reference standard (purified mAb PA-41 or mAb PA-50) was diluted in 1% pooled naive cynomolgus serum (Bioreclamation) to generate a standard curve with a range of 0.3-4000 ng/ml. Diluted test samples and standards were tested in triplicate and were incubated for one hour at room temperature.

Figure 42A:
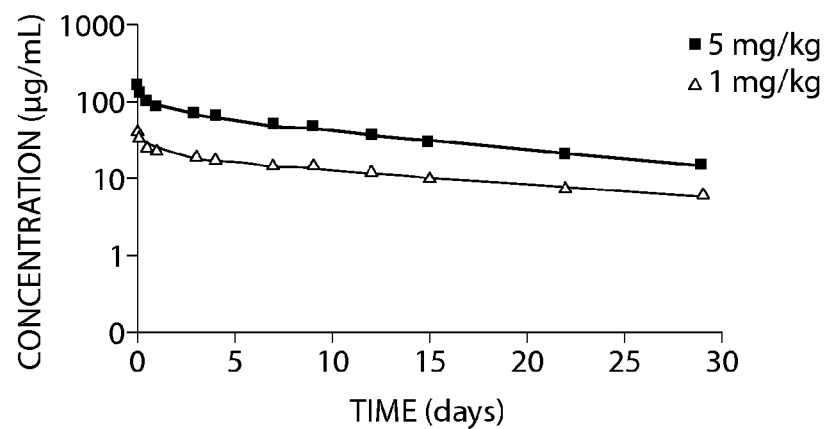
FIGS. 42A and 42B show the antibody concentration profiles resulting from the pharmacokinetic (PK) study described in Example 13 herein.
Figure 42B:
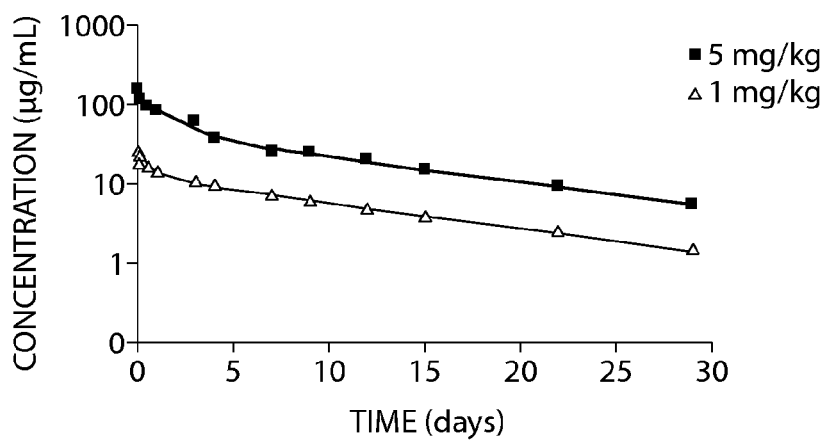

Plates were washed six times with PBS-T and incubated for one hour at room temperature with HRP-conjugated goat anti-human IgG1 (The Binding Site, San Diego, Calif.). Plates were developed with SureBlue TMB 1-component peroxidase substrate (KPL), stopped with 1N Hydrochloric acid (Thermo Fisher Scientific) and read on a SpectraMax plate reader (Molecular Devices) at 450 nm. The mAb concentration in each monkey at different time points was calculated using the standard curves. Noncompartmental pharmacokinetic analysis was performed using WinNonLin, Version 4.0 (Pharsight Corp., Mountain View, Calif.). The PK results for humanized mAb PA-50 are shown in FIG. 42A; the results for humanized mAb PA-41 are shown in FIG. 42B. For PA-50 at doses of 1 mg/kg and 5 mg/kg, the mean $T_{1/2}$ (Days) was 14.5±0.3 and 12.3±1.5, respectively. For PA-41 at doses of 1 mg/kg and 5 mg/kg, the mean $T_{1/2}$ (Days) was 8.9±1.3 and 9.2±3.3, respectively.

References

1. Bartlett, J. G., T. W. Chang, M. Gurwith, S. L. Gorbach, and A. B. Onderdonk. 1978. Antibiotic-associated pseudomembranous colitis due to toxin-producing clostridia. The New England Journal of Medicine 298:531-534.

2. Kyne, L., R. J. Farrell, and C. P. Kelly. 2001. *Clostridium difficile*. Gastroenterol. Clin North Am 30:753-777.
3. Kelly, C. P. and J. T. LaMont. 2008. *Clostridium difficile*—more difficult than ever. The New England Journal of Medicine 359:1932-1940.
4. MacCannell, D. R., T. J. Louie, D. B. Gregson, M. Layerdiere, A. C. Labbe, F. Laing, and S. Henwick. 2006. Molecular analysis of *Clostridium difficile* PCR ribotype 027 isolates from Eastern and Western Canada. J Clin Microbiol 44:2147-2152.
5. McDonald, L. C., G. E. Killgore, A. Thompson, R. C. Owens, Jr., S. V. Kazakova, S. P. Sambol, S. Johnson, and D. N. Gerding. 2005. An epidemic, toxin gene-variant strain of *Clostridium difficile*. The New England Journal of Medicine 353:2433-2441.
6. Warny, M., J. Pepin, A. Fang, G. Killgore, A. Thompson, J. Brazier, E. Frost, and L. C. McDonald. 2005. Toxin production by an emerging strain of *Clostridium difficile* associated with outbreaks of severe disease in North America and Europe. Lancet 366:1079-1084.
7. Babcock, G. J., T. J. Broering, H. J. Hernandez, R. B. Mandell, K. Donahue, N. Boatright, A. M. Stack, I. Lowy, R. Graziano, D. Molrine, D. M. Ambrosino, and W. D. Thomas, Jr. 2006. Human monoclonal antibodies directed against toxins A and B prevent *Clostridium difficile-induced* mortality in hamsters. Infect Immun 74:6339-6347.
8. Bartlett, J. G. 1981. Antimicrobial agents implicated in *Clostridium difficile* toxin-associated diarrhea of colitis. Johns Hopkins Med J 149:6-9.
9. McFarland, L. V., M. E. Mulligan, R. Y. Kwok, and W. E. Stamm. 1989. Nosocomial acquisition of *Clostridium difficile* infection. The New England Journal of Medicine 320:204-210.
10. Zilberberg, M. D., A. F. Shorr, and M. H. Kollef. 2008. Increase in adult *Clostridium difficile*-related hospitalizations and case-fatality rate, United States, 2000-2005. Emerg. Infect Dis 14:929-931.
11. Riley, T. V., Codde, J. P., and Rous, I. L. Increased length of hospital stay due to *Clostridium difficile*-associated diarrhoea. Lancet 345, 455-456. Feb. 18, 1995.
12. O'Brien, J. A., B. J. Lahue, J. J. Caro, and D. M. Davidson. 2007. The emerging infectious challenge of *clostridium difficile*-associated disease in Massachusetts hospitals: clinical and economic consequences. Infect Control Hosp Epidemiol. 28:1219-1227.
13. Redelings, M. D., F. Sorvillo, and L. Mascola. 2007. Increase in *Clostridium difficile*-related mortality rates, United States, 1999-2004. Emerg. Infect Dis 13:1417-1419.
14. Loo, V. G., L. Poirier, M. A. Miller, M. Oughton, M. D. Libman, S. Michaud, A. M. Bourgault, T. Nguyen, C. Frenette, M. Kelly, A. Vibien, P. Brassard, S. Fenn, K. Dewar, T. J. Hudson, R. Horn, P. Rene, Y. Monczak, and A. Dascal. 2005. A predominantly clonal multi-institutional outbreak of *Clostridium difficile*-associated diarrhea with high morbidity and mortality. The New England Journal of Medicine 353:2442-2449.
15. Warny, M. K. C. 2003. Pathogenicity of *Clostridium difficile* toxins. Washington D.C.: ASM Press 366:503-524.
16. Kelly, C. P., C. Pothoulakis, and J. T. LaMont. 1994. *Clostridium difficile* colitis. The New England Journal of Medicine 330:257-262.
17. Lyerly, D. M., D. E. Lockwood, S. H. Richardson, and T. D. Wilkins. 1982. Biological activities of toxins A and B of *Clostridium difficile*. Infect Immun. 35:1147-1150.
18. McFarland, L. V., H. W. Beneda, J. E. Clarridge, and G. J. Raugi. 2007. Implications of the changing face of *Clostridium difficile* disease for health care practitioners. Am J Infect Control 35:237-253.
19. Drudy, D., T. Quinn, R. O'Mahony, L. Kyne, P. O'Gaora, and S. Fanning 2006. High-level resistance to moxifloxacin and gatifloxacin associated with a novel mutation in gyrB in toxin-A-negative, toxin-B-positive *Clostridium difficile*. J Antimicrob Chemother 58:1264-1267.
20. Rupnik, M., N. Kato, M. Grabnar, and H. Kato. 2003. New types of toxin A-negative, toxin B-positive strains among *Clostridium difficile* isolates from Asia. J Clin Microbiol 41:1118-1125.
21. Voth, D. E. and J. D. Ballard. 2005. *Clostridium difficile* toxins: mechanism of action and role in disease. Clin Microbiol Rev 18:247-263.
22. Reineke, J., S. Tenzer, M. Rupnik, A. Koschinski, O. Hasselmayer, A. Schrattenholz, H. Schild, and C. Eichel-Streiber. 2007. Autocatalytic cleavage of *Clostridium difficile* toxin B. Nature 446:415-419.
23. Aslam, S., R. J. Hamill, and D. M. Musher. 2005. Treatment of *Clostridium difficile*-associated disease: old therapies and new strategies. Lancet Infect Dis 5:549-557.
24. Musher, D. M., S. Aslam, N. Logan, S. Nallacheru, I. Bhaila, F. Borchert, and R. J. Hamill. 2005. Relatively poor outcome after treatment of *Clostridium difficile* colitis with metronidazole. Clin Infect Dis 40:1586-1590.
25. Pepin, J., M. E. Alary, L. Valiquette, E. Raiche, J. Ruel, K. Fulop, D. Godin, and C. Bourassa. 2005. Increasing risk of relapse after treatment of *Clostridium difficile* colitis in Quebec, Canada. Clin Infect Dis 40:1591-1597.
26. Fekety, R. and A. B. Shah. 1993. Diagnosis and treatment of *Clostridium difficile* colitis. JAMA 269:71-75.
27. Fekety, R., L. V. McFarland, C. M. Surawicz, R. N. Greenberg, G. W. Elmer, and M. E. Mulligan. 1997. Recurrent *Clostridium difficile* diarrhea: characteristics of and risk factors for patients enrolled in a prospective, randomized, double-blinded trial. Clin Infect Dis 24:324-333.
28. Pothoulakis, C. and J. T. LaMont. 1993. *Clostridium difficile* colitis and diarrhea. Gastroenterol. Clin North Am 22:623-637.
29. McFarland, L. V., C. M. Surawicz, R. N. Greenberg, R. Fekety, G. W. Elmer, K. A. Moyer, S. A. Melcher, K. E. Bowen, J. L. Cox, Z. Noorani, and. 1994. A randomized placebo-controlled trial of *Saccharomyces boulardii* in combination with standard antibiotics for *Clostridium difficile* disease. JAMA 271:1913-1918.
30. McFarland, L. V., G. W. Elmer, and C. M. Surawicz. 2002. Breaking the cycle: treatment strategies for 163 cases of recurrent *Clostridium difficile* disease. Am J. Gastroenterol. 97:1769-1775.
31. Kyne, L., M. Warny, A. Qamar, and C. P. Kelly. 2000. Asymptomatic carriage of *Clostridium difficile* and serum levels of IgG antibody against toxin A. The New England Journal of Medicine 342:390-397.
32. Kyne, L., M. Warny, A. Qamar, and C. P. Kelly. 2001. Association between antibody response to toxin A and protection against recurrent *Clostridium difficile* diarrhoea. Lancet 357:189-193.
33. Leav, B., Blair, B., Leney, M., Knauber, M., Reilly, C., Lowy, I., Kohberger, R., Gerding, D. N., Kelly, C., Katchar, K., Baxter, R., and Ambrosino, D. 2008. Serum anti-toxin B antibody 35 correlates with protection from recurrent *Clostridium difficile* associated diarrhea (CDAD). ICAAC/IDSA, Poster B-1925. 2008.

34. Wilcox, M. H., W. N. Fawley, C. D. Settle, and A. Davidson. 1998. Recurrence of symptoms in *Clostridium difficile* infection—relapse or reinfection? J Hosp Infect 38:93-100.
35. Jodlowski, T. Z., R. Oehler, L. W. Kam, and I. Melnychuk. 2006. Emerging therapies in the treatment of *Clostridium difficile*-associated disease. Ann. Pharmacother 40:2164-2169.
36. Missaghi, B., A. J. Valenti, and R. C. Owens, Jr. 2008. *Clostridium difficile* Infection: A Critical Overview. Curr. Infect Dis Rep 10:165-173.
37. Optimer Pharmaceuticals, News Release, Nov. 10. 2008.
38. Louie, T. J., J. Peppe, C. K. Watt, D. Johnson, R. Mohammed, G. Dow, K. Weiss, S. Simon, J. F. John, Jr., G. Garber, S. Chasan-Taber, and D. M. Davidson. 2006. Tolevamer, a novel nonantibiotic polymer, compared with vancomycin in the treatment of mild to moderately severe *Clostridium difficile*-associated diarrhea. Clin Infect Dis 43:411-420.
39. Louie, T. G. M. G. D. e. al. 2007. Results of a phase III trial comparing tolevamer, vancomycin and metronidazole in patients with *Clostridium difficile*-associated diarrhea (CDI). 47th Interscience Conference on Antimicrobial Agents and Chemotherapy.
40. Kelly, C. P., C. Pothoulakis, J. Orellana, and J. T. LaMont. 1992. Human colonic aspirates containing immunoglobulin A antibody to *Clostridium difficile* toxin A inhibit toxin A-receptor binding. Gastroenterology 102:35-40.
41. Salcedo, J., S. Keates, C. Pothoulakis, M. Warny, I. Castagliuolo, J. T. LaMont, and C. P. Kelly. 1997. Intravenous immunoglobulin therapy for severe *Clostridium difficile* colitis. Gut 41:366-370.
42. Leung, D. Y., C. P. Kelly, M. Boguniewicz, C. Pothoulakis, J. T. LaMont, and A. Flores. 1991. Treatment with intravenously administered gamma globulin of chronic relapsing colitis induced by *Clostridium difficile* toxin. J Pediatr 118:633-637.
43. Medarex and Massachusetts Biologic Laboratories, News Release, Nov. 3, 2008.
44. Kamiya, S., K. Yamakawa, X. Q. Meng, H. Ogura, and S, Nakamura. 1991. Production of monoclonal antibody to *Clostridium difficile* toxin A which neutralizes enterotoxicity but not haemagglutination activity. FEMS Microbiol Lett 65:311-315.
45. Kink, J. A. and J. A. Williams. 1998. Antibodies to recombinant *Clostridium difficile* toxins A and B are an effective treatment and prevent relapse of *C. difficile*-associated disease in a hamster model of infection. Infect Immun 66:2018-2025.
46. Lyerly, D. M., C. J. Phelps, J. Toth, and T. D. Wilkins. 1986. Characterization of toxins A and B of *Clostridium difficile* with monoclonal antibodies. Infect Immun 54:70-76.
47. Harlow, E. and Lane, D. Antibodies, a laboratory manual. Cold Spring Harbor Laboratory Press, Cold Spring Harbor, N.Y. 1988.
48. Clark, G. F., H. C. Krivan, T. D. Wilkins, and D. F. Smith. 1987. Toxin A from *Clostridium difficile* binds to rabbit erythrocyte glycolipids with terminal Gal alpha 1-3Gal beta 1-4G1cNAc sequences. Arch Biochem Biophys 257: 217-229.
49. Anton, P. M., M. O'Brien, E. Kokkotou, B. Eisenstein, A. Michaelis, D. Rothstein, S. Paraschos, C. P. Kelly, and C. Pothoulakis. 2004. Rifalazil treats and prevents relapse of *clostridium difficile*-associated diarrhea in hamsters. Antimicrob Agents Chemother 48:3975-3979.
50. Boss, S. M., C. L. Gries, B. K. Kirchner, G. D. Smith, and P. C. Francis. 1994. Use of vancomycin hydrochloride for treatment of *Clostridium difficile* enteritis in Syrian hamsters. Lab Anim Sci 44:31-37.
51. Freeman, J., S. D. Baines, D. Jabes, and M. H. Wilcox. 2005. Comparison of the efficacy of ramoplanin and vancomycin in both in vitro and in vivo models of clindamycin-induced *Clostridium difficile* infection. J Antimicrob Chemother 56:717-725.
52. Kink, J. A. and J. A. Williams. 1998. Antibodies to recombinant *Clostridium difficile* toxins A and B are an effective treatment and prevent relapse of *C. difficile*-associated disease in a hamster model of infection. Infect Immun 66:2018-2025.
53. Kokkotou, E., A. C. Moss, A. Michos, D. Espinoza, J. W. Cloud, N. Mustafa, M. O'Brien, C. Pothoulakis, and C. P. Kelly. 2008. Comparative efficacies of rifaximin and vancomycin for treatment of *Clostridium difficile*-associated diarrhea and prevention of disease recurrence in hamsters. Antimicrob Agents Chemother 52:1121-1126.
54. Kurtz, C. B., E. P. Cannon, A. Brezzani, M. Pitruzzello, C. Dinardo, E. Rinard, D. W. Acheson, R. Fitzpatrick, P. Kelly, K. Shackett, A. T. Papoulis, P. J. Goddard, R. H. Barker, Jr., G. P. Palace, and J. D. Klinger. 2001. GT160-246, a toxin binding polymer for treatment of *Clostridium difficile* colitis. Antimicrob Agents Chemother 45:2340-2347.
55. McVay, C. S, and R. D. Rolfe. 2000. In vitro and in vivo activities of nitazoxanide against *Clostridium difficile*. Antimicrob Agents Chemother 44:2254-2258.
56. Razaq, N., S. Sambol, K. Nagaro, W. Zukowski, A. Cheknis, S. Johnson, and D. N. Gerding. 2007. Infection of hamsters with historical and epidemic BI types of *Clostridium difficile*. J Infect Dis 196:1813-1819.
57. Fernie, D. S., R. O. Thomson, I. Batty, and P. D. Walker. 1983. Active and passive immunization to protect against antibiotic associated caecitis in hamsters. Developmental Biology Standard 53:325-332.
58. Giannasca, P. J., Z. X. Zhang, W. D. Lei, J. A. Boden, M. A. Giel, T. P. Monath, and W. D. Thomas, Jr. 1999. Serum antitoxin antibodies mediate systemic and mucosal protection from *Clostridium difficile* disease in hamsters. Infect Immun 67:527-538.
59. Kim, P. H., J. P. Iaconis, and R. D. Rolfe. 1987. Immunization of adult hamsters against *Clostridium difficile*-associated ileocecitis and transfer of protection to infant hamsters. Infect Immun 55:2984-2992.
60. Lyerly, D. M., E. F. Bostwick, S. B. Binion, and T. D. Wilkins 1991. Passive immunization of hamsters against disease caused by *Clostridium difficile* by use of bovine immunoglobulin G concentrate. Infect Immun 59:2215-2218.
61. Kelly, C. P., C. Pothoulakis, F. Vavva, I. Castagliuolo, E. F. Bostwick, J. C. O'Keane, S. Keates, and J. T. LaMont. 1996. Anti-*Clostridium difficile* bovine immunoglobulin concentrate inhibits cytotoxicity and enterotoxicity of *C. difficile* toxins. Antimicrob Agents Chemother 40:373-379.
62. Delmee, M., M. Homel, and G. Wauters. 1985. Serogrouping of *Clostridium difficile* strains by slide agglutination. J Clin Microbiol 21:323-327.
63. Delmee, M., V. Avesani, N. Delferriere, and G. Burtonboy. 1990. Characterization of flagella of *Clostridium difficile* and their role in serogrouping reactions. J Clin Microbiol 28:2210-2214.
64. Barbut, F., A. Richard, K. Hamadi, V. Chomette, B. Burghoffer, and J. C. Petit. 2000. Epidemiology of recurrences or reinfections of *Clostridium difficile*-associated diarrhea. J Clin Microbiol 38:2386-2388.

65. Carswell, C. I., G. L. Plosker, and A. J. Wagstaff. 2001. Daclizumab: a review of its use in the management of organ transplantation. BioDrugs 15:745-773.
66. Wiland, A. M. and B. Philosophe. 2004. Daclizumab induction in solid organ transplantation. Expert Opin Biol Ther 4:729-740.
67. Fenton, C., L. J. Scott, and G. L. Plosker. 2004. Palivizumab: a review of its use as prophylaxis for serious respiratory syncytial virus infection. Paediatr. Drugs 6:177-197.
68. Wu, H., D. S. Pfarr, Y. Tang, L. L. An, N. K. Patel, J. D. Watkins, W. D. Huse, P. A. Kiener, and J. F. Young. 2005. Ultra-potent antibodies against respiratory syncytial virus: effects of binding kinetics and binding valence on viral neutralization. J Mol Biol 350:126-144.
69. Romero, J. R. Palivizumab prophylaxis of respiratory syncytial virus disease from 1998 to 2002: results from four years of palivizumab usage. Pediatr. Infect. Dis 22, S46-S54. 2003.
70. Carter, P., L. Presta, C. M. Gorman, J. B. Ridgway, D. Henner, W. L. Wong, A. M. Rowland, C. Kotts, M. E. Carver, and H. M. Shepard. 1992. Humanization of an anti-p185HER2 antibody for human cancer therapy. Proc Natl Acad Sci USA 89:4285-4289.
71. Emens, L. A. 2005. Trastuzumab: targeted therapy for the management of HER-2/neu-overexpressing metastatic breast cancer. Am J Ther 12:243-253.
72. Finn, R. S, and D. J. Slamon. 2003. Monoclonal antibody therapy for breast cancer: herceptin. Cancer Chemother Biol Response Modif. 21:223-233.
73. Giles, F., E. Estey, and S. O'Brien. 2003. Gemtuzumab ozogamicin in the treatment of acute myeloid leukemia. Cancer 982095-2104.
74. Siemoneit, K., S. Cardoso Mda, K. Koerner, A. Wolpl, and B. Kubanek. 1995. Human monoclonal antibodies for the immunological characterization of a highly conserved protein domain of the hepatitis C virus glycoprotein E1. Clin Exp Immunol 101:278-83.
75. Casale, T. B. 2004. Omalizumab: an effective anti-IgE treatment for allergic asthma and rhinitis. Drugs Today (Barc.) 40:367-376.
76. Holgate, S. T., R. Djukanovic, T. Casale, and J. Bousquet. 2005. Anti-immunoglobulin E treatment with omalizumab in allergic diseases: an update on anti-inflammatory activity and clinical efficacy. Clin Exp Allergy 35:408-416.
77. Presta, L. G., S. J. Lahr, R. L. Shields, J. P. Porter, C. M. Gorman, B. M. Fendly, and P. M. Jardieu. 1993. Humanization of an antibody directed against IgE. The Journal of Immunology 151:2623-2632.
78. Jordan, J. K. 2005. Efalizumab for the treatment of moderate to severe plaque psoriasis. Ann. Pharmacother 39:1476-1482.
79. Werther, W. A., T. N. Gonzalez, S. J. O'Connor, S. McCabe, B. Chan, T. Hotaling, M. Champe, J. A. Fox, P. M. Jardieu, P. W. Berman, and L. G. Presta. 1996. Humanization of an anti-lymphocyte function-associated antigen (LFA)-1 monoclonal antibody and reengineering of the humanized antibody for binding to rhesus LFA-1. The Journal of Immunology 157:4986-4995.
80. Leonardi, C. L. 2004. Current concepts and review of efalizumab in the treatment of psoriasis. Dermatol. Clin 22:427-435.
81. Ferrara, N., K. J. Hillan, H. P. Gerber, and W. Novotny. 2004. Discovery and development of bevacizumab, an anti-VEGF antibody for treating cancer. Nat Rev Drug Discov. 3:391-400.
82. Presta, L. G., H. Chen, S. J. O'Connor, V. Chisholm, Y. G. Meng, L. Krummen, M. Winkler, and N. Ferrara. 1997. Humanization of an anti-vascular endothelial growth factor monoclonal antibody for the therapy of solid tumors and other disorders. Cancer Res 57:4593-4599.
83. Steinman, L. 2005. Blocking adhesion molecules as therapy for multiple sclerosis: natalizumab. Nat Rev Drug Discov. 4:510-518.
84. Fagnani, R. 1994. The immunogenicity of foreign monoclonal antibodies in human disease applications: problems and current approaches. Immunol Ser. 61:3-22.
85. Mateo, C., E. Moreno, K. Amour, J. Lombardero, W. Harris, and R. Perez. 1997. Humanization of a mouse monoclonal antibody that blocks the epidermal growth factor receptor: recovery of antagonistic activity. Immunotechnology. 3:71-81.
86. Reichert, J. M., C. J. Rosensweig, L. B. Faden, and M. C. Dewitz. 2005. Monoclonal antibody successes in the clinic. Nat Biotechnol 23:1073-1078.
87. Stephens, S., S. Emtage, O. Vetterlein, L. Chaplin, C. Bebbington, A. Nesbitt, M. Sopwith, D. Athwal, C. Novak, and M. Bodmer. 1995. Comprehensive pharmacokinetics of a humanized antibody and analysis of residual anti-idiotypic responses. Immunology 85:668-674.
88. Co, M. S., N. M. Avdalovic, P. C. Caron, M. V. Avdalovic, D. A. Scheinberg, and C. Queen. 1992. Chimeric and humanized antibodies with specificity for the CD33 antigen. J. Immunol. 148:1149-1154.
89. Lowy, I. et al. 2010. Treatment with monoclonal antibodies against *Clostridium difficile* toxins. N. Engl. J. Med., 362, 197-205.
90. Babcock, G. J. et al. Human Monoclonal Antibodies Neutralize Toxins Produced by Epidemic Strains of *Clostridium difficile*, the Infectious Diseases Society of America 43rd Annual Meeting, Oct. 6-9, 2005; San Francisco, Calif.
91. Optimer Pharmaceuticals Reports Positive Data from its North American Phase 3 CDI Study of OPT-80. Optimer Pharmaceuticals, Press Release (2008).
92. Rothman S W, Toxicon. 1988; 26(6):583-97.
93. WO2005US0047100 to Diversa
94. Cheknis, A K. et al. Distribution of *Clostridium difficile* strains from a North American, European and Australian trial of treatment for *C. difficile* infections: 2005-2007. Anaerobe 15: 230-233 (2009).
95. Gerding D, et al. Restriction endonuclease analysis (REA) typing of *Clostridium difficile* in a phase 3 treatment trial of fidaxomicin vs vancomycin: Decreased cure rate for epidemic BI/NAP1/027 strain. 49th Interscience Conference on Antimicrobial Agents and Chemotherapy, Abstract, L1-1642, San Francisco, Calif., Sep. 12-15, 2009.

Although the invention has been described in detail for the purpose of illustration, it is understood that such detail is solely for that purpose and variations can be made by those skilled in the art without departing from the spirit and scope of the invention which is defined by the following claims.

The contents of all references, patents and published patent applications cited throughout this application are incorporated herein by reference.

The listing of any reference is not an admission that the reference is prior art.

We claim:

1. An isolated antibody or an antigen-binding fragment thereof, wherein the antibody or antigen-binding fragment thereof:
   (a) specifically binds toxin A of *C. difficile* and comprises the CDR1, CDR2, and CDR3 of the variable heavy chain (VH) and the CDR1, CDR2, and CDR 3 of the variable light chain (VL) of the monoclonal antibody produced by the hybridoma cell line deposited under ATCC Accession No. PTA-9692; or
   (b) specifically binds toxin A of *C. difficile* and comprises the CDR1, CDR2, and CDR3 of the VH and the CDR1, CDR2, and CDR 3 of the VL of the monoclonal antibody produced by the hybridoma cell line deposited under ATCC Accession No. PTA-9694; or
   (c) specifically binds toxin A of *C. difficile* and comprises the CDR1, CDR2, and CDR3 of the VH and the CDR1, CDR2, and CDR 3 of the VL of the monoclonal antibody produced by the hybridoma cell line deposited under ATCC Accession No. PTA-9888; or
   (d) specifically binds toxin B of *C. difficile* and comprises the CDR1, CDR2, and CDR3 of the VH and the CDR1, CDR2, and CDR3 of the VL of the monoclonal antibody produced by the hybridoma cell line deposited under ATCC Accession No. PTA-9693.

2. The antibody or antigen-binding fragment thereof of claim 1, wherein the antibody is selected from the group consisting of
   (a) an antibody produced by the hybridoma cell line deposited under ATCC Accession No. PTA-9692;
   (b) an antibody produced by the hybridoma cell line deposited under ATCC Accession No. PTA-9694;
   (c) an antibody produced by the hybridoma cell line deposited under ATCC Accession No. PTA-9888; and
   (d) an antibody produced by the hybridoma cell line deposited under ATCC Accession No. PTA-9693.

3. The isolated antibody or antigen-binding fragment thereof of claim 1, wherein the antibody or antigen-binding fragment neutralizes the in vivo toxicity of toxin A or toxin B, or both, of *C. difficile*.

4. The isolated antibody or antigen-binding fragment thereof of claim 1, wherein the antibody or antigen-binding fragment thereof:
   (i) is, or is from, a monoclonal antibody;
   (ii) is in a humanized form;
   (iii) is human; or
   (iv) is in chimeric form.

5. The antibody or antigen-binding fragment thereof of claim 1, wherein the antigen-binding fragment is selected from an Fab fragment, an F(ab')$_2$ fragment, or an Fv fragment.

6. The isolated antibody or antigen-binding fragment thereof of claim 1, wherein the antibody or antigen-binding fragment thereof comprises a single chain antibody.

7. A bispecific antibody or an antigen-binding fragment thereof which comprises:
   (i) a first antigen binding region comprising an antibody or an antigen-binding fragment thereof that specifically binds toxin B of *C. difficile* of claim 1(d); and
   (ii) a second antigen binding region comprising an antibody that specifically binds toxin A of *C. difficile* or an antigen-binding fragment thereof.

8. A composition comprising the antibody or antigen-binding fragment thereof of claim 1 and a pharmaceutically acceptable carrier, excipient, or diluent.

9. The composition of claim 8, wherein the composition further comprises an additional therapeutic agent.

10. A composition comprising (i) an antibody or antigen fragment thereof of claim 1(d) and (ii) an antibody or antigen-binding fragment thereof which specifically binds toxin A of *C. difficile*.

11. The bispecific antibody or an antigen-binding fragment there of claim 7, wherein the bispecific antibody or an antigen-binding fragment there neutralizes the toxicity of toxin A and toxin B of *C. difficile*.

12. A hybridoma cell line that produces an antibody of claim 1, wherein the hybridoma cell line is deposited under ATCC Accession No. PTA-9692, PTA-9693, PTA-9494, or PTA-9888.

13. A method of treating *C. difficile* infection, *C. difficile*-associated disease, or *C. difficile*-associated diarrhea (CDAD) in a subject, which comprises administering to the subject at least one antibody or antigen binding fragment thereof of claim 1, in an amount effective to treat the *C. difficile* infection or *C. difficile*-associated disease.

14. A method of treating *C. difficile* infection, *C. difficile*-associated disease, or *C. difficile*-associated diarrhea (CDAD) in a subject, which comprises administering to the subject the composition of claim 10 in an amount effective to treat the *C. difficile* infection or *C. difficile*-associated disease.

15. A kit comprising the antibody or antigen-binding fragment thereof of claim 1, and instructions for use.

16. An antibody, or an antigen-binding fragment thereof of claim 1, wherein the antibody or antigen-binding fragment thereof neutralizes toxin A of a hypervirulent strain of *C. difficile* as determined by an $EC_{50}$ value ranging from $7.7^{-12}$ M to $4.8^{-8}$ M and/or neutralizes toxin B of a hypervirulent strain of *C. difficile* as determined by an $EC_{50}$ value ranging from $1.1^{-11}$ M to $6.5^{-10}$ M.

17. The antibody or antigen-binding fragment thereof of claim 1 comprising a CH region selected from IgG1, IgG2a, IgG2b, IgG3, IgG4, IgA, IgE, or IgM, and a human CL region selected from the κ or λ isotype.

18. An anti-*C. difficile* toxin A antibody, or antigen-binding fragment thereof, of claim 1, wherein the antibody or antigen-binding fragment thereof specifically binds toxin A of *C. difficile* and wherein:
   (i) the V region of the L chain comprises an amino acid sequence selected from SEQ ID NO:3 or SEQ ID NO:4 and/or the V region of the H chain comprises an amino acid sequence selected from SEQ ID NO:1 or SEQ ID NO:2; or
   (ii) the V region of the L chain comprises the amino acid sequence of SEQ ID NO:7 and/or the V region of the H chain comprises an amino acid sequence from SEQ ID NO:5 or SEQ ID NO:6.

19. An anti-*C. difficile* toxin B antibody, or a fragment thereof, of claim 1, wherein the antibody of antigen-binding fragment thereof specifically binds toxin A of *C. difficile*, and wherein:
the V region of the L chain comprises an amino acid sequence as set forth in SEQ ID NO:10, and/or
the V region of the H chain comprises an amino acid sequence selected from SEQ ID NO:8 or SEQ ID NO:9.

20. An isolated antibody, or antigen-binding fragment thereof, of claim 1, wherein the antibody, or antigen-binding fragment thereof inhibits, blocks, or prevents *C. difficile* toxin A toxicity by inhibiting, blocking, or preventing toxin A internalization and cytocellular toxicity and/or inhibits, blocks, or prevents *C. difficile* toxin B toxicity by binding to an epitopic site in the N-terminal enzymatic region of toxin B.

21. An isolated antibody or an antigen-binding fragment thereof, wherein the antibody or antigen-binding fragment thereof:
(a) specifically binds toxin A of *C. difficile* and the VH comprises the CDR1, CDR2, and CDR3 of SEQ ID NO:1 or SEQ ID NO:2 and the VL comprises the CDR1, CDR2, and CDR3 of the SEQ ID NO:3 or SEQ ID NO:4; or
(b) specifically binds toxin A of *C. difficile* and the VH comprises the CDR1, CDR2, and CDR3 of SEQ ID NO:5 of SEQ ID NO:6 and the VL comprises the CDR1, CDR2, and CDR3 of SEQ ID NO:7; or
(c) specifically binds toxin B of *C. difficile* and the VH comprises the CDR1, CDR2, and CDR3 of SEQ ID NO:8 or SEQ ID NO:9 and the VL comprises the CDR1, CDR2, and CDR3 of SEQ ID NO:10.

22. An isolated antibody or an antigen-binding fragment thereof, wherein the antibody or antigen-binding fragment thereof:
(a) specifically binds toxin A of *C. difficile*, the VH comprises a CDR1 comprising amino acid residues 31 to 35 of SEQ ID NO:1, a CDR2 comprising amino acid residues 50 to 65 of SEQ ID NO:1 and a CDR3 comprising amino acid residues 95 to 102 of SEQ ID NO:1, and the VL comprises a CDR1 comprising amino acid residues 24 to 34 of SEQ ID NO:3, a CDR2 comprising amino acid residues 50 to 56 of SEQ ID NO:3, and a CDR3 comprising amino acid residues 89 to 97 of the SEQ ID NO:3; or
(b) specifically binds toxin A of *C. difficile*, the VH comprises a CDR1 comprising amino acid residues 31 to 35 of SEQ ID NO:5, a CDR2 comprising amino acid residues 50 to 55 of SEQ ID NO:3, and a CDR3 comprising amino acid residues to of SEQ ID NO: 95 to 102 of SEQ ID NO:5, and the VL comprises a CDR1 comprising amino acid residues 24 to 33 of SEQ ID NO:7, a CDR2 comprising amino acid residues 49 to 55 of SEQ ID NO:7, and a CDR3 comprising amino acid residues 88 to 94 of SEQ ID NO:7; or
(c) specifically binds toxin B of *C. difficile*, the VH comprises a CDR1 comprising amino acid residues 31 to 36 of SEQ ID NO:8, a CDR2 comprising amino acid residues 50 to 66 of SEQ ID NO:8, and a CDR3 comprising amino acid residues 99 to 108 of SEQ ID NO:8, and the VL comprises a CDR1 comprising amino acid residues 24 to 34 of SEQ ID NO:10, a CDR2 comprising amino acid residues 50 to 56 of SEQ ID NO:10, and a CDR3 comprising amino acid residues 89 to 97 of SEQ ID NO:10.

23. The bispecific antibody or an antigen-binding fragment thereof of claim 7, wherein the second antigen binding region comprises:
(a) an antibody or an antigen-binding fragment thereof that specifically binds toxin A of *C. difficile* and comprises the CDR1, CDR2, and CDR3 of the variable heavy chain (VH) and the CDR1, CDR2, and CDR 3 of the variable light chain (VL) of the monoclonal antibody produced by the hybridoma cell line deposited under ATCC Accession No. PTA-9692; or
(b) an antibody or an antigen-binding fragment thereof that specifically binds toxin A of *C. difficile* and comprises the CDR1, CDR2, and CDR3 of the VH and the CDR1, CDR2, and CDR 3 of the VL of the monoclonal antibody produced by the hybridoma cell line deposited under ATCC Accession No. PTA-9694; or
(c) an antibody or an antigen-binding fragment thereof that specifically binds toxin A of *C. difficile* and comprises the CDR1, CDR2, and CDR3 of the VH and the CDR1, CDR2, and CDR 3 of the VL of the monoclonal antibody produced by the hybridoma cell line deposited under ATCC Accession No. PTA-9888.

24. The composition of claim 10, wherein the antibody or an antigen-binding fragment thereof that specifically binds toxin A of *C. difficile* comprises:
(a) the CDR1, CDR2, and CDR3 of the variable heavy chain (VH) and the CDR1, CDR2, and CDR 3 of the variable light chain (VL) of the monoclonal antibody produced by the hybridoma cell line deposited under ATCC Accession No. PTA-9692; or
(b) the CDR1, CDR2, and CDR3 of the VH and the CDR1, CDR2, and CDR 3 of the VL of the monoclonal antibody produced by the hybridoma cell line deposited under ATCC Accession No. PTA-9694; or
(c) the CDR1, CDR2, and CDR3 of the VH and the CDR1, CDR2, and CDR 3 of the VL of the monoclonal antibody produced by the hybridoma cell line deposited under ATCC Accession No. PTA-9888.

* * * * *

SEQUENCE LISTING

<160> NUMBER OF SEQ ID NOS: 25

<210> SEQ ID NO 1
<211> LENGTH: 117
<212> TYPE: PRT
<213> ORGANISM: artificial sequence
<220> FEATURE:
<223> OTHER INFORMATION: antibody, VH region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asp His
            20                  25                  30

Asn Ile His Trp Val Arg Gln Ala Pro Gly Gln Gly Leu Glu Trp Ile
        35                  40                  45

Gly Tyr Ile Tyr Pro Tyr Ile Gly Thr Thr Val Tyr Asn Gln Lys Phe
    50                  55                  60

Lys Ser Lys Ala Thr Leu Thr Val Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Trp Gly His Arg Gly Phe Pro Tyr Trp Gly Gln Gly Thr Leu
            100                 105                 110

Val Thr Val Ser Ser
        115

<210> SEQ ID NO 2
<211> LENGTH: 117
<212> TYPE: PRT
<213> ORGANISM: artificial sequence
<220> FEATURE:
<223> OTHER INFORMATION: antibody, VH region

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asp His
            20                  25                  30

Asn Ile His Trp Val Arg Gln Ala Pro Gly Gln Gly Leu Glu Trp Ile
        35                  40                  45

Gly Tyr Ile Tyr Pro Tyr Ile Gly Thr Thr Val Tyr Asn Gln Lys Phe
    50                  55                  60

Lys Ser Lys Ala Thr Leu Thr Val Asp Asn Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Trp Gly His Arg Gly Phe Pro Tyr Trp Gly Gln Gly Thr Leu
            100                 105                 110

Val Thr Val Ser Ser
        115

<210> SEQ ID NO 3
<211> LENGTH: 107
<212> TYPE: PRT
<213> ORGANISM: artificial sequence
<220> FEATURE:
<223> OTHER INFORMATION: antibody, VL region

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Ser Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Val Tyr Tyr Cys Gln Gln Tyr Tyr Ser Tyr Pro Tyr
                85                  90                  95

Thr Phe Gly Gln Gly Thr Lys Leu Glu Ile Lys
            100                 105

<210> SEQ ID NO 4
<211> LENGTH: 107
<212> TYPE: PRT
<213> ORGANISM: artificial sequence
<220> FEATURE:
<223> OTHER INFORMATION: antibody, VL region

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Ala Pro Lys Val Leu Ile
        35                  40                  45

Tyr Ser Ala Ser Tyr Arg Tyr Ser Gly Val Ser Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Val Tyr Tyr Cys Gln Gln Tyr Tyr Ser Tyr Pro Tyr
                85                  90                  95

Thr Phe Gly Gln Gly Thr Lys Leu Glu Ile Lys
            100                 105

<210> SEQ ID NO 5
<211> LENGTH: 118
<212> TYPE: PRT
<213> ORGANISM: artificial sequence
<220> FEATURE:
<223> OTHER INFORMATION: antibody, VH region

<400> SEQUENCE: 5

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Arg Leu Glu Trp Ile
        35                  40                  45

Gly Asp Ile Asn Pro Lys Tyr Asp Ile Ile Gly His Asn Pro Lys Phe
    50                  55                  60

Met Gly Lys Ala Thr Leu Thr Val Asp Lys Ser Ala Ser Thr Ala Tyr
65              70                  75                  80

Met Glu Leu Ser Ser Leu Arg Ser Glu Asp Thr Ala Val Tyr Tyr Cys 85                  90                  95

Ala Arg Ser Asp Arg Gly Trp Tyr Phe Asp Val Trp Gly Gln Gly Thr
                100                 105                 110

Leu Val Thr Val Ser Ser
        115

<210> SEQ ID NO 6
<211> LENGTH: 118
<212> TYPE: PRT
<213> ORGANISM: artificial sequence
<220> FEATURE:
<223> OTHER INFORMATION: antibody, VH region

<400> SEQUENCE: 6

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Gln Arg Leu Glu Trp Ile
                35                  40                  45

Gly Asp Ile Asn Pro Lys Tyr Asp Ile Ile Gly His Asn Pro Lys Phe
        50                  55                  60

Met Gly Lys Ala Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Arg Gly Trp Tyr Phe Asp Val Trp Gly Gln Gly Thr
                100                 105                 110

Leu Val Thr Val Ser Ser
        115

<210> SEQ ID NO 7
<211> LENGTH: 104
<212> TYPE: PRT
<213> ORGANISM: artificial sequence
<220> FEATURE:
<223> OTHER INFORMATION: antibody, VL region

<400> SEQUENCE: 7

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val Asn Tyr Met
                20                  25                  30

Asn Trp Tyr Gln Gln Lys Pro Gly Gln Ala Pro Arg Pro Arg Ile Tyr
                35                  40                  45

Ala Thr Ser Asn Leu Ala Ser Gly Val Pro Ala Arg Phe Ser Gly Ser
        50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Trp Ser Ser Arg Thr Phe Gly
                85                  90                  95

Gly Gly Thr Lys Val Glu Ile Lys
        100

<210> SEQ ID NO 8
<211> LENGTH: 119
<212> TYPE: PRT
<213> ORGANISM: artificial sequence
<220> FEATURE:

<223> OTHER INFORMATION: antibody, VH region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Asn Tyr
            20                  25                  30

Phe Met His Trp Val Arg Gln Ala Pro Gly Gln Arg Leu Glu Trp Ile
        35                  40                  45

Gly Arg Ile Asn Pro Tyr Asn Gly Ala Thr Ser Tyr Ser Leu Asn Phe
    50                  55                  60

Arg Asp Lys Ala Thr Leu Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Ile Thr Ser Pro Leu Leu Asp Phe Trp Gly Gln Gly
            100                 105                 110

Thr Leu Val Thr Val Ser Ser
        115

<210> SEQ ID NO 9
<211> LENGTH: 119
<212> TYPE: PRT
<213> ORGANISM: artificial sequence
<220> FEATURE:
<223> OTHER INFORMATION: antibody, VH region

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Asn Tyr
            20                  25                  30

Phe Met His Trp Val Arg Gln Ala Pro Gly Gln Arg Leu Glu Trp Ile
        35                  40                  45

Gly Arg Ile Asn Pro Tyr Asn Gly Ala Thr Ser Tyr Ser Leu Asn Phe
    50                  55                  60

Arg Asp Lys Ala Thr Ile Thr Leu Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Ile Thr Ser Pro Leu Leu Asp Phe Trp Gly Gln Gly
            100                 105                 110

Thr Leu Val Thr Val Ser Ser
        115

<210> SEQ ID NO 10
<211> LENGTH: 107
<212> TYPE: PRT
<213> ORGANISM: artificial sequence
<220> FEATURE:
<223> OTHER INFORMATION: antibody, VL region

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Thr Ser
            20                  25                  30

Ile His Trp Tyr Gln Gln Lys Pro Gly Gln Ala Pro Arg Leu Leu Ile

```
                35                  40                  45
Lys Phe Ala Ser Glu Ser Ile Ser Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Ser Asn Lys Trp Pro Phe
                 85                  90                  95

Thr Phe Gly Gln Gly Thr Lys Leu Glu Ile Lys
            100                 105
```

<210> SEQ ID NO 11
<211> LENGTH: 30
<212> TYPE: DNA
<213> ORGANISM: artificial sequence
<220> FEATURE:
<223> OTHER INFORMATION: oligonucleotide primer

<400> SEQUENCE: 11
tatatctaga attcccccccc cccccccccc                                        30

<210> SEQ ID NO 12
<211> LENGTH: 46
<212> TYPE: DNA
<213> ORGANISM: artificial sequence
<220> FEATURE:
<223> OTHER INFORMATION: oligonucleotide primer

<400> SEQUENCE: 12
tatagagctc aagcttggat ggtgggaaga tggatacagt tggtgc                       46

<210> SEQ ID NO 13
<211> LENGTH: 54
<212> TYPE: DNA
<213> ORGANISM: artificial sequence
<220> FEATURE:
<223> OTHER INFORMATION: oligonucleotide primer

<400> SEQUENCE: 13
tatagagctc aagcttccag tggatagacc atgatggggg ctgttcgttt tggc              54

<210> SEQ ID NO 14
<211> LENGTH: 467
<212> TYPE: PRT
<213> ORGANISM: artificial sequence
<220> FEATURE:
<223> OTHER INFORMATION: antibody, heavy chain

<400> SEQUENCE: 14

```
Met Glu Trp Ser Gly Val Phe Ile Phe Leu Leu Ser Val Thr Ala Gly
 1               5                  10                  15

Val His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Asp Tyr Asn Met Asp Trp Val Arg Gln Ala Pro Gly Gln Arg Leu
 50                  55                  60

Glu Trp Ile Gly Asp Ile Asn Pro Lys Tyr Asp Ile Ile Gly His Asn
 65                  70                  75                  80

Pro Lys Phe Met Gly Lys Ala Thr Ile Thr Val Asp Lys Ser Ala Ser
                 85                  90                  95

Thr Ala Tyr Met Glu Leu Ser Ser Leu Arg Ser Glu Asp Thr Ala Val
```

Tyr Tyr Cys Ala Arg Ser Asp Arg Gly Trp Tyr Phe Asp Val Trp Gly
            115                 120                 125

Gln Gly Thr Leu Val Thr Val Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Ser Leu Gly Thr Gln Thr Tyr Ile Cys Asn Val Asn His
                210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
                290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
                370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
                435                 440                 445

His Glu Ala Leu His Asn His Tyr Thr Gln Lys Ser Leu Ser Leu Ser
                450                 455                 460

Pro Gly Lys
465

<210> SEQ ID NO 15
<211> LENGTH: 1404
<212> TYPE: DNA
<213> ORGANISM: artificial sequence
<220> FEATURE:
<223> OTHER INFORMATION: antibody, heavy chain

<400> SEQUENCE: 15

```
atggaatggt ccggcgtgtt catcttttg ctgtcagtca ccgctggcgt gcactctcaa      60
gtccagcttg ttcagagcgg agcagaagtg aagaagccag gggccagcgt caaggtttct    120
tgtaaagcca gtggttatac ctttactgat tacaacatgg attgggtacg tcaggcaccc    180
ggacaacggc tggagtggat tggcgacatc aatcccaaat acgacattat cggccataac    240
cctaagttta tggaaaggc taccattaca gtagataagt ctgcttccac cgcttacatg    300
gagctctcct ctctgcgcag tgaggatacc gcagtgtact attgcgccag gagtgaccga    360
ggctggtatt tcgacgtttg ggggcagggt acattggtga ctgtgtcaag cgccagcaca    420
aagggcccat cggtcttccc cctggcaccc tctagcaaga gcacctctgg gggcacagcg    480
gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcagcttgg gcacccagac ctacatctgc    660
aacgtgaatc acaagcccag caacaccaag gtggacaaga gagttgagcc caaatcttgt    720
gacaaaactc acacatgccc accgtgccca gcacctgaac tcctgggggg accgtcagtc    780
ttcctcttcc cccaaaaacc caaggacacc ctcatgatct cccggacccc tgaggtcaca    840
tgcgtggtgg tggacgtgag ccacgaagac cctgaggtca agttcaactg gtacgtggac    900
ggcgtggagg tgcataatgc caagacaaag ccgcgggagg agcagtacaa cagcacgtac    960
cgtgtggtca gcgtcctcac cgtcctgcac caggactggc tgaatggcaa ggagtacaag   1020
tgcaaggtct ccaacaaagc cctcccagcc cccatcgaga aaaccatctc caaagccaaa   1080
gggcagcccc gagaaccaca ggtgtacacc ctgcccccat cccgggagga tgaccaag     1140
aaccaggtca gcctgacctg cctggtcaaa ggcttctatc ccagcgacat cgccgtggag   1200
tgggagagca atgggcagcc ggagaacaac tacaagacca cgcctcccgt gctggactcc   1260
gacggctcct tcttcctcta tagcaagctc accgtggaca agagcaggtg gcagcagggg   1320
aacgtcttct catgctccgt gatgcatgag gctctgcaca accactacac gcagaagagc   1380
ctctccctgt ctccgggtaa atga                                          1404
```

<210> SEQ ID NO 16
<211> LENGTH: 233
<212> TYPE: PRT
<213> ORGANISM: artificial sequence
<220> FEATURE:
<223> OTHER INFORMATION: antibody, light chain

<400> SEQUENCE: 16

```
Met Asp Phe Gln Val Gln Ile Phe Ser Phe Leu Leu Ile Ser Ala Ser
  1               5                  10                  15

Val Ile Met Ser Arg Gly Glu Ile Val Leu Thr Gln Ser Pro Ala Thr
             20                  25                  30

Leu Ser Leu Ser Pro Gly Glu Arg Ala Thr Leu Ser Cys Arg Ala Ser
         35                  40                  45

Ser Ser Val Asn Tyr Met Asn Trp Tyr Gln Gln Lys Pro Gly Gln Ala
     50                  55                  60

Pro Arg Pro Arg Ile Tyr Ala Thr Ser Asn Leu Ala Ser Gly Val Pro
 65                  70                  75                  80

Ala Arg Phe Ser Gly Ser Gly Ser Gly Thr Asp Tyr Thr Leu Thr Ile
             85                  90                  95

Ser Ser Leu Glu Pro Glu Asp Phe Ala Val Tyr Tyr Cys Gln Gln Trp
```

```
            100                 105                 110
Ser Ser Arg Thr Phe Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 17
<211> LENGTH: 657
<212> TYPE: DNA
<213> ORGANISM: artificial sequence
<220> FEATURE:
<223> OTHER INFORMATION: antibody, light chain

<400> SEQUENCE: 17

```
atggatttc aagttcagat attctccttt cttctcatta gcgccagtgt gattatgtca      60
agagggaga ttgtcctgac acagagtccc gccacactta gcctgtcccc cggagagcgt     120
gctacactct cttgtcgcgc ttccagctct gtcaactaca tgaactggta tcagcagaaa    180
cccggtcagg cccctagacc ccggatctat gccacatcta atcttgcctc cggagtgcct    240
gcccgattca gcgggagcgg aagtggtacc gattacaccc tcacaatctc tagcttggaa    300
ccagaggact ttgcagtcta ttactgccaa cagtggtcta gtcgcacttt cggtggtggc    360
accaaattgg agatcaagag gactgtcgct gccccaagtg tgttcatctt cctccatcc    420
gatgagcagc tgaagagtgg aaccgcatcc gtggtttgcc tgctgaacaa cttttaccct    480
cgggaagcta aagtgtcagt aaccgaacaa gattccaagg actccaccta ctctctctca    540
tctaccttga ccctgtcaaa ggccgactat gaaaaacaca aggtttacgc atgtgaggta    600
actcatcaag gcttagctc tccagtcact aagagcttta caggggcga atgctag        657
```

<210> SEQ ID NO 18
<211> LENGTH: 538
<212> TYPE: PRT
<213> ORGANISM: artificial sequence
<220> FEATURE:
<223> OTHER INFORMATION: antibody, heavy chain

<400> SEQUENCE: 18

```
Met Glu Trp Ser Gly Val Phe Ile Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Asn Asp His Asn Ile His Trp Val Arg Gln Ala Pro Gly Gln Gly Leu
    50                  55                  60
```

-continued

```
Glu Trp Ile Gly Tyr Ile Tyr Pro Tyr Ile Gly Thr Val Tyr Asn
65                  70                  75                  80

Gln Lys Phe Lys Ser Lys Ala Thr Leu Thr Val Asp Thr Ser Thr Ser
            85                  90                  95

Thr Ala Tyr Met Glu Leu Arg Ser Leu Arg Ser Asp Asp Thr Ala Val
                100                 105                 110

Tyr Tyr Cys Ser Arg Trp Gly His Arg Gly Phe Pro Tyr Trp Gly Gln
            115                 120                 125

Gly Thr Leu Val Thr Val Ser Ser Ala Ser Thr Lys Gly Pro Ser Val
        130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Gln Thr Tyr Ile Cys Asn Val Asn His Lys
210                 215                 220

Pro Ser Asn Thr Lys Val Asp Lys Arg Val Gly Glu Arg Pro Ala Gln
225                 230                 235                 240

Gly Gly Arg Val Ser Ala Gly Ser Gln Ala Gln Arg Ser Cys Leu Asp
                245                 250                 255

Ala Ser Arg Leu Cys Ser Pro Ser Pro Gly Gln Gln Gly Arg Pro Arg
            260                 265                 270

Leu Pro Leu His Pro Glu Ala Ser Ala Arg Pro Thr His Ala Gln Gly
        275                 280                 285

Glu Gly Leu Leu Ala Phe Ser Pro Gly Ser Gly Gln Ala Gln Ala Arg
    290                 295                 300

Cys Pro Glu Pro Lys Ser Cys Asp Lys Thr His Thr Cys Pro Pro Cys
305                 310                 315                 320

Pro Ala Pro Glu Leu Leu Gly Gly Pro Ser Val Phe Leu Phe Pro Pro
                325                 330                 335

Lys Pro Lys Asp Thr Leu Met Ile Ser Arg Thr Pro Glu Val Thr Cys
            340                 345                 350

Val Val Val Asp Val Ser His Glu Asp Pro Glu Val Lys Phe Asn Trp
        355                 360                 365

Tyr Val Asp Gly Val Glu Val His Asn Ala Lys Thr Lys Pro Arg Glu
    370                 375                 380

Glu Gln Tyr Asn Ser Thr Tyr Arg Val Val Ser Val Leu Thr Val Leu
385                 390                 395                 400

His Gln Asp Trp Leu Asn Gly Lys Glu Tyr Lys Cys Lys Val Ser Asn
                405                 410                 415

Lys Ala Leu Pro Ala Pro Ile Glu Lys Thr Ile Ser Lys Ala Lys Gly
            420                 425                 430

Gln Pro Arg Glu Pro Gln Val Tyr Thr Leu Pro Pro Ser Arg Glu Glu
        435                 440                 445

Met Thr Lys Asn Gln Val Ser Leu Thr Cys Leu Val Lys Gly Phe Tyr
    450                 455                 460

Pro Ser Asp Ile Ala Val Glu Trp Glu Ser Asn Gly Gln Pro Glu Asn
465                 470                 475                 480
```

Asn Tyr Lys Thr Thr Pro Pro Val Leu Asp Ser Asp Gly Ser Phe Phe
                485                 490                 495

Leu Tyr Ser Lys Leu Thr Val Asp Lys Ser Arg Trp Gln Gln Gly Asn
            500                 505                 510

Val Phe Ser Cys Ser Val Met His Glu Ala Leu His Asn His Tyr Thr
        515                 520                 525

Gln Lys Ser Leu Ser Leu Ser Pro Gly Lys
    530                 535

<210> SEQ ID NO 19
<211> LENGTH: 1617
<212> TYPE: DNA
<213> ORGANISM: artificial sequence
<220> FEATURE:
<223> OTHER INFORMATION: antibody, heavy chain

<400> SEQUENCE: 19

```
atggagtggt ccggagtgtt catctttctg ctctctgtta ccgctggcgt acatagccaa     60
gtccagcttg tccagtctgg cgccgaggtc aagaaaccag gggccagcgt gaaagttagt    120
tgtaaggcat ccggctatac cttcaacgat cacaatatcc actgggtacg acaggctcca    180
ggccaagggc tggaatggat tggttacata taccccttaca ttggaacaac agtgtataac   240
cagaagttca atccaaggc aactcttact gtggatacat caacctcaac tgcctacatg     300
gaattgagat ccctgaggag tgacgacact gctgtctatt actgcagtcg gtggggacat    360
cgcggctttc cttattgggg tcaggggaca ctcgttactg tgagctctgc cagtaccaag    420
ggcccatcgg tcttcccccct ggcaccctct agcaagagca cctctggggg cacagcggcc    480
ctgggctgcc tggtcaagga ctacttcccc gaaccggtga cggtgtcgtg aactcaggc     540 gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttggtgagag gccagcacag    720
ggagggaggg tgtctgctgg aagccaggct cagcgctcct gcctggacgc atcccggcta    780
tgcagtccca gtccagggca gcaaggcagg ccccgtctgc ctcttcaccc ggaggcctct    840
gcccgcccca ctcatgctca gggagagggt cttctggctt ttccccagg ctctgggcag     900 gcacaggcta ggtgccccga gcccaaatct tgtgacaaaa ctcacacatg cccaccgtgc    960
ccagcacctg aactcctggg gggaccgtca gtcttcctct tccccccaaa acccaaggac   1020
accctcatga tctcccggac ccctgaggtc acatgcgtgg tggtggacgt gagccacgaa   1080
gaccctgagg tcaagttcaa ctggtacgtg gacggcgtgg aggtgcataa tgccaagaca   1140
aagccgcggg aggagcagta caacagcacg taccgtgtgg tcagcgtcct caccgtcctg   1200
caccaggact ggctgaatgg caaggagtac aagtgcaagg tctccaacaa agccctccca   1260 gccccatcg agaaaaccat ctccaaagcc aagggcagc cccgagaacc acaggtgtac    1320
accctgcccc catcccggga ggagatgacc aagaaccagg tcagcctgac ctgcctggtc   1380
aaaggcttct atcccagcga catcgccgtg gagtgggaga gcaatgggca gccggagaac   1440
aactacaaga ccacgcctcc cgtgctggac tccgacggct ccttcttcct ctatagcaag   1500
ctcaccgtgg acaagagcag gtggcagcag gggaacgtct tctcatgctc cgtgatgcat   1560
gaggctctgc acaaccacta cacgcagaag agcctctccc tgtctccggg taaatga      1617
```

<210> SEQ ID NO 20
<211> LENGTH: 234

```
<212> TYPE: PRT
<213> ORGANISM: artificial sequence
<220> FEATURE:
<223> OTHER INFORMATION: antibody, light chain

<400> SEQUENCE: 20
```

| | | | | | | | | | | | | | | | |
|---|---|---|---|---|---|---|---|---|---|---|---|---|---|---|---|
| Met | Glu | Ser | Gln | Thr | Gln | Val | Phe | Val | Tyr | Met | Leu | Leu | Trp | Leu | Ser |
| 1 | | | | 5 | | | | | 10 | | | | | 15 | |
| Gly | Val | Asp | Gly | Asp | Ile | Gln | Met | Thr | Gln | Ser | Pro | Ser | Ser | Leu | Ser |
| | | | 20 | | | | | 25 | | | | | 30 | | |
| Ala | Ser | Val | Gly | Asp | Arg | Val | Thr | Ile | Thr | Cys | Lys | Ala | Ser | Gln | Asn |
| | | | 35 | | | | | 40 | | | | | 45 | | |
| Val | Gly | Thr | Asn | Val | Ala | Trp | Tyr | Gln | Gln | Lys | Pro | Gly | Lys | Ala | Pro |
| | | 50 | | | | | 55 | | | | | 60 | | | |
| Lys | Ala | Leu | Ile | Tyr | Ser | Ala | Ser | Tyr | Arg | Tyr | Ser | Gly | Val | Ser | Ser |
| 65 | | | | | 70 | | | | | 75 | | | | | 80 |
| Arg | Phe | Ser | Gly | Ser | Gly | Ser | Gly | Thr | Asp | Phe | Thr | Leu | Thr | Ile | Ser |
| | | | | 85 | | | | | 90 | | | | | 95 | |
| Ser | Leu | Gln | Pro | Glu | Asp | Phe | Ala | Val | Tyr | Tyr | Cys | Gln | Gln | Tyr | Tyr |
| | | | 100 | | | | | 105 | | | | | 110 | | |
| Ser | Tyr | Pro | Tyr | Thr | Phe | Gly | Gln | Gly | Thr | Lys | Leu | Glu | Ile | Lys | Arg |
| | | 115 | | | | | 120 | | | | | 125 | | | |
| Thr | Val | Ala | Ala | Pro | Ser | Val | Phe | Ile | Phe | Pro | Pro | Ser | Asp | Glu | Gln |
| | 130 | | | | | 135 | | | | | 140 | | | | |
| Leu | Lys | Ser | Gly | Thr | Ala | Ser | Val | Val | Cys | Leu | Leu | Asn | Asn | Phe | Tyr |
| 145 | | | | | 150 | | | | | 155 | | | | | 160 |
| Pro | Arg | Glu | Ala | Lys | Val | Gln | Trp | Lys | Val | Asp | Asn | Ala | Leu | Gln | Ser |
| | | | | 165 | | | | | 170 | | | | | 175 | |
| Gly | Asn | Ser | Gln | Glu | Ser | Val | Thr | Glu | Gln | Asp | Ser | Lys | Asp | Ser | Thr |
| | | | 180 | | | | | 185 | | | | | 190 | | |
| Tyr | Ser | Leu | Ser | Ser | Thr | Leu | Thr | Leu | Ser | Lys | Ala | Asp | Tyr | Glu | Lys |
| | | | 195 | | | | | 200 | | | | | 205 | | |
| His | Lys | Val | Tyr | Ala | Cys | Glu | Val | Thr | His | Gln | Gly | Leu | Ser | Ser | Pro |
| | 210 | | | | | 215 | | | | | 220 | | | | |
| Val | Thr | Lys | Ser | Phe | Asn | Arg | Gly | Glu | Cys | | | | | | |
| 225 | | | | | 230 | | | | | | | | | | |

```
<210> SEQ ID NO 21
<211> LENGTH: 705
<212> TYPE: DNA
<213> ORGANISM: artificial sequence
<220> FEATURE:
<223> OTHER INFORMATION: antibody, light chain

<400> SEQUENCE: 21
atggaatctc agactcaagt gtttgtgtac atgttgctgt ggctgagcgg cgttgacggt      60
gacattcaga tgacccaaag cccctcaagt ctttctgcta gcgtggggga cagggtgacc     120
ataacatgca aagccagcca aaatgtgggg actaacgttg cctggtatca gcagaaacca     180
ggtaaagcac ccaaggctct gatctacagt gcaagttatc gatactccgg cgtgtcctct     240
cggttttctg gctctgggag cggaaccgat tcactctga ccattagttc actccaacca      300
gaagatttcg cagtctacta ttgtcagcag tactatagtt acccatatac atttggacag     360
ggcaccaagc tggaaatcaa gagaaccgtt gccgctcctt cagtattcat cttccctccc     420
tccgatgagc agttgaagtc cggcacagca agcgtcgtat gccttttgaa caatttctat     480
ccacgcgagg ccaaagtgca atggaaggtc gacaacgctc tgcagtcagg caactcccaa     540
```

```
gagtcagtca cagagcagga cagcaaagat tccacttatt ctctctcttc tacactcact      600
ctgagcaagg ccgactatga aagcataag gtttacgcct gcgaagtgac ccaccaggga       660
ttgagttccc ctgtcactaa gtcctttaac cgtggggagt gttag                      705
```

<210> SEQ ID NO 22
<211> LENGTH: 540
<212> TYPE: PRT
<213> ORGANISM: artificial sequence
<220> FEATURE:
<223> OTHER INFORMATION: antibody, heavy chain

<400> SEQUENCE: 22

```
Met Gly Trp Ser Trp Ile Phe Leu Phe Leu Leu Ser Gly Thr Ala Gly
1               5                   10                  15

Gly Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Pro Phe
        35                  40                  45

Thr Asn Tyr Phe Met His Trp Val Arg Gln Ala Pro Gly Gln Arg Leu
    50                  55                  60

Glu Trp Ile Gly Arg Ile Asn Pro Tyr Asn Gly Ala Thr Ser Tyr Ser
65                  70                  75                  80

Leu Asn Phe Arg Asp Lys Ala Thr Ile Thr Leu Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Ser Thr Ile Thr Ser Pro Leu Leu Asp Phe Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Gly Glu Arg Pro
225                 230                 235                 240

Ala Gln Gly Gly Arg Val Ser Ala Gly Ser Gln Ala Gln Arg Ser Cys
                245                 250                 255

Leu Asp Ala Ser Arg Leu Cys Ser Pro Ser Gly Gln Gln Gly Arg
            260                 265                 270

Pro Arg Leu Pro Leu His Pro Glu Ala Ser Ala Arg Pro Thr His Ala
        275                 280                 285

Gln Gly Glu Gly Leu Leu Ala Phe Ser Pro Gly Ser Gln Ala Gln
    290                 295                 300

Ala Arg Cys Pro Glu Pro Lys Ser Cys Asp Lys Thr His Thr Cys Pro
305                 310                 315                 320

Pro Cys Pro Ala Pro Glu Leu Leu Gly Gly Pro Ser Val Phe Leu Phe
                325                 330                 335
```

```
Pro Pro Lys Pro Lys Asp Thr Leu Met Ile Ser Arg Thr Pro Glu Val
            340                 345                 350
Thr Cys Val Val Val Asp Val Ser His Glu Asp Pro Glu Val Lys Phe
            355                 360                 365
Asn Trp Tyr Val Asp Gly Val Glu Val His Asn Ala Lys Thr Lys Pro
        370                 375                 380
Arg Glu Glu Gln Tyr Asn Ser Thr Tyr Arg Val Val Ser Val Leu Thr
385                 390                 395                 400
Val Leu His Gln Asp Trp Leu Asn Gly Lys Glu Tyr Lys Cys Lys Val
                405                 410                 415
Ser Asn Lys Ala Leu Pro Ala Pro Ile Glu Lys Thr Ile Ser Lys Ala
            420                 425                 430
Lys Gly Gln Pro Arg Glu Pro Gln Val Tyr Thr Leu Pro Pro Ser Arg
            435                 440                 445
Glu Glu Met Thr Lys Asn Gln Val Ser Leu Thr Cys Leu Val Lys Gly
        450                 455                 460
Phe Tyr Pro Ser Asp Ile Ala Val Glu Trp Glu Ser Asn Gly Gln Pro
465                 470                 475                 480
Glu Asn Asn Tyr Lys Thr Thr Pro Pro Val Leu Asp Ser Asp Gly Ser
                485                 490                 495
Phe Phe Leu Tyr Ser Lys Leu Thr Val Asp Lys Ser Arg Trp Gln Gln
            500                 505                 510
Gly Asn Val Phe Ser Cys Ser Val Met His Glu Ala Leu His Asn His
            515                 520                 525
Tyr Thr Gln Lys Ser Leu Ser Leu Ser Pro Gly Lys
        530                 535                 540

<210> SEQ ID NO 23
<211> LENGTH: 765
<212> TYPE: DNA
<213> ORGANISM: artificial sequence
<220> FEATURE:
<223> OTHER INFORMATION: antibody, heavy chain

<400> SEQUENCE: 23
atgggatgga gctggatttt cttgttcctc ctttccggga ctgctggcgg actgtcccaa      60
gtccagttgg tgcagagcgg cgctgaggtt aagaagcccg gtgcctctgt caaagttagt     120
tgcaaagcaa gtggctaccc tttcacaaac tactttatgc actgggtgcg ccaggcccct     180
gggcaaagac tcgaatggat cggtcgtatc aatccataca atggggcaac tagttattct     240
ctcaacttca gggataaggc taccattaca ctggacaagt ctgcctctac cgcctatatg     300
gagctgagct ccctgcggag tgaagatact gctgtctatt actgtgcacg atccaccata     360
acctctcccc tgctggactt ttggggccag ggcacacttg tgactgtatc atcagcatcc     420
acaaagggcc catcggtctt ccccctggca cctctagca agagcaccto tggggcaca     480 gcggccctgg gctgcctggt caaggactac ttccccgaac cggtgacggt gtcgtggaac     540
tcaggcgccc tgaccagcgg cgtgcacacc ttcccggctg tcctacagtc ctcaggactc     600
tactccctca gcagcgtggt gaccgtgccc tccagcagct tgggcaccca gacctacatc     660
tgcaacgtga atcacaagcc cagcaacacc aaggtggaca gagagttgg tgagaggcca     720 gcacagggag ggagggtgtc tgctggaagc caggctcagc gctcc                     765

<210> SEQ ID NO 24
<211> LENGTH: 234
```

<212> TYPE: PRT
<213> ORGANISM: artificial sequence
<220> FEATURE:
<223> OTHER INFORMATION: antibody, light chain

<400> SEQUENCE: 24

```
Met Ser Val Pro Thr Gln Val Leu Gly Leu Leu Leu Leu Trp Leu Thr
1               5                   10                  15

Asp Ala Arg Cys Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Gly Thr Ser Ile His Trp Tyr Gln Gln Lys Pro Gly Gln Ala Pro
    50                  55                  60

Arg Leu Leu Ile Lys Phe Ala Ser Glu Ser Ile Ser Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Ser Asn
            100                 105                 110

Lys Trp Pro Phe Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 25
<211> LENGTH: 705
<212> TYPE: DNA
<213> ORGANISM: artificial sequence
<220> FEATURE:
<223> OTHER INFORMATION: antibody, light chain

<400> SEQUENCE: 25

| | |
|---|---|
| atgtccgttc ctactcaagt gctgggactg cttcttctgt ggctcactga cgcaaggtgt | 60 |
| gagatcgtgc tgacccagag tccagccaca ctcagcttgt cacccgggga acgggctaca | 120 |
| ctgtcctgtc gtgcatcaca gagcgtgggt acatcaattc actggtatca gcagaagccc | 180 |
| ggtcaggctc ccagactcct gataaagttt gcctccgaat ccatttctgg cattccagcc | 240 |
| cgcttctccg gctccggcag tggaactgat tcacccctca ccattagttc tttggagcct | 300 |
| gaagattttg cagtatacta ctgtcaacag tctaacaagt ggccttttac ttttgggcag | 360 |
| ggaactaaac tggagatcaa gcgcactgtc gctgctccaa gcgtattcat ctttcctccc | 420 |
| tccgacgagc agttgaaatc agggacagcc tctgtggtct gctgctgaa caatttctac | 480 |
| ccaagggaag ccaaagtgca gtggaaggtc gataatgcac ttcaatcagg taattctcaa | 540 |

-continued

```
gagagtgtga ccgagcagga ttccaaggac agtacctact ctctcagctc aaccctgacc      600
ctttctaaag ctgactatga aaaacataaa gtctacgcct gcgaagtgac acaccagggt      660
ctgagtagcc ctgttaccaa gagctttaac cgaggcgagt gctag                      705
```